US012692548B2

(12) United States Patent
Lin

(10) Patent No.: US 12,692,548 B2
(45) Date of Patent: Jul. 28, 2026

(54) BCOR REARRANGEMENTS AND USES THEREOF

(71) Applicant: Foundation Medicine, Inc., Cambridge, MA (US)

(72) Inventor: Douglas I. Lin, Cambridge, MA (US)

(73) Assignee: Foundation Medicine, Inc., Boston, MA (US)

( * ) Notice: Subject to any disclaimer, the term of this patent is extended or adjusted under 35 U.S.C. 154(b) by 870 days.

(21) Appl. No.: 17/908,847

(22) PCT Filed: Mar. 3, 2021

(86) PCT No.: PCT/US2021/020752
§ 371 (c)(1),
(2) Date: Sep. 1, 2022

(87) PCT Pub. No.: WO2021/178595
PCT Pub. Date: Sep. 10, 2021

(65) Prior Publication Data

US 2023/0295734 A1 Sep. 21, 2023

Related U.S. Application Data

(60) Provisional application No. 62/985,227, filed on Mar. 4, 2020.

(51) Int. Cl.
*C12Q 1/68* (2018.01)
*C12Q 1/6869* (2018.01)
*C12Q 1/6886* (2018.01)

(52) U.S. Cl.
CPC ......... *C12Q 1/6886* (2013.01); *C12Q 1/6869* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS 3,773,919 A 11/1973 Boswell
4,683,195 A 7/1987 Mullis et al.
4,816,567 A 3/1989 Cabilly et al.
5,223,409 A 6/1993 Ladner et al.
5,225,539 A 7/1993 Winter
5,545,806 A 8/1996 Lonberg et al.
5,545,807 A 8/1996 Surani et al.
5,569,825 A 10/1996 Lonberg et al.
5,624,821 A 4/1997 Winter et al.
5,625,126 A 4/1997 Lonberg et al.
5,633,425 A 5/1997 Lonberg et al.
5,648,260 A 7/1997 Winter et al.
5,661,016 A 8/1997 Lonberg et al.
5,776,688 A 7/1998 Bittner et al.
9,340,830 B2 5/2016 Lipson et al.
2016/0108380 A1 4/2016 Iavarone et al.
2018/0045727 A1 2/2018 Spetzler et al.
2019/0367613 A1 12/2019 Harvey et al.

FOREIGN PATENT DOCUMENTS

EP 171496 A2 2/1986
EP 173494 A2 3/1986
EP 184187 A2 6/1986
EP 125023 B1 6/1991
WO WO-1986001533 A1 3/1986
WO WO-1987002671 A1 10/1987
WO WO-1990002809 A1 3/1990
WO WO-1991010741 A1 7/1991
WO WO-1992001047 A1 7/1991
WO WO-1991017271 A1 11/1991
WO WO-1992009690 A2 6/1992
WO WO-1992015679 A1 9/1992
WO WO-1992018619 A1 10/1992
WO WO-1992020791 A1 11/1992
WO WO-1993001288 A1 1/1993
WO WO-1994029351 A2 12/1994
WO WO-1996033735 A1 10/1996
WO WO-1996034096 A1 10/1996
WO WO-1998024893 A2 6/1998
WO WO-2005016894 A1 2/2005

(Continued)

OTHER PUBLICATIONS

Hoang et al. (The American Journal of Surgical Pathology 41(1):p. 12-24, Jan. 2017) (Year: 2017).*
Luke et al. (Clin Cancer Res (2012) 18 (9): 2638-2647) (Year: 2012).*
Kao et al. (Am J Surg Pathol 2018;42:604-615) (Year: 2018).*
Brahmi et al. ( Annals of Oncology, (Oct. 2019) vol. 30, Supplement 5, pp. v702-v703 Meeting Info: 44th ESMO Congress. Barcelona, Spain. Sep. 27, 2019-Oct. 1, 2019) (Year: 2019).*
Allen et al., (2017). "A recurrent endometrial stromal sarcoma harbors the novel fusion JAZFI-BCORL1," Gyriecologic Oncology Reports, 20:51-53.
Alonso et al., (1994). "Biodegradable microspheres as controlled-release tetanus toxoid delivery systems," Vaccine, 12(4):299-306.
Arias-Stella et al., (2019). "Novel PLAG1 Gene Rearrangement Distinguishes a Subset of Uterine Myxoid Leiomyosarcoma From Other Uterine Myxoid Mesenchymal Tumors," Am. J. Surg. Pathol., 43:382-388, 13 pages.

(Continued)

*Primary Examiner* — Juliet C Switzer
(74) *Attorney, Agent, or Firm* — MORRISON & FOERSTER LLP

(57) ABSTRACT

Provided herein are methods related to detecting rearrangements in the B-cell lymphoma 6 (BCL6) corepressor (BCOR) or BCL6 corepressor-like protein I (BCORL1) gene, as well as methods of treatment, uses, and kits related thereto. As demonstrated herein, detection of BCOR rearrangements can be used to identify individuals that may benefit from treatment with a targeted therapeutic, such as a CDK inhibitor, an MDM2 inhibitor, a tyrosine kinase inhibitor, a MEK inhibitor, an mTOR inhibitor, or a Hh inhibitor. In some embodiments, the BCOR rearrangement is a fusion gene between BCOR and L3MBTL2, EP300, NUTM2G, MAP7D2, RALGPS1 RGAG1, CREBBP, ING3, NUGGC, or KMT 2D.

10 Claims, 18 Drawing Sheets

Specification includes a Sequence Listing.

(56) References Cited

FOREIGN PATENT DOCUMENTS

| | | | |
|---|---|---|---|
| WO | WO-2012092426 | A1 | 7/2012 |
| WO | WO-2012139134 | A2 | 10/2012 |
| WO | WO-2015016718 | A1 | 2/2015 |
| WO | WO-2017070497 | A1 | 4/2017 |
| WO | WO-2019178081 | A1 | 9/2019 |
| WO | WO-2020033585 | A1 | 2/2020 |

OTHER PUBLICATIONS

Astolfi et al., (2019). "BCOR involvement in cancer," Epigenomics, 11:835-855, 33 pages.

Beidler et al., (1988). "Cloning and high level expression of a chimeric antibody with specificity for human carcinoembryonic antigen," J. Immunol., 141(11):4053-4060.

Benson et al., (2017). "Uterine sarcoma—current perspectives," Int. J. Womens Health, 9:597-606.

Better et al. (1988). "*Escherichia coli* secretion of an active chimeric antibody fragment," Science, 240(4855):1041-1043.

Brahmi et al., (2020). "Molecular Classification of Endometrial Stromal Sarcomas Using RNA Sequencing Defines Nosological and Prognostic Subgroups with Different Natural History," Cancers (Basel), 12(9):2604, 12 pages.

Bruggeman et al., (1993). "Designer mice: the production of human antibody repertoires in transgenic animals," The Year in Immunology, 7:33-40.

Carrel et al., (2005). "X-inactivation profile reveals extensive variability in X-linked gene expression in females," Nature, 434:400-404.

Cerami et al., (2012). "The cBio cancer genomics portal: an open platform for exploring multidimensional cancer genomics data," Cancer Discov., 2:401-404.

Chalmers et al., (2017). "Analysis of 100,000 human cancer genomes reveals the landscape of tumor mutational burden," Genome Med., 9(1):34, 14 pages.

Chothia et al., (1987). "Canonical structures for the hypervariable regions of immunoglobulins," Mol. Biol., 196:901-917.

Clackson et al., (1991). "Making antibody fragments using phage display libraries," Nature, 352(6336):624-628.

Cole et al., (1985). "The EBV-Hybridoma Technique and its Application to Human Lung Cancer," Monoclonal Antibodies and Cancer Therapy, pp. 77-96.

Connelly et al., (2018). "Abstract 1227: Somatic genome alterations in cancer as compared to inferred patient ancestry," Cancer Research: AACR, 2 pages.

Cuppens et al., (2018). "Integrated genome analysis of uterine leiomyosarcoma to identify novel driver genes and targetable pathways," Int. J. Cancer, 142:1230-1243.

Dickson et al., (2018). "NUTM1 Gene Fusions Characterize a Subset of Undifferentiated Soft Tissue and Visceral Tumors," American Journal of Surgical Pathology, 42(5):636-645, 19 pages.

Diehl, (2002). "Cycling to cancer with cyclin D1," Cancer Biol. Ther., 1:226-231.

Duncan et al., (1988). "The binding site for C1q on lgG," Nature, 322(6166):738-740.

Eldridge et al., (1991). "Biodegradable microspheres as a vaccine delivery system," Molec. Immunol., 28:287-294.

Elvin et al., (2017). "Clinical Benefit in Response to Palbociclib Treatment in Refractory Uterine Leiomyosarcomas with a Common CDKN2A Alteration," Oncologist, 22:416-421.

Emens, (2008). "Cancer vaccines: on the threshold of success," Expert Opin Emerg Drugs, 13(2):295-308, 22 pages.

FDA (2020). "FDA approves pembrohzumab for adults and children with 1MB-H solid tumors," Available online at <https://www.fda.gov/drugs/drug-approvals-and-databases/fda-approves-pembrolizumab-adults-and-children-tmb-h-solid-tumors>, 2 pages.

Fellouse et al., (2004). "Synthetic antibodies from a four-amino-acid code: a dominant role for tyrosine in antigen recognition," Proc. Natl. Acad. Sci. USA, 101(34):12467-12472.

Fishwild et al., (1996). "High-avidity human IgGK monoclonal antibodies from a novel strain of minilocus transgenic mice," Nature Biotechnol., 14:845-851.

Frampton et al., (2013). "Development and validation of a clinical cancer genomic profiling test based on massively parallel DNA sequencing," Nature Biotechnology, 31(11):1023-1031.

Fuchs et al., (1991). "Targeting Recombinant Antibodies to the Surface of *Escherichia coli*: Fusion to a Peptidoglycan Associated Lipoprotein," Nature Biotechnology, 9:1370-1372.

Gao et al., (2013). "Integrative analysis of complex cancer genomics and clinical profiles using the cBioPortal," Sci. Signal, 6(269):pl1, 34 pages.

Griffiths et al., (1993). "Human anti-self antibodies with high specificity from phage display libraries," EMBO J., 12(2):725-734.

Hamers-Casterman et al., (1993). "Naturally occurring antibodies devoid of light chains," Nature, 363:446-448.

Hay et al., (1992). "Bacteriophage cloning and *Escherichia coli* expression of a human lgM Fab," Hum. Antibod. Hybridomas, 3(2):81-85.

He et al. (2016). "Integrated genomic DNA/RNA profiling of hematologic malignancies in the clinical setting" Blood vol. 127, No. 24, pp. 3004-3014.

Hemming et al., (2017). "YWHAE-rearranged high-grade endometrial stromal sarcoma: Two-center case series and response to chemotherapy," Gynecol. Oncol., 145:531-535, 11 pages.

Hoang et al., (2017). "Novel High-grade Endometrial Stromal Sarcoma: A Morphologic Mimicker of Myxoid Leiomyosarcoma," Am. J Surg. Pathol., 41:12-24, 21 pages.

Hongo et al., (1995). "Development and characterization of murine monoclonal antibodies to the latency-associated peptide of transforming growth factor beta 1," Hybridoma, 14(3):253-260.

Hu et al., (1998). "The immunostimulating complex (ISCOM) is an efficient mucosal delivery system for respiratory syncytial virus (RSV) envelope antigens inducing high local and systemic antibody responses," Clin. Exp. Immunol., 113:235-243.

Huse et al., (1989). "Generation of a large combinatorial library of the immunoglobulin repertoire in phage lambda," Science, 246(4935):1275-1281.

International Search Report and Written Opinion received for International Patent Application No. PCT/US2021/020752 mailed on Sep. 2, 2021, 26 pages.

Jakobovits et al., (1993). "Analysis of homozygous mutant chimeric mice: deletion of the immunoglobulin heavy-chain joining region blocks B-cell development and antibody production," Proc. Acad Sci USA, 90:2551-5.

Jakobovits et al., (1993). "Germ-line transmission and expression of a human-derived yeast artificial chromosome" Nature, 362:255-258.

Jones et al., (1986). "Replacing the complementarity-determining regions in a human antibody with those from a mouse," Nature, 321(6069):552-525.

Jones et al., (1995). "Protection of mice from Bordetella pertussis respiratory infection using microencapsulated pertussis fimbriae," Vaccine, 13:675-681.

Kao et al., (2017). "Expanding the molecular signature of ossifying fibromyxoid tumors with two novel gene fusions: CREBBP-BCORL1 and KDM2A-WWTR1," Genes, Chromosomes, Cancer, 56:42-50, 15 pages.

Kao et al., (2018). "BCOR-CCNB3 Fusion Positive Sarcomas: A Clinicopathologic and Molecular Analysis of 36 Cases With Comparison to Morphologic Spectrum and Clinical Behavior of Other Round Cell Sarcomas," Am. J. Surg. Pathol., 42:604-615, 23 pages.

Kohler et al., (1975). "Continuous cultures of fused cells secreting antibody of predefined specificity," Nature, 256(5517):495-497.

Kozbor et al., (1983). "The production of monoclonal antibodies from human lymphocytes," Immunol. Today, 4(3):72-79.

Lee et al., (2004). "Bivalent antibody phage display mimics natural immunoglobulin," J. Immunol. Methods, 284(1-2):119-132.

Lee et al., (2004). "High-affinity human antibodies from phage-displayed synthetic Fab libraries with a single framework scaffold," J. Mol. Biol., 340(5):1073-1093.

(56) References Cited

OTHER PUBLICATIONS

Lewis et al., (2018). "ZC3H7B-BCOR high-grade endometrial stromal sarcomas: a report of 17 cases of a newly defined entity," Mod Pathol., 31:674-684.
Li et al., (2011). "Somatic mutations in the transcriptional corepressor gene BCORL1 in adult acute myelogenous leukemia," Blood J, 18:5914-5917.
Li et al., (2016). "HDACs and HDAC Inhibitors in Cancer Development and Therapy," Cold Spring Harb Perspect Med, 6(10):a026831, 34 pages.
Lin et al., (2019). "SMARCA4 inactivation defines a subset of undifferentiated uterine sarcomas with rhabdoid and small cell features and germline mutation association," Mod. Pathol, 32(11):1675-1687.
Lipson et al., (2012). "Identification of new ALK and RET gene fusions from colorectal and lung cancer biopsies," Nat. Med., 18(3):382-384.
Liu et al., (1987). "Chimeric mouse-human lgG1 antibody that can mediate lysis of cancer cells," Proc. Natl. Acad. Sci. USA, 84(10):3439-3443.
Liu et al., (1987). "Production of a mouse-human chimeric monoclonal antibody to CD20 with potent Fc-dependent biologic activity," J Immunol. 139(10):3521-3526.
Lonberg et al., (1994). "Antigen-specific human antibodies from mice comprising four distinct genetic modifications," Nature, 368:856-859.
Lonberg et al., (1995). "Human antibodies from transgenic mice," Int. Rev. Immunol., 13(1):65-93.
Makinen et al., (2016). "Exome Sequencing of Uterine Leiomyosarcomas Identifies Frequent Mutations in TP53, ATRX, and MED12," PLoS Genet., 12:e1005850, 13 pages.
Marino-Enriquez et al., (2018). "BCOR Internal Tandem Duplication in High-grade Uterine Sarcomas," Am. J Surg. Pathol., 42:335-341.
Marks et al., (1992). "By-passing immunization. Human antibodies from V-gene libraries displayed on phage," J Mol Biol., 222(3):581-597.
Marks et al., (1992). "By-Passing Immunization: Building High Affinity Human Antibodies by Chain Shuffling," BioTechnology, 10:779-783.
Metzker (2010). "Sequencing technologies—the next generation," Nature Biotechnology Reviews, 11(1):31-46.
Micci et al., (2016). "Cytogenetic and molecular profile of endometrial stromal sarcoma," Genes Chromosom Cancer, 55:834-846.
Morrison (1985). "Transfectomas provide novel chimeric antibodies," Science, 229(4719):1202-1207.
Morrison, (1994). "Success in specification," Nature, 368:812-813.
Mullis et al., (1987). "Specific enzymatic amplification of DNA in vitro: the polymerase chain reaction," Cold Spring Harbor Symp. Quant. Biol. 51:263-73.
Neuberger, (1996). "Generating high-avidity human Mabs in mice," Nature Biotechnol, 14:826, 1 page.
Nishimura et al., (1987). "Recombinant human-mouse chimeric monoclonal antibody specific for common acute lymphocytic leukemia antigen," Cancer Res., 47(4):999-1005.
Oi et al., (1986). "Chimeric antibodies," BioTechniques, 4(3), 214-221.
Pardoll, (2012). "The blockade of immune checkpoints in cancer immunotherapy," Nat Rev Cancer, 12(4):252-64.
Pietrantonio et al., (2017). "ALK, ROS1, and NTRK Rearrangements in Metastatic Colorectal Cancer," J Natl Cancer Inst, 109(12), 10 pages.
Pisapia et al., (2020). "Fusions involving BCOR and CREBBP are rare events in infiltrating glioma," Acta Neuropathologica Communications, 8(1):80, 11 pages.
See et al., (2012). "Sensitivity of glioblastomas to clinically available MEK inhibitors is defined by neurofibromin 1 deficiency," Cancer Res., 72:3350-3359.
Shaw et al., (1988). "Mouse/human chimeric antibodies to a tumor-associated antigen: biologic activity of the four human lgG subclasses," J. Natl. Cancer Inst. 80(19):1553-1559.
Sheriff et al., (1996). "Redefining the minimal antigen-binding fragment," Nature Struct., 3:733-736.
Sidhu et al., (2004). "Phage-displayed antibody libraries of synthetic heavy chain complementarity determining regions," J Mot Biol., 338(2):299-310.
Silva et al., (2015). "Refractory angiosarcoma of the breast with VEGFR2 upregulation successfully treated with sunitinib," Breast J, 21(2):205-207.
Specht et al., (2016). "Novel BCOR-MAML3 and ZC3H7B-BCOR Gene Fusions in Undifferentiated Small Blue Round Cell Sarcomas," Am. J. Surg. Pathol., 40:433-442, 20 pages.
Sun et al., (1987). "Chimeric antibody with human constant regions and mouse variable regions directed against carcinoma-associated antigen 17-1A," Proc. Natl. Acad. Sci. USA, 84(1):214-218.
Takahashi et al., (1990). "Induction of CD8+ cytotoxic T cells by immunization with purified HIV-1 envelope protein in ISCOMs," Nature, 344:873-875.
Tam, (1988). "Synthetic peptide vaccine design: synthesis and properties of a high-density multiple antigenic peptide system," Proc. Natl Acad. Sci. U.S.A., 85:5409-5413.
Tam, (1996). "Recent advances in multiple antigen peptides," J. Immunol. Methods, 196:17-32.
Torre et al., (2019). "Recurrent EP300-BCOR Fusions in Pediatric Gliomas with Distinct Clinicopathologic Features," Journal of Neuropathology and Experimental Neurology, 78(4):305-314.
Turner et al., (2015). "Palbociclib in Hormone-Receptor-Positive Advanced Breast Cancer," N. Engl. J. Med., 373:209-219.
Turner et al., (2018). "Overall Survival with Palbociclib and Fulvestrant in Advanced Breast Cancer," N. Engl. J. Med., 379:1926-1936.
Verhoeyan et al., (1988). "Reshaping human antibodies: grafting an antilysozyme activity," Science, 239(4847):1534-1536.
Vitiello et al., (1995). "Development of a lipopeptide-based therapeutic vaccine to treat chronic HBV infection. I. Induction of a primary cytotoxic T lymphocyte response in humans," J. Clin. Invest., 95:341-9.
Von Hoff et al., (2009). "Inhibition of the hedgehog pathway in advanced basal-cell carcinoma" N. Engl. J. Med., 361:1164-1172.
Wang et al., (2020). "Emerging Roles of ALK in Immunity and Insights for Immunotherapy," Cancers, 12(2):426, 5 pages.
Wong et al., (2020)."Structure and Role of BCOR PUFD in Noncanonical PRC1 Assembly and Disease," Biochemistry, 59:2718-2728, 22 pages.
Wood et al., (1985). "The synthesis and in vivo assembly of functional antibodies in yeast," Nature, 314(6010):446-449.
Xu et al., (2000). "Diversity in the CDR3 region of V(H) is sufficient for most antibody specificities," Immunity, 13:37-45.
Yamada et al., (2013). "Next-generation peptide vaccines for advanced cancer," Cancer Sci, 104:14-21.
Yamamoto et al., (2014). "Clarifying the Impact of Polycomb Complex Component Disruption in Human Cancers," Molecular Cancer Research, 12(4):479-84.
Yankauckas et al., (1993). "Long-Term Anti-Nucleoprotein Cellular and Humoral Immunity Is Induced by Intramuscular Injection of Plasmid DNA Containing NP Gene," DNA Cell Biol., 12:771-776.
Yoon et al., (2019). "Myxoid smooth muscle neoplasia of the uterus: comprehensive analysis by next-generation sequencing and nucleic acid hybridization," Mod. Pathol., 32:1688-1697.
Ali et al., (2015). "Exceptional Response on Addition of Everolimus to Taxane in Urothelial Carcinoma Bearing an NF2 Mutation," Eur. Urol., 67:1195-1196.
De Duenas et al., (2018). "Preclinical and clinical development of palbociclib and future perspectives," Clin Transl. Oncol., 20:1136-1144.
Debiec-Rychter et al., (2004). "Use of c-KIT/PDGFRA mutational analysis to predict the clinical response to imatinib in patients with advanced gastrointestinal stromal tumours entered on phase I and II studies of the EORTC Soft Tissue and Bone Sarcoma Group," Eur. J. Cancer, 40:689-695.

(56) References Cited

OTHER PUBLICATIONS

Ferreira et al., (2018). "Recent advances in the histological and molecular classification of endometrial stromal neoplasms," Virchows Arch., 473:665-678.
Juckett et al., (2018). "A Pan-Cancer Landscape Analysis Reveals a Subset of Endometrial Stromal and Pediatric Tumors Defined by Internal Tandem Duplications of BCOR," Oncology, 96:101-109.
Lin et al., (2020). "Genomic profiling of BCOR-rearranged uterine sarcomas reveals novel gene fusion partners, frequent CDK4 amplification and CDKN2A loss," Gynecol Oncol, 157:357-366.
Malouf et al., (2013). "Prognostic factors and outcome of undifferentiated endometrial sarcoma treated by multimodal therapy," Int. J. Gynaecol. Obstet., 122:57-61.
Meurer et al., (2019). "Localized high grade endometrial stromal sarcoma and localized undifferentiated uterine sarcoma: a retrospective series of the French Sarcoma Group," Int. J. Gynecol. Cancer, 29:691-698.
Muthukumarana et al., (2020). "BCOR Expression in Mullerian Adenosarcoma: A Potential Diagnostic Pitfall," Am. J Surg. Pathol., 44:765-770, 13 pages.
Pautier et al., (2014). "Gynecologic Cancer InterGroup (GCIG) consensus review for high-grade undifferentiated sarcomas of the uterus," Int. J. Gynecol. Cancer, 24:S73-S77.
Plevin et al., (2005). "The LxxLL motif: a multifunctional binding sequence in transcriptional regulation," Trends Biochem. Sci., 30:66-69.
Schaefer et al., (2017). "Abnormal p53 and p16 staining patterns distinguish uterine leiomyosarcoma from inflammatory myofibroblastic tumour," Histopathology, 70:1138-1146.
Serrano, (1997). "The tumor suppressor protein p16INK4a," Exp. Cell Res., 237:7-13.
Totoki et al., (2011). "High-resolution characterization of a hepatocellular carcinoma genome," Nat Genet., 43:464-471.
Partial Supplementary European Search Report received for Patent Application No. 21764573.8, mailed on Apr. 1, 2025, 16 pages.
Lewis et al., (2017). "ZC3H7B-BCOR High-grade endometrial stromal sarcomas: a report of 17 cases of a newly defined entity," Modern Pathology, 31(4):674-684.
Vaha-Koskela et al., (2018). "Expanding the Utility of Midostaurin in Acute Myeloid Leukemia—Predictive Mutational Signatures in Patient Samples without FLT3 mutations and Clinically Applicable Synergistic Drug Combinations," Blood, 132:2743, 3 pages.
Yoshizato et al., (2015). "Somatic Mutations and Clonal Hematopoiesis in Aplastic Anemia," The New England Journal of Medicine, 373(1):35-47.
Extended European Search Report received for Patent Application No. 21764573.8, mailed on Jul. 25, 2025, 17 pages.
Fares et al., (2018). "Bcor Mutations Cooperate with Tet2 Deficiency to Promote RAS Transformation of Mouse Hematopoietic Progenitors," Blood, 132:888, 3 pages.
International Search Report and Written Opinion received for International Patent Application No. PCT/US2024/018905 mailed on Jun. 21, 2024, 8 pages.
Linares-Saldana et al., (2021). "BRD4 orchestrates genome folding to promote neural crest differentiation," Nature Genetics, 53(10):1480-1492, 42 pages.
Sturm et al., (2016). "New Brain Tumor Entities Emerge from Molecular Classification of CNS-PNETs," Cell, 164(5):1060-1072.
Yu et al., (2023). "Structural mechanism of BRD4-NUT and p300 bipartite interaction in propagating aberrant gene transcription in chromatin in NUT carcinoma," Nat Commun, 14:378, 16 pages.

* cited by examiner

1300

1302  OBTAINING A PLURALITY OF SEQUENCE READS OF NUCLEIC ACID(S) FROM A SAMPLE

1304  ANALYZING THE PLURALITY OF SEQUENCE READS FOR THE PRESENCE OF A GENETIC ALTERATION COMPRISING A REARRANGEMENT IN A BCOR GENE OR AN ALTERATION IN A BCORL1 GENE

1306  DETECTING, BASED ON THE ANALYSIS, A REARRANGEMENT IN A BCOR GENE OR AN ALTERATION IN A BCORL1 GENE, OR A PORTION THEREOF

SEQUENCE LISTING

```
<160> NUMBER OF SEQ ID NOS: 2

<210> SEQ ID NO 1
<211> LENGTH: 6808
<212> TYPE: DNA
<213> ORGANISM: Homo sapiens

<400> SEQUENCE: 1

agacggagcc tgggctccca gcggcaaggt gaggcagagc tgcgctcctc gctgaacgcg      60

ggccgagctc ggcggctgcg ggggagacgc gcaggagccc agaccgcgac cgagagcggg     120

agctaggcgg gcggcggcgg cggaggggga gcccgcgagc cgccgggcgg agagcccaag     180

ccgcgctgtc gccgcgcagg gacgacttgg ccaacactca cacacactca cacacaccca     240

gcccgagcgg gcgctcgcgg cgaaccgtca acatggcgct ggggctcctg cccgagcgcg     300

ggcggcggcg gcagcgcggg agctgctgag ctcggccaag cccagtccag ctgcgggagc     360

ccggaggatc gcacggggct gtcgccacct gcccggaggc cccgagcccg ccccgccccg     420

cccccacccg gcccagagcc cacccctcgg cggggccgac cccgagggca gccggctgcc     480
```

-continued

```
agcagacggc gagggagtcg agtgagcgcg gcgccgcgag cgggctgcgg gcagccgggg    540
accgcaaact ttgctgctcg ccgcgcttct ccggcccggc tccttctccg ctcgttaacg    600
tcgccaaccc cccccacccc tcatatctct ctccacccac ccaaccgccc cccgctcctt    660
ctcgccgcct cgagtccgct tgggggaaaa cttcaaagag ccggatcgca ggctccctgc    720
ctactccccc accggggatt tcagactaga cgcttgaagc aaagctgcca tcccagaaga    780
cgacatgctc tcagcaaccc ccctgtatgg gaacgttcac agctggatga acagcgagag    840
ggtccgcatg tgtggggcga gcgaagacag gaaaatcctt gtaaatgatg gtgacgcttc    900
aaaagccaga ctggaactga gggaagagaa tcccttgaac cacaacgtgg tggatgcgag    960
cacggcccat aggatcgatg gcctggcagc actgagcatg gaccgcactg gcctgatccg   1020
ggaagggctg cgggtcccgg gaaacatcgt ctattctagc ttgtgtggac tgggctcaga   1080
gaaaggtcgg gaggctgcca caagcactct aggtggcctt gggttttctt cggaaagaaa   1140
tccagagatg cagttcaaac cgaatacacc cgagacagtg gaggcttctg ccgtctctgg   1200
aaaacccccca aatggcttca gtgctatata caaaacaccg cctggaatac aaaaaagtgc   1260
tgtagccaca gcagaagcgc tgggcttgga caggcctgcc agcgacaaac agagccctct   1320
caacatcaat ggtgctagtt atctgcggct gccctgggtc aatccttaca tggagggtgc   1380
cacgccagcc atctaccctt tcctcgactc gccaaataag tattcactga acatgtacaa   1440
ggccttgcta cctcagcagt cctacagctt ggcccagccg ctgtattctc cagtctgcac   1500
caatggggag cgctttctct acctgccgcc acctcactac gtcggtcccc acatcccatc   1560
gtccttggca tcacccatga ggctctcgac accttcggcc tccccagcca tcccgcctct   1620
cgtccattgc gcagacaaaa gcctcccgtg gaagatgggc gtcagccctg ggaatcctgt   1680
tgattcccac gcctatcctc acatccagaa cagtaagcag cccagggttc cctctgccaa   1740
ggcggtcacc agtggcctgc cgggggacac agctctcctg ttgccccccct cgcctcggcc   1800
gtcaccccga gtccaccttc ccacccagcc tgctgcagac acctactcgg agttccacaa   1860
gcactatgcc aggatctcca cctctccttc agttgccctg tcaaagccat acatgacagt   1920
tagcagcgag ttccccgcgg ccaggctctc caatggcaag tatcccaagg ctccggaagg   1980
gggcgaaggt gcccagccag tgcccgggca tgcccggaag acagcggttc aagacagaaa   2040
agatggcagc tcacctcctc tgttggagaa gcagaccgtt accaaagacg tcacagataa   2100
gccactagac ttgtcttcta aagtggtgga tgtagatgct tccaaagctg accacatgaa   2160
aaagatggct cccacggtcc tggttcacag cagggctgga agtggcttag tgctctccgg   2220
aagtgagatt ccgaaagaaa cactatctcc tccaggaaat ggttgtgcta tctatagatc   2280
tgaaatcatc agcactgctc cctcatcctg ggtggtgccc gggccaagtc ctaacgaaga   2340
gaacaatggc aaaagcatgt cgctgaaaaa caaggcattg gactgggcga taccacagca   2400
gcggagttca tcatgcccgc gcatgggcgg caccgatgct gtcatcacta acgtttcagg   2460
gtcagtgtcg agtgcaggcc gcccagcctc cgcatcaccc gcccccaatg ccaatgcaga   2520
tggcaccaaa accagcagga gctctgtaga aaccacacca tccgttattc agcacgtggg   2580
ccagcccccg gccactcctg ccaagcacag tagcagcacc agcagcaagg gcgccaaagc   2640
cagcaaccca gaaccgagtt tcaaagcaaa cgagaacggc cttccaccaa gctctatatt   2700
tctgtctcca aatgaggcat tcaggtcccc accaattccc taccccagga gttacctccc   2760
ttacccagcc cctgagggca ttgctgtaag tcccctctcc ttacatggca aaggacctgt   2820
ctaccctcac ccagttttgt tacccaatgg cagtctgttt cctgggcacc ttgccccaaa   2880
```

-continued gcctgggctg ccctatgggc ttcccaccgg ccgtccagag tttgtgacct accaagatgc 2940
cctggggttg ggcatggtgc atcccatgtt gataccacac acgcccatag agattactaa 3000
agaggagaaa ccagagagga gatcccggtc ccatgagaga gcccgttacg aggacccaac 3060
cctccggaat cggttttccg agattttgga aactagcagc accaagttac atccagatgt 3120
ccccaccgac aagaacctaa agccgaaccc caactggaat caagggaaga ctgttgtcaa 3180
aagcgacaag cttgtctacg tagaccttct ccgagaagaa ccagatgcta aaactgacac 3240
aaacgtgtcc aaacccagct ttgcagcaga gagtgttggc cagagcgctg agccccccaa 3300
gccctcagtt gagccggccc tgcagcagca ccgtgatttc atcgccctga gagaggagtt 3360
ggggcgcatc agtgacttcc acgaaactta tactttcaaa cagccagtct tcaccgtaag 3420
caaggacagt gttctggcag gtaccaacaa agagaaccta gggttgccag tctcgactcc 3480
attcctggag ccacctctgg ggagcgatgg ccctgctgta acttttggta aaacccaaga 3540
ggatcccaaa ccattttgtg tgggcagtgc ccccaccaagt gtggatgtga cccccaccta 3600
taccaaagat ggagctgatg aggctgaatc aaatgatggc aaagttctga aaccgaagcc 3660
atctaagctg gcaaagagaa tcgccaactc agcgggttac gtgggtgacc gattcaaatg 3720
tgtcactacc gaactgtatg cagattccag tcagctcagc cgggagcaac gggcattgca 3780
gatggaagga ttacaagagg acagtatttt atgtctaccc gctgcttact gtgagcgtgc 3840
aatgatgcgc ttctcagagt tggagatgaa agaaagagaa ggtggccacc cagcaaccaa 3900
agactccgag atgtgcaaat tcagcccagc cgactgggaa aggttgaaag gaaatcagga 3960
caaaaagcca aagtcggtca ccctggagga ggccattgca gaacagaacg aaagtgagag 4020
atgcgagtat agtgttggaa acaagcaccg tgatcccttt gaagccccag aggacaaaga 4080
tcttcctgtg gagaagtact ttgtggagag gcagcctgtg agcgagcctc ccgcagacca 4140
ggtggcctcg gacatgcctc acagccccac cctccgggtg gacaggaaac gcaaagtctc 4200
aggtgacagc agccacactg agaccactgc ggaggaggtg ccagaggacc ctctgctgaa 4260
agccaaacgc cgacgagtct ctaaagggct ccatcctaaa aaacaacgcc acttgctgca 4320
ccttagagaa cgatgggagc agcaggtgtc ggcagcagat ggcaaacctg gccggcaaag 4380
caggaaggaa gtgacccagg ccactcagcc tgaggccatt cctcagggga ctaacatcac 4440
tgaagagaaa cctggcagga aaagggcaga ggccaaaggc aacagaagct ggtcggaaga 4500
gtctcttaaa cccagtgaca atgaacaagg cttgcctgtg ttctccggct ctccgcccat 4560
gaagagtctt tcatccacca gtgcaggcgg caaaaagcag gctcagccaa gctgcgcacc 4620
agcctccagg ccgcctgcca aacagcagaa aattaaagaa aaccagaaga cagatgtgct 4680
gtgtgcagac gaagaagagg attgccaggc tgcctccctg ctgcagaaat acaccgacaa 4740
cagcgagaag ccatccggga agagactgtg caaaaccaaa cacttgatcc ctcaggagtc 4800
caggcgggga ttgccactga caggggaata ctacgtggag aatgccgatg gcaaggtgac 4860
tgtccggaga ttcagaaagc ggccggagcc cagttcggac tatgatctgt caccagccaa 4920
gcaggagcca aagcccttcg accgcttgca gcaactgcta ccagcctccc agtccacaca 4980
gctgccatgc tcaagttccc ctcaggagac cacccagtct cgccctatgc cgccggaagc 5040
acggagactt attgtcaata agaacgctgg cgagaccctt ctgcagcggg cagccaggct 5100
tggctatgag gaagtggtcc tgtactgctt agagaacaag atttgtgatg taaatcatcg 5160
ggacaacgca ggttactgcg ccctgcatga agcttgtgct aggggctggc tcaacattgt 5220
gcgacacctc cttgaatatg gcgctgatgt caactgtagt gcccaggatg gaaccaggcc 5280
tctgcacgat gctgttgaga acgatcactt ggaaattgtc cgactacttc tctcttatgg 5340
tgctgacccc accttggcta cgtactcagg tagaaccatc atgaaaatga cccacagtga 5400
acttatggaa aagttcttaa cagattattt aaatgacctc cagggtcgca atgatgatga 5460
cgccagtggc acttgggact tctatggcag ctctgtttgt gaaccagatg atgaaagtgg 5520
ctatgatgtt ttagccaacc ccccaggacc agaagaccag gatgatgatg acgatgccta 5580
tagcgatgtg tttgaatttg aattttcaga gacccccctc ttaccgtgtt ataacatcca 5640
agtatctgtg gctcaggggc cacgaaactg gctactgctt tcggatgtcc ttaagaaatt 5700
gaaaatgtcc tcccgcatat ttcgctgcaa ttttccaaac gtggaaattg tcaccattgc 5760
agaggcagaa ttttatcggc aggtttctgc aagtctcttg ttctcttgct ccaaagacct 5820
ggaagccttc aaccctgaaa gtaaggagct gttagatctg gtggaattca cgaacgaaat 5880
tcagactctg ctgggctcct ctgtagagtg gctccacccc agtgatctgg cctcagacaa 5940
ctactggtga gcaagctgga cccaccatgt acagtgtgtt atagtgttaa tccttgtgca 6000
tatgtgtcat aatacaacta tttctgtaaa gaaaggacac tattacatat gaaaatatct 6060
cttctttata taagagaaat tactccagtc agaaggactt agaaacatgt tttttttcctt 6120 ttaaactttt aagtcagttt ttatgaagtt gttataatgt ttctttactt ttcaatgcac 6180
acatgctttg ggatacgttt gtttttactt ggaacatttg tttcttttct tttttaagga 6240
gaaaaaaaaa tgagtaaaag gagctccaca ctttgactta atttcataca aagctctgat 6300
gacaggccat gactgtagag tggtcagaac tgtgtggttg gtttgaggga gcgaattcgg 6360
ggaaggcact tggtgatata actttgtttt gtttacagag tacctgctcg ggccaggtaa 6420
atgctattgg atgtaatcca gtagtgtgta atataaattc aaaccatatc cacacacaac 6480
aactaattgt atgaaacttt tatatcctaa tttaaaagct gtgaaattag ttttcacgca 6540
tcaaaccgga ttgtttatat gtttaaacat tttatgctct tatttaaaga agactttgag 6600
ctattttttt ctgtaccctg taaaatattg aaaactaaca taatatgttg aggttgcttg 6660
gaaatgtaca taaaactaaa attttctgaa tcgtgtgttt atgtttgaaa tctgtgtttt 6720
aactttgtaa gtaaattctc tgcctttgta tttatatttt acaaaaattt tcttaaaagg 6780
caataaaact gttgaggaaa ggagaaaa 6808

<210> SEQ ID NO 2
<211> LENGTH: 7772
<212> TYPE: DNA
<213> ORGANISM: Homo sapiens

<400> SEQUENCE: 2
agatcggcgg ggccgcgagc ggagggaggg aggcccgcgg cggcgcggcg gcagcgaagg 60
ccagcttccg cggagtttgt gcccgggctt cccgggctct ggccgcctca cgcgcacaaa 120
tggggctagg ggactgagtg gtaagcaact ccgagtgtta gacggtgatc gggcggcgat 180
tccgggaaaa gcgaggaaag acacagtctg cgattgtgcc gcacccccca cccacctctt 240
agcatctgga ttctgctctc gtagtggggg ccgcggaccc tccccgccac agtcctttta 300
ctctccagca ctcccaccgc cttccccctt cttcagccat ctgactctcc tagggggtcg 360
gcgtggcgaa ggacggctag ccttggaggg aaagtagcca ccagtccaac tcgggtcgcc 420
cccaccatta tttcggggga gtggccacag caggtcctat ctggtggtga gtggctgtca 480
tgatctctac agcaccgctc tacagcggcg tgcacaactg gaccagttct gaccggattc 540

-continued

```
gcatgtgtgg catcaacgag gagagaagag cacctctttc tgatgaggag tcaacgacag    600
gcgactgcca gcactttgga tctcaggagt tttgtgtcag cagcagtttt tccaaggtgg    660
agctcacggc agttggaagt ggcagcaatg cccggggggc agacccagat ggcagtgcta    720
cagaaaaact tgggcacaag tcagaagaca agcctgacga tccccagcca aaaatggact    780
acgctgggaa cgtggcagag gctgagggcc tcttggtgcc cctgagcagc ccaggagacg    840
ggctcaagct tcccgcatct gacagcgccg aggccagcaa cagcagggcc gactgctcct    900
ggactccact caacacccaa atgagcaaac aggttgactg ctcacccgcc ggagtaaagg    960
ctttggactc tcggcaaggt gttggagaga agaatacttt cattttggca actctgggaa   1020
ctggagtccc tgtggagggg accctgcccc tggttaccac taacttcagt cctctgccag   1080
cccctatctg tccccctgct cccggttcgg cctctgtgcc ccactctgtt ccagatgcat   1140
tccaggttcc cctctccgtc cctgccccag tcccccattc agggcttgtt ccagtccaag   1200
ttgccacttc ggttccagct ccttcccctc ccttagcacc tgtcccggct ctggctccag   1260
cgccaccgtc agtgcccacg ctcatctctg actcgaaccc cctttctgtt tcggcctcag   1320
tcttggtgcc tgtgccagct tctgctcccc cttcaggccc ggttcccttg tcggctccag   1380
ctcctgcccc gctttcagtc ccagtttcag ctcctccctt ggctctcatc caggctcctg   1440
tgccccctte agctccgacc ttggttctcg ctcccgtccc cactccggtt ctggctccca   1500
tgccagcatc cacgcctcca gcggcccctg cccctccgtc tgtgcccatg cccactccaa   1560
ccccatcttc cggcccacct tctaccccca ccctcatccc cgcctttgct cctacaccgg   1620
tgcctgcacc caccccagcc cccatcttta ctccagcccc tacacccatg cctgctgcca   1680
cgccagctgc cattcccacc tctgcaccca tcccggcctc cttcagtttg agtagagtgt   1740
gctttcctgc agctcaggca ccagctatgc aaaaagtccc cctgtccttt cagccaggga   1800
cagtgctgac ccccgagcag ccgctggtat atatcccgcc tccaagctgt gggcagccac   1860
tcagtgtggc cacactgcca accactctag ggtttcctc cactcttacg ctccctgtcc    1920
tgccgtccta cctgcaggac aggtgtctcc caggcgtgct agcctccccc gagctccgtt   1980
cttacccgta tgcattttct gtggcccggc ctctgacttc ggattccaag ctggtatctc   2040
tggaggtgaa caggctcccc tgcacttccc catccggtag caccaccacc cagcctgcac   2100
ccgatggggt ccctgggcct ttggcagata cctccccttgt tactgcttct gccaaggtgc   2160
ttccaactcc acagcctctg ctgccagccc ccagtgggag ctcagcccca ccgcaccccg   2220
ccaagatgcc cagtggcacc gagcagcaaa cagaagggac ttccgttacc ttctctcctc   2280
ttaagtcacc gccacagctg gaacgagaga tggcctctcc acctgagtgc agcgagatgc   2340
cccttgatct gtcctccaag tccaaccgcc agaagcttcc attgccgaac cagcgcaaga   2400
caccccccat gcctgtgttg acccccgtgc acaccagcag caaggccctc ctctccacag   2460
tcctgtctag gtctcagcgc acaacccagg ctgccggtgg caatgtcacc tcctgcctgg   2520
gctccacttc ctcgcccttt gtcatctttc ccgagatcgt gaggaatggg gacccgagca   2580
cctgggtgaa gaactcaact gcactgatca gcaccattcc tggcacctac gtgggagtgg   2640
ccaacccagt gcctgcatcc ctgctgctga acaaagaccc caacctgggc ctcaaccgtg   2700
acccccgcca tctccccaag caggagccca tctccatcat tgatcaagga gagcctaagg   2760
gcactggtgc cacgtgtggc aaaaagggca gccaggctgg tgctgaggga cagccaagca   2820
cagtgaaacg atatactcca gcccgcattg cccctgggct gccagggtgc caaaccaagg   2880
```

-continued

```
aactctcttt gtggaaaccc acggggccgg caaatattta tccccggtgt tcagtcaatg   2940
ggaaacctac cagcacccag gtcctgcctg ttggctggtc cccgtaccac caggcgtctc   3000
tgctttccat tggcatttcc agtgccgggc agctgacccc cagtcagggg gcgcccatca   3060
ggcccaccag cgttgtttcg gagttttctg gtgtgccatc tctcagctcc agcgaagccg   3120
tgcacggact tcctgagggg caaccacggc ctgggggctc cttcgttcca gagcaggacc   3180
ctgttacaaa gaacaaaact tgccggattg ctgccaagcc ttatgaagaa caagtcaatc   3240
ctgtcctctt gaccctcagc cctcagactg ggaccctggc actgtctgtt cagcctagcg   3300
gtggggacat tcgaatgaat caggggcctg aggaatcaga gagccacctc tgctctgaca   3360
gcactcctaa gatggaaggc ccccaggggg cttgtggcct gaagctggca ggagacacga   3420
agcctaagaa ccaagtgctg gccacctaca tgtcccatga gctggtcctg gccacccccc   3480
agaacctgcc taagatgcct gagctgcctt tgctacctca cgacagccac cccaaggaac   3540
ttatattgga cgtggttccg agcagcagga ggggctccag cacagagcgc ccacagcttg   3600
gaagccaggt ggatctgggg cgagtgaaaa tggagaaggt ggatggtgat gtggtcttca   3660
atttagccac ctgcttccgg gctgatggcc tcccagtggc tccccagagg ggccaagctg   3720
aagttcgggc taaggccggg caggctcgag tgaaacagga aagcgtaggg gtctttgctt   3780
gcaagaacaa gtggcagcca gatgatgtga cggaatctct gccgcccaag aagatgaagt   3840
gcggcaaaga gaaggacagt gaagagcagc agctccagcc acaagccaag gccgtggtcc   3900
ggagttccca cagacccaag tgccggaagc tgcccagtga cccccaggaa tccaccaaga   3960
aaagccccag gggggcttca gattcaggaa aagagcacaa tggagtcagg ggaaagcaca   4020
agcaccggaa gccgacaaag ccggagtccc agtctccagg aaaacgagcc gacagccacg   4080
aggaaggttc cttggaaaag aaagcaaaga gcagtttccg tgactttatt cctgtggttc   4140
tgagcacccg cacgcgcagt cagtctggaa gcatctgtag ctcctttgct ggcatggcag   4200
acagtgacat gggaagccag gaagtcttcc ccacagaaga agaagaggag gtaaccccca   4260
ccccagctaa gcgtcgaaag gtgagaaaga cccaacggga cacccagtat cgcagccacc   4320
atgcccagga caagtctctg ctgagccagg gccgaaggca cctgtggcga gcccgagaaa   4380
tgccctggag gacagaggct gcccggcaaa tgtgggacac caatgaggag gaggaggaag   4440
aagaggagga gggcctgctg aagaggaaga aacgaagacg gcagaagagc cgaaaatatc   4500
agactgggga gtacctgaca gagcaagaag acgagcagcg gcggaaaggg agagcagatt   4560
taaaggcccg taagcagaag acttcctcct cccaaagttt ggagcaccgc ctcaggaaca   4620
ggaaccttct cttgcccaac aaagtccagg ggatctcgga ttcaccaaac ggtttcctcc   4680
caaataacct ggaagagcca gcctgccttg aaaattcaga aaagccatca ggaaaacgaa   4740
agtgcaagac caagcacatg gcaaccgtct cagaagaggc aaagggcaaa ggtcgttgga   4800
gccagcagaa gacacgatct cccaaatctc ccaccccagt gaaacccaca gaaccatgta   4860
caccctctaa gtcccgaagt gccagctcag aggaggcctc agagtcacct acagcccggc   4920
agatccccc  agaggcacgt cggctcatag tgaacaaaaa tgctggtgag accctcctgc   4980
agagggcggc gcgtcttggc tataaggatg ttgttctcta ctgcctccag aaagacagtg   5040
aagatgtgaa tcaccgtgac aatgctggct acacagccct gcatgaggct tgttcccggg   5100
gctggaccga catcctgaac atcctgctgg agcacggggc caacgtgaac tgcagtgcgc   5160
aggacggcac gaggccagtt catgatgcgg tggtcaatga caacctggag accatctggc   5220
tcctgctgtc ctatggggcc gatcccacac tggctaccta ctcgggtcag acagccatga   5280
```

-continued agctggccag cagcgacacc atgaagcgct ttctcagtga tcacctctcg gatcttcagg 5340
gccgggcaga gggtgatccc ggtgtatcct gggattttta cagcagttct gtgttggagg 5400
aaaaagacgg gtttgcctgt gacctcctac ataatcctcc tgggagctca gatcaagaag 5460
gagacgatcc gatggaggag gatgatttca tgtttgaact ctcagacaag cctcttctcc 5520
cttgctacaa cctccaagtg tcagtgtccc gcgggccctg caactggttc ctcttttccg 5580
atgtcttgaa gaggctgaag ctttcctcga ggatctttca ggcccggttc ccgcactttg 5640
aaatcaccac catgcccaag gccgagttct acaggcaggt ggcctccagt cagctgctga 5700
cccctgccga gaggcctgga ggcttggacg acagatcccc cccaggctcc tctgagactg 5760
tggagctggt gcggtacgag ccagacctac ttcggctcct agggtccgag gtggaattcc 5820
agtcttgcaa cagttgaccg ggaaaacagc cctcctcttt ctttctcctt ccgagttcgc 5880
ccttccccca cctccttgtc tttccccgac cgagcaccag actgcagaat gaggcaataa 5940
tacggaccaa caagaagccg ccttatcaat gccagcatta gcgactggac tgtttttgtt 6000
tttttggtta caattagttc tcatctccct gtcgtcgtca ttgttatcgt ggttgctgat 6060
gggggtggaa agttgaactc catgtctgag gacaagaggt cccgggggtg gtgggaggtg 6120
gcgccggggt cccttggact ggcctccttg ttcatgacca agaccaaacc tgggccctgg 6180
atggccttgg cctgtcccga ggagaaatga gaaaatccca gatctctgag cgccccccaa 6240
ctccattccc ctgtgttctt ctgtcttctg tagtatttat tttattagta tttaatttgt 6300
attgtttcat tggtttctga taagtctgta tcactgtgac gatttgagac aacttgttgt 6360
attgagggac tttctgtacc tccttttctt tttctttgtt gatgagctct gacaaagcta 6420
ttccctggtg tttttttccc ccactgggga gggggtgagg tggaatgggg tgggggaaca 6480
tggacttgtg actaacgaag ctggttgctg ctggcccagg gctgggggct tgggggtaaa 6540
tcctgaggct ttggtgctcc cccacccacc cattcccgcc ctttgcagca gccccgctat 6600
cttgagatta gtgttgacag ggaggggagg attgtgaggt gaggggttaa taagttactc 6660
taataaagga gcgtggagaa gggatctgag gggtgagggt ggccccccctc ctcacgcctt 6720
cttcactgcc cccctcagag tgcacaatac gagtttgttc ctgcctccac tctcccaccc 6780
cgttctggcc tccctgtctc aagatactga gcctctcacc tcccagccct cagccacccc 6840
catccctgcc ccttctgaga ctcacagcac ccctttcctt cctctcctcc cacctcctcc 6900
ctcagcccct cattctcctt gggaatctgc agagggctct gggactcact gccggatgtg 6960
aaatccaggc gtcagctgtt tcctaggcaa gggcaggaaa gtggtctcca gcccttgctc 7020
cactcatgcc tgggggcctg gggctgagtg gtatccctac ctggcctccc cctggcctct 7080
gggcctccag cgctgggttt gtcgagtgag agagagagag gagcttgggt tgcttccctg 7140
tccccgcccc ctctgtggca ttgtccctcc cactcttatt tttctaccaa ttgctatttt 7200
tccgaacaat ccttgtagag tatgtaccat ccaaaggcag gagggcctcg ccgtggccgg 7260
ctctggttgg agatggtaca gttttattgt acaggtgcta aaacaacaac aacaaaaaag 7320
aaaatggaaa aaaaaaagat taaaaaaaaa aggaaaaaaa aaaagccagt ttgaggatgg 7380
gacaatctgt tctctagagg ctcctgagcc atgcgggagc attggtggtt attttctttg 7440
tattgtgttt gttctttgtt cctggggggg aagttctcgg ccccccttctg taggactgct 7500
ccccaccccc accatactgc ccagttggtt ttgaacagtt gttttccctt tttaagaaaa 7560
aaaaatacat atatatatac atatatatat ataaagttga ggggttttgg actttaattt 7620

-continued

| | | |
|---|---|---|
| gttggttttg ttggggttcc tggtattgtg tagtttattt catgttctgt ttgcctttcc | 7680 |
| ttttttcgca tttgggtgta tattctggct gccctttatg tttcatttta agcaactggc | 7740 |
| tgtggagtca aaaacacttg catactgaaa aa | 7772 |

BCOR REARRANGEMENTS AND USES THEREOF

CROSS-REFERENCE TO RELATED APPLICATIONS

This application is a national stage application under 35 U.S.C. § 371 of International Application No. PCT/US2021/020752, filed internationally on Mar. 3, 2021, which claims the benefit of U.S. Provisional Application No. 62/985,227, filed Mar. 4, 2020, the contents of each of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 197102003400SEQLIST.txt, date recorded: Aug. 22, 2022, size: 17,959 bytes).

FIELD

Provided herein are methods related to detecting rearrangements in the B-cell lymphoma 6 (BCL6) corepressor (BCOR) or BCL6 corepressor-like protein 1 (BCORL1) gene, as well as methods of diagnosis/treatment, uses, and kits related thereto.

BACKGROUND

Endometrial stromal sarcomas are currently sub-divided as either low-grade or high-grade in the 2014 World Health Organization classification, based on their morphological and molecular features (Kurman, R. J. et al. (2014) *WHO Classification of Tumours of Female Reproductive Organs*). Low-grade endometrial stromal sarcomas often harbor either JAZF1 or PHF1 gene rearrangements, while the current 2014 classification recognizes only YWHAE-rearranged tumors as high-grade endometrial stromal sarcomas (Kurman, R. J. et al. (2014) *WHO Classification of Tumours of Female Reproductive Organs*). However, the classification of uterine sarcomas is an evolving and expanding field with recent characterization of new molecularly defined and aggressive subgroups such as SMARCA4-deficient undifferentiated uterine sarcomas and BCOR-mutated uterine sarcomas, the latter likely of endometrial stromal origin (Lin, D. I et al. (2019) *Mod. Pathol.* June doi:10.1038/s41379-019-0303-z; Juckett, L. T. et al. (2018) *Oncology* October: 1-9). Endometrial stromal sarcomas containing genomic alterations of BCOR may exhibit either ZC3H7B-BCOR rearrangements or internal tandem duplications in 3' region of the BCOR gene (Hoang, L. N. et al. (2017) *Am. J. Surg. Pathol.* 41:12-24; Lewis, N. et al. (2018) *Mod. Pathol.* 31:674-684; Mariño-Enriquez A. et al. (2018) *Am. J. Surg. Pathol.* 42:335-341). BCOR-altered tumors often show spindle cell morphology with brisk mitotic activity, uniform spindle to oval nuclei and a myxoid or collagenous stromal background (Lewis, N. et al. (2018) *Mod. Pathol.* 31:674-684). Additionally, uterine sarcomas harboring BCOR internal tandem duplication is distinctive in harboring a round cell component (Juckett, L. T. et al. (2018) *Oncology* October: 1-9). Because of their unique morphological features and potentially more aggressive biological behavior than low-grade endometrial stromal sarcomas, BCOR-altered uterine sarcomas have been provisionally classified as high-grade endometrial stromal sarcomas (Ferreira, J. et al. (2018) *Virchows Arch.* 473:665-678).

Prior immunohistochemistry characterization of BCOR-mutated uterine sarcomas suggests that activation of the CDK4 kinase complex occurs in this rare subset of uterine sarcomas, which may be therapeutically relevant as specific CDK4 inhibitor drugs are clinically available and currently FDA-approved in estrogen receptor-positive breast cancer (de Dueñas E. M. et al. (2018) *Clin. Transl. Oncol.* 20:1136-1144). By immunohistochemistry, BCOR-altered uterine sarcomas often show expression of cyclin D1, CD10, and BCOR, with variable expression of ER, PR. In addition, BCOR-mutated uterine sarcomas typically do not express muscle markers, with a minority of tumors expressing SMA and caldesmon, but not desmin (Lewis, N. et al. (2018) *Mod Pathol.* 31:674-684). Cyclin D1 protein overexpression occurs in the majority (>95%) of BCOR-rearranged tumor cells (Lewis, N. et al. (2018) *Mod. Pathol.* 31:674-684; Ferreira, J. et al. (2018) *Virchows Arch.* 473:665-678), likely resulting in activation of the CDK4 kinase complex. Cyclin D1 physiologically binds to and activates CDK4 during cell cycle progression and cellular proliferation (Diehl, J. A. (2002) *Cancer Biol. Ther.* 1:226-231). In contrast, activity of the CDK4 kinase is inhibited by p16 (also known as $p16^{INK4a}$ and/or cyclin-dependent kinase inhibitor 2A, encoded by the CDKN2A gene), which binds to the cyclin D1-CDK4 complex and inhibits CDK4 kinase activity (Serrano, M. (1997) *Exp. Cell Res.* 237:7-13).

Rare cases of endometrial stromal sarcomas with BCORL1 alterations have been reported (Allen, A. J. et al. (2017) *Gynecol. Oncol. Reports* 20:51-53; Brahmi, M. et al. (2020) *Cancers* (*Basel*) 12:1-12); however, the clinicopathological features and mutational landscape of BCORL1-altered uterine sarcomas have not been systematically investigated. BCORL1 is a transcriptional corepressor homologous to BCOR; both have related biological functions during transcriptional regulation as they may interchangeably form polycomb repression complex 1 (PRC1) variants (Wong, S. J. et al. (2020) *Biochemistry* 59:2718-2728). Recently, uterine sarcomas with genomic alterations in BCOR via rearrangements or internal tandem duplication (ITD) have become a newly recognized, distinct subtype of high-grade endometrial stromal sarcomas with aggressive behavior and unique morphology (Lewis, N. et al. (2018) *Mod. Pathol.* 31:674-684; Juckett, L. T. et al. (2018) *Oncology* October: 1-9; Lin, D. I., et al. (2020) *Gynecol Oncol* 157:357-366). Similar to BCOR, disruption of PRC1 via genomic alterations of the homologous BCORL1 has been reported in several cancer types, such as ossifying fibromyxoid tumor with CREBBP-BCORL1 fusion (Kao, Y. C. et al. (2017) *Genes. Chromosom. Cancer* 56:42-50), myelodysplastic syndrome (MDS) or acute myeloid leukemia (AML) with inactivating BCORL1 truncating mutations (Li, M. et al. (2011) *Blood* 118:5914-5917), and hepatocellular carcinoma with BCORL1-ELF4 fusion (Totoki, Y. et al. (2011) *Nat Genet.* 43:464-471). In addition, JAZF1-BCORL1 fusions have been previously reported in a case of uterine adenosarcoma (Muthukumarana, V. et al. (2020) *Am. J. Surg. Pathol.* 44:765-770) as well as in a recurrent endometrial stromal sarcoma (Allen, A. J. et al. (2017) *Gynecol. Oncol. Reports* 20:51-53). However, the morphological spectrum and biological behavior of BCORL1-altered uterine sarcomas and adenosarcomas are not well defined.

Therefore, there remains a need for treatment options for cancers such as uterine sarcoma characterized by BCOR-BCORL1 mutations, gene fusions, or other rearrangements.

All references cited herein, including patent applications and publications, are incorporated by reference in their entirety.

SUMMARY

To meet these and other needs, provided herein are methods related to detecting rearrangements in the B-cell lymphoma 6 (BCL6) corepressor (BCOR) or BCL6 corepressor-like protein 1 (BCORL1) gene, as well as methods of treatment, uses, and kits related thereto. These methods are based at least in part on the analysis, presented herein, of the largest cohort of BCOR-rearranged endometrial stromal sarcomas (ESS) to date (n=40), which included 31 cases with canonical ZC3H7B-BCOR fusion as well as 8 cases with novel BCOR gene rearrangement partners, such as BCOR-L3MBTL2, EP300-BCOR, BCOR-NUTM2G, BCOR-RALGPS1, BCOR-MAP7D2, RGAG1-BCOR, ING3-BCOR, BCOR-NUGGC, KMT2D-BCOR, CREBBP-BCOR and 1 case with BCOR internal rearrangement. These novel BCOR gene fusions are thought to be of diagnostic utility. BCOR-rearranged uterine sarcomas were found to exhibit frequent genomic alterations leading to CDK4 activation, suggesting that most BCOR-mutated uterine sarcoma patients may be eligible for clinical trials with CDK4 or MDM2 inhibitors and the like, including without limitation palbociclib. Additionally, these methods are based at least in part on the analysis, presented herein, of the largest cohorts of BCORL1-altered uterine sarcomas (n=12) and uterine adenosarcomas (n=6). These cohorts included 5 uterine sarcoma cases with BCORL1 rearrangements (JAZF1-BCORL1, EP300-BCORL1, or internal BCORL1 rearrangement), 5 cases with inactivating BCORL1 mutations (T53fs*22, P600fs*1, R945*, R1196*, or R1265fs*4) and 2 cases with homozygous BCORL1 deletion, and 4 uterine sarcoma cases harboring JAZF1-BCORL1 fusions, and BCORL1 L461fs*5, or H1426fs*29. BCORL1-altered uterine sarcomas and adenosarcomas were found to exhibit frequent genomic alterations leading to CDK4 activation, and less frequent NF1 and NF2-mTOR pathway alterations, expanding potential therapeutic targets.

In certain aspects, provided herein is a method of identifying an individual having cancer who may benefit from a treatment comprising a targeted therapeutic, the method comprising detecting a rearrangement in a B-cell lymphoma 6 (BCL6) corepressor (BCOR) gene in a sample from the individual, wherein the presence of the BCOR gene rearrangement in the sample identifies the individual as one who may benefit from the targeted therapeutic. In other aspects, provided herein is a method of selecting a therapy for an individual having cancer, the method comprising detecting a rearrangement in a B-cell lymphoma 6 (BCL6) corepressor (BCOR) gene in a sample from the individual, wherein the presence of the BCOR gene rearrangement in the sample identifies the individual as one who may benefit from a targeted therapeutic. In other aspects, provided herein is a method of identifying one or more treatment options for an individual having cancer, the method comprising: (a) detecting a rearrangement in a B-cell lymphoma 6 (BCL6) corepressor (BCOR) gene in a sample from the individual; and (b) generating a report comprising one or more treatment options identified for the individual based at least in part on the presence of the BCOR gene rearrangement in the sample, wherein the one or more treatment options comprise a targeted therapeutic. In other aspects, provided herein is a method of treating or delaying progression of cancer, comprising: acquiring knowledge of a rearrangement in a B-cell lymphoma 6 (BCL6) corepressor (BCOR) gene in a sample from an individual; and, responsive to said knowledge, administering to the individual an effective amount of a targeted therapeutic. In other aspects, provided herein is a method of identifying one or more treatment options for an individual having cancer, the method comprising: (a) acquiring knowledge of a rearrangement in a B-cell lymphoma 6 (BCL6) corepressor (BCOR) gene in a sample from the individual; and (b) generating a report comprising one or more treatment options identified for the individual based at least in part on said knowledge, wherein the one or more treatment options comprise a targeted therapeutic. In other aspects, provided herein is a method of treating or delaying progression of cancer, comprising administering to an individual an effective amount of a targeted therapeutic, wherein the cancer comprises a rearrangement in a B-cell lymphoma 6 (BCL6) corepressor (BCOR) gene. In other aspects, provided herein is a method of treating or delaying progression of cancer, comprising: (a) detecting a rearrangement in a B-cell lymphoma 6 (BCL6) corepressor (BCOR) gene in a sample from the individual; and (b) administering to the individual an effective amount of a targeted therapeutic. In other aspects, provided herein is a method of treating or delaying progression of cancer, comprising: (a) detecting a rearrangement in a B-cell lymphoma 6 (BCL6) corepressor (BCOR) gene in a sample from the individual; and (b) administering an effective amount of a targeted therapeutic to the individual in whose sample a BCOR rearrangement was detected. In other aspects, provided herein is a targeted therapeutic for use in a method of treating or delaying progression of cancer, wherein the method comprises administering the targeted therapeutic to the individual, wherein a rearrangement in a B-cell lymphoma 6 (BCL6) corepressor (BCOR) gene is detected in a sample obtained from the individual. In other aspects, provided herein is a targeted therapeutic for use in the manufacture of a medicament for treating or delaying progression of cancer, wherein the targeted therapeutic is to be administered to an individual from whom a sample comprising a rearrangement in a B-cell lymphoma 6 (BCL6) corepressor (BCOR) gene has been obtained. In other aspects, provided herein is a targeted therapeutic for use in the manufacture of a medicament for treating or delaying progression of cancer, wherein the medicament is to be administered to an individual, wherein a rearrangement in a B-cell lymphoma 6 (BCL6) corepressor (BCOR) gene has been detected in a sample obtained from the individual, and wherein the targeted therapeutic is selected from the group consisting of a CDK inhibitor, an MDM2 inhibitor, a tyrosine kinase inhibitor, a MEK inhibitor, an mTOR inhibitor, and a Hh inhibitor. In some embodiments of any of the above embodiments, the targeted therapeutic is selected from the group consisting of a CDK inhibitor, an MDM2 inhibitor, a tyrosine kinase inhibitor, a MEK inhibitor, an mTOR inhibitor, and a Hh inhibitor.

In certain aspects, provided herein is a method of identifying an individual having cancer who may benefit from a treatment comprising a targeted therapeutic, the method comprising detecting a genetic alteration comprising a rearrangement in a B-cell lymphoma 6 (BCL6) corepressor (BCOR) gene or an alteration in a BCL6 corepressor-like protein 1 (BCORL1) gene in a sample from the individual, wherein the presence of the BCOR gene rearrangement or BCORL1 alteration in the sample identifies the individual as one who may benefit from the targeted therapeutic, wherein the targeted therapeutic is a CDK inhibitor, an MDM2 inhibitor, a tyrosine kinase inhibitor, a MEK inhibitor, an mTOR inhibitor, PIK3CA or AKT inhibitor, or a Hh inhibitor.

In certain aspects, provided herein is a method of selecting a therapy for an individual having cancer, the method comprising detecting a genetic alteration comprising a rearrangement in a BCOR gene or an alteration in a BCORL1 gene in a sample from the individual, wherein the presence of the BCOR gene rearrangement or BCORL1 alteration in the sample identifies the individual as one who may benefit from a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

In certain aspects, provided herein is a method of identifying one or more treatment options for an individual having cancer, the method comprising: detecting a rearrangement in a BCOR gene or an alteration in a BCORL1 gene in a sample from the individual; and generating a report comprising one or more treatment options identified for the individual based at least in part on the presence of the BCOR gene rearrangement or BCORL1 alteration in the sample, wherein the one or more treatment options comprise a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

In certain aspects, provided herein is a method of identifying one or more treatment options for an individual having cancer, the method comprising: acquiring knowledge of a rearrangement in a BCOR gene or an alteration in a BCORL1 gene in a sample from the individual; and generating a report comprising one or more treatment options identified for the individual based at least in part on said knowledge, wherein the one or more treatment options comprise a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

In certain aspects, provided herein is a method of selecting treatment for an individual having cancer, comprising acquiring knowledge of a rearrangement in a BCOR gene or an alteration in a BCORL1 gene in a sample from an individual having cancer, wherein responsive to the acquisition of said knowledge: (i) the individual is classified as a candidate to receive treatment with a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor; and/or (ii) the individual is identified as likely to respond to a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

In certain aspects, provided herein is a method of treating or delaying progression of cancer, comprising administering to an individual an effective amount of a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor, wherein the cancer comprises a rearrangement in a BCOR gene or an alteration in a BCORL1 gene.

In certain aspects, provided herein is a method of treating or delaying progression of cancer, comprising, responsive to knowledge of a rearrangement in a BCOR gene or an alteration in a BCORL1 gene in a sample from an individual, administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

In certain aspects, provided herein is a method of treating or delaying progression of cancer, comprising: acquiring knowledge of a rearrangement in a BCOR gene or an alteration in a BCORL1 gene in a sample from an individual; and responsive to said knowledge, administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

In certain aspects, provided herein is a method of treating or delaying progression of cancer, comprising: detecting a rearrangement in a BCOR gene or an alteration in a BCORL1 gene in a sample from an individual; and administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

In certain aspects, provided herein is a method of monitoring an individual having cancer, comprising acquiring knowledge of a rearrangement in a BCOR gene or an alteration in a BCORL1 gene in a sample from the individual, wherein responsive to the acquisition of said knowledge, the individual is predicted to have increased risk of uterine sarcoma, as compared to an individual whose cancer does not comprise a rearrangement in a BCOR gene or an alteration in a BCORL1 gene.

In certain aspects, provided herein is a method of predicting survival of an individual having cancer, comprising acquiring knowledge of a rearrangement in a BCOR gene or an alteration in a BCORL1 gene in a sample from the individual, wherein responsive to the acquisition of said knowledge, the individual is predicted to have shorter survival, as compared to survival of an individual whose cancer does not comprise a rearrangement in a BCOR gene or an alteration in a BCORL1 gene.

In certain aspects, provided herein is a method of evaluating an individual having cancer, comprising acquiring knowledge of a rearrangement in a BCOR gene or an alteration in a BCORL1 gene in a sample from the individual, wherein responsive to the acquisition of said knowledge, the individual is predicted to have increased risk of recurrence, as compared to an individual whose cancer does not comprise a rearrangement in a BCOR gene or an alteration in a BCORL1 gene.

In certain aspects, provided herein is a method of screening an individual having cancer, comprising acquiring knowledge of a rearrangement in a BCOR gene or an alteration in a BCORL1 gene in a sample from the individual, wherein responsive to the acquisition of said knowledge, the individual is predicted to have increased risk of recurrence, as compared to an individual whose cancer does not comprise a rearrangement in a BCOR gene or an alteration in a BCORL1 gene.

In some embodiments according to any of the embodiments described herein, the cancer further comprises one or more genomic alterations leading to increased expression and/or activity of Cyclin D/Cdk4 complex. In some embodiments, the cancer further comprises amplification of a gene selected from the group consisting of MDM2, FRS2, CCND2, and CDK4. In some embodiments, the cancer further comprises deletion (e.g., a homozygous deletion) of a gene selected from the group consisting of CDKN2A and CDKN2B.

In some embodiments according to any of the embodiments described herein, the targeted therapeutic is a CDK inhibitor. In some embodiments, the CDK inhibitor is a CDK4/CDK6 inhibitor. In some embodiments, the targeted therapeutic is (a) a small molecule that inhibits one or more enzymatic activities of CDK4, (b) an antibody that inhibits one or more activities of CDK4, or (c) a nucleic acid that inhibits expression of CDK4. In some embodiments, the targeted therapeutic is palbociclib, ribociclib, or abemaciclib. In some embodiments, the targeted therapeutic is an MDM2 inhibitor. In some embodiments, the targeted therapeutic is (a) a small molecule that inhibits one or more activities of MDM2, (b) an antibody that inhibits one or more activities of MDM2, or (c) a nucleic acid that inhibits expression of MDM2. In some embodiments, the targeted therapeutic is nutlin-3a, RG7112, idasanutlin, AMG-232, MI-63, MI-291, MI-391, MI-77301, APG-115, DS-3032b, NVP-CGM097, or HDM-201. In some embodiments, the targeted therapeutic comprises a combination of a CDK inhibitor and an MDM2 inhibitor.

In some embodiments according to any of the embodiments described herein, the cancer further comprises amplification of a gene selected from the group consisting of PDGFRA, KDR, ERBB3, and KIT.

In some embodiments according to any of the embodiments described herein, the targeted therapeutic is a tyrosine kinase inhibitor. In some embodiments, the targeted therapeutic is (a) a small molecule that inhibits one or more enzymatic activities of a tyrosine kinase, (b) an antibody that inhibits one or more activities of a tyrosine kinase, or (c) a nucleic acid that inhibits expression of a tyrosine kinase. In some embodiments, the tyrosine kinase inhibitor is selected from the group consisting of imatinib, crenolanib, linifanib, ninetedanib, axitinib, dasatinib, imetelstat, midostaurin, pazopanib, sorafenib, sunitinb, motesanib, masitinib, vatalanib, cabozanitinib, tivozanib, OSI-930, Ki8751, telatinib, dovitinib, tyrphostin AG 1296, amuvatinib, and pharmaceutically acceptable salts thereof.

In some embodiments according to any of the embodiments described herein, the cancer further comprises loss-of-function mutation in a gene selected from the group consisting of NF1 and NF2.

In some embodiments according to any of the embodiments described herein, the targeted therapeutic is a MEK or mTOR inhibitor. In some embodiments, the targeted therapeutic is (a) a small molecule that inhibits one or more enzymatic activities of MEK, (b) an antibody that inhibits one or more activities of MEK, or (c) a nucleic acid that inhibits expression of MEK. In some embodiments, the MEK inhibitor is selected from the group consisting of trametinib, cobimetinib, binimetinib, CI-1040, PD0325901, selumetinib, AZD8330, TAK-733, GDC-0623, refametinib, pimasertib, RO4987655, RO5126766, WX-544, HL-085, and pharmaceutically acceptable salts thereof.

In some embodiments according to any of the embodiments described herein, the targeted therapeutic is (a) a small molecule that inhibits one or more enzymatic activities of mTOR, (b) an antibody that inhibits one or more activities of mTOR, or (c) a nucleic acid that inhibits expression of mTOR. In some embodiments, the mTOR inhibitor is selected from the group consisting of temsirolimus, everolimus, ridaforolimus, dactolisib, GSK2126458, XL765, AZD8055, AZD2014, MLN128, PP242, NVP-BEZ235, LY3023414, PQR309, PKI587, OSI027, and pharmaceutically acceptable salts thereof.

In some embodiments according to any of the embodiments described herein, the cancer further comprises loss-of-function mutation in a PTCH1 gene.

In some embodiments according to any of the embodiments described herein, the targeted therapeutic is a Hh inhibitor. In some embodiments, the targeted therapeutic is (a) a small molecule that inhibits one or more enzymatic activities of Hh, (b) an antibody that inhibits one or more activities of Hh, or (c) a nucleic acid that inhibits expression of Hh. In some embodiments, the targeted therapeutic is selected from the group consisting of sonidegib, vismodegib, erismodegib, saridegib, BMS833923, PF-04449913, LY2940680, and pharmaceutically acceptable salts thereof.

In some embodiments according to any of the embodiments described herein, the BCOR rearrangement results in a fusion gene between BCOR and ZC3H7B. In some embodiments, a sample obtained from the cancer comprises spindle cells arranged in a fascicular growth pattern.

In some embodiments, the genetic alteration comprises a BCOR rearrangement. In some embodiments, the BCOR rearrangement results in a fusion gene between BCOR and a gene selected from the group consisting of L3MBTL2, EP300, NUTM2G, MAP7D2, RALGPS1, RGAG1, CREBBP, ING3, NUGGC, and KMT2D. In some embodiments, the fusion gene is selected from the group consisting of BCOR-L3MBTL2, EP300-BCOR, BCOR-NUTM2G, BCOR-RALGPS1, BCOR-MAP7D2, RGAG1-BCOR, ING3-BCOR, BCOR-NUGGC, KMT2D-BCOR and CREBBP-BCOR. In some embodiments, the BCOR rearrangement is an internal BCOR gene rearrangement characterized by a chromosome X inversion.

In some embodiments according to any of the embodiments described herein, a sample obtained from the cancer comprises spindle, epithelioid, or small round cells. In some embodiments, the sample further comprises myxoid stroma. In some embodiments, the sample further comprises collagen fibrosis. In some embodiments, the sample further comprises spiral arterioles. In some embodiments, a sample obtained from the cancer is characterized by a mitotic count that is between about 3 per 10 high power fields (HPF) and about 30 per 10 HPF. In some embodiments, a sample obtained from the cancer exhibits expression of one or more of cyclin D1, CD10, and BCOR. In some embodiments, a sample obtained from the cancer exhibits cyclin D1 overexpression. In some embodiments, a sample obtained from the cancer does not exhibit desmin expression. In some embodiments, a sample obtained from the cancer lacks a mutation in one or more of the TP53, BRCA2, PLAG1, RB1, ATRX, PTEN or MED12 genes. In some embodiments, a sample obtained from the cancer lacks a mutation in any of the TP53, BRCA2, PLAG1, RB1, ATRX, PTEN or MED12 genes.

In some embodiments, the genetic alteration comprises a BCORL1 alteration. In some embodiments, the BCORL1 alteration comprises a frameshift, nonsense, or truncating mutation. In some embodiments, the BCORL1 alteration comprises a T513fs*22, P600fs*1, R945*, R1196*, R1265fs*4, L461fs*5, or H1426fs*29 mutation. In some embodiments, the BCORL1 alteration comprises a deletion. In some embodiments, the deletion is a homozygous deletion. In some embodiments, the BCORL1 alteration comprises an internal BCORL1 rearrangement. In some embodiments, the BCORL1 alteration comprises a rearrangement resulting in a BCORL1 fusion gene. In some embodiments, the BCORL1 rearrangement results in a fusion gene between BCORL1 and JAZF1 or EP300. In some embodiments, the BCORL1 fusion gene is a JAZF1-BCORL1, BCORL1-JAZF1, or EP300-BCORL1 fusion gene. In some embodiments, the BCORL1 fusion gene is a JAZF1-BCORL1 fusion gene comprising breakpoints at exon 3 of JAZF1 and exon 5 of BCORL1. In some embodiments, the BCORL1 fusion gene is a JAZF1-BCORL1 fusion gene comprising exons 1-3 of JAZF1 fused to exons 5-12 of BCORL1. In some embodiments, the BCORL1 fusion gene is a JAZF1-BCORL1 fusion gene comprising breakpoints at exon 3 of JAZF1 and exon 6 of BCORL1. In some embodiments, the BCORL1 fusion gene is a JAZF1-BCORL1 fusion gene comprising exons 1-3 of JAZF1 fused to exons 6-12 of BCORL1. In some embodiments, the BCORL1 fusion gene is a JAZF1-BCORL1 fusion gene comprising breakpoints at exon 3 of JAZF1 and exon 7 of BCORL1. In some embodiments, the BCORL1 fusion gene is a JAZF1-BCORL1 fusion gene comprising exons 1-3 of JAZF1 fused to exons 7-12 of BCORL1. In some embodiments, the BCORL1 fusion gene is a BCORL1-JAZF1 fusion gene comprising breakpoints at exon 4 of BCORL1 and exon 4 of JAZF1. In some embodiments, the BCORL1 fusion gene is a BCORL1-JAZF1 fusion gene comprising exons 1-4 of BCORL1 fused to exons 4-5 of JAZF1. In some embodiments, the BCORL1 fusion gene is an EP300-BCORL1 fusion gene comprising breakpoints at exon 31 of EP300 and exon 4 of BCORL1. In some embodiments, the BCORL1 fusion gene is an EP300-BCORL1 fusion gene comprising exons 1-31 of EP300 fused to exons 4-12 of BCORL1.

In some embodiments according to any of the embodiments described herein, a sample obtained from the cancer is characterized by intermediate or low tumor burden. In some embodiments, the cancer is characterized by intermediate or low tumor burden. In some embodiments, a sample obtained from the cancer is characterized by 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, or 6 or fewer mutations per megabase (Mb). In some embodiments, the cancer is characterized by 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, or 6 or fewer mutations per megabase (Mb). In some embodiments, a sample obtained from the cancer is microsatellite stable. In some embodiments, the cancer is microsatellite stable.

In some embodiments according to any of the embodiments described herein, the cancer is resistant or refractory to treatment with conventional chemotherapy. In some embodiments, the methods further comprise selectively enriching for one or more nucleic acids comprising a rearrangement in a BCOR gene or an alteration in a BCORL1 gene to produce an enriched sample. In some embodiments, the treatment or the one or more treatment options further comprise a second therapeutic agent, e.g., a chemotherapeutic agent, immune checkpoint inhibitor (ICI), cancer immunotherapy, cell-based therapy, or nucleic acid-based therapy.

In some embodiments according to any of the embodiments described herein, the cancer is endometrial stromal sarcoma (ESS). In some embodiments, the cancer is a high grade ESS. In some embodiments, the cancer is uterine sarcoma. In some embodiments, the cancer was previously classified as myxoid leiomyosarcoma.

In some embodiments according to any of the embodiments described herein, the sample from the individual comprises fluid, cells, or tissue. In some embodiments, the sample from the individual comprises a tumor biopsy or a circulating tumor cell. In some embodiments, the sample from the individual is a nucleic acid sample. In some embodiments, the nucleic acid sample comprises mRNA, genomic DNA, circulating tumor DNA, cell-free DNA, or cell-free RNA. In some embodiments, the BCOR gene rearrangement or BCORL1 alteration is detected in the sample by one or more methods selected from the group consisting of a nucleic acid hybridization assay, an amplification-based assay, a polymerase chain reaction-restriction fragment length polymorphism (PCR-RFLP) assay, real-time PCR, sequencing, next-generation sequencing, a screening analysis, fluorescence in situ hybridization (FISH), spectral karyotyping, multicolor FISH (mFISH), comparative genomic hybridization, in situ hybridization, sequence-specific priming (SSP) PCR, high-performance liquid chromatography (HPLC), and mass-spectrometric genotyping. In some embodiments, the methods further comprise obtaining more than one sample from the individual at different time points.

In other aspects, provided herein is a targeted therapeutic for use in any of the methods described herein. In other aspects, provided herein is a targeted therapeutic for use in a method of treating or delaying progression of cancer, wherein the method comprises administering the targeted therapeutic to an individual, wherein a rearrangement in a BCOR gene or an alteration in a BCORL1 gene is detected in a sample obtained from the individual. In other aspects, provided herein is a targeted therapeutic for use in manufacturing a medicament for use in any of the methods described herein. In other aspects, provided herein is a targeted therapeutic for use in manufacturing a medicament for a rearrangement in a BCOR gene or an alteration in a BCORL1 gene has been detected in a sample obtained from the individual. In some embodiments, the targeted therapeutic is a CDK inhibitor, an MDM2 inhibitor, a tyrosine kinase inhibitor, a MEK inhibitor, an mTOR inhibitor, PIK3CA or AKT inhibitor, or a Hh inhibitor.

In other aspects, provided herein is a method of detecting a rearrangement in B-cell lymphoma 6 (BCL6) corepressor (BCOR) gene, the method comprising detecting (e.g., in vitro) an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D in a sample from an individual. In other aspects, provided herein is a method of diagnosing a rearrangement in B-cell lymphoma 6 (BCL6) corepressor (BCOR) gene, the method comprising: (a) detecting (e.g., in vitro) an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D in a sample from an individual; and (b) providing a diagnosis of a rearrangement in a B-cell lymphoma 6 (BCL6) corepressor (BCOR) gene. In other aspects, provided herein is a method of assessing a rearrangement in B-cell lymphoma 6 (BCL6) corepressor (BCOR) gene, the method comprising: (a) detecting (e.g., in vitro) an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D in a sample from an individual; and (b) providing an assessment of a rearrangement in a B-cell lymphoma 6 (BCL6) corepressor (BCOR) gene. In other aspects, provided herein is a method of diagnosing endometrial stromal sarcoma (ESS) in an individual, the method comprising: (a) detecting (e.g., in vitro) an internal rearrangement in B-cell lymphoma 6 (BCL6) corepressor (BCOR) gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT72D in a sample from the individual; and (b) providing a diagnosis of endometrial stromal sarcoma in the individual. In other aspects, provided herein is a method of diagnosing uterine sarcoma in an individual, the method comprising: (a) detecting (e.g., in vitro) an internal rearrangement in B-cell lymphoma 6 (BCL6) corepressor (BCOR) gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D in a sample from the individual; and (b) providing a diagnosis of uterine sarcoma in the individual. In other aspects, provided herein is an in vitro use of one or more oligonucleotides for detecting a rearrangement in a B-cell lymphoma 6 (BCL6) corepressor (BCOR) gene, wherein the BCOR gene rearrangement results in an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D. In other aspects, provided herein is a kit comprising one or more oligonucleotides for detecting (e.g., in vitro) a rearrangement in a B-cell lymphoma 6 (BCL6) corepressor (BCOR) gene, wherein the BCOR gene rearrangement results in an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D.

In other aspects, provided herein is a method of detecting a BCORL1 gene alteration, the method comprising detecting (e.g., in vitro) BCORL1 gene comprising a frameshift, nonsense, or truncating mutation; deletion; internal rearrangement; or fusion gene in a sample from an individual. In other aspects, provided herein is a method of diagnosing a BCORL1 gene alteration, the method comprising: (a) detecting (e.g., in vitro) a BCORL1 gene comprising a frameshift, nonsense, or truncating mutation; deletion; internal rearrangement; or fusion gene in a sample from an individual; and (b) providing a diagnosis of a BCORL1 gene alteration. In other aspects, provided herein is a method of assessing a BCORL1 gene alteration, the method comprising: (a) detecting (e.g., in vitro) a BCORL1 gene comprising a frameshift, nonsense, or truncating mutation; deletion; internal rearrangement; or fusion gene in a sample from an individual; and (b) providing an assessment of a BCORL1 gene alteration. In other aspects, provided herein is a method of diagnosing endometrial stromal sarcoma (ESS) in an individual, the method comprising: (a) detecting (e.g., in vitro) a BCORL1 gene comprising a frameshift, nonsense, or truncating mutation; deletion; internal rearrangement; or fusion gene in a sample from the individual; and (b) providing a diagnosis of endometrial stromal sarcoma in the individual. In other aspects, provided herein is a method of diagnosing uterine sarcoma in an individual, the method comprising: (a) detecting (e.g., in vitro) a BCORL1 gene comprising a frameshift, nonsense, or truncating mutation; deletion; internal rearrangement; or fusion gene in a sample from the individual; and (b) providing a diagnosis of uterine sarcoma in the individual. In other aspects, provided herein is an in vitro use of one or more oligonucleotides for detecting a BCORL1 gene alteration, wherein the BCORL1 gene alteration comprises a frameshift, nonsense, or truncating mutation; deletion; internal rearrangement; or fusion gene. In other aspects, provided herein is a kit comprising one or more oligonucleotides for detecting (e.g., in vitro) BCORL1 gene alteration, wherein the BCORL1 gene alteration comprises a frameshift, nonsense, or truncating mutation; deletion; internal rearrangement; or fusion gene.

In other aspects, provided herein is a method of detecting a rearrangement in a BCOR gene or an alteration in a BCORL1 gene, comprising: providing a plurality of nucleic acids obtained from a sample from an individual, wherein the plurality of nucleic acids comprises nucleic acids encoding a BCOR gene or a BCORL1 gene; optionally, ligating one or more adaptors onto one or more nucleic acids from the plurality of nucleic acids; amplifying nucleic acids from the plurality of nucleic acids; optionally, capturing a plurality of nucleic acids corresponding to the BCOR and/or BCORL1 gene(s); sequencing, by a sequencer, the plurality of nucleic acids to obtain a plurality of sequence reads corresponding to the BCOR and/or BCORL1 gene(s); analyzing the plurality of sequence reads; and based on the analysis, detecting a rearrangement in the BCOR gene or an alteration in the BCORL1 gene. In some embodiments, the plurality of nucleic acids corresponding to the BCOR and/or BCORL1 gene(s) are captured from the amplified nucleic acids by hybridization with a bait molecule.

In other aspects, provided herein is a system comprising: a memory configured to store one or more program instructions, and one or more processors configured to execute the one or more program instructions, the one or more program instructions when executed by the one or more processors are configured to: obtain a plurality of sequence reads of one or more nucleic acids, wherein the one or more nucleic acids are derived from a sample obtained from an individual; analyze the plurality of sequence reads for the presence of a genetic alteration comprising a rearrangement in a B-cell lymphoma 6 (BCL6) corepressor (BCOR) gene or an alteration in a BCL6 corepressor-like protein 1 (BCORL1) gene, or of a portion thereof; and detect, based on the analyzing, a rearrangement in a BCOR gene or an alteration in a BCORL1 gene, or a portion thereof, in the sample.

In other aspects, provided herein is a computer readable storage medium (e.g., a non-transitory computer readable storage medium) comprising one or more programs executable by one or more computer processors for performing a method, comprising: obtaining, using the one or more processors, a plurality of sequence reads of one or more nucleic acids, wherein the one or more nucleic acids are derived from a sample obtained from an individual; analyzing, using the one or more processors, the plurality of sequence reads for the presence of a genetic alteration comprising a rearrangement in a B-cell lymphoma 6 (BCL6) corepressor (BCOR) gene or an alteration in a BCL6 corepressor-like protein 1 (BCORL1) gene, or of a portion thereof; and detecting, using the one or more processors and based on the analyzing, a rearrangement in a BCOR gene or an alteration in a BCORL1 gene, or a portion thereof, in the sample.

In some embodiments according to any of the embodiments described herein, the fusion gene is selected from the group consisting of BCOR-L3MBTL2, EP300-BCOR, BCOR-NUTM2G, BCOR-RALGPS1, BCOR-MAP7D2, RGAG1-BCOR, ING3-BCOR, BCOR-NUGGC, KMT2D-BCOR and CREBBP-BCOR. In some embodiments, the BCOR rearrangement is an internal BCOR gene rearrangement characterized by a chromosome X inversion.

In some embodiments according to any of the embodiments described herein, the BCORL1 gene comprises: a T513fs*22, P600fs*1, R945*, R1196*, R1265fs*4, L461fs*5, or H1426fs*29 mutation; a deletion; an internal rearrangement; or a JAZF1-BCORL1, BCORL1-JAZF1, or EP300-BCORL1 fusion gene.

In some embodiments according to any of the embodiments described herein, a sample obtained from the cancer comprises spindle, epithelioid, or small round cells. In some embodiments, the sample further comprises myxoid stroma. In some embodiments, the sample further comprises collagen fibrosis. In some embodiments, the sample further comprises spiral arterioles. In some embodiments, a sample obtained from the cancer is characterized by a mitotic count that is between about 3 per 10 high power fields (HPF) and about 30 per 10 HPF. In some embodiments, a sample obtained from the cancer exhibits expression of one or more of cyclin D1, CD10, and BCOR. In some embodiments, a sample obtained from the cancer exhibits cyclin D1 overexpression. In some embodiments, a sample obtained from the cancer does not exhibit desmin expression. In some embodiments, a sample obtained from the cancer lacks a mutation in one or more of the TP53, BRCA2, PLAG1, RB1, ATRX, PTEN or MED12 genes. In some embodiments, a sample obtained from the cancer lacks a mutation in any of the TP53, BRCA2, PLAG1, RB1, ATRX, PTEN or MED12 genes. In some embodiments, a sample obtained from the cancer is characterized by intermediate or low tumor burden. In some embodiments, the cancer is characterized by intermediate or low tumor burden. In some embodiments, a sample obtained from the cancer is characterized by 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, or 6 or fewer mutations per megabase (Mb). In some embodiments, the cancer is characterized by 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, or 6 or fewer mutations per megabase (Mb). In some embodiments, a sample obtained from the cancer is microsatellite stable. In some embodiments, the cancer is microsatellite stable.

In other aspects, provided herein is a kit comprising a probe or bait for detecting a rearrangement in a BCOR gene or an alteration in a BCORL1 gene. In other aspects, provided herein is a vector comprising a rearrangement in a BCOR gene or an alteration in a BCORL1 gene, or fragments thereof. In other aspects, provided herein is a host cell comprising the vector according to any one of the above embodiments.

In other aspects, provided herein is an antibody or antibody fragment that specifically binds to a polypeptide encoded by a BCOR fusion gene or an internal BCOR gene rearrangement. In some embodiments according to any of the embodiments described herein, the BCOR fusion gene comprises a fusion between BCOR and a gene selected from the group consisting of L3MBTL2, EP300, NUTM2G, MAP7D2, RALGPS1, RGAG1, CREBBP, ING3, NUGGC, and KMT2D.

In other aspects, provided herein is an antibody or antibody fragment that specifically binds to a polypeptide encoded by a BCORL1 gene comprising a frameshift, nonsense, or truncating mutation; an internal rearrangement; or a fusion gene. In other aspects, provided herein is a kit comprising an antibody or antibody fragment that specifically binds to a polypeptide encoded by a BCORL1 gene comprising a frameshift, nonsense, or truncating mutation; an internal rearrangement; or a fusion gene. In some embodiments according to any of the embodiments described herein, the BCORL1 gene comprises: a T513fs*22, P600fs*1, R945*, R1196*, R1265fs*4, L461fs*5, or H1426fs*29 mutation; an internal rearrangement; or a JAZF1-BCORL1, BCORL1-JAZF1, or EP300-BCORL1 fusion gene.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIGS. 2A & 2B: uterine sarcoma with internal BCOR rearrangement without fusion gene partner with cellular spindle to (FIG. 2A) epithelioid morphology and clear cytoplasm, transitioning to (FIG. 2B) hypocellular fibromyxoid spindle cell areas. FIGS. 2C & 2D: uterine sarcoma with novel RGAG1-BCOR gene rearrangement epithelioid (FIG. 2C) and round cell (FIG. 2D) morphology. FIG. 2E: BCOR-NUTM2G rearranged uterine sarcoma with small round cell morphology. FIG. 2F: KMT2D-BCOR rearranged uterine sarcoma with small round cell morphology with sharp transition to hypocellular spindle cell myxoid morphology.

FIG. 5A provides a schematic representation of the protein domains of BCORL1 and the positions and types of mutations in BCORL1 (NM_021946) identified in the endometrial stromal sarcoma and uterine adenosarcoma cohorts (top), as well as the homologous BCOR protein domains and the location of the previously described internal tandem duplications (bottom). CTBP1 binding site; NLS, nuclear localization signal; LXXLL, Leu-$X_{aa}$-$X_{aa}$-Leu-Leu motif, where $X_{aa}$ is any amino acid; ANK, ankyrin repeats; PUFD, PUFD (PCGF Ub-like fold discriminator) domain; ITD, internal tandem duplications (denoted by arrow); and BBD, BCL6-binding domain. FIG. 5B provides schematic diagrams of RNA fusion transcripts involving BCORL1 and JAZF1, or BCORL1 and EP300 fusions identified in endometrial stromal sarcoma and uterine adenosarcoma cases. Specific exons for BCORL1 and the gene partner identified for each fusion transcript are labeled. Two additional cases also harbored homozygous BCORL1 gene deletion and one additional case had an internal BCORL1 rearrangement (not represented). Reference sequences: JAZF1 (NM_175061), BCORL1 (NM_021946), EP300 (NM_001429), BCOR (NM_017745).

FIGS. 6A-6D: endometrial stromal sarcoma (case #1) with JAZF1-BCORL1 demonstrating alternating hypercellular and hypocellular areas and myxoid stroma on low power view (FIG. 6A), hypercellular area with spindle cells and mild to moderate atypia (FIG. 6B), hypocellular and spindle cell area with low-grade atypia and myxoid stromal change (FIG. 6C), and hypercellular, epithelioid area with high-grade nuclear atypia and prominent nucleoli (FIG. 6D). FIGS. 6E-6F: endometrial stromal sarcoma (case #2) with EP300-BCORL1 rearrangement characterized by epithelioid morphology with pink cytoplasm (FIG. 6E) and hypocellular myxoid and spindle cell areas (FIG. 6F).

FIGS. 7A-7C: endometrial stromal sarcoma with epithelioid and spindle areas (FIG. 7A), spiral arterioles (FIG. 7B), myxoid stroma and mild to moderate atypia (FIG. 7C). FIGS. 7D-7F: endometrial stromal sarcoma with hypercellular spindle cell area with collagen fibrosis (FIG. 7D), hypocellular fibromyxoid areas (FIG. 7E), and focal epithelioid areas with high-grade atypia adjacent to spindle cell and myxoid areas (FIG. 7F).

FIGS. 8A-8C: uterine sarcoma with BCORL1 R1265fs*4 frameshift mutation, previously diagnosed as low grade endometrial stromal sarcoma, characterized by epithelioid morphology with clear to pale cytoplasm and moderate to high grade atypia (FIG. 8A), spindle to epithelioid areas with collagen fibrosis (FIG. 8B), and spindle cell areas with myxoid stroma and lower grade atypia (FIG. 8C). FIG. 8D: uterine sarcoma, previously diagnosed as myxoid leiomyosarcoma, harboring BCORL1 T513fs*22 frameshift mutation as the only oncogenic genomic alteration, and exhibiting spindle cell morphology with myxoid stroma and collagen fibrosis. FIGS. 8E-8F: uterine sarcoma, previously diagnosed as spindle cell neoplasm consistent with leiomyosarcoma, with BCORL1 P600fs*1 frameshift mutation, featuring epithelioid areas with high grade atypia, and spindle cell area with lower grade atypia (FIG. 8E) and myxoid change.

FIGS. 9A-9D: uterine adenosarcoma with JAZF1-BCORL1 fusion, characterized by low power phyllodes architecture (FIG. 9A), peri-glandular stromal cuffing of hypercellular spindle cells transitioning to hypocellular myxoid areas (FIG. 9B), hypocellular fibromyxoid component (FIG. 9C) and epithelioid areas with higher grade atypia (FIG. 9D). FIG. 9E: uterine adenosarcoma with BCORL1 L461fs*5 frameshift mutation and EPC1-PHF1 fusion with morphology of the sarcomatous component resembling low grade endometrial stromal sarcoma. FIG. 9F: uterine adenosarcoma with BCORL1 H1426fs*29 frameshift mutation, featuring higher grade atypia and myxoid stromal change.

DETAILED DESCRIPTION

Figure 1A:
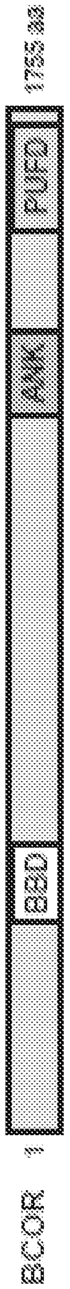
FIG. 1A provides a schematic diagram of the protein domains of BCOR. BBD, BCL-6 binding domain; ANK, ankyrin repeat; PUFD, PCGF Ub-like fold discriminator.

The present disclosure relates generally to detecting rearrangements in the B-cell lymphoma 6 (BCL6) corepressor (BCOR) or BCL6 corepressor-like protein 1 (BCORL1) gene, as well as methods of treatment, uses, and kits related thereto. The present disclosure describes analyses undertaken on the largest cohort of BCOR-rearranged ESS to date (n=40), which included 31 cases with canonical ZC3H7B-BCOR fusion as well as 8 cases with novel BCOR gene rearrangement partners, such as BCOR-L3MBTL2, EP300-BCOR, BCOR-NUTM2G, BCOR-RALGPS1, BCOR-MAP7D2, RGAG1-BCOR, ING3-BCOR, BCOR-NUGGC, KMT2D-BCOR, CREBBP-BCOR and 1 case with BCOR internal rearrangement. Re-review of cases with novel rearrangements demonstrated sarcomas with spindle, epithelioid or small round cell components and frequent myxoid stromal change. Comprehensive genomic profiling revealed high frequency of CDK4 and MDM2 amplification in 38% and 45% of BCOR-rearranged cases, respectively, and homozygous deletion of CDKN2A, which encodes an inhibitor of CDK4, in 28% of cases. Notably, CDK4 and MDM2 amplification was absent in all cases from an independent cohort of 15 ESS cases harboring BCOR ITD.

Without wishing to be bound to theory, it is thought that activation of the CDK4/MDM2 pathway, for which targeted therapies are clinically available, via CDK4 or MDM2 amplification and/or CDKN2A loss, contributes to the pathogenesis of BCOR-rearranged uterine sarcomas. Gene amplifications leading to potential activation of other pathways, such as tyrosine kinases, MEK, mTOR, and Hh, were also observed and suggest corresponding targeted therapies.

The present disclosure further describes analysis of the largest cohorts of BCORL1-altered uterine sarcomas (n=12) and uterine adenosarcomas (n=6). These cohorts included 5 uterine sarcoma cases with BCORL1 rearrangements (JAZF1-BCORL1, EP300-BCORL1, or internal BCORL1 rearrangement), 5 cases with inactivating BCORL1 mutations (T513fs*22, P600fs*1, R945*, R1196*, or R1265fs*4) and 2 cases with homozygous BCORL1 deletion, and 4 uterine sarcoma cases harboring JAZF1-BCORL1 fusions, and BCORL1 L146fs*5, or H1426fs*29. BCORL1-altered uterine sarcomas and adenosarcomas were found to exhibit frequent genomic alterations leading to CDK4 activation, and less frequent NF1 and NF2-mTOR pathway alterations, expanding potential therapeutic targets. Without wishing to be bound to theory, it is thought that activation of the CDK4, NF1, or NF2-mTOR pathways, for which targeted therapies are clinically available, contributes to the pathogenesis of BCORL1-altered uterine sarcomas.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2*: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, 1, or 2 cancer. Examples of a cancer include, but are not limited to, a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor. In certain embodiments, the cancer is endometrial stromal sarcoma (ESS), e.g., a high grade ESS. In certain embodiments, the cancer is uterine sarcoma.

The term "tumor," as used herein, refers to all neoplastic cell growth and proliferation, whether malignant or benign, and all pre-cancerous and cancerous cells and tissues. The terms "cancer," "cancerous," and "tumor" are not mutually exclusive as referred to herein.

As used herein, the term "B-cell lymphoma 6 (BCL6) corepressor (BCOR)" refers to a gene encoding a BCOR mRNA or polypeptide, as well as fusions or rearrangements thereof. BCOR encodes a corepressor of BCL6, which is a POZ/zinc finger transcriptional repressor. BCOR is also known as MAA2, ANOP2, and MCOPS2. In some embodiments, a BCOR gene is a human BCOR gene. An exemplary BCOR gene is represented by NCBI Gene ID No. 54880. An exemplary BCOR mRNA sequence is represented by NCBI Ref. Seq. NM_017745:

```
                                                             (SEQ ID NO: 1)
AGACGGAGCCTGGGCTCCCAGCGGCAAGGTGAGGCAGAGCTGCGCTCCTCGCTGAACGCGGGCCGAGCTC

GGCGGCTGCGGGGGAGACGCGCAGGAGCCCAGACCGCGACCGAGAGCGGGAGCTAGGCGGGCGGCGGCGG

CGGAGGGGGAGCCCGCGAGCCGCCGGGCGGAGAGCCCAAGCCGCGCTGTCGCCGCGCAGGGACGACTTGG

CCAACACTCACACACACTCACACACACCCAGCCCGAGCGGGCGCTCGCGGCGAACCGTCAACATGGCGCT

GGGGCTCCTGCCCGAGCGCGGGCGGCGGCGGCAGCGCGGGAGCTGCTGAGCTCGGCCAAGCCCAGTCCAG

CTGCGGGAGCCCGGAGGATCGCACGGGGCTGTCGCCACCTGCCCGGAGGCCCCGAGCCCGCCCCGCCCCG

CCCCCACCCGGCCCAGAGCCCACCCCTCGGCGGGGCCGACCCCGAGGGCAGCCGGCTGCCAGCAGACGGC

GAGGGAGTCGAGTGAGCGCGGCGCCGCGAGCGGGCTGCGGGCAGCCGGGGACCGCAAACTTTGCTGCTCG

CCGCGCTTCTCCGGCCCGGCTCCTTCTCCGCTCGTTAACGTCGCCAACCCCCCCCACCCCTCATATCTCT

CTCCACCCACCCAACCGCCCCCCGCTCCTTCTCGCCGCCTCGAGTCCGCTTGGGGGAAAACTTCAAAGAG

CCGGATCGCAGGCTCCCTGCCTACTCCCCCACCGGGGATTTCAGACTAGACGCTTGAAGCAAAGCTGCCA

TCCCAGAAGACGACATGCTCTCAGCAACCCCCCTGTATGGGAACGTTCACAGCTGGATGAACAGCGAGAG

GGTCCGCATGTGTGGGGCGAGCGAAGACAGGAAAATCCTTGTAAATGATGGTGACGCTTCAAAAGCCAGA

CTGGAACTGAGGGAAGAGAATCCCTTGAACCACAACGTGGTGGATGCGAGCACGGCCCATAGGATCGATG

GCCTGGCAGCACTGAGCATGGACCGCACTGGCCTGATCCGGGAAGGGCTGCGGGTCCCGGGAAACATCGT

CTATTCTAGCTTGTGTGGACTGGGCTCAGAGAAAGGTCGGGAGGCTGCCACAAGCACTCTAGGTGGCCTT

GGGTTTTCTTCGGAAAGAAATCCAGAGATGCAGTTCAAACCGAATACACCCGAGACAGTGGAGGCTTCTG

CCGTCTCTGGAAAACCCCCAAATGGCTTCAGTGCTATATACAAAACACCGCCTGGAATACAAAAAAGTGC

TGTAGCCACAGCAGAAGCGCTGGGCTTGGACAGGCCTGCCAGCGACAAACAGAGCCCTCTCAACATCAAT

GGTGCTAGTTATCTGCGGCTGCCCTGGGTCAATCCTTACATGGAGGGTGCCACGCCAGCCATCTACCCTT

TCCTCGACTCGCCAAATAAGTATTCACTGAACATGTACAAGGCCTTGCTACCTCAGCAGTCCTACAGCTT

GGCCCAGCCGCTGTATTCTCCAGTCTGCACCAATGGGGAGCGCTTTCTCTACCTGCCGCCACCTCACTAC

GTCGGTCCCCACATCCCATCGTCCTTGGCATCACCCATGAGGCTCTCGACACCTTCGGCCTCCCCAGCCA

TCCCGCCTCTCGTCCATTGCGCAGACAAAAGCCTCCCGTGGAAGATGGGCGTCAGCCCTGGGAATCCTGT

TGATTCCCACGCCTATCCTCACATCCAGAACAGTAAGCAGCCCAGGGTTCCCTCTGCCAAGGCGGTCACC

AGTGGCCTGCCGGGGGACACAGCTCTCCTGTTGCCCCCCTCGCCTCGGCCGTCACCCCGAGTCCACCTTC

CCACCCAGCCTGCTGCAGACACCTACTCGGAGTTCCACAAGCACTATGCCAGGATCTCCACCTCTCCTTC

AGTTGCCCTGTCAAAGCCATACATGACAGTTAGCAGCGAGTTCCCCGCGGCCAGGCTCTCCAATGGCAAG

TATCCCAAGGCTCCGGAAGGGGGCGAAGGTGCCCAGCCAGTGCCCGGGCATGCCCGGAAGACAGCGGTTC

AAGACAGAAAAGATGGCAGCTCACCTCCTCTGTTGGAGAAGCAGACCGTTACCAAAGACGTCACAGATAA

GCCACTAGACTTGTCTTCTAAAGTGGTGGATGTAGATGCTTCCAAAGCTGACCACATGAAAAAGATGGCT

CCCACGGTCCTGGTTCACAGCAGGGCTGGAAGTGGCTTAGTGCTCTCCGGAAGTGAGATTCCGAAAGAAA

CACTATCTCCTCCAGGAAATGGTTGTGCTATCTATAGATCTGAAATCATCAGCACTGCTCCCTCATCCTG

GGTGGTGCCCGGGCCAAGTCCTAACGAAGAGAACAATGGCAAAAGCATGTCGCTGAAAAACAAGGCATTG
```

-continued

GACTGGGCGATACCACAGCAGCGGAGTTCATCATGCCCGCGCATGGGCGGCACCGATGCTGTCATCACTA

ACGTTTCAGGGTCAGTGTCGAGTGCAGGCCGCCCAGCCTCCGCATCACCCGCCCCCAATGCCAATGCAGA

TGGCACCAAAACCAGCAGGAGCTCTGTAGAAACCACACCATCCGTTATTCAGCACGTGGGCCAGCCCCCG

GCCACTCCTGCCAAGCACAGTAGCAGCACCAGCAGCAAGGGCGCCAAAGCCAGCAACCCAGAACCGAGTT

TCAAAGCAAACGAGAACGGCCTTCCACCAAGCTCTATATTTCTGTCTCCAAATGAGGCATTCAGGTCCCC

ACCAATTCCCTACCCCAGGAGTTACCTCCCTTACCCAGCCCCTGAGGGCATTGCTGTAAGTCCCCTCTCC

TTACATGGCAAAGGACCTGTCTACCCTCACCCAGTTTTGTTACCCAATGGCAGTCTGTTTCCTGGGCACC

TTGCCCCAAAGCCTGGGCTGCCCTATGGGCTTCCCACCGGCCGTCCAGAGTTTGTGACCTACCAAGATGC

CCTGGGGTTGGGCATGGTGCATCCCATGTTGATACCACACACGCCCATAGAGATTACTAAAGAGGAGAAA

CCAGAGAGGAGATCCCGGTCCCATGAGAGAGCCCGTTACGAGGACCCAACCCTCCGGAATCGGTTTTCCG

AGATTTTGGAAACTAGCAGCACCAAGTTACATCCAGATGTCCCCACCGACAAGAACCTAAAGCCGAACCC

CAACTGGAATCAAGGGAAGACTGTTGTCAAAAGCGACAAGCTTGTCTACGTAGACCTTCTCCGAGAAGAA

CCAGATGCTAAAACTGACACAAACGTGTCCAAACCCAGCTTTGCAGCAGAGAGTGTTGGCCAGAGCGCTG

AGCCCCCCAAGCCCTCAGTTGAGCCGGCCCTGCAGCAGCACCGTGATTTCATCGCCCTGAGAGAGGAGTT

GGGGCGCATCAGTGACTTCCACGAAACTTATACTTTCAAACAGCCAGTCTTCACCGTAAGCAAGGACAGT

GTTCTGGCAGGTACCAACAAAGAGAACCTAGGGTTGCCAGTCTCGACTCCATTCCTGGAGCCACCTCTGG

GGAGCGATGGCCCTGCTGTAACTTTTGGTAAAACCCAAGAGGATCCCAAACCATTTTGTGTGGGCAGTGC

CCCACCAAGTGTGGATGTGACCCCCACCTATACCAAAGATGGAGCTGATGAGGCTGAATCAAATGATGGC

AAAGTTCTGAAACCGAAGCCATCTAAGCTGGCAAAGAGAATCGCCAACTCAGCGGGTTACGTGGGTGACC

GATTCAAATGIGTCACTACCGAACTGTATGCAGATTCCAGTCAGCTCAGCCGGGAGCAACGGGCATTGCA

GATGGAAGGATTACAAGAGGACAGTATTTTATGTCTACCCGCTGCTTACTGTGAGCGTGCAATGATGCGC

TTCTCAGAGTTGGAGATGAAAGAAAGAGAAGGTGGCCACCCAGCAACCAAAGACTCCGAGATGTGCAAAT

TCAGCCCAGCCGACTGGGAAAGGTTGAAAGGAAATCAGGACAAAAAGCCAAAGTCGGTCACCCTGGAGGA

GGCCATTGCAGAACAGAACGAAAGTGAGAGATGCGAGTATAGTGTTGGAAACAAGCACCGTGATCCCTTT

CCGCAGACCAGGTGGCCTCGGACATGCCTCACAGCCCCACCCTCCGGGTGGACAGGAAACGCAAAGTCTC

AGGTGACAGCAGCCACACTGAGACCACTGCGGAGGAGGTGCCAGAGGACCCTCTGCTGAAAGCCAAACGC

CGACGAGTCTCTAAAGGGCTCCATCCTAAAAAACAACGCCACTTGCTGCACCTTAGAGAACGATGGGAGC

AGCAGGTGTCGGCAGCAGATGGCAAACCTGGCCGGCAAAGCAGGAAGGAAGTGACCCAGGCCACTCAGCC

TGAGGCCATTCCTCAGGGGACTAACATCACTGAAGAGAAACCTGGCAGGAAAAGGGCAGAGGCCAAAGGC

AACAGAAGCTGGTCGGAAGAGTCTCTTAAACCCAGTGACAATGAACAAGGCTTGCCTGTGTTCTCCGGCT

CTCCGCCCATGAAGAGTCTTTCATCCACCAGTGCAGGCGGCAAAAAGCAGGCTCAGCCAAGCTGCGCACC

AGCCTCCAGGCCGCCTGCCAAACAGCAGAAAATTAAAGAAAACCAGAAGACAGATGTGCTGTGTGCAGAC

GAAGAAGAGGATTGCCAGGCTGCCTCCCTGCTGCAGAAATACACCGACAACAGCGAGAAGCCATCCGGGA

AGAGACTGTGCAAAACCAAACACTTGATCCCTCAGGAGTCCAGGCGGGGATTGCCACTGACAGGGGAATA

CTACGTGGAGAATGCCGATGGCAAGGTGACTGTCCGGAGATTCAGAAAGCGGCCGGAGCCCAGTTCGGAC

TATGATCTGTCACCAGCCAAGCAGGAGCCAAAGCCCTTCGACCGCTTGCAGCAACTGCTACCAGCCTCCC

AGTCCACACAGCTGCCATGCTCAAGTTCCCCTCAGGAGACCACCCAGTCTCGCCCTATGCCGCCGGAAGC

ACGGAGACTTATTGTCAATAAGAACGCTGGCGAGACCCTTCTGCAGCGGGCAGCCAGGCTTGGCTATGAG

GAAGTGGTCCTGTACTGCTTAGAGAACAAGATTTGTGATGTAAATCATCGGGACAACGCAGGTTACTGCG

CCCTGCATGAAGCTTGTGCTAGGGGCTGGCTCAACATTGTGCGACACCTCCTTGAATATGGCGCTGATGT

-continued

```
CAACTGTAGTGCCCAGGATGGAACCAGGCCTCTGCACGATGCTGTTGAGAACGATCACTTGGAAATTGTC
CGACTACTTCTCTCTTATGGTGCTGACCCCACCTTGGCTACGTACTCAGGTAGAACCATCATGAAAATGA
CCCACAGTGAACTTATGGAAAAGTTCTTAACAGATTATTTAAATGACCTCCAGGGTCGCAATGATGATGA
CGCCAGTGGCACTTGGGACTTCTATGGCAGCTCTGTTTGTGAACCAGATGATGAAAGTGGCTATGATGTT
TTAGCCAACCCCCCAGGACCAGAAGACCAGGATGATGATGACGATGCCTATAGCGATGTGTTTGAATTTG
AATTTTCAGAGACCCCCCTOTTACCGTGTTATAACATCCAAGTATCTGTGGCTCAGGGGCCACGAAACTG
GCTACTGCTTTCGGATGTCCTTAAGAAATTGAAAATGTCCTCCCGCATATTTCGCTGCAATTTTCCAAAC
GTGGAAATTGTCACCATTGCAGAGGCAGAATTTTATCGGCAGGTTTCTGCAAGTCTCTTGTTCTCTTGCT
CCAAAGACCTGGAAGCCTTCAACCCTGAAAGTAAGGAGCTGTTAGATCTGGTGGAATTCACGAACGAAAT
TCAGACTCTGCTGGGCTCCTCTGTAGAGTGGCTCCACCCCAGTGATCTGGCCTCAGACAACTACTGGTGA
GCAAGOTGGACCCACCATGTACAGTGTGTTATAGTGTTAATCCTTGTGCATATGTGTCATAATACAACTA
TTTCTGTAAAGAAAGGACACTATTACATATGAAAATATCTCTTCTTTATATAAGAGAAATTACTCCAGTC
AGAAGGACTTAGAAACATGTTTTTTTCCTTTTAAACTTTTAAGTCAGTTTTTATGAAGTTGTTATAATGT
TTCTTTACTTTTCAATGCACACATGCTTTGGGATACGTTTGTTTTTACTTGGAACATTTGTTTCTTTTCT
TTTTTAAGGAGAAAAAAAAATGAGTAAAAGGAGCTCCACACTTTGACTTAATTTCATACAAAGCTCTGAT
GACAGGCCATGACTGTAGAGTGGTCAGAACTGTGTGGTTGGTTTGAGGGAGCGAATTCGGGGAAGGCACT
TGGTGATATAACTTTGTTTTGTTTACAGAGTACCTGCTCGGGCCAGGTAAATGCTATTGGATGTAATCCA
GTAGTGTGTAATATAAATTCAAACCATATCCACACACAACAACTAATTGTATGAAACTTTTATATCCTAA
TTTAAAAGCTGTGAAATTAGTTTTCACGCATCAAACCGGATTGTTTATATGTTTAAACATTTTATGCTCT
TATTTAAAGAAGACTTTGAGCTATTTTTTTCTGTACCCTGTAAAATATTGAAAACTAACATAATATGTTG
AGGTTGCTTGGAAATGTACATAAAACTAAAATTTTCTGAATCGTGTGTTTATGTTTGAAATCTGTGTTTT
AACTTTGTAAGTAAATTCTCTGCCTTTGTATTTATATTTTACAAAAATTTTCTTAAAAGGCAATAAAACT
GTTGAGGAAAGGAGAAAA
```

As used herein, the term “BCL6 corepressor-like protein 1 (BCORL1)” refers to a gene encoding a BCORL1 mRNA or polypeptide, as well as fusions or rearrangements thereof. BCORL1 encodes a transcriptional corepressor of BCL6 similar to BCOR, which is a POZ/zinc finger transcriptional repressor. BCORL1 is also known as SHUVER, BCoR-L1, and CXorf10. In some embodiments, a BCORL1 gene is a human BCORL1 gene. An exemplary BCORL1 gene is represented by NCBI Gene ID No. 63035. An exemplary BCORL1 mRNA sequence is represented by NCBI Ref. Seq. NM_001184772:

(SEQ ID NO: 2)

```
AGATCGGCGGGGCCGCGAGCGGAGGGAGGGAGGCCCGCGGCGGCGCGGCGGCAGCGAAGGCCAGCTTCCG
CGGAGTTTGTGCCCGGGCTTCCCGGGCTCTGGCCGCCTCACGCGCACAAATGGGGCTAGGGGACTGAGTG
GTAAGCAACTCCGAGTGTTAGACGGTGATCGGGCGGCGATTCCGGGAAAAGCGAGGAAAGACACAGTCTG
CGATTGTGCCGCACCCCCCACCCACCTCTTAGCATCTGGATTCTGCTCTCGTAGTGGGGGCCGCGGACCC
TCCCCGCCACAGTCCTTTTACTCTCCAGCACTCCCACCGCCTTCCCCCTTCTTCAGCCATCTGACTCTCC
TAGGGGGTCGGCGTGGCGAAGGACGGCTAGCCTTGGAGGGAAAGTAGCCACCAGTCCAACTCGGGTCGCC
CCCACCATTATTTCGGGGGAGTGGCCACAGCAGGTCCTATCTGGTGGTGAGTGGCTGTCATGATCTCTAC
AGCACCGCTCTACAGCGGCGTGCACAACTGGACCAGITCTGACCGGATTCGCATGTGTGGCATCAACGAG
GAGAGAAGAGCACCTCTTTCTGATGAGGAGTCAACGACAGGCGACTGCCAGCACTTTGGATCTCAGGAGT
```

-continued

TTTGTGTCAGCAGCAGTTTTTCCAAGGTGGAGCTCACGGCAGTTGGAAGTGGCAGCAATGCCCGGGGGGC

AGACCCAGATGGCAGTGCTACAGAAAAACTTGGGCACAAGTCAGAAGACAAGCCTGACGATCCCCAGCCA

AAAATGGACTACGCTGGGAACGTGGCAGAGGCTGAGGGCCTCTTGGTGCCCCTGAGCAGCCCAGGAGACG

GGCTCAAGCTTCCCGCATCTGACAGCGCCGAGGCCAGCAACAGCAGGGCCGACTGCTCCTGGACTCCACT

CAACACCCAAATGAGCAAACAGGTTGACTGCTCACCCGCCGGAGTAAAGGCTTTGGACTCTCGGCAAGGT

GTTGGAGAGAAGAATACTTTCATTTTGGCAACTCTGGGAACTGGAGTCCCTGTGGAGGGGACCCTGCCCC

TGGTTACCACTAACTTCAGTCCTCTGCCAGCCCCTATCTGTCCCCCTGCTCCCGGTTCGGCCTCTGTGCC

CCACTCTGTTCCAGATGCATTCCAGGTTCCCCTCTCCGTCCCTGCCCCAGTCCCCCATTCAGGGCTTGTT

CCAGTCCAAGTTGCCACTTCGGTTCCAGCTCCTTCCCCTCCCTTAGCACCTGTCCCGGCTCTGGCTCCAG

CGCCACCGTCAGTGCCCACGCTCATCTCTGACTCGAACCCCCTTTCTGTTTCGGCCTCAGTCTTGGTGCC

TGTGCCAGCTTCTGCTCCCCCTTCAGGCCCGGTTCCCTTGTCGGCTCCAGCTCCTGCCCCGCTTTCAGTC

CCAGPTTCAGCTCCTCCCTTGGCTCTCATCCAGGCTCCTGTGCCCCCTTCAGCTCCGACCTTGGTTCTCG

CTCCCGTCCCCACTCCGGTTCTGGCTCCCATGCCAGCATCCACGCCTCCAGCGGCCCCTGCCCCTCCGTC

TGTGCCCATGCCCACTCCAACCCCATCTTCCGGCCCACCTTCTACCCCCACCCTCATCCCCGCCTTTGCT

CCTACACCGGTGCCTGCACCCACCCCAGCCCCCATCTTTACTCCAGCCCCTACACCCATGCCTGCTGCCA

CGCCAGCTGCCATTCCCACCTCTGCACCCATCCCGGCCTCCTTCAGTTTGAGTAGAGTGTGCTTTCCTGC

AGCTCAGGCACCAGCTATGCAAAAAGTCCCCCTGTCCTTTCAGCCAGGGACAGTGCTGACCCCGAGCCAG

CCGCTGGTATATATCCCGCCTCCAAGCTGTGGGCAGCCACTCAGTGTGGCCACACTGCCAACCACTCTAG

GGGTTTCCTCCACTCTTACGCTCCCTGTCCTGCCGTCCTACCTGCAGGACAGGTGTCTCCCAGGCGTGCT

AGCCTCCCCCGAGCTCCGTTCTTACCCGTATGCATTTTCTGTGGCCCGGCCTCTGACTTCGGATTCCAAG

CTGGTATCTCTGGAGGTGAACAGGCTCCCCTGCACTTCCCCATCCGGTAGCACCACCACCCAGCCTGCAC

CCGATGGGGTCCCTGGGCCTTTGGCAGATACCTCCCTTGTTACTGCTTCTGCCAAGGTGCTTCCAACPCC

ACAGCCTCTGCTGCCAGCCCCCAGTGGGAGCTCAGCCCCACCGCACCCCGCCAAGATGCCCAGTGGCACC

GAGCAGCAAACAGAAGGGACTTCCGTTACCTTCTCTCCTCTTAAGTCACCGCCACAGCTGGAACGAGAGA

TGGCCTCTCCACCTGAGTGCAGCGAGATGCCCCTTGATCTGTCCTCCAAGTCCAACCGCCAGAAGCTTCC

ATTGCCGAACCAGCGCAAGACACCCCCCATGCCTGTGTTGACCCCCGTGCACACCAGCAGCAAGGCCCTC

CTCTCCACAGTCCTGTCTAGGTCTCAGCGCACAACCCAGGCTGCCGGTGGCAATGTCACCTCCTGCCTGG

GCTCCACTTCCTCGCCCTTTGTCATCTTTCCCGAGATCGTGAGGAATGGGGACCCGAGCACCTGGGTGAA

GAACTCAACTGCACTGATCAGCACCATTCCTGGCACCTACGTGGGAGTGGCCAACCCAGTGCCTGCATCC

CTGCTGCTGAACAAAGACCCCAACCTGGGCCTCAACCGTGACCCCCGCCATCTCCCCAAGCAGGAGCCCA

TCTCCATCATTGATCAAGGAGAGCCTAAGGGCACTGGTGCCACGTGTGGCAAAAAGGGCAGCCAGGCTGG

TGCTGAGGGACAGCCAAGCACAGTGAAACGATATACTCCAGCCCGCATTGCCCCTGGGCTGCCAGGGTGC

CAAACCAAGGAACTCTCTTTGTGGAAACCCACGGGGCCGGCAAATATTTATCCCCGGTGTTCAGTCAATG

GGAAACCTACCAGCACCCAGGTCCTGCCTGTTGGCTGGTCCCCGTACCACCAGGCGTCTCTGCTTTCCAT

TGGCATTTCCAGTGCCGGGCAGCTGACCCCCAGTCAGGGGGCGCCCATCAGGCCCACCAGCGTTGTTTCG

GAGTTTTCTGGTGTGCCATCTCTCAGCTCCAGCGAAGCCGTGCACGGACTTCCTGAGGGGCAACCACGGC

CTGGGGGCTCCTTCGTTCCAGAGCAGGACCCTGTTACAAAGAACAAAACTTGCCGGATTGCTGCCAAGCC

TTATGAAGAACAAGTCAATCCTGTCCTCTTGACCCTCAGCCCTCAGACTGGGACCCTGGCACTGTCTGTT

CAGCCTAGCGGTGGGGACATTCGAATGAATCAGGGGCCTGAGGAATCAGAGAGCCACCTCTGCTCTGACA

GCACTCCTAAGATGGAAGGCCCCCAGGGGGCTTGTGGCCTGAAGCTGGCAGGAGACACGAAGCCTAAGAA

CCAAGTGCTGGCCACCTACATGTCCCATGAGCTGGTCCTGGCCACCCCCCAGAACCTGCCTAAGATGCCT

-continued

GAGCTGCCTTTGCTACCTCACGACAGCCACCCCAAGGAACTTATATTGGACGTGGTTCCGAGCAGCAGGA

GGGGCTCCAGCACAGAGCGCCCACAGCTTGGAAGCCAGGTGGATCTGGGGCGAGTGAAAATGGAGAAGGT

GGATGGTGATGTGGTCTTCAATTTAGCCACCTGCTTCCGGGCTGATGGCCTCCCAGTGGCTCCCCAGAGG

GGCCAAGCTGAAGTTCGGGCTAAGGCCGGGCAGGCTCGAGTGAAACAGGAAAGCGTAGGGGTCTTTGCTT

GCAAGAACAAGTGGCAGCCAGATGATGTGACGGAATCTCTGCCGCCCAAGAAGATGAAGTGCGGCAAAGA

GAAGGACAGTGAAGAGCAGCAGCTCCAGCCACAAGCCAAGGCCGTGGTCCGGAGTTCCCACAGACCCAAG

TGCCGGAAGCTGCCCAGTGACCCCCAGGAATCCACCAAGAAAAGCCCCAGGGGGGCTTCAGATTCAGGAA

AAGAGCACAATGGAGTCAGGGGAAAGCACAAGCACCGGAAGCCGACAAAGCCGGAGTCCCAGTCTCCAGG

AAAACGAGCCGACAGCCACGAGGAAGGTTCCTTGGAAAAGAAAGCAAAGAGCAGTTTCCGTGACTTTATT

CCTGTGGTTCTGAGCACCCGCACGCGCAGTCAGTCTGGAAGCATCTGTAGCTCCTTTGCIGGCATGGCAG

ACAGTGACATGGGAAGCCAGGAAGTCTTCCCCACAGAAGAAGAAGAGGAGGTAACCCCCACCCCAGCTAA

GCGTCGAAAGGTGAGAAAGACCCAACGGGACACCCAGTATCGCAGCCACCATGCCCAGGACAAGTCTCTG

CTGAGCCAGGGCCGAAGGCACCTGTGGCGAGCCCGAGAAATGCCCTGGAGGACAGAGGCTGCCCGGCAAA

TGTGGGACACCAATGAGGAGGAGGAGGAAGAAGAGGAGGAGGGCCTGCTGAAGAGGAAGAAACGAAGACG

GCAGAAGAGCCGAAAATATCAGACTGGGGAGTACCTGACAGAGCAAGAAGACGAGCAGCGGCGGAAAGGG

AGAGCAGATTTAAAGGCCCGTAAGCAGAAGACTTCCTCCTCCCAAAGTTTGGAGCACCGCCTCAGGAACA

GGAACCTTCTCTTGCCCAACAAAGTCCAGGGGATCTCGGATTCACCAAACGGTTTCCTCCCAAATAACCT

GGAAGAGCCAGCCTGCCTTGAAAATTCAGAAAAGCCATCAGGAAAACGAAAGTGCAAGACCAAGCACATG

GCAACCGTCTCAGAAGAGGCAAAGGGCAAAGGTCGTTGGAGCCAGCAGAAGACACGATCTCCCAAATCTC

CCACCCCAGTGAAACCCACAGAACCATGTACACCCTCTAAGTCCCGAAGTGCCAGCTCAGAGGAGGCCTC

AGAGTCACCTACAGCCCGGCAGATCCCCCCAGAGGCACGTCGGCTCATAGTGAACAAAAATGCTGGTGAG

ACCCTCCTGCAGAGGGCGGCGCGTCTTGGCTATAAGGATGTTGTTCTCTACTGCCTCCAGAAAGACAGTG

AAGATGTGAATCACCGTGACAATGCTGGCTACACAGCCCTGCATGAGGCTTGTTCCCGGGGCTGGACCGA

CATCCTGAACATCCTGCTGGAGCACGGGGCCAACGTGAACTGCAGTGCGCAGGACGGCACGAGGCCAGTT

CATGATGCGGTGGTCAATGACAACCTGGAGACCATCTGGCTCCTGCTGTCCTATGGGGCCGATCCCACAC

TGGCTACCTACTCGGGTCAGACAGCCATGAAGCTGGCCAGCAGCGACACCATGAAGCGCTTTCTCAGTGA

TCACCTCTCGGATCTTCAGGGCCGGGCAGAGGGTGATCCCGGTGTATCCTGGGATTTTTACAGCAGTTCT

GTGTTGGAGGAAAAAGACGGGTTTGCCTGTGACCTCCTACATAATCCTCCTGGGAGCTCAGATCAAGAAG

GAGACGATCCGATGGAGGAGGATGATTTCATGTTTGAACTCTCAGACAAGCCTCTTCTCCCTTGCTACAA

CCTCCAAGTGTCAGTGTCCCGCGGGCCCTGCAACTGGTTCCTCTTTTCCGATGTCTTGAAGAGGCTGAAG

CTTTCCTCGAGGATCTTTCAGGCCCGGTTCCCGCACTTTGAAATCACCACCATGCCCAAGGCCGAGTTCT

ACAGGCAGGTGGCCTCCAGTCAGCTGCTGACCCCTGCCGAGAGGCCTGGAGGCTTGGACGACAGATCCCC

CCCAGGCTCCTCTGAGACTGTGGAGCTGGTGCGGTACGAGCCAGACCTACTTCGGCTCCTAGGGTCCGAG

GTGGAATTCCAGTCTTGCAACAGTTGACCGGGAAAACAGCCCCTCCTCTTCTTTCTCCTTCCGAGTTCGC

CCTTCCCCCACCTCCTTGTCTTTCCCCGACCGAGCACCAGACTGCAGAATGAGGCAATAATACGGACCAA

CAAGAAGCCGCCTTATCAATGCCAGCATTAGCGACTGGACTGTTTTTGTTTTTTTGGTTACAATTAGTTC

TCATCTCCCTGTCGTCGTCATTGTTATCGTGGTTGCTGATGGGGGTGGAAAGTTGAACTCCATGTCTGAG

GACAAGAGGTCCCGGGGGTGGTGGGAGGTGGCGCCGGGGTCCCTTGGACTGGCCTCCPTGTTCATGACCA

AGACCAAACCTGGGCCCTGGATGGCCTTGGCCTGTCCCGAGGAGAAATGAGAAAATCCCAGATCTCTGAG

CGCCCCCCAACTCCATTCCCCTGTGTTCTTCTGTCTTCTGTAGTATTTATTTTATTAGTATTTAATTTGT

-continued

```
ATTGTTTCATTGGTTTCTGATAAGTCTGTATCACTGTGACGATTTGAGACAACTTGTTGTATTGAGGGAC

TTTCTGTACCTCCTTTTCTTTTTCTTTGTTGATGAGCTCTGACAAAGCTATTCCCTGGTGTTTTTTTCCC

CCACTGGGGAGGGGGTGAGGTGGAATGGGGTGGGGGAACATGGACTTGTGACTAACGAAGCTGGTTGCTG

CTGGCCCAGGGCTGGGGGCTTGGGGGTAAATCCTGAGGCTTTGGTGCTCCCCCACCCACCCATTCCCGCC

CTTTGCAGCAGCCCCGCTATCTTGAGATTAGTGTTGACAGGGAGGGGAGGATTGTGAGGTGAGGGGTTAA

TAAGTTACTCTAATAAAGGAGCGTGGAGAAGGGATCTGAGGGGTGAGGGTGGCCCCCCTCCTCACGCCTT

CTTCACTGCCCCCCTCAGAGTGCACAATACGAGTTTGTTCCTGCCTCCACTCTCCCACCCCGTTCTGGCC

TCCCTGTCTCAAGATACTGAGCCTCTCACCTCCCAGCCCTCAGCCACCCCCATCCCTGCCCCTTCTGAGA

CTCACAGCACCCCTTTCCTTCCTCTCCTCCCACCTCCTCCCTCAGCCCCTCATTCTCCTTGGGAATCTGC

AGAGGGCTCTGGGACTCACTGCCGGATGTGAAATCCAGGCGTCAGCTGTTTCCTAGGCAAGGGCAGGAAA

GTGGTCTCCAGCCCTTGCTCCACTCATGCCTGGGGGCCTGGGGCTGAGTGGTATCCCTACCTGGCCTCCC

CCTGGCCTCTGGGCCTCCAGCGCTGGGTTTGTCGAGTGAGAGAGAGAGAGGAGCTTGGGTTGCTTCCCTG

TCCCCGCCCCCTCTGTGGCATTGTCCCTCCCACTCTTATTTTTCTACCAATTGCTATTTTTCCGAACAAT

CCTTGTAGAGTATGTACCATCCAAAGGCAGGAGGGCCTCGCCGTGGCCGGCTCTGGTTGGAGATGGTACA

GTTTTATTGTACAGGTGCTAAAACAACAACAACAAAAAAGAAAATGGAAAAAAAAAAGATTAAAAAAAAA

AGGAAAAAAAAAAAAGCCAGTTTGAGGATGGGACAATCTGTTCTCTAGAGGCTCCTGAGCCATGCGGGAGC

ATTGGTGGTTATTTTCTTTGTATTGTGTTTGTTCTTTGTTCCTGGGGGGGAAGTTCTCGGCCCCCTTCTG

TAGGACTGCTCCCCACCCCCACCATACTGCCCAGTTGGTTTTGAACAGTTGTTTTCCCTTTTTAAGAAAA

AAAAATACATATATATATACATATATATATATAAAGTTGAGGGGTTTTGGACTTTAATTTGTTGGTTTTG

TTGGGGTTCCTGGTATTGTGTAGTTTATTTCATGTTCTGTTTGCCTTTCCTTTTTTCGCATTTGGGTGTA

TATTCTGGCTGCCCTTTATGTTTCATTTTAAGCAACTGGCTGTGGAGTCAAAAACACTTGCATACTGAAA

AA
```

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, and the like) and with charged linkages (e.g., phosphorothioates, phosphorodithioates, and the like), those containing pendant moieties, such as, for example, proteins (e.g., nucleases, toxins, antibodies, signal peptides, poly-L-lysine, and the like), those with intercalators (e.g., acridine, psoralen, and the like), those containing chelators (e.g., metals, radioactive metals, boron, oxidative metals, and the like), those containing alkylators, those with modified linkages (e.g., alpha anomeric nucleic acids), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-0-methyl-, 2'-0-allyl-, 2'-fluoro-, or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments w herein phosphate is replaced by P(0)S ("thioate"), P(S)S ("dithioate"), "(0)$NR_2$ ("amidate"), P(0)R, P(0)OR', CO or $CH_2$ ("formacetal"), in which each R or R' is independently H or substituted or unsubstituted alkyl (1-20 C) optionally containing an ether (-0-) linkage, aryl, alkenyl, cycloalkyl, cycloalkenyl or araldyl. Not all linkages in a polynucleotide need be identical. A polynucleotide can contain one or more different types of modifications as described herein and/or multiple modifications of the same type. The preceding description applies to all polynucleotides referred to herein, including RNA and DNA.

"Oligonucleotide," as used herein, generally refers to short, single stranded, polynucleotides that are, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "isolated" antibody is one which has been identified and separated and/or recovered from a component of its natural environment. Contaminant components of its natural environment are materials which would interfere with research, diagnostic, and/or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. An isolated antibody includes the antibody in situ within recombinant cells since at least one component of the antibody's natural environment will not be present. Ordinarily, however, an isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "light chains" of antibodies (immunoglobulins) from any mammalian species can be assigned to one of two clearly distinct types, called kappa ("κ") and lambda ("λ"), based on the amino acid sequences of their constant domains.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2, and CH3 domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The term "hypervariable region," "HVR," or "HV," as used herein, refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, for example, Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, for example, Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196-901-917 (1987)). The AbM HVRs represent a compromise between the Kabat HVRs and Chothia structural loops, and are used by Oxford Molecular's AbM antibody modeling software.

The "contact" HVRs are based on an analysis of the available complex crystal structures. The residues from each of these HVRs are noted below

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence mam contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody comprising the antigen-binding region thereof. In some embodiments, the antibody fragment described herein is an antigen-binding fragment. Examples of antibody fragments include Fab, Fab', F(ab')2, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target-binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target-binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target-binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, Nature 256:495-97 (1975); Hongo et al., Hybridoma 14 (3): 253-260 (1995), Harlow et al., Antibodies: A Laboratory Manual (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101 (34): 12467-12472 (2004); and Lee et al., J. Immunol. Methods 284(1-2): 119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg et al., Intern. Rev. Immunol. 13: 65-93 (1995)).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody.

A "humanized form" of an antibody, e.g., a non-human antibody, refers to an antibody that has undergone humanization.

A "blocking" antibody or an "antagonist" antibody is one which inhibits or reduces biological activity of the antigen it binds. For example, blocking antibodies or antagonist antibodies substantially or completely inhibit the biological activity of the antigen.

As used herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of <1 μM, <100 nM, <10 nM, <1 nM, or <0.1 nM. In certain embodiments, an antibody specifically binds to an epitope on a protein that is conserved among the protein from different species. In another embodiment, specific binding can include, but does not require exclusive binding.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California. The ALIGN-2 program should be compiled for use on a UNIX operating system, for example, digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "detection" includes any means of detecting, including direct and indirect detection. The term "biomarker" as used herein refers to an indicator, e.g., predictive, diagnostic, and/or prognostic, which can be detected in a sample. The biomarker may serve as an indicator of a particular subtype of a disease or disorder (e.g., cancer) characterized by certain, molecular, pathological, histological, and/or clinical features (e.g., responsiveness to therapy including a checkpoint inhibitor). In some embodiments, a biomarker is a collection of genes or a collective number of mutations/alterations (e.g., somatic mutations) in a collection of genes. Biomarkers include, but are not limited to, polynucleotides (e.g., DNA and/or RNA), polynucleotide alterations (e.g., polynucleotide copy number alterations, e.g., DNA copy number alterations), polypeptides, polypeptide and polynucleotide modifications (e.g., post-translational modifications), carbohydrates, and/or glycolipid-based molecular markers.

The "amount" or "number" of somatic mutations associated with an increased clinical benefit to an individual is a detectable level in a biological sample. These can be measured by methods known to one skilled in the art and also disclosed herein. The amount of a somatic mutation assessed can be used to determine the response to the treatment.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The technique of "polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified.

The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., Cold Spring Harbor Symp. Quant. Biol. 51:263 (1987) and Erlich, ed., PCR Technology (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, for instance, by histopathological criteria, or by molecular features (e.g., a subtype characterized by expression of one or a combination of biomarkers (e.g., particular genes or proteins encoded by said genes)).

The term "aiding diagnosis" is used herein to refer to methods that assist in making a clinical determination regarding the presence, or nature, of a particular type of symptom or condition of a disease or disorder (e.g., cancer). For example, a method of aiding diagnosis of a disease or condition (e.g., cancer) can comprise measuring certain somatic mutations in a biological sample from an individual.

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, plasma, serum, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof. In some instances, the sample is a whole blood sample, a plasma sample, a serum sample, or a combination thereof. In some embodiments, the sample is from a tumor (e.g., a "tumor sample"), such as from a biopsy. In some embodiments, the sample is a formalin-fixed paraffin-embedded (FFPE) sample.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

A "reference sample," "reference cell," "reference tissue," "control sample," "control cell," or "control tissue," as used herein, refers to a sample, cell, tissue, standard, or level that is used for comparison purposes.

By "correlate" or "correlating" is meant comparing, in any way, the performance and/or results of a first analysis or protocol with the performance and/or results of a second analysis or protocol. For example, one may use the results of a first analysis or protocol in carrying out a second protocol and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down or complete arrest; (2) a reduction in tumor size; (3) inhibition (i.e., reduction, slowing down, or complete stopping) of cancer cell infiltration into adjacent peripheral organs and/or tissues; (4) inhibition (i.e. reduction, slowing down, or complete stopping) of metastasis; (5) relief, to some extent, of one or more symptoms associated with the disease or disorder (e.g., cancer); (6) increase or extension in the length of survival, including overall survival and progression free survival; and/or (7) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and/or progression-free survival); resulting in an objective response (including a complete response or a partial response); or improving signs or symptoms of cancer.

An "effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and in some embodiments stop) cancer cell infiltration into peripheral organs; inhibit (i.e., slow to some extent and in some embodiments stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), response rates (e.g., CR and PR), duration of response, and/or quality of life.

The term "tumor," as used herein, refers to all neoplastic cell growth and proliferation, whether malignant or benign, and all pre-cancerous and cancerous cells and tissues. The terms "cancer," "cancerous," and "tumor" are not mutually exclusive as referred to herein.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies (e.g., antibody-based checkpoint inhibitors) are used to delay development of a disease or to slow the progression of a disease.

As used herein, the terms "individual," "patient," or "subject" are used interchangeably and refer to any single animal, e.g., a mammal (including such non-human animals as, for example, dogs, cats, horses, rabbits, zoo animals, cows, pigs, sheep, and non-human primates) for which treatment is desired. In particular embodiments, the patient herein is a human.

As used herein, "administering" is meant a method of giving a dosage of a compound (e.g., an antagonist) or a pharmaceutical composition (e.g., a pharmaceutical composition including an antagonist) to a subject (e.g., a patient). Administering can be by any suitable means, including parenteral, intrapulmonary, and intranasal, and, if desired for local treatment, intralesional administration. Parenteral infusions include, for example, intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the symptoms of the disorder being treated, the presence or size of metastases, or the size of the primary tumor.

The term "package insert" is used to refer to instructions customarily included in commercial packages of therapeutic products, that contain information about the indications, usage, dosage, administration, combination therapy, contraindications, and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker (e.g., a BCOR rearrangement or BCORL1 alteration) described herein. In certain embodiments, the manufacture or kit is promoted, distributed, or sold as a unit for performing the methods described herein.

The phrase "based on" when used herein means that the information about one or more biomarkers is used to inform a treatment decision, information provided on a package insert, or marketing/promotional guidance, etc.

III. Methods, Systems, and Devices

In one aspect, provided herein are methods of identifying an individual having cancer who may benefit from a treatment comprising a targeted therapeutic. In some embodiments, the methods comprise detecting a rearrangement in a BCOR gene or an alteration in a BCORL1 gene in a sample from the individual, wherein the presence of the BCOR gene rearrangement or BCORL1 alteration in the sample identifies the individual as one who may benefit from a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor).

In another aspect, provided herein are methods of selecting a therapy for an individual having cancer. In some embodiments, the methods comprise detecting a rearrangement in a BCOR gene or an alteration in a BCORL1 gene in a sample from the individual, wherein the presence of the BCOR gene rearrangement or BCORL1 alteration in the sample identifies the individual as one who may benefit from a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor).

In another aspect, provided herein are methods of identifying one or more treatment options for an individual having cancer. In some embodiments, the methods comprise detecting, or acquiring knowledge of, a rearrangement in a BCOR gene or an alteration in a BCORL1 gene in a sample from the individual and generating a report comprising one or more treatment options identified for the individual based at least in part on the presence of the BCOR gene rearrangement or BCORL1 alteration in the sample, wherein the one or more treatment options comprise a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor).

In another aspect, provided herein are methods of selecting treatment for an individual having cancer. In some embodiments, the methods comprise acquiring knowledge of a rearrangement in a BCOR gene or an alteration in a BCORL1 gene in a sample from an individual having cancer, wherein responsive to the acquisition of said knowledge: (i) the individual is classified as a candidate to receive treatment with a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor; and/or (ii) the individual is identified as likely to respond to a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

In another aspect, provided herein are methods of treating or delaying progression of cancer. In some embodiments, the methods comprise administering to an individual an effective amount of a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor), wherein the cancer comprises a rearrangement in a BCOR gene or an alteration in a BCORL1 gene. In some embodiments, the methods comprise, responsive to knowledge of a rearrangement in a BCOR gene or an alteration in a BCORL1 gene in a sample from an individual, administering to the individual an effective amount of a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor). In some embodiments, the methods comprise detecting or acquiring knowledge of a rearrangement in a BCOR gene or an alteration in a BCORL1 gene in a sample from the individual. In some embodiments, the methods comprise detecting a rearrangement in a BCOR gene or an alteration in a BCORL1 gene in a sample from the individual and administering to the individual an effective amount of a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor).

In another aspect, provided herein are methods of monitoring an individual having cancer. In some embodiments, the methods comprise acquiring knowledge of a rearrangement in a BCOR gene or an alteration in a BCORL1 gene in a sample from the individual, wherein responsive to the acquisition of said knowledge, the individual is predicted to have increased risk of uterine sarcoma, e.g., as compared to an individual whose cancer does not comprise a rearrangement in a BCOR gene or an alteration in a BCORL1 gene.

In another aspect, provided herein are methods of predicting survival of an individual having cancer. In some embodiments, the methods comprise acquiring knowledge of a rearrangement in a BCOR gene or an alteration in a BCORL1 gene in a sample from the individual, wherein responsive to the acquisition of said knowledge, the individual is predicted to have shorter survival, e.g., as compared to survival of an individual whose cancer does not comprise a rearrangement in a BCOR gene or an alteration in a BCORL1 gene.

In another aspect, provided herein are methods of evaluating an individual having cancer. In some embodiments, the methods comprise acquiring knowledge of a rearrangement in a BCOR gene or an alteration in a BCORL1 gene in a sample from the individual, wherein responsive to the acquisition of said knowledge, the individual is predicted to have increased risk of recurrence, e.g., as compared to an individual whose cancer does not comprise a rearrangement in a BCOR gene or an alteration in a BCORL1 gene.

In another aspect, provided herein are methods of screening an individual having cancer. In some embodiments, the methods comprise acquiring knowledge of a rearrangement in a BCOR gene or an alteration in a BCORL1 gene in a sample from the individual, wherein responsive to the acquisition of said knowledge, the individual is predicted to have increased risk of recurrence, e.g., as compared to an individual whose cancer does not comprise a rearrangement in a BCOR gene or an alteration in a BCORL1 gene.

In another aspect, provided herein are methods of detecting a rearrangement in a BCOR gene. In some embodiments, the methods comprise detecting an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D in a sample from an individual.

In another aspect, provided herein are methods of detecting an alteration in a BCORL1 gene. In some embodiments, the methods comprise detecting a BCORL1 gene comprising a frameshift, nonsense, or truncating mutation; deletion; internal rearrangement; or fusion gene in a sample from an individual.

In another aspect, provided herein are methods of diagnosing or assessing a rearrangement in a BCOR gene. In some embodiments, the methods comprise detecting an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D in a sample from an individual and providing a diagnosis/assessment of a rearrangement in a BCOR gene.

In another aspect, provided herein are methods of diagnosing or assessing an alteration in a BCORL1 gene. In some embodiments, the methods comprise detecting a BCORL1 gene comprising a frameshift, nonsense, or truncating mutation; deletion; internal rearrangement; or fusion gene in a sample from an individual and providing a diagnosis/assessment of an alteration in a BCORL1 gene.

In another aspect, provided herein are methods of diagnosing endometrial stromal sarcoma (ESS) in an individual. In some embodiments, the methods comprise detecting an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D in a sample from the individual and optionally providing a diagnosis of endometrial stromal sarcoma in the individual. In some embodiments, the cancer was previously classified as myxoid leiomyosarcoma. In some embodiments, the individual was previously diagnosed with myxoid leiomyosarcoma.

In another aspect, provided herein are methods of diagnosing endometrial stromal sarcoma (ESS) in an individual. In some embodiments, the methods comprise detecting a BCORL1 gene alteration in a sample from the individual and optionally providing a diagnosis of endometrial stromal sarcoma in the individual. In some embodiments, the cancer was previously classified as myxoid leiomyosarcoma. In some embodiments, the individual was previously diagnosed with myxoid leiomyosarcoma.

In another aspect, provided herein are methods of diagnosing a uterine sarcoma in an individual. In some embodiments, the methods comprise detecting an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D in a sample from the individual and optionally providing a diagnosis of uterine sarcoma in the individual. In some embodiments, the cancer was previously classified as myxoid leiomyosarcoma. In some embodiments, the individual was previously diagnosed with myxoid leiomyosarcoma.

In another aspect, provided herein are methods of diagnosing a uterine sarcoma in an individual. In some embodiments, the methods comprise detecting a BCORL1 gene alteration in a sample from the individual and optionally providing a diagnosis of uterine sarcoma in the individual. In some embodiments, the cancer was previously classified as myxoid leiomyosarcoma. In some embodiments, the individual was previously diagnosed with myxoid leiomyosarcoma.

In another aspect, provided herein are methods of detecting a rearrangement in a BCOR gene or an alteration in a BCORL1 gene, e.g., in a sample from an individual. In some embodiments, the methods comprise providing a plurality of nucleic acids obtained from a sample from an individual, wherein the plurality of nucleic acids comprises nucleic acids encoding a BCOR gene or a BCORL1 gene; optionally, ligating one or more adaptors onto one or more nucleic acids from the plurality of nucleic acids; amplifying nucleic acids from the plurality of nucleic acids; optionally, capturing a plurality of nucleic acids corresponding to the BCOR and/or BCORL1 gene(s); sequencing, by a sequencer, the plurality of nucleic acids to obtain a plurality of sequence reads corresponding to the BCOR and/or BCORL1 gene(s); analyzing the plurality of sequence reads; and based on the analysis, detecting a rearrangement in the BCOR gene or an alteration in the BCORL1 gene. In some embodiments, the plurality of nucleic acids corresponding to the BCOR and/or BCORL1 gene(s) are captured from the amplified nucleic acids by hybridization with a bait molecule.

In another aspect, provided herein are uses (e.g., in vitro uses) of one or more oligonucleotides for detecting a rearrangement in a BCOR gene. In some embodiments, the BCOR gene rearrangement results in an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D.

In another aspect, provided herein are uses (e.g., in vitro uses) of one or more oligonucleotides for detecting an alteration in a BCORL1 gene. In some embodiments, the BCORL1 gene alteration comprises a T513fs*22, P600fs*1, R945*, R1196*, R1265fs*4, L461fs*5, or H1426fs*29 mutation; an internal rearrangement; or a JAZF1-BCORL1, BCORL1-JAZF1, or EP300-BCORL1 fusion gene.

In another aspect, provided herein are kits or articles of manufacture comprising one or more oligonucleotides for detecting a rearrangement in a BCOR gene. In some embodiments, the BCOR gene rearrangement results in an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D.

In another aspect, provided herein are kits or articles of manufacture comprising one or more oligonucleotides for detecting an alteration in a BCORL1 gene. In some embodiments, the BCORL1 gene alteration comprises a T513fs*22, P600fs*1, R945*, R1196*, R1265fs*4, L461fs*5, or H1426fs*29 mutation; an internal rearrangement; or a JAZF1-BCORL1, BCORL1-JAZF1, or EP300-BCORL1 fusion gene.

In another aspect, provided herein are kits or articles of manufacture comprising a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor) and a package insert comprising instructions for using the targeted therapeutic in a method of treating or delaying progression of cancer, e.g., by administration to an individual from whom a sample comprising a BCOR gene rearrangement or BCORL1 gene alteration has been obtained.

In another aspect, provided herein are targeted therapeutics (e.g., a CDK inhibitor, an MDM2 inhibitor, a tyrosine kinase inhibitor, a MEK inhibitor, an mTOR inhibitor, PIK3CA or AKT inhibitor, or a Hh inhibitor) for use in a method of treating or delaying progression of cancer. In some embodiments, the method comprises administering the targeted therapeutic to an individual, and a BCOR gene rearrangement or BCORL1 gene alteration has been detected in a sample from the individual.

In another aspect, provided herein are targeted therapeutics (e.g., a CDK inhibitor, an MDM2 inhibitor, a tyrosine kinase inhibitor, a MEK inhibitor, an mTOR inhibitor, PIK3CA or AKT inhibitor, or a Hh inhibitor) for use in the manufacture of a medicament for treating or delaying progression of cancer, e.g., in an individual from whom a sample comprising a BCOR gene rearrangement or BCORL1 gene alteration has been obtained. In some embodiments, the method comprises administering the targeted therapeutic to an individual, and a BCOR gene rearrangement or BCORL1 gene alteration has been detected in a sample from the individual.

In another aspect, provided herein are systems, e.g., comprising a memory and one or more processors. In some embodiments, the systems comprise a memory configured to store one or more program instructions; and one or more processors configured to execute the one or more program instructions, the one or more program instructions when executed by the one or more processors are configured to: (a) obtain a plurality of sequence reads of one or more nucleic acids, wherein the one or more nucleic acids are derived from a sample obtained from an individual; (b) analyze the plurality of sequence reads for the presence of a genetic alteration comprising a rearrangement in a B-cell lymphoma 6 (BCL6) corepressor (BCOR) gene or an alteration in a BCL6 corepressor-like protein 1 (BCORL1) gene, or of a portion thereof; and (c) detect, based on the analyzing, a rearrangement in a BCOR gene or an alteration in a BCORL1 gene, or a portion thereof, in the sample.

In another aspect, provided herein are computer-readable storage media. In some embodiments, the computer-readable storage media comprise one or more programs executable by one or more computer processors for performing a method, comprising: (a) obtaining, using the one or more processors, a plurality of sequence reads of one or more nucleic acids, wherein the one or more nucleic acids are derived from a sample obtained from an individual; (b) analyzing, using the one or more processors, the plurality of sequence reads for the presence of a genetic alteration comprising a rearrangement in a B-cell lymphoma 6 (BCL6) corepressor (BCOR) gene or an alteration in a BCL6 corepressor-like protein 1 (BCORL1) gene, or of a portion thereof; and (c) detecting, using the one or more processors and based on the analyzing, a rearrangement in a BCOR gene or an alteration in a BCORL1 gene, or a portion thereof, in the sample. In some embodiments, the computer-readable storage media are non-transitory. In some embodiments, the computer-readable storage media are transitory.

BCOR Rearrangements/BCORL1 Alterations and Detection

Certain aspects of the present disclosure relate to detection of a BCOR rearrangement. A BCOR rearrangement of the present disclosure may relate to any chromosomal translocation, fusion, or rearrangement involving the locus of a BCOR gene. In some embodiments, detection of a BCOR rearrangement as described herein is performed in vitro.

In some embodiments, a BCOR rearrangement results in a gene fusion involving at least a portion of the BCOR gene and at least a portion of another gene. In some embodiments, the BCOR rearrangement results in a fusion gene between BCOR and ZC3H7B. In some embodiments, the BCOR rearrangement results in a fusion gene between BCOR and L3MBTL2, EP300, NUTM2G, MAP7D2, RALGPS1, RGAG1, CREBBP, ING3, NUGGC, or KMT2D. For example, in some embodiments, the BCOR rearrangement results in a fusion gene selected from the group consisting of BCOR-L3MBTL2, EP300-BCOR, BCOR-NUTM2G, BCOR-RALGPS1, BCOR-MAP7D2, RGAG1-BCOR, ING3-BCOR, BCOR-NUGGC, KMT72D-BCOR and CREBBP-BCOR. Exemplary and non-limiting BCOR rearrangements are described infra and/or in Table 2.

In some embodiments, the BCOR rearrangement results in a gene fusion involving BCOR and L3MBTL2. In some embodiments, the BCOR rearrangement results in a gene fusion that comprises, from Y to 3, exons 1-4 of BCOR (e.g., according to the sequence of NM_017745) and exons 1-17 of L3MBTL2 (e.g., according to the sequence of NM_031488), optionally including the 3' UTR of L3MBTL2. In some embodiments, the BCOR rearrangement results in a gene fusion comprising the following breakpoints: chrX 39931624-39931664 and chr22 41605711-41605751.

In some embodiments, the BCOR rearrangement results in a gene fusion involving BCOR and EP300. In some embodiments, the BCOR rearrangement results in a gene fusion that comprises, from 5' to 3', exons 1-31 of EP300 (e.g., according to the sequence of NM_001429) and exons 5-15 of BCOR (e.g., according to the sequence of NM_017745). In some embodiments, the BCOR rearrangement results in a gene fusion comprising the following breakpoints: chr22 41573723-41573763 and chrX 39930323-39930363.

In some embodiments, the BCOR rearrangement results in a gene fusion involving BCOR and NUTM2G. In some embodiments, the BCOR rearrangement results in a gene fusion that comprises, from 5' to 3, exons 1-2 of BCOR (e.g., according to the sequence of NM_017745) and exons 3-7 of NUTM2G (e.g., according to the sequence of NM_001045477). In some embodiments, the BCOR rearrangement results in a gene fusion comprising the following breakpoints: chrX 39937113-39937153 and chr9 99697663-99697703.

In some embodiments, the BCOR rearrangement results in a gene fusion involving BCOR and MAP7D2. In some embodiments, the BCOR rearrangement results in a gene fusion that comprises, from 5' to 3, exons 1-6 of BCOR (e.g., according to the sequence of NM_017745) and exons 8-16 of MAP7D2 (e.g., according to the sequence of NM_152780). In some embodiments, the BCOR rearrangement results in a gene fusion comprising the following breakpoints: chrX 39930257-39930297 and chrX 20043983-20044023.

In some embodiments, the BCOR rearrangement results in a gene fusion involving BCOR and RGAG1. In some embodiments, the BCOR rearrangement results in a gene fusion that comprises, from 5' to 3', exons 1-3 of RGAG1 (e.g., according to the sequence of NM_020769) and exons 4-15 of BCOR (e.g., according to the sequence of NM_017745). In some embodiments, the BCOR rearrangement results in a gene fusion comprising the following breakpoints: RGAG1 exon 3 and BCOR exon 4. In some embodiments, a cancer of the present disclosure (e.g., comprising a BCOR gene rearrangement/gene fusion described herein) further comprises an X chromosome duplication fragment comprising the following breakpoints: chrX 39932547-39932587 and chrX 109695012-109695052.

In some embodiments, the BCOR rearrangement results in a gene fusion involving BCOR and RALGPS1. In some embodiments, the BCOR rearrangement results in a gene fusion that comprises, from 5' to 3', exons 1-6 of BCOR (e.g., according to the sequence of NM_017745) and exons 9-19 of RALGPS1 (e.g., according to the sequence of NM_014636). In some embodiments, the BCOR rearrangement results in a gene fusion comprising the following breakpoints: chrX 39930273-39930313 and chr9 129928344-129928384.

In some embodiments, the BCOR rearrangement results in a gene fusion involving BCOR and CREBBP. In some embodiments, the BCOR rearrangement results in a gene fusion that comprises, from 5' to 3', exons 1-10 of BCOR (e.g., according to the sequence of NM_017745) and exon 31 of CREBBP (e.g., according to the sequence of NM_004380). In some embodiments, the BCOR rearrangement results in a gene fusion comprising the following breakpoints: chr16 3779817-3779857 and chrX 39921385-39921425.

In some embodiments, the BCOR rearrangement results in a gene fusion involving BCOR and NUGGC. In some embodiments, the BCOR rearrangement results in a gene fusion that comprises, from 5' to 3', exons 1-8 of BCOR (e.g., according to the sequence of NM_017745) and exons 11-19 of NUGGC (e.g., according to the sequence of NM_001010906). In some embodiments, the BCOR rearrangement results in a gene fusion comprising the following breakpoints: BCOR exon 8 and NUGGC intron 10. In some embodiments, the BCOR rearrangement results in a gene fusion comprising the following breakpoints: chrX 39923698-39923738 and chr8 27905006-27905046.

In some embodiments, the BCOR rearrangement results in a gene fusion involving BCOR and ING3. In some embodiments, the BCOR rearrangement results in a gene fusion that comprises, from 5' to 3', exons 1-8 of ING3 (e.g., according to the sequence of NM_019071) and exons 8-15 of BCOR (e.g., according to the sequence of NM_017745). In some embodiments, the BCOR rearrangement results in a gene fusion comprising the following breakpoints: ING3 intron 8 and BCOR exon 8.

In some embodiments, the BCOR rearrangement results in a gene fusion involving BCOR and KMT2D. In some embodiments, the BCOR rearrangement results in a gene fusion that comprises, from 5' to 3', exons 1-34 of KMT2D (e.g., according to the sequence of NM_003482) and exons 8-15 of BCOR (e.g., according to the sequence of NM_017745). In some embodiments, the BCOR rearrangement results in a gene fusion comprising the following breakpoints: KMT2D intron 34 and BCOR intron 7. In some embodiments, the BCOR rearrangement results in a gene fusion comprising the following breakpoints: chrX 39922861-39923209 and chr12 49430901-49432454. In some embodiments, the BCOR rearrangement results in a gene fusion that comprises, from 5' to 3', exons 1-4 of BCOR (e.g., according to the sequence of NM_017745) and exons 20-54 of KMT2D (e.g., according to the sequence of NM_003482). In some embodiments, the BCOR rearrangement results in a gene fusion comprising the following breakpoints: BCOR exon 4 and KMT2D exon 20. In some embodiments, the BCOR rearrangement results in a gene fusion comprising the following breakpoints: chrX 39922861-39923209 and chr12 49430901-49432454. In some embodiments, a cancer of the present disclosure (e.g., comprising a BCOR gene rearrangement/gene fusion described herein) further comprises a chromosome 12 deletion fragment. In some embodiments, the deletion fragment comprises the following breakpoints: exons 1-20 of KMT2D (e.g., according to the sequence of NM_003482) and exons 35-54 of KMT2D (e.g., according to the sequence of NM_003482). In some embodiments, the deletion fragment comprises the following breakpoints: KMT2D exon 20 and KMT2D intron 34.

In some embodiments, a BCOR rearrangement results in a genetic rearrangement within (e.g., internal to) the BCOR locus, including but not limited to X chromosome inversions. In some embodiments, the BCOR rearrangement results in an X chromosome inversion fragment comprising a 3' rearrangement breakpoint at intron 6 of BCOR. In some embodiments, the BCOR rearrangement results in a gene rearrangement comprising the following breakpoints: chrX 39930205-39930543 and chrX 13323245-13323522.

Certain aspects of the present disclosure relate to detection of a BCORL1 alteration. A BCORL1 alteration of the present disclosure may relate to any involving the locus of a BCORL1 gene, including but not limited to frameshift mutations, nonsense mutations, truncating mutations, deletions, internal rearrangements, and rearrangements resulting in a BCORL1 fusion gene (e.g., at least a portion of a BCORL1 gene fused with another gene). In some embodiments, detection of a BCORL1 alteration as described herein is performed in vitro.

In some embodiments, the BCORL1 alteration results in a frameshift, nonsense, or truncating mutation. For example, in some embodiments, the BCORL1 alteration comprises a T513fs*22, P600fs*1, R945*, R1196*, R1265fs*4, L461fs*5, or H1426fs*29 mutation.

In some embodiments, the BCORL1 alteration results in a deletion, e.g., a homozygous deletion.

In some embodiments, the BCORL1 alteration results in a BCORL1 rearrangement within (e.g., internal to) the BCORL1 locus, including but not limited to X chromosome inversions.

In some embodiments, a BCORL1 rearrangement results in a gene fusion involving at least a portion of the BCORL1 gene and at least a portion of another gene. In some embodiments, the BCORL1 rearrangement results in a fusion gene between BCORL1 and JAZF1 or EP300. For example, in some embodiments, the BCORL1 rearrangement results in a fusion gene selected from the group consisting of JAZF1-BCORL1, BCORL1-JAZF1, or EP300-BCORL1. Exemplary and non-limiting BCORL1 rearrangements are described infra and/or in Table 3.

In some embodiments, the BCORL1 rearrangement results in a gene fusion involving BCORL1 and JAZF1. In some embodiments, the BCORL1 rearrangement results in a BCORL1-JAZF1 fusion gene. In some embodiments, the BCORL1 rearrangement results in a gene fusion that comprises, from 5' to 3', exons 1-4 of BCORL1 (e.g., according to the sequence of NM_001184772) and exons 4-5 of JAZF1 (e.g., according to the sequence of NM_175061), optionally including the 3' UTR of JAZF1. In some embodiments, the BCORL1 rearrangement results in a gene fusion that comprises breakpoints at exon 4 of BCORL1 (e.g., according to the sequence of NM_001184772) and exon 4 of JAZF1 (e.g., according to the sequence of NM_175061).

In some embodiments, the BCORL1 rearrangement results in a JAZF1-BCORL1 fusion gene. In some embodiments, the BCORL1 rearrangement results in a gene fusion that comprises, from 5' to 3', exons 1-3 of JAZF1 (e.g., according to the sequence of NM_175061) and exons 5-12 of BCORL1 (e.g., according to the sequence of NM_001184772), optionally including the 3' UTR of BCORL1. In some embodiments, the BCORL1 rearrangement results in a gene fusion that comprises breakpoints at exon 3 of JAZF1 (e.g., according to the sequence of NM_175061) and exon 5 of BCORL1 (e.g., according to the sequence of NM_001184772). In some embodiments, the BCORL1 rearrangement results in a gene fusion that comprises, from 5' to 3', exons 1-3 of JAZF1 (e.g., according to the sequence of NM_175061) and exons 6-12 of BCORL1 (e.g., according to the sequence of NM_001184772), optionally including the 3' UTR of BCORL1. In some embodiments, the BCORL1 rearrangement results in a gene fusion that comprises breakpoints at exon 3 of JAZF1 (e.g., according to the sequence of NM_175061) and exon 6 of BCORL1 (e.g., according to the sequence of NM_001184772). In some embodiments, the BCORL1 rearrangement results in a gene fusion that comprises, from 5' to 3', exons 1-3 of JAZF1 (e.g., according to the sequence of NM_175061) and exons 7-12 of BCORL1 (e.g., according to the sequence of NM_001184772), optionally including the 3' UTR of BCORL1. In some embodiments, the BCORL1 rearrangement results in a gene fusion that comprises breakpoints at exon 3 of JAZF1 (e.g., according to the sequence of NM_175061) and exon 7 of BCORL1 (e.g., according to the sequence of NM_001184772).

In some embodiments, the BCORL1 rearrangement results in an EP300-BCORL1 fusion gene. In some embodiments, the BCORL1 rearrangement results in a gene fusion that comprises, from 5' to 3', exons 1-31 of EP300 (e.g., according to the sequence of NM_001362843) and exons 4-12 of BCORL1 (e.g., according to the sequence of NM_001184772), optionally including the 3' UTR of BCORL1. In some embodiments, the BCORL1 rearrangement results in a gene fusion that comprises breakpoints at exon 31 of EP300 (e.g., according to the sequence of NM_001362843) and exon 4 of BCORL1 (e.g., according to the sequence of NM_001184772).

Certain aspects of the present disclosure relate to detection of a BCOR rearrangement or BCORL1 alteration of the present disclosure in a sample, e.g., a patient sample. In some embodiments, the BCOR rearrangement/BCORL1 alteration is detected in vitro. Methods for detecting a BCOR rearrangement/BCORL1 alteration of the present disclosure are known in the art. For example, in some embodiments, a BCOR rearrangement/BCORL1 alteration is detected by sequencing part or all of the BCOR-BCORL1 gene, e.g., by next-generation or other sequencing of DNA, RNA, or cDNA. In some embodiments, a BCOR rearrangement/BCORL1 alteration is detected by PCR amplification of DNA, RNA, or cDNA. In some embodiments, a BCOR rearrangement/BCORL1 alteration is detected by in situ hybridization using one or more polynucleotides that hybridize to the BCOR/BCORL1 locus or a rearrangement/fusion thereof, e.g., using fluorescence in sins hybridization (FISH). In some embodiments, a BCOR rearrangement/BCORL1 alteration of the present disclosure is detected in a cancer cell, e.g., using tumor tissue, such as from a tumor biopsy or other tumor specimen. Exemplary and non-limiting methods for detecting BCOR rearrangement/BCORL1 alteration in tumor samples are described herein.

In some embodiments, a cancer of the present disclosure (e.g., comprising a BCOR gene rearrangement/gene fusion or BCORL1 alteration described herein) further comprises one or more genomic alterations leading to increased expression and/or activity of the Cyclin D/Cdk4 complex, e.g., leading to amplification of one or more gene(s) whose products potentiate expression and/or activity of the Cyclin D/Cdk4 complex, or leading to loss-of-function (e.g., deletion) of one or more gene(s) whose products lower expression and/or activity of the Cyclin D/Cdk4 complex. For example, in some embodiments, the cancer further comprises amplification of a gene selected from the group consisting of MDM2, FRS2, CCND2, and CDK4. In some embodiments, MDM2 refers to a human MDM2 gene (also known as HDMX, LSKB, hdm2, and ACTFS), known to encode an E3 ubiqutin ligase, e.g., as represented by NCBI Gene ID No. 4193 and NCBI Ref. Seq. Accession No. NP_001138809. In some embodiments, FRS2 refers to a human FRS2 gene (also known as SNT, SNT1, FRS1A, FRS2A, SNT-1, and FRS2alpha), known to encode a fibroblast growth factor receptor substrate, e.g., as represented by NCBI Gene ID No. 10818 and NCBI Ref. Seq. Accession No. NP_001036020. In some embodiments, CCND2 refers to a human (CCND2 gene (also known as MPPH3 and KIAK0002), known to encode a cyclin D2, e.g., as represented by NCBI Gene ID No. 894 and NCBI Ref. Seq. Accession No. NP_001750. In some embodiments, CDK4 refers to a human CDK4 gene (also known as CMM3 and PSK-J3), known to encode a cyclin-dependent kinase 4 protein, e.g., as represented by NCBI Gene ID No. 1019 and NCBI Ref. Seq. Accession No. NP_000066. In some embodiments, the cancer further comprises deletion (e.g., homozygous deletion) of a gene selected from the group consisting of CDKN2A and CDKN2B. In some embodiments, CDKN2A refers to a human CDKN2A gene (also known as ARF, CDK4I, CDKN2, CMM2, MLM, P14, P16, P19, INK4, MTS1, TP16, INK4A, MTS-1, P14ARF, P19ARF, P16INK4, P16INK4A, and P16-INK4A), known to encode a cyclin-dependent kinase inhibitor 2A, e.g., as represented by NCBI Gene ID No. 1029 and NCBI Ref. Seq. Accession No. NP_000068. In some embodiments, CDKN2B refers to a human CDKN2B gene (also known as P15, MTS2, TP15, CDK41, INK4B, and p15INK4Bi), known to encode a cyclin-dependent kinase inhibitor 2B, e.g., as represented by NCBI Gene ID No. 1030 and NCBI Ref. Seq. Accession No. NP_004927.

In some embodiments, a cancer of the present disclosure (e.g., comprising a BCOR gene rearrangement/gene fusion described herein) further comprises one or more genomic alterations leading to increased expression and/or activity of a tyrosine kinase, such as PDGFRA, VEGFR (KDR), ERBB3, or KIT. For example, in some embodiments, the cancer further comprises amplification of a gene selected from the group consisting of PDGFRA, KDR, ERBB3, and KIT. In some embodiments, PDGFRA refers to a human PDGFRA gene (also known as CD140A, PDGFR2, and PDGFR-2), known to encode a platelet derived growth factor receptor alpha, e.g., as represented by NCBI Gene ID No. 5156 and NCBI Ref. Seq. Accession No. NP_001334756. In some embodiments, KDR refers to a human KDR gene (also known as FLK1, CD309, VEGFR, and VEGFR2), known to encode a vascular endothelial growth factor or kinase insert domain receptor, e.g., as represented by NCBI Gene ID No. 3791 and NCBI Ref. Seq. Accession No. NP_002244. In some embodiments, ERBB3 refers to a human ERBB3 gene (also known as HER3, FERKL, LCCS2, ErbB-3, c-erbB3, erbB3-2, MDA-BF-1, c-erbB-3, p180-ErbB3, p45-sErbB3, and p85-sErbB3), known to encode an erb-b2 receptor tyrosine kinase 3, e.g., as represented by NCBI Gene ID No. 2065 and NCBI Ref. Seq. Accession No. NP_001005915. In some embodiments, KIT refers to a human KIT gene (also known as PBT, SCRF, C-Kit, CD117, and MASTC), known to encode a KIT proto-oncogene or type 3 transmembrane receptor for mast cell growth factor or stem cell factor, e.g., as represented by NCBI Gene ID No. 3815 and NCBI Ref. Seq. Accession No. NP_000213.

In some embodiments, a cancer of the present disclosure (e.g., comprising a BCOR gene rearrangement/gene fusion or BCORL1 alteration described herein) further comprises one or more genomic alterations leading to loss-of-function in NF1 and/or NF2. Deficiencies in NF1 and/or NF2 have been implicated in activation of both the Akt/mTOR and Raf/MEK/ERK pathways. In some embodiments, NF1 refers to a human NF1 gene (also known as WSS, NFNS, and VRNF), known to encode a neurofibromin 1, e.g., as represented by NCBI Gene ID No. 4763 and NCBI Ref. Seq. Accession No. NP_000258. In some embodiments, NF2 refers to a human NF2 gene (also known as ACN, SCH, and BANE), known to encode a neurofibromin 2, e.g., as represented by NCBI Gene ID No. 4771 and NCBI Ref. Seq. Accession No. NP_000259.

In some embodiments, a cancer of the present disclosure (e.g., comprising a BCOR gene rearrangement/gene fusion described herein) further comprises one or more genomic alterations leading to loss-of-function in PTCH1. In some embodiments, PTCH1 refers to a human PTCH1 gene (also known as PTC, BCNS, PTC1, PTCH, and NBCCS), known to encode a patched 1 receptor of the hedgehog (Hh) family of ligands, e.g., as represented by NCBI Gene ID No. 5727 and NCBI Ref. Seq. Accession No. NP_000255.

In some embodiments, a sample obtained from a cancer of the present disclosure (e.g., comprising a BCOR gene rearrangement/gene fusion or BCORL1 alteration described herein) comprises spindle cells arranged in a fascicular growth pattern. In some embodiments, the cancer comprises a fusion gene between BCOR and ZC3H7B.

In some embodiments, a sample obtained from a cancer of the present disclosure (e.g., comprising a BCOR gene rearrangement/gene fusion or BCORL1 alteration described herein) comprises spindle cells. In some embodiments, a sample obtained from a cancer of the present disclosure (e.g., comprising a BCOR gene rearrangement/gene fusion or BCORL1 alteration described herein) comprises small cells. In some embodiments, a sample obtained from a cancer of the present disclosure (e.g., comprising a BCOR gene rearrangement/gene fusion or BCORL1 alteration described herein) comprises epithelioid cells. In some embodiments, a sample obtained from a cancer of the present disclosure (e.g., comprising a BCOR gene rearrangement/gene fusion or BCORL1 alteration described herein) comprises uniform nuclei. In some embodiments, a sample obtained from a cancer of the present disclosure (e.g., comprising a BCOR gene rearrangement/gene fusion or BCORL1 alteration described herein) comprises variable nuclei. In some embodiments, a sample obtained from a cancer of the present disclosure (e.g., comprising a BCOR gene rearrangement/gene fusion or BCORL1 alteration described herein) comprises myxoid stroma. In some embodiments, a sample obtained from a cancer of the present disclosure (e.g., comprising a BCOR gene rearrangement/gene fusion or BCORL1 alteration described herein) does not comprise myxoid stroma. In some embodiments, a sample obtained from a cancer of the present disclosure (e.g., comprising a BCOR gene rearrangement/gene fusion or BCORL1 alteration described herein) comprises collagen fibrosis. In some embodiments, a sample obtained from a cancer of the present disclosure (e.g., comprising a BCOR gene rearrangement/gene fusion or BCORL1 alteration described herein) does not comprise collagen fibrosis. In some embodiments, a sample obtained from a cancer of the present disclosure (e.g., comprising a BCOR gene rearrangement/gene fusion or BCORL1 alteration described herein) comprises spiral arterioles. In some embodiments, a sample obtained from a cancer of the present disclosure (e.g., comprising a BCOR gene rearrangement/gene fusion or BCORL1 alteration described herein) does not comprise spiral arterioles. In some embodiments, a sample obtained from a cancer of the present disclosure (e.g., comprising a BCOR gene rearrangement/gene fusion or BCORL1 alteration described herein) is characterized by a mitotic count that is between about 3 per 10 high power fields (HPF) and about 30 per 10 HPF. In some embodiments, the cancer comprises a fusion gene between BCOR and a gene selected from the group consisting of L3MBTL2, EP300, NUTM2G, MAP7D2, RAL- GPS1, RGAG1, CREBBP, ING3, NUGGC, and KMT2D. In some embodiments, a sample obtained from a cancer of the present disclosure (e.g., comprising a BCOR gene rearrangement/gene fusion described herein) is characterized by one or more of the properties of a single sample described in Table 1 infra.

In some embodiments, a sample obtained from a cancer of the present disclosure (e.g., comprising a BCOR gene rearrangement/gene fusion described herein) is characterized by expression of one or more of cyclin D1, CD10, and BCOR. In some embodiments, a sample obtained from a cancer of the present disclosure (e.g., comprising a BCOR gene rearrangement/gene fusion described herein) is characterized by cyclin D1 overexpression. In some embodiments, a sample obtained from a cancer of the present disclosure (e.g., comprising a BCOR gene rearrangement/gene fusion described herein) is not characterized by desmin expression. In some embodiments, a sample obtained from a cancer of the present disclosure (e.g., comprising a BCOR gene rearrangement/gene fusion described herein) is not characterized by a mutation in one or more of the TP53, BRCA2, PLAG1, RB1, ATRX, PTEN or MED12 genes. In some embodiments, a sample obtained from a cancer of the present disclosure (e.g., comprising a BCOR gene rearrangement/gene fusion described herein) lacks a mutation in any of the TP53, BRCA2, PLAG1, RB1, ATRX, PTEN or MED12 genes.

In some embodiments, a sample obtained from a cancer of the present disclosure (e.g., comprising a BCOR gene rearrangement/gene fusion or BCORL1 alteration described herein) is characterized by intermediate or low tumor burden. In some embodiments, a sample obtained from a cancer of the present disclosure (e.g., comprising a BCOR gene rearrangement/gene fusion or BCORL1 alteration described herein) is characterized by 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, or 6 or fewer mutations per megabase (Mb).

In some embodiments, a sample obtained from a cancer of the present disclosure (e.g., comprising a BCOR gene rearrangement/gene fusion or BCORL1 alteration described herein) is microsatellite stable. In some embodiments, a sample obtained from a cancer of the present disclosure (e.g., comprising a BCOR gene rearrangement/gene fusion or BCORL1 alteration described herein) is not microsatellite unstable. In some embodiments, a cancer of the present disclosure (e.g., comprising a BCOR gene rearrangement/gene fusion or BCORL1 alteration described herein) is microsatellite stable. In some embodiments, a cancer of the present disclosure (e.g., comprising a BCOR gene rearrangement/gene fusion or BCORL1 alteration described herein) is not microsatellite unstable.

Methods for ascertaining one or more properties of a cancer of the present disclosure are known in the art; exemplary and non-limiting methods are described in Examples 1 and 2 below. In some embodiments, a sample obtained from an individual (e.g., a tumor sample or specimen, such as from a biopsy) is analyzed.

In some embodiments, the sample is a formalin-fixed paraffin-embedded (FFPE) sample. In some embodiments, the sample comprises nucleic acids, e.g., genomic DNA, cDNA, or mRNA. In some embodiments, the sample is obtained from an individual having a cancer, such as a cancer described herein. A variety of materials (such as tissues) can be the source of the nucleic acid samples used in the methods provided herein. For example, the source of the sample can be solid tissue as from a fresh, frozen and/or preserved organ, tissue sample, biopsy, resection, smear, or aspirate, blood or any blood constituents; bodily fluids such as cerebrospinal fluid, amniotic fluid, urine, saliva, sputum, peritoneal fluid or interstitial fluid; or cells from any time in gestation or development of an individual. In some embodiments, the source of the sample is blood or blood constituents. In some embodiments, the source of the sample is a tumor sample. In some embodiments, the sample is or comprises biological tissue or fluid. In some embodiments, the sample can contain compounds that are not naturally intermixed with the tissue in nature, such as preservatives, anticoagulants, buffers, fixatives, nutrients, antibiotics or the like. In some embodiments, a BCOR or BCORL1 nucleic acid molecule is detected in a sample comprising genomic or subgenomic DNA fragments, or RNA, such as mRNA isolated from a sample, e.g., a tumor sample, a normal adjacent tissue (NAT) sample, a tissue sample, or a blood sample obtained from an individual. In some embodiments, the sample comprises cDNA derived from an mRNA sample or from a sample comprising mRNA. In some embodiments, the tissue is preserved as a frozen sample or as a formaldehyde- or paraformaldehyde-fixed paraffin-embedded (FFPE) tissue preparation. For example, the sample can be embedded in a matrix, e.g., an FFPE block or a frozen sample.

In some embodiments, the sample comprises cell-free DNA (cfDNA). In some embodiments, the sample comprises cell-free RNA (cfRNA). In some embodiments, the sample comprises circulating tumor DNA (ctDNA).

In some embodiments, a sample may be or comprise bone marrow; a bone marrow aspirate; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as ductal lavages or bronchoalveolar lavages; aspirates; scrapings; bone marrow specimens; tissue biopsy specimens; surgical specimens; other body fluids, secretions, and/or excretions; and/or cells therefrom. In some embodiments, a biological sample is or comprises cells obtained from an individual.

In some embodiments, a sample is a primary sample obtained directly from a source of interest by any appropriate means. For example, in some embodiments, a primary biological sample is obtained by a method chosen from biopsy (e.g., fine needle aspiration or tissue biopsy), surgery, or collection of body fluid (e.g., blood, lymph, or feces). In some embodiments, as will be clear from context, the term "sample" refers to a preparation that is obtained by processing (e.g., by removing one or more components of and/or by adding one or more agents to) a primary sample. Such a processed sample may comprise, for example nucleic acids or proteins extracted from a sample or obtained by subjecting a primary sample to techniques such as amplification or reverse transcription of mRNA, or isolation and/or purification of certain components.

In one embodiment, the sample comprises one or more cells associated with a tumor, e.g., tumor cells or tumor-infiltrating lymphocytes (TIL). In one embodiment, the sample includes one or more premalignant or malignant cells. In one embodiment, the sample is acquired from a hematologic malignancy (or pre-malignancy), e.g., a hematologic malignancy (or pre-malignancy) described herein. In one embodiment, the sample is acquired from a cancer, such as a cancer described herein. In some embodiments, the sample is acquired from a solid tumor, a soft tissue tumor or a metastatic lesion. In other embodiments, the sample includes tissue or cells from a surgical margin. In another embodiment, the sample includes one or more circulating tumor cells (CTCs) (e.g., a CTC acquired from a blood sample). In one embodiment, the sample is a cell not associated with a tumor, e.g., a non-tumor cell or a peripheral blood lymphocyte.

In some embodiments, the sample comprises tumor nucleic acids, such as nucleic acids from a tumor or a cancer sample, e.g., genomic DNA, RNA, or cDNA derived from RNA, from a tumor or cancer sample. In certain embodiments, a tumor nucleic acid sample is purified or isolated (e.g., it is removed from its natural state).

In some embodiments, the sample is a control nucleic acid sample or a reference nucleic acid sample, e.g., genomic DNA, RNA, or cDNA derived from RNA, not containing a mutation or gene fusion described herein. In certain embodiments, the reference or control nucleic acid sample comprises a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

In some embodiments, a BCOR or BCORL1 nucleic acid molecule of the disclosure is detected in a sample comprising cell-free DNA (cfDNA), cell-free RNA, or circulating tumor DNA (ctDNA).

Also provided herein are methods of detecting a BCOR or BCORL1 polypeptide of the disclosure, or a fragment thereof. A BCOR or BCORL1 polypeptide provided herein, or a fragment thereof, may be detected or measured, e.g., in a sample obtained from an individual, using any method known in the art, such as using antibodies (e.g., an antibody described herein), mass spectrometry (e.g., tandem mass spectrometry), a reporter assay (e.g., a fluorescence-based assay), immunoblots such as a Western blot, immunoassays such as enzyme-linked immunosorbent assays (ELISA), immunohistochemistry, other immunological assays (e.g., fluid or gel precipitin reactions, immunodiffusion, immunoelectrophoresis, radioimmunoassay (RIA), immunofluorescent assays), and analytic biochemical methods (e.g., electrophoresis, capillary electrophoresis, high performance liquid chromatography (HPLC), thin layer chromatography (TLC), hyperdiffusion chromatography).

In some embodiments, a BCOR or BCORL1 polypeptide of the disclosure, or a fragment thereof, can be distinguished from a reference polypeptide, e.g., a non-mutant or wild type BCOR or BCORL1 protein or polypeptide, with an antibody or antibody fragment that reacts differentially with a mutant protein or polypeptide (e.g., a BCOR or BCORL1 polypeptide provided herein or a fragment thereof) as compared to a reference protein or polypeptide. In some embodiments, a BCOR or BCORL1 polypeptide of the disclosure, or a fragment thereof, can be distinguished from a reference polypeptide, e.g., a non-mutant or wild type BCOR or BCORL1 protein or polypeptide, by reaction with a detection reagent, e.g., a substrate, e.g., a substrate for catalytic activity, e.g., phosphorylation.

In some aspects, methods of detection of a BCOR or BCORL1 polypeptide of the disclosure, or a fragment thereof, are provided, comprising contacting a sample, e.g., a sample described herein, comprising a BCOR or BCORL1 polypeptide described herein, with a detection reagent provided herein (e.g., an antibody of the disclosure), and determining if the BCOR or BCORL1 polypeptide is present in the sample.

In some embodiments, a sample for use according to the methods of detection of a BCOR or BCORL1 polypeptide of the disclosure, is a solid tissue, e.g., from a fresh, frozen and/or preserved organ, tissue sample, biopsy (e.g., a tumor biopsy), resection, smear, or aspirate; blood or any blood constituents; bodily fluids such as cerebrospinal fluid, amniotic fluid, urine, saliva, sputum, peritoneal fluid or interstitial fluid; or cells such as tumor cells. In some embodiments, the source of the sample is blood or blood constituents. In some embodiments, the source of the sample is a tumor sample. In some embodiments, the sample is or comprises biological tissue or fluid. In some embodiments, the sample is preserved as a frozen sample or as a formaldehyde- or paraformaldehyde-fixed paraffin-embedded (FFPE) tissue preparation. In some embodiments, the sample comprises circulating tumor cells (CTCs).

In some embodiments, a sample for use according to the methods of detection of a BCOR or BCORL1 polypeptide described herein is a sample of proteins isolated or obtained from a solid tissue, e.g., from a fresh, frozen and/or preserved organ, tissue sample, biopsy (e.g., a tumor biopsy), resection, smear, or aspirate; from blood or any blood constituents; from bodily fluids such as cerebrospinal fluid, amniotic fluid, urine, saliva, sputum, peritoneal fluid or interstitial fluid; or from cells such as tumor cells. In some embodiments, the sample is a sample of proteins isolated or obtained from a preserved sample, such as a frozen sample or a formaldehyde- or paraformaldehyde-fixed paraffin-embedded (FFPE) tissue preparation. In some embodiments, the sample is a sample of proteins isolated or obtained from circulating tumor cells (CTCs). In some embodiments, the sample can contain compounds that are not naturally intermixed with the tissue in nature, such as preservatives, anticoagulants, buffers, fixatives, nutrients, antibiotics or the like.

In some embodiments, a sample may be or comprise bone marrow; a bone marrow aspirate; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as ductal lavages or bronchoalveolar lavages; aspirates; scrapings; bone marrow specimens; tissue biopsy specimens; surgical specimens; other body fluids, secretions, and/or excretions; and/or cells therefrom. In some embodiments, a biological sample is or comprises cells obtained from an individual.

In some embodiments, a sample is a primary sample obtained directly from a source of interest by any appropriate means. For example, in some embodiments, a primary biological sample is obtained by a method chosen from biopsy (e.g., fine needle aspiration or tissue biopsy), surgery, or collection of body fluid (e.g., blood, lymph, or feces). In some embodiments, as will be clear from context, the term "sample" refers to a preparation that is obtained by processing (e.g., by removing one or more components of and/or by adding one or more agents to) a primary sample. Such a processed sample may comprise, for example, proteins extracted from a sample or obtained by subjecting a primary sample to techniques such as isolation and/or purification of certain components.

In one embodiment, the sample comprises one or more cells associated with a tumor, e.g., tumor cells or tumor-infiltrating lymphocytes (TIL). In one embodiment, the sample includes one or more premalignant or malignant cells. In one embodiment, the sample is acquired from a hematologic malignancy (or pre-malignancy), e.g., a hematologic malignancy (or pre-malignancy) described herein. In one embodiment, the sample is acquired from a cancer, such as a cancer described herein. In some embodiments, the sample is acquired from a solid tumor, a soft tissue tumor or a metastatic lesion. In other embodiments, the sample includes tissue or cells from a surgical margin. In another embodiment, the sample includes one or more circulating tumor cells (CTCs) (e.g., a CTC acquired from a blood sample). In one embodiment, the sample is a cell not associated with a tumor, e.g., a non-tumor cell or a peripheral blood lymphocyte.

In some embodiments, the sample comprises tumor proteins or polypeptides, such as proteins or polypeptides from a tumor or a cancer sample. In certain embodiments, the proteins are purified or isolated (e.g., removed from their natural state).

In some embodiments, the sample is a control sample or a reference sample, e.g., not containing a BCOR or BCORL1 polypeptide described herein. In certain embodiments, the reference sample is purified or isolated (e.g., it is removed from its natural state). In other embodiments, the reference sample is from a non-tumor sample, e.g., a blood control, a normal adjacent tumor (NAT), or any other non-cancerous sample from the same or a different subject.

In some embodiments, a cancer of the present disclosure is endometrial stromal sarcoma (ESS), e.g., a high grade ESS. In some embodiments, a cancer of the present disclosure is a uterine sarcoma. In some embodiments, a cancer of the present disclosure was previously classified as myxoid leiomyosarcoma.

In some embodiments, a BCOR or BCORL1 nucleic acid molecule of the disclosure is detected using any suitable method known in the art, such as a nucleic acid hybridization assay, an amplification-based assay (e.g., polymerase chain reaction, PCR), a PCR-RFLP assay, real-time PCR, sequencing (e.g., Sanger sequencing or next-generation sequencing), a screening analysis (e.g., using karyotype methods), fluorescence in situ hybridization (FISH), break away FISH, spectral karyotyping, multiplex-FISH, comparative genomic hybridization, in situ hybridization, single specific primer-polymerase chain reaction (SSP-PCR), high performance liquid chromatography (HPLC), or mass-spectrometric genotyping. Methods of analyzing samples, e.g., to detect a nucleic acid molecule, are described in U.S. Pat. No. 9,340,830 and in WO2012092426A1, which are hereby incorporated by reference in their entirety.

In some embodiments, a BCOR or BCORL1 nucleic acid molecule of the disclosure is detected using an in situ hybridization method, such as a fluorescence in situ hybridization (FISH) method.

In some embodiments, FISH analysis is used to identify the chromosomal rearrangement resulting in the mutations as described herein. In some embodiments, FISH analysis is used to identify an RNA molecule comprising a BCOR or BCORL1 nucleic acid described herein. Methods for performing FISH are known in the art and can be used in nearly any type of tissue. In FISH analysis, nucleic acid probes which are detectably labeled, e.g. fluorescently labeled, are allowed to bind to specific regions of DNA, e.g., a chromosome, or an RNA, e.g., an mRNA, and then examined, e.g., through a microscope. See, for example, U.S. Pat. No. 5,776,688. DNA or RNA molecules are first fixed onto a slide, the labeled probe is then hybridized to the DNA or RNA molecules, and then visualization is achieved, e.g., using enzyme-linked label-based detection methods known in the art. Generally, the resolution of FISH analysis is on the order of detection of 60 to 100000 nucleotides, e.g., 60 base pairs (bp) up to 100 kilobase pairs of DNA. Nucleic acid probes used in FISH analysis comprise single stranded nucleic acids. Such probes are typically at least about 50 nucleotides in length. In some embodiments, probes comprise about 100 to about 500 nucleotides. Probes that hybridize with centromeric DNA and locus-specific DNA or RNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA or other sources of nucleic acids through standard techniques. Examples of probes, labeling and hybridization methods are known in the art.

Several variations of FISH methods are known in the art and are suitable for use according to the methods of the disclosure, including single-molecule RNA FISH, Fiber FISH, Q-FISH, Flow-FISH, MA-FISH, break-away FISH, hybrid fusion-FISH, and multi-fluor FISH or mFISH. In some embodiments, "break-away FISH" is used in the methods provided herein. In break-away FISH, at least one probe targeting a fusion junction or breakpoint and at least one probe targeting an individual gene of the fusion, e.g., at one or more exons and or introns of the gene, are utilized. In normal cells (i.e., cells not having a fusion nucleic acid molecule described herein), both probes are observed (or a secondary color is observed due to the close proximity of the two genes of the gene fusion); and in cells having a fusion nucleic acid molecule described herein, only a single gene probe is observed due to the presence of a rearrangement resulting in the fusion nucleic acid molecule.

In some embodiments, a BCOR or BCORL1 nucleic acid molecule of the disclosure is detected using an array-based method, such as array-based comparative genomic hybridization (CGH) methods. In array-based CGH methods, a first sample of nucleic acids (e.g., from a sample, such as from a tumor) is labeled with a first label, while a second sample of nucleic acids (e.g., a control, such as from a healthy cell/tissue) is labeled with a second label. In some embodiments, equal quantities of the two samples are mixed and co-hybridized to a DNA microarray of several thousand evenly spaced cloned DNA fragments or oligonucleotides, which have been spotted in triplicate on the array. After hybridization, digital imaging systems are used to capture and quantify the relative fluorescence intensities of each of the hybridized fluorophores. The resulting ratio of the fluorescence intensities is proportional to the ratio of the copy numbers of DNA sequences in the two samples. In some embodiments, where there are chromosomal deletions or multiplications, differences in the ratio of the signals from the two labels are detected and the ratio provides a measure of the copy number. Array-based CGH can also be performed with single-color labeling. In single color CGH, a control (e.g., control nucleic acid sample, such as from a healthy cell/tissue) is labeled and hybridized to one array and absolute signals are read, and a test sample (e.g., a nucleic acid sample obtained from an individual or from a tumor) is labeled and hybridized to a second array (with identical content) and absolute signals are read. Copy number differences are calculated based on absolute signals from the two arrays.

In some embodiments, a BCOR or BCORL1 nucleic acid molecule of the disclosure is detected using an amplification-based method. As is known in the art, in such amplification-based methods, a sample of nucleic acids, such as a sample obtained from an individual or from a tumor, is used as a template in an amplification reaction (e.g., Polymerase Chain Reaction (PCR)) using one or more oligonucleotides or primers, e.g., such as one or more oligonucleotides or primers provided herein. The presence of a BCOR or BCORL1 nucleic acid molecule of the disclosure in the sample can be determined based on the presence or absence of an amplification product. Quantitative amplification methods are also known in the art and may be used according to the methods provided herein. Methods of measurement of DNA copy number at microsatellite loci using quantitative PCR analysis are known in the art. The known nucleotide sequence for genes is sufficient to enable one of skill in the art to routinely select primers to amplify any portion of the gene. Fluorogenic quantitative PCR can also be used. In fluorogenic quantitative PCR, quantitation is based on the amount of fluorescence signals, e.g., TaqMan and Sybr green.

Other amplification methods suitable for use according to the methods provided herein include, e.g., ligase chain reaction (LCR), transcription amplification, self-sustained sequence replication, dot PCR, and linker adapter PCR.

In some embodiments, a BCOR or BCORL1 nucleic acid molecule of the disclosure is detected using a sequencing method. Any method of sequencing known in the art can be used to detect a BCOR or BCORL1 nucleic acid molecule provided herein. Exemplary sequencing methods that may be used to detect a BCOR or BCORL1 nucleic acid molecule provided herein include those based on techniques developed by Maxam and Gilbert or Sanger. Automated sequencing procedures may also be used, e.g., including sequencing by mass spectrometry.

In some embodiments, a BCOR or BCORL1 nucleic acid molecule of the disclosure is detected using hybrid capture-based sequencing (hybrid capture-based NGS), e.g., using adaptor ligation-based libraries. See, e.g., Frampton, G. M. et al. (2013) Nat. Biotech. 31:1023-1031. In some embodiments, a BCOR or BCORL1 nucleic acid molecule of the disclosure is detected using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules may be sequenced simultaneously). Next generation sequencing methods suitable for use according to the methods provided herein are known in the art and include, without limitation, massively parallel short-read sequencing, template-based sequencing, pyrosequencing, real-time sequencing comprising imaging the continuous incorporation of dye-labeling nucleotides during DNA synthesis, nanopore sequencing, sequencing by hybridization, nano-transistor array based sequencing, polony sequencing, scanning tunneling microscopy (STM)-based sequencing, or nanowire-molecule sensor based sequencing. See, e.g., Metzker, M. (2010) *Nature Biotechnology Reviews* 11:31-46, which is hereby incorporated by reference. Exemplary NGS methods and platforms that may be used to detect a BCOR or BCORL1 nucleic acid molecule provided herein include, without limitation, the HeliScope Gene Sequencing system from Helicos BioSciences (Cambridge, MA., USA), the PacBio RS system from Pacific Biosciences (Menlo Park, CA, USA), massively parallel short-read sequencing such as the Solexa sequencer and other methods and platforms from Illumina Inc. (San Diego, CA, USA), 454 sequencing from 454 LifeSciences (Branford, CT, USA), Ion Torrent sequencing from ThermoFisher (Waltham, MA, USA), or the SOLiD sequencer from Applied Biosystems (Foster City, CA, USA). Additional exemplary methods and platforms that may be used to detect a BCOR or BCORL1 nucleic acid molecule provided herein include, without limitation, the Genome Sequencer (GS) FLX System from Roche (Basel, CHE), the G.007 polonator system, the Solexa Genome Analyzer, HiSeq 2500, HiSeq3000, HiSeq 4000, and NovaSeq 6000 platforms from Illumina Inc. (San Diego, CA, USA).

In some aspects, provided herein are reagents for detecting a BCOR or BCORL1 nucleic acid molecule of the disclosure or a fragment thereof, e.g., according to the methods of detection provided herein. In some embodiments, a detection reagent provided herein comprises a nucleic acid molecule, e.g., a DNA, RNA, or mixed DNA/RNA molecule, comprising a nucleotide sequence that is complementary to a nucleotide sequence on a target nucleic acid, e.g., a nucleic acid that comprises a BCOR or BCORL1 nucleic acid molecule described herein or a fragment or portion thereof.

In some embodiments, nucleic acids corresponding to the BCOR and/or BCORL1 gene(s) are captured (e.g., from amplified nucleic acids) by hybridization with a bait molecule. Provided herein are baits suitable for the detection of a BCOR or BCORL1 nucleic acid molecule of the disclosure.

In some embodiments, the bait comprises a capture nucleic acid molecule configured to hybridize to a target nucleic acid molecule comprising a BCOR or BCORL1 nucleic acid molecule provided herein, or a fragment or portion thereof. In some embodiments, the capture nucleic acid molecule is configured to hybridize to the BCOR or BCORL1 nucleic acid molecule of the target nucleic acid molecule.

In some embodiments, the capture nucleic acid molecule is configured to hybridize to a fragment of the BCOR or BCORL1 nucleic acid molecule. In some embodiments, the fragment comprises (or is) between about 5 and about 25 nucleotides, between about 5 and about 300 nucleotides, between about 100 and about 300 nucleotides, between about 130 and about 230 nucleotides, or between about 150 and about 200 nucleotides. In some embodiments, the capture nucleic acid molecule is between about 5 and about 25 nucleotides, between about 5 and about 300 nucleotides, between about 100 and about 300 nucleotides, between about 130 and about 230 nucleotides, or between about 150 and about 200 nucleotides. In some embodiments, the fragment comprises (or is) about 100 nucleotides, about 125 nucleotides, about 150 nucleotides, about 175 nucleotides, about 200 nucleotides, about 225 nucleotides, about 250 nucleotides, about 275 nucleotides, or about 300 nucleotides in length. In some embodiments, the capture nucleic acid molecule comprises (or is) about 100 nucleotides, about 125 nucleotides, about 150 nucleotides, about 175 nucleotides, about 200 nucleotides, about 225 nucleotides, about 250 nucleotides, about 275 nucleotides, or about 300 nucleotides in length.

In some embodiments, the capture nucleic acid molecule is configured to hybridize to a BCOR or BCORL1 breakpoint, and may further hybridize to between about 10 and about 100 nucleotides or more, e.g., any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides flanking either side of the BCOR or BCORL1 breakpoint.

In some embodiments, the capture nucleic acid molecule is configured to hybridize to a nucleotide sequence in an intron or an exon of BCOR or BCORL1, or in a BCOR or BCORL1 breakpoint joining the introns or exons of BCOR or BCORL1 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides) to another intron or exon of BCOR or BCORL1 (e.g., in case of internal rearrangements), or to the intron or exon of another gene (e.g., a fusion partner of BCOR or BCORL1, e.g., as described herein).

In some embodiments, the capture nucleic acid molecule is a DNA, RNA, or a DNA/RNA molecule. In some embodiments, the capture nucleic acid molecule comprises any of between about 50 and about 1000 nucleotides, between about 50 and about 500 nucleotides, between about 100 and about 500 nucleotides, between about 100 and about 300 nucleotides, between about 130 and about 230 nucleotides, or between about 150 and about 200 nucleotides. In some embodiments, the capture nucleic acid molecule comprises any of between about 50 nucleotides and about 100 nucleotides, about 100 nucleotides and about 150 nucleotides, about 150 nucleotides and about 200 nucleotides, about 200 nucleotides and about 250 nucleotides, about 250 nucleotides and about 300 nucleotides, about 300 nucleotides and about 350 nucleotides, about 350 nucleotides and about 400 nucleotides, about 400 nucleotides and about 450 nucleotides, about 450 nucleotides and about 500 nucleotides, about 500 nucleotides and about 550 nucleotides, about 550 nucleotides and about 600 nucleotides, about 600 nucleotides and about 650 nucleotides, about 650 nucleotides and about 700 nucleotides, about 700 nucleotides and about 750 nucleotides, about 750 nucleotides and about 800 nucleotides, about 800 nucleotides and about 850 nucleotides, about 850 nucleotides and about 900 nucleotides, about 900 nucleotides and about 950 nucleotides, or about 950 nucleotides and about 1000 nucleotides. In some embodiments, the capture nucleic acid molecule comprises about 150 nucleotides. In some embodiments, the capture nucleic acid molecule is about 150 nucleotides. In some embodiments, the capture nucleic acid molecule comprises about 170 nucleotides. In some embodiments, the capture nucleic acid molecule is about 170 nucleotides.

In some embodiments, a bait provided herein comprises a DNA, RNA, or a DNA/RNA molecule. In some embodiments, a bait provided herein includes a label or a tag. In some embodiments, the label or tag is a radiolabel, a fluorescent label, an enzymatic label, a sequence tag, biotin, or another ligand. In some embodiments, a bait provided herein includes a detection reagent such as a fluorescent marker. In some embodiments, a bait provided herein includes (e.g., is conjugated to) an affinity tag, e.g., that allows capture and isolation of a hybrid formed by a bait and a nucleic acid hybridized to the bait. In some embodiments, the affinity tag is an antibody, an antibody fragment, biotin, or any other suitable affinity tag or reagent known in the art. In some embodiments, a bait is suitable for solution phase hybridization.

Baits can be produced and used according to methods known in the art, e.g., as described in WO2012092426A1 and/or or in Frampton et al. (2013) Nat Biotechnol, 31:1023-1031, incorporated herein by reference. For example, biotinylated baits (e.g., RNA baits) can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

In some embodiments, a bait provided herein is between about 100 nucleotides and about 300 nucleotides. In some embodiments, a bait provided herein is between about 130 nucleotides and about 230 nucleotides. In some embodiments, a bait provided herein is between about 150 nucleotides and about 200 nucleotides. In some embodiments, a bait provided herein comprises a target-specific bait sequence (e.g., a capture nucleic acid molecule described herein) and universal tails on each end. In some embodiments, the target-specific sequence, e.g., a capture nucleic acid molecule described herein, is between about 40 nucleotides and about 300 nucleotides. In some embodiments, the target-specific sequence, e.g., a capture nucleic acid molecule described herein, is between about 100 nucleotides and about 200 nucleotides. In some embodiments, the target-specific sequence, e.g., a capture nucleic acid molecule described herein, is between about 120 nucleotides and about 170 nucleotides. In some embodiments, the target-specific sequence, e.g., a capture nucleic acid molecule described herein, is about 150 nucleotides or about 170 nucleotides. In some embodiments, a bait provided herein comprises an oligonucleotide comprising about 200 nucleotides, of which about 150 nucleotides or about 170 nucleotides are target-specific (e.g., a capture nucleic acid molecule described herein), and the other 50 nucleotides or 30 nucleotides (e.g., 25 or 15 nucleotides on each end of the bait) are universal arbitrary tails, e.g., suitable for PCR amplification.

In some embodiments, a bait provided herein hybridizes to a nucleotide sequence comprising a nucleotide sequence in an intron or an exon of one gene of a fusion molecule described herein (e.g., BCOR or BCORL1), in an intron or an exon of the other gene of a fusion molecule described herein, and/or a BCOR or BCORL1 breakpoint joining the introns and/or exons.

The baits described herein can be used for selection of exons and short target sequences.

In some embodiments, a bait of the disclosure distinguishes a nucleic acid, e.g., a genomic or transcribed nucleic acid, e.g., a cDNA or RNA, having a BCOR or BCORL1 breakpoint described herein, from a reference nucleotide sequence, e.g., a nucleotide sequence not having the breakpoint.

In some embodiments, the bait hybridizes to the BCOR or BCORL1 breakpoint, and a sequence on either side of the BCOR or BCORL1 breakpoint (e.g., any of 1, 2, 3, 4, 5, 6, 7, 8, 9, or 10 nucleotides on either side of the BCOR or BCORL1 breakpoint, or any of between 1 and about 5, about 5 and about 10, about 10 and about 15, about 15 and about 20, about 20 and about 25, about 25 and about 30, about 30 and about 35, about 35 and about 40, about 40 and about 45, about 45 and about 50, about 50 and about 55, about 55 and about 60, about 60 and about 65, about 70 and about 75, about 75 and about 80, about 80 and about 85, about 85 and about 90, about 90 and about 95, or about 95 and about 100, or more nucleotides on either side of the BCOR or BCORL1 breakpoint).

Also provided herein are probes, e.g., nucleic acid molecules, suitable for the detection of a BCOR or BCORL1 nucleic acid molecule provided herein. In some embodiments, a probe provided herein comprises a nucleic acid sequence configured to hybridize to a target nucleic acid molecule comprising a BCOR or BCORL1 nucleic acid molecule provided herein, or a fragment or portion thereof. In some embodiments, the probe comprises a nucleic acid sequence configured to hybridize to the BCOR or BCORL1 nucleic acid molecule, or the fragment or portion thereof, of the target nucleic acid molecule. In some embodiments, the probe comprises a nucleic acid sequence configured to hybridize to a fragment or portion of the BCOR or BCORL1 nucleic acid molecule of the target nucleic acid molecule. In some embodiments, the fragment or portion comprises between about 5 and about 25 nucleotides, between about 5 and about 300 nucleotides, between about 100 and about 300 nucleotides, between about 130 and about 230 nucleotides, or between about 150 and about 200 nucleotides.

In some embodiments, the probe comprises a nucleotide sequence configured to hybridize to a BCOR or BCORL1 breakpoint, and may be further configured to hybridize to between about 10 and about 100 nucleotides or more, e.g., any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides flanking either side of the BCOR or BCORL1 breakpoint.

In some embodiments, the probe comprises a nucleotide sequence configured to hybridize to a nucleotide sequence in an intron or an exon of BCOR or BCORL1, or in a BCOR or BCORL1 break-point joining the introns or exons of BCOR or BCORL1 (e.g., plus or minus any of between about 10 and about 20, about 20 and about 30, about 30 and about 40, about 40 and about 50, about 50 and about 60, about 60 and about 70, about 70 and about 80, about 80 and about 90, or about 90 and about 100, or more nucleotides) to another intron or exon of BCOR or BCORL1 (e.g., in case of internal rearrangements), or to the intron or exon of another gene (e.g., a fusion partner of BCOR or BCORL1, e.g., as described herein).

In some embodiments, the probe comprises a nucleic acid molecule which is a DNA, RNA, or a DNA/RNA molecule. In some embodiments, the probe comprises a nucleic acid molecule comprising any of between about 10 and about 20 nucleotides, between about 12 and about 20 nucleotides, between about 10 and about 1000 nucleotides, between about 50 and about 500 nucleotides, between about 100 and about 500 nucleotides, between about 100 and about 300 nucleotides, between about 130 and about 230 nucleotides, or between about 150 and about 200 nucleotides. In some embodiments, the probe comprises a nucleic acid molecule comprising any of 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides. In some embodiments, the probe comprises a nucleic acid molecule comprising any of between about 40 nucleotides and about 50 nucleotides, about 50 nucleotides and about 100 nucleotides, about 100 nucleotides and about 150 nucleotides, about 150 nucleotides and about 200 nucleotides, about 200 nucleotides and about 250 nucleotides, about 250 nucleotides and about 300 nucleotides, about 300 nucleotides and about 350 nucleotides, about 350 nucleotides and about 400 nucleotides, about 400 nucleotides and about 450 nucleotides, about 450 nucleotides and about 500 nucleotides, about 500 nucleotides and about 550 nucleotides, about 550 nucleotides and about 600 nucleotides, about 600 nucleotides and about 650 nucleotides, about 650 nucleotides and about 700 nucleotides, about 700 nucleotides and about 750 nucleotides, about 750 nucleotides and about 800 nucleotides, about 800 nucleotides and about 850 nucleotides, about 850 nucleotides and about 900 nucleotides, about 900 nucleotides and about 950 nucleotides, or about 950 nucleotides and about 1000 nucleotides. In some embodiments, the probe comprises a nucleic acid molecule comprising between about 12 and about 20 nucleotides.

In some embodiments, a probe provided herein comprises a DNA, RNA, or a DNA/RNA molecule. In some embodiments, a probe provided herein includes a label or a tag. In some embodiments, the label or tag is a radiolabel (e.g., a radioisotope), a fluorescent label (e.g., a fluorescent compound), an enzymatic label, an enzyme co-factor, a sequence tag, biotin, or another ligand. In some embodiments, a probe provided herein includes a detection reagent such as a fluorescent marker. In some embodiments, a probe provided herein includes (e.g., is conjugated to) an affinity tag, e.g., that allows capture and isolation of a hybrid formed by a probe and a nucleic acid hybridized to the probe. In some embodiments, the affinity tag is an antibody, an antibody fragment, biotin, or any other suitable affinity tag or reagent known in the art. In some embodiments, a probe is suitable for solution phase hybridization.

In some embodiments, probes provided herein may be used according to the methods of detection of BCOR or BCORL1 nucleic acid molecules provided herein. For example, a probe provided herein may be used for detecting a BCOR or BCORL1 nucleic acid molecule provided herein in a sample, e.g., a sample obtained from an individual. In some embodiments, the probe may be used for identifying cells or tissues that express a BCOR or BCORL1 nucleic acid molecule provided herein, e.g., by measuring levels of the BCOR or BCORL1 nucleic acid molecule. In some embodiments, the probe may be used for detecting levels of a BCOR or BCORL1 nucleic acid molecule, e.g., mRNA levels, in a sample of cells from an individual.

In some embodiments, a probe provided herein specifically hybridizes to a nucleic acid comprising a rearrangement (e.g., a deletion, inversion, insertion, duplication, or other rearrangement) resulting in a BCOR or BCORL1 fusion gene or rearranged nucleic acid molecule described herein.

In some embodiments, a probe of the disclosure distinguishes a nucleic acid, e.g., a genomic or transcribed nucleic acid, e.g., a cDNA or RNA, having a BCOR or BCORL1 breakpoint described herein, from a reference nucleotide sequence, e.g., a nucleotide sequence not having the breakpoint.

Also provided herein are isolated pairs of allele-specific probes, wherein, for example, the first probe of the pair specifically hybridizes to a BCOR or BCORL1 nucleic acid molecule described herein, and the second probe of the pair specifically hybridizes to a corresponding wild type sequence (e.g., a wild type BCOR or BCORL1 nucleic acid molecule). Probe pairs can be designed and produced for any of the fusion nucleic acid molecules described herein and are useful in detecting a somatic mutation in a sample. In some embodiments, a first probe of a pair specifically hybridizes to a mutation (e.g., the BCOR or BCORL1 breakpoint of an alteration, rearrangement, inversion, duplication, deletion, insertion or translocation resulting in a BCOR or BCORL1 nucleic acid molecule described herein), and a second probe of a pair specifically hybridizes to a sequence upstream or downstream of the mutation.

In some embodiments, one or more probes provided herein are suitable for use in in situ hybridization methods, e.g., as described above, such as FISH.

Chromosomal probes, e.g., for use in the FISH methods described herein, are typically about 50 to about $10^5$ nucleotides in length. Longer probes typically comprise smaller fragments of about 100 to about 500 nucleotides. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). Probes of the disclosure may also hybridize to RNA molecules, e.g., mRNA, such as an RNA comprising a BCOR or BCORL1 nucleic acid provided herein.

In some embodiments, probes, such as probes for use in the FISH methods described herein, are used for determining whether a cytogenetic abnormality is present in one or more cells, e.g., in a region of a chromosome or an RNA bound by one or more probes provided herein. The cytogenetic abnormality may be a cytogenetic abnormality that results in a BCOR or BCORL1 nucleic acid molecule described herein. Examples of such cytogenetic abnormalities include, without limitation, deletions (e.g., deletions of entire chromosomes or deletions of fragments of one or more chromosomes), duplications (e.g., of entire chromosomes, or of regions smaller than an entire chromosome), translocations (e.g., non-reciprocal translocations, balanced translocations), intra-chromosomal inversions, point mutations, deletions, gene copy number changes, germ-line mutations, and gene expression level changes.

In some embodiments, probes, such as probes for use in the FISH methods described herein, are labeled such that a chromosomal region or a region on an RNA to which the probes hybridize can be detected. Probes typically are directly labeled with a fluorophore, allowing the probe to be visualized without a secondary detection molecule. Probes can also be labeled by nick translation, random primer labeling or PCR labeling. Labeling may be accomplished using fluorescent (direct)-or haptene (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin(BIO)-11-dUTP, Digoxygenin(DIG)-11-dUTP and Dinitrophenyl (DNP)-11-dUTP. Probes can also be indirectly labeled with biotin or digoxygenin, or labeled with radioactive isotopes such as $^{32}P$ and $^{3}H$, and secondary detection molecules are used, or further processing is performed, to visualize the probes. For example, a probe labeled with biotin can be detected by avidin conjugated to a detectable marker, e.g., avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase. Probes can also be prepared such that a fluorescent or other label is added after hybridization of the probe to its target to detect that the probe hybridized to the target. For example, probes can be used that have antigenic molecules incorporated into the nucleotide sequence. After hybridization, these antigenic molecules are detected, for example, using specific antibodies reactive with the antigenic molecules. Such antibodies can, for example, themselves incorporate a fluorochrome, or can be detected using a second antibody with a bound fluorochrome. For fluorescent probes, e.g., used in FISH techniques, fluorescence can be viewed with a fluorescence microscope equipped with an appropriate filter for each fluorophore, or by using dual or triple band-pass filter sets to observe multiple fluorophores. Alternatively, techniques such as flow cytometry can be used to examine the hybridization pattern of the chromosomal probes.

In some embodiments, the probe hybridizes to the BCOR or BCORL1 breakpoint, and a sequence on either side of the BCOR or BCORL1 breakpoint (e.g., any of 1, 2, 3, 4, 5, 6, 7, 8, 9, or 10 nucleotides on either side of the BCOR or BCORL1 breakpoint, or any of between 1 and about 5, about 5 and about 10, about 10 and about 15, about 15 and about 20, about 20 and about 25, about 25 and about 30, about 30 and about 35, about 35 and about 40, about 40 and about 45, about 45 and about 50, about 50 and about 55, about 55 and about 60, about 60 and about 65, about 70 and about 75, about 75 and about 80, about 80 and about 85, about 85 and about 90, about 90 and about 95, or about 95 and about 100, or more nucleotides on either side of the BCOR or BCORL1 breakpoint).

In some aspects, provided herein are oligonucleotides, e.g., useful as primers. In some embodiments, an oligonucleotide, e.g., a primer, provided herein comprises a nucleotide sequence configured to hybridize to a target nucleic acid molecule comprising a BCOR or BCORL1 nucleic acid molecule provided herein, or a fragment or portion thereof. In some embodiments, the oligonucleotide comprises a nucleotide sequence configured to hybridize to the BCOR or BCORL1 nucleic acid molecule of the target nucleic acid molecule. In some embodiments, the oligonucleotide comprises a nucleotide sequence configured to hybridize to a fragment or portion of the BCOR or BCORL1 nucleic acid molecule of the target nucleic acid molecule.

In some embodiments, the oligonucleotide, e.g., the primer, comprises a nucleotide sequence configured to hybridize to a BCOR or BCORL1 breakpoint, and may be further configured to hybridize to between about 10 and about 12, about 12 and about 15, about 15 and about 17, about 17 and about 20, about 20 and about 25, or about 25 and about 30, or more nucleotides flanking either side of the BCOR or BCORL1 breakpoint.

In some embodiments, the oligonucleotide, e.g., the primer, comprises a nucleotide sequence configured to hybridize to a nucleotide sequence in an intron or an exon of BCOR or BCORL1 breakpoint joining the introns or exons of BCOR or BCORL1 (e.g., plus or minus any of between about 10 and about 12, about 12 and about 15, about 15 and about 17, about 17 and about 20, about 20 and about 25, or about 25 and about 30, or more nucleotides) to another intron or exon of BCOR or BCORL1 (e.g., in case of internal rearrangements), or to the intron or exon of another gene (e.g., a fusion partner of BCOR or BCORL1, e.g., as described herein).

In some embodiments, the oligonucleotide comprises a nucleotide sequence corresponding to a BCOR or BCORL1 nucleic acid molecule provided herein. In some embodiments, the oligonucleotide comprises a nucleotide sequence corresponding to a fragment or a portion of a BCOR or BCORL1 nucleic acid molecule provided herein. In some embodiments, the fragment or portion comprises between about 10 and about 30 nucleotides, between about 12 and about 20 nucleotides, or between about 12 and about 17 nucleotides. In some embodiments, the oligonucleotide comprises a nucleotide sequence complementary to a BCOR or BCORL1 nucleic acid molecule provided herein. In some embodiments, the oligonucleotide comprises a nucleotide sequence complementary to a fragment or a portion of a BCOR or BCORL1 nucleic acid molecule provided herein. In some embodiments, the fragment or portion comprises between about 10 and about 30 nucleotides, between about 12 and about 20 nucleotides, or between about 12 and about 17 nucleotides.

In some embodiments, an oligonucleotide, e.g., a primer, provided herein comprises a nucleotide sequence that is sufficiently complementary to its target nucleotide sequence such that the oligonucleotide specifically hybridizes to a nucleic acid molecule comprising the target nucleotide sequence, e.g., under high stringency conditions. In some embodiments, an oligonucleotide, e.g., a primer, provided herein comprises a nucleotide sequence that is sufficiently complementary to its target nucleotide sequence such that the oligonucleotide specifically hybridizes to a nucleic acid molecule comprising the target nucleotide sequence under conditions that allow a polymerization reaction (e.g., PCR) to occur.

In some embodiments, an oligonucleotide, e.g., a primer, provided herein may be useful for initiating DNA synthesis via PCR (polymerase chain reaction) or a sequencing method. In some embodiments, the oligonucleotide may be used to amplify a nucleic acid molecule comprising a BCOR or BCORL1 nucleic acid molecule provided herein, or a fragment thereof, e.g., using PCR. In some embodiments, the oligonucleotide may be used to sequence a nucleic acid molecule comprising a BCOR or BCORL1 nucleic acid molecule provided herein, or a fragment thereof. In some embodiments, the oligonucleotide may be used to amplify a nucleic acid molecule comprising a BCOR or BCORL1 breakpoint provided herein, e.g., using PCR. In some embodiments, the oligonucleotide may be used to sequence a nucleic acid molecule comprising a BCOR or BCORL1 breakpoint.

In some embodiments, pairs of oligonucleotides, e.g., pairs of primers, are provided herein, which are configured to hybridize to a nucleic acid molecule comprising a BCOR or BCORL1 nucleic acid molecule provided herein, or a fragment thereof. In some embodiments, a pair of oligonucleotides of the disclosure may be used for directing amplification of the BCOR or BCORL1 nucleic acid molecule or fragment thereof, e.g., using a PCR reaction. In some embodiments, pairs of oligonucleotides, e.g., pairs of primers, are provided herein, which are configured to hybridize to a nucleic acid molecule comprising a BCOR or BCORL1 breakpoint provided herein, e.g., for use in directing amplification of the BCOR or BCORL1 nucleic acid molecule or fragment thereof, e.g., using a PCR reaction.

In some embodiments, an oligonucleotide, e.g., a primer, provided herein is a single stranded nucleic acid molecule, e.g., for use in sequencing or amplification methods. In some embodiments, an oligonucleotide provided herein is a double stranded nucleic acid molecule. In some embodiments, a double stranded oligonucleotide is treated, e.g., denatured, to separate its two strands prior to use, e.g., in sequencing or amplification methods. Oligonucleotides provided herein comprise a nucleotide sequence of sufficient length to hybridize to their target, e.g., a BCOR or BCORL1 nucleic acid molecule provided herein, or a fragment thereof, and to prime the synthesis of extension products, e.g., during PCR or sequencing.

In some embodiments, an oligonucleotide, e.g., a primer, provided herein comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more deoxyribonucleotides or ribonucleotides. In some embodiments, an oligonucleotide provided herein comprises at least about 8 deoxyribonucleotides or ribonucleotides. In some embodiments, an oligonucleotide provided herein comprises at least about 10 deoxyribonucleotides or ribonucleotides. In some embodiments, an oligonucleotide provided herein comprises at least about 12 deoxyribonucleotides or ribonucleotides. In some embodiments, an oligonucleotide provided herein comprises at least about 15 deoxyribonucleotides or ribonucleotides. In some embodiments, an oligonucleotide provided herein comprises at least about 20 deoxyribonucleotides or ribonucleotides. In some embodiments, an oligonucleotide provided herein comprises at least about 30 deoxyribonucleotides or ribonucleotides. In some embodiments, an oligonucleotide provided herein comprises between about 10 and about 30 deoxyribonucleotides or ribonucleotides. In some embodiments, an oligonucleotide provided herein comprises between about 10 and about 25 deoxyribonucleotides or ribonucleotides. In some embodiments, an oligonucleotide provided herein comprises between about 10 and about 20 deoxyribonucleotides or ribonucleotides. In some embodiments, an oligonucleotide provided herein comprises between about 10 and about 15 deoxyribonucleotides or ribonucleotides. In some embodiments, an oligonucleotide provided herein comprises between about 12 and about 20 deoxyribonucleotides or ribonucleotides. In some embodiments, an oligonucleotide provided herein comprises between about 17 and about 20 deoxyribonucleotides or ribonucleotides. In some embodiments, the length and nucleotide sequence of an oligonucleotide provided herein is determined according to methods known in the art, e.g., based on factors such as the specific application (e.g., PCR, sequencing library preparation, sequencing), reaction conditions (e.g., buffers, temperature), and the nucleotide composition of the nucleotide sequence of the oligonucleotide or of its target complementary sequence.

In some embodiments, an oligonucleotide, e.g., a primer, of the disclosure distinguishes a nucleic acid, e.g., a genomic or transcribed nucleic acid, e.g., a cDNA or RNA, having a BCOR or BCORL1 described herein, from a reference nucleotide sequence, e.g., a nucleotide sequence not having the breakpoint.

In one aspect, provided herein is a primer or primer set for amplifying a nucleic acid molecule comprising a cytogenetic abnormality such as an alteration, rearrangement, chromosomal inversion, deletion, translocation, duplication, or other rearrangement resulting in a BCOR or BCORL1 nucleic acid molecule described herein. In another aspect, provided herein is a primer or primer set for amplifying a nucleic acid molecule comprising an alteration, rearrangement, chromosomal inversion, insertion, deletion, translocation, duplication or other rearrangement resulting in a BCOR or BCORL1 nucleic acid molecule described herein. In certain aspects, provided herein are allele-specific oligonucleotides, e.g., primers, wherein a first oligonucleotide of a pair specifically hybridizes to a mutation (e.g., the BCOR or BCORL1 nucleic acid molecule described herein), and a second oligonucleotide of a pair specifically hybridizes to a sequence upstream or downstream of the mutation. In certain aspects, provided herein are pairs of oligonucleotides, e.g., primers, wherein a first oligonucleotide of a pair specifically hybridizes to a sequence upstream of a mutation (e.g., the BCOR or BCORL1 nucleic acid molecule described herein), and a second oligonucleotide of the pair specifically hybridizes to a sequence downstream of the mutation.

In some embodiments, the oligonucleotide, e.g., the primer, hybridizes to the BCOR or BCORL1 nucleic acid, and a sequence on either side of the BCOR or BCORL1 nucleic acid (e.g., any of 1, 2, 3, 4, 5, 6, 7, 8, 9, or 10 nucleotides on either side of the BCOR or BCORL1 nucleic acid, or any of between 1 and about 5, about 5 and about 10, about 10 and about 15, about 15 and about 20, about 20 and about 25, about 25 and about 30, about 30 and about 35, about 35 and about 40, about 40 and about 45, about 45 and about 50, about 50 and about 55, about 55 and about 60, about 60 and about 65, about 70 and about 75, about 75 and about 80, about 80 and about 85, about 85 and about 90, about 90 and about 95, or about 95 and about 100, or more nucleotides on either side of the BCOR or BCORL1 nucleic acid).

Provided herein are antibodies or antibody fragments that specifically bind to a BCOR or BCORL1 polypeptide of the disclosure, or a portion thereof. The antibody may be of any suitable type of antibody, including, but not limited to, a monoclonal antibody, a polyclonal antibody, a multi-specific antibody (e.g., a bispecific antibody), or an antibody fragment, so long as the antibody or antibody fragment exhibits a specific antigen binding activity (e.g., binding to a BCOR or BCORL1 polypeptide of the disclosure, or a portion thereof).

In some embodiments, a BCOR or BCORL1 polypeptide of the disclosure, or a fragment thereof, is used as an immunogen to generate one or more antibodies of the disclosure, e.g., using standard techniques for polyclonal and monoclonal antibody preparation. In some embodiments, a BCOR or BCORL1 polypeptide provided herein, is used to provide antigenic peptide fragments (e.g., comprising any of at least about 8, at least about 10, at least about 15, at least about 20, at least about 30 or more amino acids) for use as immunogens to generate one or more antibodies of the disclosure, e.g., using standard techniques for polyclonal and monoclonal antibody preparation. As is known in the art, an antibody of the disclosure may be prepared by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptides, e.g., a BCOR or BCORL1 polypeptide provided herein, or a fragment thereof. The preparation can further include an adjuvant, such as Freund's complete or incomplete adjuvant, or a similar immunostimulatory agent.

In some embodiments, an antibody provided herein is a polyclonal antibody. Methods of producing polyclonal antibodies are known in the art. In some embodiments, an antibody provided herein is a monoclonal antibody, wherein a population of the antibody molecules contain only one species of an antigen binding site capable of immunoreacting or binding with a particular epitope, e.g., an epitope on a BCOR or BCORL1 polypeptide provided herein. Methods of preparation of monoclonal antibodies are known in the art, e.g., using standard hybridoma techniques originally described by Kohler and Milstein (1975) *Nature* 256:495-497, human B cell hybridoma techniques (see Kozbor et al., 1983, *Immunol. Today* 4:72), EBV-hybridoma techniques (see Cole et al., pp. 77-96 In *Monoclonal Antibodies and Cancer Therapy*, Alan R. Liss, Inc., 1985), or trioma techniques. The technology for producing hybridomas is well known (see generally *Current Protocols in Immunology*, Coligan et al. ed., John Wiley & Sons, New York, 1994). A monoclonal antibody of the disclosure may also be identified and isolated by screening a recombinant combinatorial immunoglobulin library (e.g., an antibody phage display library) with the polypeptide of interest, e.g., a BCOR or BCORL1 polypeptide provided herein or a fragment thereof. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display libraries can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; and Griffiths et al. (1993) *EMBO J.* 12:725-734. In some embodiments, monoclonal antibodies of the disclosure are recombinant antibodies, such as chimeric and humanized monoclonal antibodies, comprising both human and non-human portions. Such chimeric and/or humanized monoclonal antibodies can be produced by recombinant DNA techniques known in the art, for example, using methods described in PCT Publication No. WO 87/02671; European Patent Application 184,187, European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559; Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060. In some embodiments, a monoclonal antibody of the disclosure is a human monoclonal antibody. In some embodiments, human monoclonal antibodies are prepared using methods known in the art, e.g., using transgenic mice which are incapable of expressing endogenous immunoglobulin heavy and light chains genes, but which can express human heavy and light chain genes. For an overview of this technology for producing human antibodies, see Lonberg and Huszar (1995) *Int. Rev. Immunol.* 13:65-93. For a detailed discussion of this technology for producing human antibodies and human monoclonal antibodies, and protocols for producing such antibodies, see, e.g., U.S. Pat. Nos. 5,625,126; 5,633,425; 5,569,825; 5,661,016, and 5,545,806.

In some embodiments, the antibody or antibody fragment of the disclosure is an isolated antibody or antibody fragment, which has been separated from a component of its natural environment or a cell culture used to produce the antibody or antibody fragment. In some embodiments, an antibody of the disclosure is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods.

In some embodiments, an antibody of the disclosure can be used to isolate a BCOR or BCORL1 polypeptide provided herein, or a fragment thereof, by standard techniques, such as affinity chromatography or immunoprecipitation. In some embodiments, an antibody of the disclosure can be used to detect a BCOR or BCORL1 polypeptide provided herein, or a fragment thereof, e.g., in a tissue sample, cellular lysate, or cell supernatant, in order to evaluate the level and/or pattern of expression of the BCOR or BCORL1 polypeptide. Detection can be facilitated by coupling the antibody to a detectable substance. Thus, in some embodiments, an antibody of the disclosure is coupled to a detectable substance, such as enzymes, prosthetic groups, fluorescent materials, luminescent materials, bioluminescent materials, and radioactive materials. Non-limiting examples of suitable enzymes include, e.g., horseradish peroxidase, alkaline phosphatase, β-galactosidase, or acetylcholinesterase; examples of suitable prosthetic group complexes include, e.g., streptavidin/biotin and avidin/biotin; examples of suitable fluorescent materials include, e.g., umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, e.g., luciferase, luciferin, and aequorin; and examples of suitable radioactive materials include, e.g., $^{125}$I, $^{131}$, $^{35}$S or $^{3}$H.

An antibody or antibody fragment of the disclosure may also be used diagnostically, e.g., to detect and/or monitor protein levels (e.g., protein levels of a BCOR or BCORL1 polypeptide provided herein) in tissues or body fluids (e.g., in a tumor cell-containing tissue or body fluid), e.g., according to the methods provided herein.

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$M to $10^{-13}$ M). Methods of measuring antibody affinity (e.g., Kd) are known in the art, and include, without limitation, a radiolabeled antigen binding assay (RIA) and a BIACORE® surface plasmon resonance assay. In some embodiments, antibody affinity (e.g., Kd) is determined using the Fab version of an antibody of the disclosure and its antigen (e.g., a BCOR or BCORL1 polypeptide provided herein). In some embodiments, a RIA is performed with the Fab version of an antibody of the disclosure and its antigen (e.g., a BCOR or BCORL1 polypeptide provided herein).

In certain embodiments, an antibody provided herein is an antibody fragment. Antibody fragments include, but are not limited to, Fab, Fab', Fab'-SH, $F(ab')_2$, Fv, and single-chain antibody molecules (e.g., scFv) fragments, and other fragments described herein.

In certain embodiments, an antibody provided herein is a diabody. Diabodies are antibody fragments with two antigen-binding sites that may be bivalent or bispecific. In certain embodiments, an antibody provided herein is a triabody or a tetrabody.

In certain embodiments, an antibody provided herein is a single-domain antibody. Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody, as well as production by recombinant host cells (e.g., *E. coli* or phage), as known in the art and as described herein.

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey), and a human constant region. In a further example, a chimeric antibody is a "class switched" antibody, in which the class or subclass of the antibody has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof), are derived from a non-human antibody, and framework regions (FRs) (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanized antibodies and methods of making them are known in the art. Human framework regions that may be used for humanization include but are not limited to: framework regions selected using the "best-fit" method; framework regions derived from the consensus sequence of human antibodies of a particular subgroup of light or heavy chain variable regions; human mature (somatically mutated) framework regions or human germline framework regions; and framework regions derived from screening FR libraries.

In certain embodiments, an antibody provided herein is a human antibody. Human antibodies can be produced using various techniques known in the art. For example, human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or are present extrachromosomally or integrated randomly into the animal's chromosomes. In such transgenic animals, e.g., mice, the endogenous immunoglobulin loci have generally been inactivated. Human variable regions from intact antibodies generated by such animals may be further modified, e.g., by combining with a different human constant region. Human antibodies can also be made by hybridoma-based methods known in the art, e.g., using known human myeloma and mouse-human heteromyeloma cell lines for the production of human monoclonal antibodies. Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies of the disclosure may be isolated by screening combinatorial libraries for antibodies with the desired activity or activities. For example, a variety of methods are known in the art for generating phage display libraries and screening such libraries for antibodies possessing the desired binding characteristics. In certain phage display methods, repertoires of VH and VL genes are separately cloned by polymerase chain reaction (PCR) and recombined randomly in phage libraries, which can then be screened for antigen-binding phage. Phage typically display antibody fragments, either as single-chain Fv (scFv) fragments or as Fab fragments. Libraries from immunized sources provide high-affinity antibodies to the immunogen without the requirement of constructing hybridomas. Alternatively, a naive antibody repertoire can be cloned (e.g., from human) to provide a single source of antibodies to a wide range of non-self and also self antigens without any immunization. Naive libraries can also be made synthetically by cloning un-rearranged V-gene segments from stem cells, and using PCR primers containing random sequences to amplify the highly variable CDR3 regions and to accomplish rearrangement in vitro. Antibodies or antibody fragments isolated from human antibody libraries are considered human antibodies or human antibody fragments herein.

In certain embodiments, an antibody provided herein is a multispecific antibody, e.g., a bispecific antibody. Multispecific antibodies are monoclonal antibodies that have binding specificities for at least two different sites or at least two different antigens. For example, one of the binding specificities can be to an immune checkpoint protein of the present disclosure, and the other can be to any other antigen, e.g., a BCOR or BCORL1 polypeptide provided herein. Multispecific antibodies can be prepared as full length antibodies or as antibody fragments. Techniques for making multispecific antibodies are known in the art and include, but are not limited to, recombinant co-expression of two immunoglobulin heavy chain-light chain pairs having different specificities, and "knob-in-hole" engineering. Multispecific antibodies may also be made by engineering electrostatic steering effects (e.g., by introducing mutations in the constant region) for making heterodimeric Fcs; cross-linking two or more antibodies or fragments; using leucine zippers to produce bispecific antibodies; using "diabody" technology for making bispecific antibody fragments; using single-chain Fv (scFv) dimers; and preparing trispecific antibodies. Engineered antibodies with three or more functional antigen binding sites, including "Octopus antibodies," are also included in the disclosure. Antibodies or antibody fragments of the disclosure also include "Dual Acting FAbs" or "DAF," e.g., comprising an antigen binding site that binds to an immune checkpoint protein as well as another, different antigen.

In certain embodiments, amino acid sequence variants of the antibodies provided herein are contemplated. For example, it may be desirable to improve the binding affinity and/or other biological properties of the antibody. Amino acid sequence variants of an antibody of the disclosure may be prepared by introducing appropriate modifications into the nucleotide sequence encoding the antibody, or by peptide synthesis. Such modifications include, for example, deletions, and/or insertions, and/or substitutions of residues within the amino acid sequences of the antibody. Any combination of deletions, insertions, and substitutions can be made to arrive at the final antibody, provided that the final antibody possesses the desired characteristics, e.g., antigen-binding.

In certain embodiments, antibody variants having one or more amino acid substitutions are provided. Sites of interest for substitutional mutagenesis include the HVRs and FRs. Amino acid substitutions may be introduced into an antibody of interest, and the products may be screened for a desired activity, e.g., retained/improved antigen binding, decreased immunogenicity, or improved or reduced antibody-dependent cell-mediated cytotoxicity (ADCC) and/or complement-dependent cytotoxicity (CDC).

In certain embodiments, an antibody of the present disclosure is altered to increase or to decrease the extent to which the antibody is glycosylated. Addition or deletion of glycosylation sites to an antibody may be conveniently accomplished by altering the amino acid sequence of the antibody, such that one or more glycosylation sites is created or removed. Antibody variants having bisected oligosaccharides are further provided, e.g., in which a biantennary oligosaccharide attached to the Fc region of the antibody is bisected by GlcNAc. In some embodiments, antibody variants of the disclosure may have increased fucosylation. In some embodiments, antibody variants of the disclosure may have reduced fucosylation. In some embodiments, antibody variants of the disclosure may have improved ADCC function. In some embodiments, antibody variants of the disclosure may have decreased ADCC function. Antibody variants with at least one galactose residue in the oligosaccharide attached to the Fc region are also provided. Such antibody variants may have improved CDC function. In some embodiments, antibody variants of the disclosure may have increased CDC function. In some embodiments, antibody variants of the disclosure may have decreased CDC function.

In certain embodiments, one or more amino acid modifications may be introduced into the Fc region of an antibody of the present disclosure, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the present disclosure contemplates an antibody variant that possesses some but not all effector functions, which make it a desirable candidate for applications in which the half-life of the antibody in vivo is important, yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc-gamma-R binding (hence likely lacking ADCC activity), but retains FcRn binding ability. The primary cells that mediate ADCC, e.g., NK cells, express Fc-gamma-RIII only, whereas monocytes express Fc-gamma-RI, Fc-gamma-RII and Fc-gamma-RIII. Antibodies with reduced effector function include those with substitution of one or more of Fc region residues 238, 265, 269, 270, 297, 327 and 329. Such Fc mutants include Fc mutants with substitutions at two or more of amino acid positions 265, 269, 270, 297 and 327, including the so-called "DANA" Fc mutant with substitutions of residues 265 and 297 to alanine. Antibody variants with improved or diminished binding to FcRs are also included in the disclosure. In certain embodiments, an antibody variant comprises an Fc region with one or more amino acid substitutions that improve ADCC, e.g., substitutions at positions 298, 333, and/or 334 of the Fc region. In some embodiments, number of Fc region residues is according to EU numbering of residues. In some embodiments, alterations are made in the Fc region that result in altered (i.e., either improved or diminished) C1q binding and/or CDC. In some embodiments, antibodies of the disclosure include antibodies with increased half-lives and improved binding to the neonatal Fc receptor (FcRn), e.g., comprising one or more substitutions that improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434. See, also, Duncan & Winter, *Nature* 322:73840 (1988); U.S. Pat. Nos. 5,648,260; 5,624,821; and WO 94/29351 for other examples of Fc region variants.

In certain embodiments, an antibody provided herein is a cysteine-engineered antibody, e.g., "thioMAb," in which one or more residues of the antibody are substituted with cysteine residues. In some embodiments, the substituted residues occur at accessible sites of the antibody. By substituting those residues with cysteine, reactive thiol groups are thereby positioned at accessible sites of the antibody, and may be used to conjugate the antibody to other moieties, such as drug moieties or linker-drug moieties, e.g., to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine-engineered antibodies may be generated using any suitable method known in the art.

In some embodiments, an antibody or antibody fragment provided herein comprises a label or a tag. In some embodiments, the label or tag is a radiolabel, a fluorescent label, an enzymatic label, a sequence tag, biotin, or other ligands. Examples of labels or tags include, but are not limited to, 6×His-tag, biotin-tag, Glutathione-S-transferase (GST)-tag, green fluorescent protein (GFP)-tag, c-myc-tag, FLAG-tag, Thioredoxin-tag, Glu-tag, Nus-tag, V5-tag, calmodulin-binding protein (CBP)-tag, Maltose binding protein (MBP)-tag, Chitin-tag, alkaline phosphatase (AP)-tag, HRP-tag, Biotin Caboxyl Carrier Protein (BCCP)-tag, Calmodulin-tag, S-tag, Strep-tag, haemoglutinin (HA)-tag, digoxigenin (DIG)-tag, DsRed, RFP, Luciferase, Short Tetracysteine Tags, Halo-tag, and Nus-tag. In some embodiments, the label or tag comprises a detection agent, such as a fluorescent molecule or an affinity reagent or tag.

In some embodiments, an antibody or antibody fragment provided herein is conjugated to a drug molecule, e.g., an anti-cancer agent described herein, or a cytotoxic agent such as mertansine or monomethyl auristatin E (MMAE).

In certain embodiments, an antibody or antibody fragment provided herein may be further modified to contain additional nonproteinaceous moieties. Such moieties may be suitable for derivatization of the antibody, e.g., including but not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyamino acids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, polyethylene glycol propionaldehyde, and mixtures thereof. The polymers may be of any molecular weight, and may be branched or unbranched. The number of polymers attached to the antibody may vary, and if more than one polymer is attached, the polymers can be the same or different molecules. In general, the number and/or type of polymers used for derivatization can be determined based on considerations including, but not limited to, the particular properties or functions of the antibody to be improved, or whether the antibody derivative will be used in a therapy under defined conditions. In some embodiments, provided herein are antibodies conjugated to carbon nanotubes, e.g., for use in methods to selectively heat the antibody using radiation to a temperature at which cells proximal to the antibody are killed.

In some embodiments, the methods provided herein comprise generating a report, and/or providing a report to party.

In some embodiments, a report according to the present disclosure comprises information about one or more of: a BCOR or BCORL1 nucleic acid molecule or polypeptide of the disclosure; a cancer of the disclosure, e.g., comprising a BCOR or BCORL1 nucleic acid molecule or polypeptide of the disclosure; or a treatment, a therapy, or one or more treatment options for an individual having a cancer, such as a cancer of the disclosure (e.g., comprising a BCOR or BCORL1 nucleic acid molecule or polypeptide described herein).

In some embodiments, a report according to the present disclosure comprises information about the presence or absence of a BCOR or BCORL1 nucleic acid molecule or polypeptide of the disclosure in a sample obtained from an individual, such as an individual having a cancer, e.g., a cancer provided herein. In one embodiment, a report according to the present disclosure indicates that a BCOR or BCORL1 nucleic acid molecule or polypeptide of the disclosure is present in a sample obtained from the individual. In one embodiment, a report according to the present disclosure indicates that a BCOR or BCORL1 nucleic acid molecule or polypeptide of the disclosure is not present in a sample obtained from the individual. In one embodiment, a report according to the present disclosure indicates that a BCOR or BCORL1 nucleic acid molecule or polypeptide of the disclosure has been detected in a sample obtained from the individual. In one embodiment, a report according to the present disclosure indicates that a BCOR or BCORL1 nucleic acid molecule or polypeptide of the disclosure has not been detected in a sample obtained from the individual. In some embodiments, the report comprises an identifier for the individual from which the sample was obtained.

In some embodiments, the report includes information on the role of a BCOR or BCORL1 nucleic acid molecule or polypeptide of the disclosure, or its wild type counterparts, in disease, such as in cancer. Such information can include one or more of: information on prognosis of a cancer, such as a cancer provided herein, e.g., comprising a BCOR or BCORL1 nucleic acid molecule or polypeptide described herein; information on resistance of a cancer, such as a cancer provided herein, e.g., comprising a BCOR or BCORL1 nucleic acid molecule or polypeptide described herein, to one or more treatments; information on potential or suggested therapeutic options (e.g., such as an anti-cancer therapy provided herein, or a treatment selected or identified according to the methods provided herein); or information on therapeutic options that should be avoided. In some embodiments, the report includes information on the likely effectiveness, acceptability, and/or advisability of applying a therapeutic option (e.g., such as an anti-cancer therapy provided herein, or a treatment selected or identified according to the methods provided herein) to an individual having a cancer, such as a cancer provided herein, e.g., comprising a BCOR or BCORL1 nucleic acid molecule or polypeptide described herein and identified in the report. In some embodiments, the report includes information or a recommendation on the administration of a treatment (e.g., an anti-cancer therapy provided herein, or a treatment selected or identified according to the methods provided herein). In some embodiments, the information or recommendation includes the dosage of the treatment and/or a treatment regimen (e.g., in combination with other treatments, such as a second therapeutic agent). In some embodiments, the report comprises information or a recommendation for at least one, at least two, at least three, at least four, at least five, at least six, at least seven, at least eight, at least nine, at least ten, or more treatments.

Also provided herein are methods of generating a report according to the present disclosure. In some embodiments, a report according to the present disclosure is generated by a method comprising one or more of the following steps: obtaining a sample, such as a sample described herein, from an individual, e.g., an individual having a cancer, such as a cancer provided herein; detecting a BCOR or BCORL1 nucleic acid molecule or polypeptide of the disclosure in the sample, or acquiring knowledge of the presence of a BCOR or BCORL1 nucleic acid molecule or polypeptide of the disclosure in the sample; and generating a report. In some embodiments, a report generated according to the methods provided herein comprises one or more of: information about the presence or absence of a BCOR or BCORL1 nucleic acid molecule or polypeptide of the disclosure in the sample; an identifier for the individual from which the sample was obtained; information on the role of a BCOR or BCORL1 nucleic acid molecule or polypeptide of the disclosure, or its wild type counterparts, in disease (e.g., such as in cancer); information on prognosis, resistance, or potential or suggested therapeutic options (such as an anti-cancer therapy provided herein, or a treatment selected or identified according to the methods provided herein); information on the likely effectiveness, acceptability, or the advisability of applying a therapeutic option (such as an anti-cancer therapy provided herein, or a treatment selected or identified according to the methods provided herein) to the individual; a recommendation or information on the administration of a treatment (such as an anti-cancer therapy provided herein, or a treatment selected or identified according to the methods provided herein); or a recommendation or information on the dosage or treatment regimen of a treatment (such as an anti-cancer therapy provided herein, or a treatment selected or identified according to the methods provided herein), e.g., in combination with other treatments (e.g., a second therapeutic agent). In some embodiments, the report generated is a personalized cancer report.

A report according to the present disclosure may be in an electronic, web-based, or paper form. The report may be provided to an individual or a patient (e.g., an individual or a patient with a cancer, such as a cancer provided herein, e.g., comprising a BCOR or BCORL1 nucleic acid molecule or polypeptide of the disclosure), or to an individual or entity other than the individual or patient (e.g., other than the individual or patient with the cancer), such as one or more of a caregiver, a physician, an oncologist, a hospital, a clinic, a third party payor, an insurance company, or a government entity. In some embodiments, the report is provided or delivered to the individual or entity within any of about 1 day or more, about 7 days or more, about 14 days or more, about 21 days or more, about 30 days or more, about 45 days or more, or about 60 days or more from obtaining a sample from an individual (e.g., an individual having a cancer). In some embodiments, the report is provided or delivered to an individual or entity within any of about 1 day or more, about 7 days or more, about 14 days or more, about 21 days or more, about 30 days or more, about 45 days or more, or about 60 days or more from detecting a BCOR or BCORL1 nucleic acid molecule or polypeptide of the disclosure in a sample obtained from an individual (e.g., an individual having a cancer). In some embodiments, the report is provided or delivered to an individual or entity within any of about 1 day or more, about 7 days or more, about 14 days or more, about 21 days or more, about 30 days or more, about 45 days or more, or about 60 days or more from acquiring knowledge of the presence of a BCOR or BCORL1 nucleic acid molecule or polypeptide of the disclosure in a sample obtained from an individual (e.g., an individual having a cancer).

The method steps of the methods described herein are intended to include any suitable method of causing one or more other parties or entities to perform the steps, unless a different meaning is expressly provided or otherwise clear from the context. Such parties or entities need not be under the direction or control of any other party or entity, and need not be located within a particular jurisdiction. Thus, for example, a description or recitation of "adding a first number to a second number" includes causing one or more parties or entities to add the two numbers together. For example, if person X engages in an arm's length transaction with person Y to add the two numbers, and person Y indeed adds the two numbers, then both persons X and Y perform the step as recited: person Y by virtue of the fact that he actually added the numbers, and person X by virtue of the fact that he caused person Y to add the numbers. Furthermore, if person X is located within the United States and person Y is located outside the United States, then the method is performed in the United States by virtue of person X's participation in causing the step to be performed.

Software, Systems, and Devices

In some other aspects, provided herein are non-transitory computer-readable storage media. In some embodiments, the non-transitory computer-readable storage media comprise one or more programs for execution by one or more processors of a device, the one or more programs including instructions which, when executed by the one or more processors, cause the device to perform the method according to any of the embodiments described herein.

Figure 11:
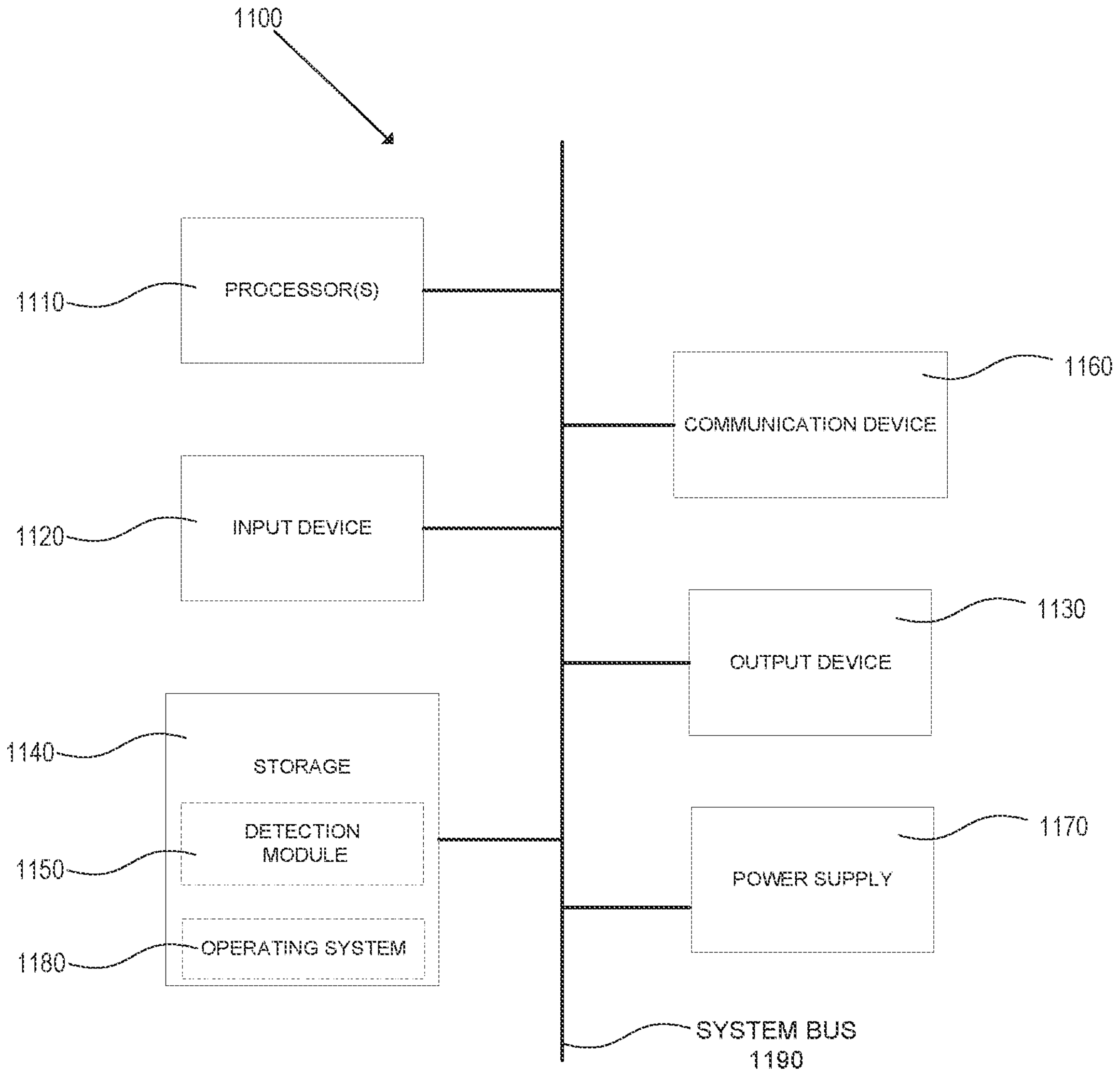
FIG. 11 depicts an exemplary device, in accordance with some embodiments.

FIG. 11 illustrates an example of a computing device in accordance with one embodiment. Device 1100 can be a host computer connected to a network. Device 300 can be a client computer or a server. As shown in FIG. 11, device 1100 can be any suitable type of microprocessor-based device, such as a personal computer, workstation, server or handheld computing device (portable electronic device) such as a phone or tablet. The device can include, for example, one or more of processor(s) 1110, input device 1120, output device 1130, storage 1140, communication device 1160, power supply 1170, operating system 1180, and system bus 1190. Input device 1120 and output device 1130 can generally correspond to those described herein, and can either be connectable or integrated with the computer.

Input device 1120 can be any suitable device that provides input, such as a touch screen, keyboard or keypad, mouse, or voice-recognition device. Output device 1130 can be any suitable device that provides output, such as a touch screen, haptics device, or speaker.

Storage 1140 can be any suitable device that provides storage (e.g., an electrical, magnetic or optical memory including a RAM (volatile and non-volatile), cache, hard drive, or removable storage disk). Communication device 1160 can include any suitable device capable of transmitting and receiving signals over a network, such as a network interface chip or device. The components of the computer can be connected in any suitable manner, such as via a wired media (e.g., a physical bus, ethernet, or any other wire transfer technology) or wirelessly (e.g., Bluetooth®, Wi-Fi®, or any other wireless technology). For example, in FIG. 11, the components are connected by System Bus 1190.

Detection module 1150, which can be stored as executable instructions in storage 1140 and executed by processor(s) 1110, can include, for example, the processes that embody the functionality of the present disclosure (e.g., as embodied in the devices as described herein).

Detection module 1150 can also be stored and/or transported within any non-transitory computer-readable storage medium for use by or in connection with an instruction execution system, apparatus, or device, such as those described herein, that can fetch instructions associated with the software from the instruction execution system, apparatus, or device and execute the instructions. In the context of this disclosure, a computer-readable storage medium can be any medium, such as storage 1140, that can contain or store processes for use by or in connection with an instruction execution system, apparatus, or device. Examples of computer-readable storage media may include memory units like hard drives, flash drives and distribute modules that operate as a single functional unit. Also, various processes described herein may be embodied as modules configured to operate in accordance with the embodiments and techniques described above. Further, while processes may be shown and/or described separately, those skilled in the art will appreciate that the above processes may be routines or modules within other processes.

Detection module 1150 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Figure 12:
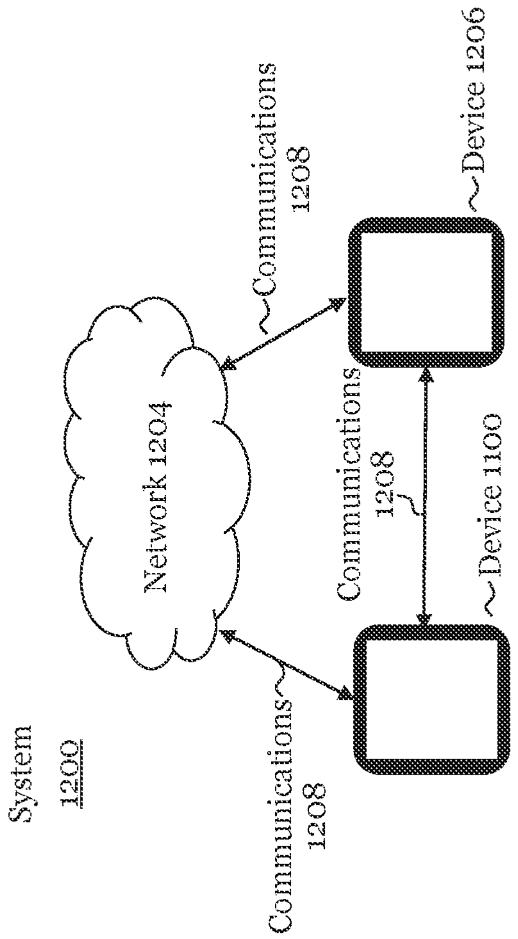
FIG. 12 depicts an exemplary system, in accordance with some embodiments.

Device 1100 may be connected to a network (e.g., Network 404, as shown in FIG. 12 and/or described below), which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1100 can implement any operating system (e.g., Operating System 1180) suitable for operating on the network. Detection module 1150 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example. In some embodiments, Operating System 1180 is executed by one or more processors, e.g., Processor(s) 1110.

Device 1100 can further include Power Supply 1170, which can be any suitable power supply.

FIG. 12 illustrates an example of a computing system in accordance with one embodiment. In System 1200, Device 1100 (e.g., as described above and illustrated in FIG. 11) is connected to Network 1204, which is also connected to Device 1206. In some embodiments, Device 1206 is a sequencer. Exemplary sequencers can include, without limitation, Roche/454's Genome Sequencer (GS) FLX System, Illumina/Solexa's Genome Analyzer (GA), Illumina's HiSeq 2500, HiSeq 3000, HiSeq 4000 and NovaSeq 6000 Sequencing Systems, Life/APG's Support Oligonucleotide Ligation Detection (SOLiD) system, Polonator's G.007 system, Helicos BioSciences' HeliScope Gene Sequencing system, or Pacific Biosciences' PacBio RS system. Devices 1100 and 1206 may communicate, e.g., using suitable communication interfaces via Network 1204, such as a Local Area Network (LAN), Virtual Private Network (VPN), or the Internet. In some embodiments, Network 1204 can be, for example, the Internet, an intranet, a virtual private network, a cloud network, a wired network, or a wireless network. Devices 1100 and 1206 may communicate, in part or in whole, via wireless or hardwired communications, such as Ethernet, IEEE 802.11b wireless, or the like. Additionally, Devices 1100 and 1206 may communicate, e.g., using suitable communication interfaces, via a second network, such as a mobile/cellular network. Communication between Devices 1100 and 1206 may further include or communicate with various servers such as a mail server, mobile server, media server, telephone server, and the like. In some embodiments, Devices 1100 and 1206 can communicate directly (instead of, or in addition to, communicating via Network 1204), e.g., via wireless or hardwired communications, such as Ethernet, IEEE 802.11b wireless, or the like. In some embodiments, Devices 1100 and 1206 communicate via Communications 1208, which can be a direct connection or can occur via a network (e.g., Network 1204).

One or all of Devices 1100 and 1206 generally include logic (e.g., http web server logic) or is programmed to format data, accessed from local or remote databases or other sources of data and content, for providing and/or receiving information via Network 404 according to various examples described herein.

Figure 13:
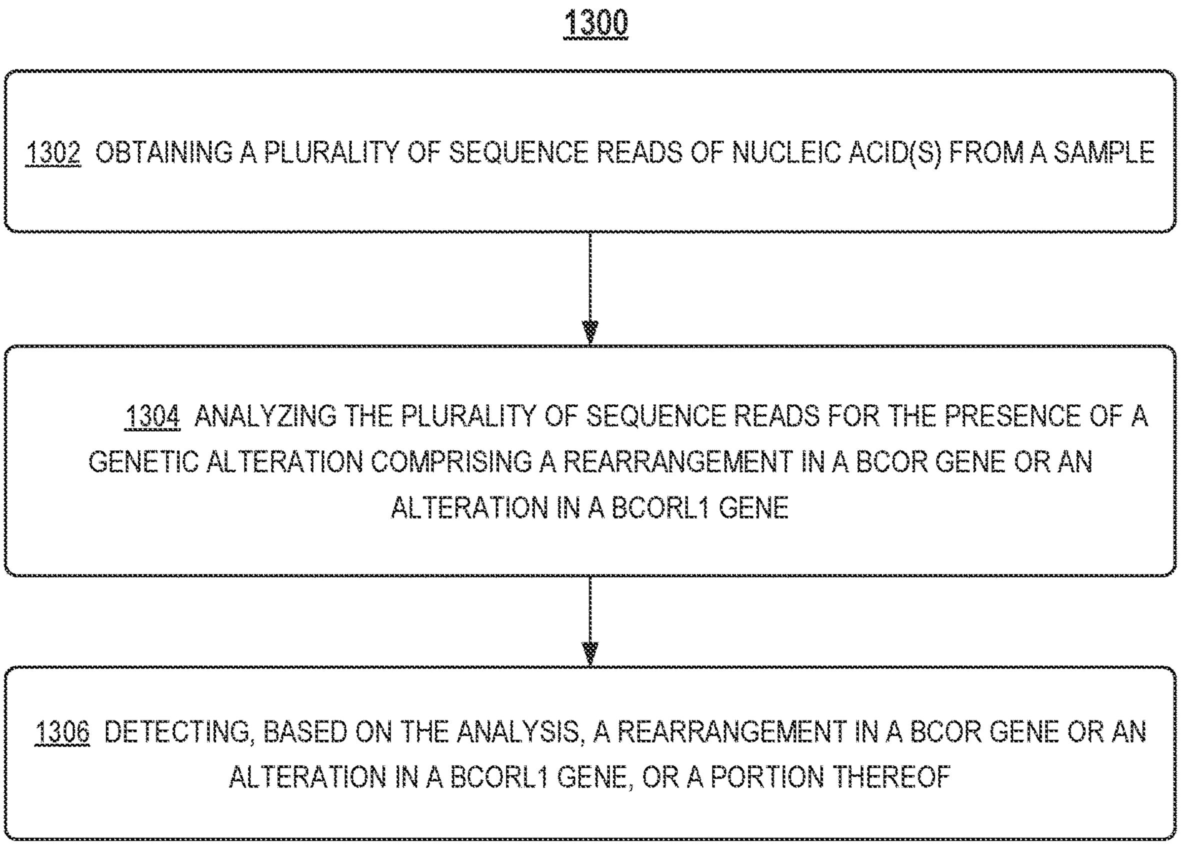
FIG. 13 depicts a block diagram of an exemplary process for detecting a rearrangement in a BCOR gene or an alteration in a BCORL1 gene (or of a portion thereof), in accordance with some embodiments.

FIG. 13 illustrates an exemplary process 1300 for detecting a rearrangement in a BCOR gene or an alteration in a BCORL1 gene, or a portion thereof, in accordance with some embodiments. Process 1300 is performed, for example, using one or more electronic devices implementing a software program. In some examples, process 1300 is performed using a client-server system, and the blocks of process 1300 are divided up in any manner between the server and a client device. In other examples, the blocks of process 1300 are divided up between the server and multiple client devices. Thus, while portions of process 1300 are described herein as being performed by particular devices of a client-server system, it will be appreciated that process 1300 is not so limited. In some embodiments, the executed steps can be executed across many systems, e.g., in a cloud environment. In other examples, process 1300 is performed using only a client device or only multiple client devices. In process 1300, some blocks are, optionally, combined, the order of some blocks is, optionally, changed, and some blocks are, optionally, omitted. In some examples, additional steps may be performed in combination with the process 1300. Accordingly, the operations as illustrated (and described in greater detail below) are exemplary by nature and, as such, should not be viewed as limiting.

At block 1302, a plurality of sequence reads of one or more nucleic acids is obtained, wherein the one or more nucleic acids are derived from a sample obtained from an individual. In some embodiments, the sequence reads are obtained using a sequencer, e.g., as described herein or otherwise known in the art. In some embodiments, the nucleic acid(s) comprise one or more nucleic acids corresponding to a BCOR or BCORL1 gene of the present disclosure, or portion thereof. Optionally, prior to obtaining the sequence reads, the sample is purified, enriched (e.g., for nucleic acid(s) corresponding to a BCOR or BCORL1 gene of the present disclosure, or portion thereof), and/or subjected to PCR amplification. At block 1304, an exemplary system (e.g., one or more electronic devices) analyzes the plurality of sequence reads for the presence of a genetic alteration comprising a rearrangement in a BCOR gene and/or an alteration in a BCORL1 gene, or a portion thereof. At block 1306, the system detects (e.g., based on the analysis) a rearrangement in a BCOR gene or an alteration in a BCORL1 gene, or a portion thereof, in the sample.

Targeted Therapeutics

Certain aspects of the present disclosure relate to targeted therapeutics, as well as methods for identifying an individual who may benefit from treatment with a targeted therapeutic, methods for selecting a targeted therapeutic for treating an individual, methods for identifying a targeted therapeutic as a treatment option, methods for treating or delaying progression of cancer comprising administration of a targeted therapeutic, uses for targeted therapeutics (e.g., in methods of treating or delaying progression of cancer in an individual, or in methods for manufacturing a medicament for treating or delaying progression of cancer), and the like. These methods and uses are based, at least in part, on the observations demonstrated herein that certain genetic mutations were found in tumors harboring BCOR gene rearrangements/gene fusions, e.g., in uterine sarcoma. For example, a high frequency of genomic alterations leading to the activation of the cyclin D1-CDK4 kinase (e.g., via CDK4 amplification, CCND2 amplification or CDKN2A loss), often coincident with MDM2 amplification, was observed in BCOR-rearranged uterine sarcomas. In addition, targetable genomic alterations such as alterations in receptor kinases, inactivating truncating mutations in NF1 or NF2, and inactivating truncating mutations in PTCH1 were also identified in BCOR-rearranged uterine sarcomas. Without wishing to be bound to theory, it is thought that these genomic alterations can identify patients that would benefit from appropriate targeted therapeutics, including but not limited to CDK inhibitors, MDM2 inhibitors, tyrosine kinase inhibitors (TKIs), MEK inhibitors, mTOR inhibitors, and Hh inhibitors.

In some embodiments, the targeted therapeutic comprises a small molecule (e.g., chemical inhibitor) that inhibits one or more activities (e.g., enzymatic activities) of its target. In some embodiments, the targeted therapeutic comprises an antibody or other biologic that binds to and inhibits one or more activities of its target, binds to and inhibits expression (e.g., cell surface expression) of its target, and/or binds to and inhibits one or more activities of a cell expressing its target (e.g., by inducing antibody-dependent cellular cytotoxicity, ADCC, or phagocytosis, ADCP). In some embodiments, the targeted therapeutic comprises a nucleic acid that inhibits expression of its target, e.g., an antisense oligonucleotide, miRNA, siRNA, morpholino, CRISPR-based therapeutic, and the like.

In some embodiments (e.g., for treatment of tumors comprising one or more genomic alterations leading to increased expression and/or activity of Cyclin D/Cdk4 complex), the targeted therapeutic is a cyclin-dependent kinase (CDK) inhibitor. In some embodiments, the CDK inhibitor inhibits CDK4. In some embodiments, the CDK inhibitor inhibits Cyclin D/CDK4. In some embodiments, the targeted therapeutic/CDK inhibitor is (a) a small molecule that inhibits one or more enzymatic activities of CDK4, (b) an antibody that inhibits one or more activities of CDK4 (e.g., by binding to and inhibiting one or more activities of CDK4, binding to and inhibiting expression of CDK4, and/or binding to and inhibiting one or more activities of a cell expressing CDK4, such as by inducing antibody-dependent cellular cytotoxicity, ADCC, or phagocytosis, ADCP), or (c) a nucleic acid that inhibits expression of CDK4 (e.g., an antisense oligonucleotide, miRNA, siRNA, morpholino, CRISPR-based therapeutic, and the like). In some embodiments, the CDK inhibitor inhibits CDK4 and CDK6. In some embodiments, the CDK inhibitor is a small molecule inhibitor of CDK4 (e.g., a competitive or non-competitive inhibitor). Non-limiting examples of CDK inhibitors include palbociclib, ribociclib, and abemaciclib, as well as pharmaceutically acceptable salts thereof.

In some embodiments (e.g., for treatment of tumors comprising one or more genomic alterations leading to increased expression and/or activity of MDM2), the targeted therapeutic is a murine double minute 2 homolog (MDM2) inhibitor. In some embodiments, the targeted therapeutic/MDM2 inhibitor is (a) a small molecule that inhibits one or more activities of MDM2 (e.g., binding to p53), (b) an antibody that inhibits one or more activities of MDM2 (e.g., by binding to and inhibiting one or more activities of MDM2, binding to and inhibiting expression of MDM2, and/or binding to and inhibiting one or more activities of a cell expressing MDM2, such as by inducing antibody-dependent cellular cytotoxicity, ADCC, or phagocytosis, ADCP), or (c) a nucleic acid that inhibits expression of MDM2 (e.g., an antisense oligonucleotide, miRNA, siRNA, morpholino, CRISPR-based therapeutic, and the like). In some embodiments, the MDM2 inhibitor is a small molecule inhibitor of MDM2 (e.g., a competitive or non-competitive inhibitor). Non-limiting examples of MDM2 inhibitors include nutlin-3a, RG7112, idasanutlin (RG7388), AMG-232, MI-63, MI-291, MI-391, MI-77301 (SAR405838), APG-115, DS-3032b, NVP-CGM097, and HDM-201 (siremadlin), as well as pharmaceutically acceptable salts thereof. In some embodiments, the MDM2 inhibitor inhibits or disrupts interaction between MDM2 and p53. In some embodiments, an MDM2 inhibitor is administered with another therapeutic agent, including without limitation an antimetabolite, DNA-damaging agent, or platinum-containing therapeutic (e.g., 5-azacitadine, 5-fluorouracil, acadesine, busulfan, carboplatin, cisplatin, chlorambucil, CPT-11, cytarabine, daunorubicin, decitabine, doxorubicin, etoposide, fludarabine, gemcitabine, idarubicin, radiation, oxaliplatin, temozolomide, topotecan, trabectedin, GSK2830371, or rucaparib); a pro-apoptotic agent (e.g., a BCL2 inhibitor or downregulator, SMAC mimetic, or TRAIL agonist such as ABT-263, ABT-737, oridonin, venetoclax, combination of venetoclax and an anti-CD20 antibody such as obinutuzumab or rituximab, 1396-11, ABT-10, SM-164, D269H/E195R, or rhTRAIL); a tyrosine kinase inhibitor (e.g., as described herein); an inhibitor of RAS, RAF, MEK, or the MAPK pathway (e.g., AZD6244, dabrafenib, LGX818, PD0325901, pimasertib, trametinib, or vemurafenib); an inhibitor of PI3K, mTOR, or Akt (e.g., as described herein); a CDK inhibitor (e.g., as described herein); a PKC inhibitor (e.g., LXS196 or sotrastaurin); an antibody-based therapeutic (e.g., an anti-PD-1 or anti-PDL1 antibody such as atezolizumab, pembrolizumab, nivolumab, or spartalizumab; an anti-CD20 antibody such as obinutuzumab or rituximab; or an anti-DRS antibody such as drozitumab); a proteasome inhibitor (e.g., bortezomib, carfilzomib, ixazomib, or MG-132); an HDAC inhibitor (e.g., SAHA or VPA); an antibiotic (e.g., actinomycin D); a zinc-containing therapeutic (e.g., zinc or ZMC1); an HSP inhibitor (e.g., geldanamycin); an ATPase inhibitor (e.g., archazolid); a mitotic inhibitor (e.g., paclitaxel or vincristine); metformin; methotrexate; tanshinone IIA; and/or P5091.

In some embodiments, treatment with a targeted therapeutic as described herein comprises administration of a CDK inhibitor of the present disclosure and an MDM2 inhibitor of the present disclosure, e.g., a combination of a CDK inhibitor and an MDM2 inhibitor.

In some embodiments (e.g., for treatment of tumors comprising amplification of a gene selected from the group consisting of PDGFRA, KDR, ERBB3, and KIT), the targeted therapeutic is a tyrosine kinase inhibitor. In some embodiments, the tyrosine kinase inhibitor inhibits one or more activities of PDGFRA, KDR, ERBB3 (also known as HER3), and KIT. In some embodiments, the targeted therapeutic/tyrosine kinase inhibitor is (a) a small molecule that inhibits one or more enzymatic activities of a tyrosine kinase, (b) an antibody that inhibits one or more activities of a tyrosine kinase (e.g., by binding to and inhibiting one or more activities of the tyrosine kinase, binding to and inhibiting expression, such as cell surface expression, of the tyrosine kinase, and/or binding to and inhibiting one or more activities of a cell expressing the tyrosine kinase, such as by inducing antibody-dependent cellular cytotoxicity, ADCC, or phagocytosis, ADCP), or (c) a nucleic acid that inhibits expression of a tyrosine kinase (e.g., an antisense oligonucleotide, miRNA, siRNA, morpholino, CRISPR-based therapeutic, and the like). In some embodiments, the tyrosine kinase inhibitor is a small molecule inhibitor of a tyrosine kinase (e.g., a competitive or non-competitive inhibitor). Non-limiting examples of tyrosine kinase inhibitors include imatinib, crenolanib, linifanib, ninetedanib, axitinib, dasatinib, imetelstat, midostaurin, pazopanib, sorafenib, sunitinb, motesanib, masitinib, vatalanib, cabozanitinib, tivozanib, OSI-930, Ki8751, telatinib, dovitinib, tyrphostin AG 1296, and amuvatinib, as well as pharmaceutically acceptable salts thereof.

In some embodiments (e.g., for treatment of tumors comprising a loss-of-function mutation in NF1 or NF2), the targeted therapeutic is a mitogen-activated protein kinase (MEK) inhibitor. In some embodiments, the MEK inhibitor inhibits one or more activities of MEK1 and/or MEK2. In some embodiments, the targeted therapeutic/MEK inhibitor is (a) a small molecule that inhibits one or more enzymatic activities of MEK, (b) an antibody that inhibits one or more activities of MEK (e.g., by binding to and inhibiting one or more activities of MEK, binding to and inhibiting expression of MEK, and/or binding to and inhibiting one or more activities of a cell expressing MEK, such as by inducing antibody-dependent cellular cytotoxicity, ADCC, or phagocytosis, ADCP), or (c) a nucleic acid that inhibits expression of MEK (e.g., an antisense oligonucleotide, miRNA, siRNA, morpholino, CRISPR-based therapeutic, and the like). In some embodiments, the MEK inhibitor is a small molecule inhibitor of MEK (e.g., a competitive or non-competitive inhibitor). Non-limiting examples of MEK inhibitors include trametinib, cobimetinib, binimetinib, CI-1040, PD0325901, selumetinib, AZD8330, TAK-733, GDC-0623, refametinib, pimasertib, RO4987655, RO5126766, WX-544, and HL-085, as well as pharmaceutically acceptable salts thereof. In some embodiments, the targeted therapeutic inhibits one or more activities of the Raf/MEK/ERK pathway, including inhibitors of Raf, MEK, and/or ERK.

In some embodiments (e.g., for treatment of tumors comprising a loss-of-function mutation in NF1 or NF2), the targeted therapeutic is a mammalian target of rapamycin (mTOR) inhibitor. In some embodiments, the targeted therapeutic/mTOR inhibitor is (a) a small molecule that inhibits one or more enzymatic activities of mTOR, (b) an antibody that inhibits one or more activities of mTOR (e.g., by binding to and inhibiting one or more activities of mTOR, binding to and inhibiting expression of mTOR, and/or binding to and inhibiting one or more activities of a cell expressing mTOR, such as by inducing antibody-dependent cellular cytotoxicity, ADCC, or phagocytosis, ADCP), or (c) a nucleic acid that inhibits expression of mTOR (e.g., an antisense oligonucleotide, miRNA, siRNA, morpholino, CRISPR-based therapeutic, and the like). In some embodiments, the mTOR inhibitor is a small molecule inhibitor of mTOR (e.g., a competitive inhibitor, such as an ATP-competitive inhibitor, or a non-competitive inhibitor, such as a rapamycin analog). Non-limiting examples of mTOR inhibitors include temsirolimus, everolimus, ridaforolimus, dactolisib, GSK2126458, XL765, AZD8055, AZD2014, MLN128, PP242, NVP-BEZ235, LY3023414, PQR309, PKI587, and OSI027, as well as pharmaceutically acceptable salts thereof. In some embodiments, the targeted therapeutic inhibits one or more activities of the Akt/mTOR pathway, including inhibitors of Akt and/or mTOR.

In some embodiments (e.g., for treatment of tumors comprising a loss-of-function mutation in PIK3R1 or gain-of-function mutation in AKT1), the targeted therapeutic is a PI3K inhibitor or Akt inhibitor. In some embodiments, the PI3K inhibitor inhibits one or more activities of PI3K. In some embodiments, the targeted therapeutic/PI3K inhibitor is (a) a small molecule that inhibits one or more enzymatic activities of PI3K, (b) an antibody that inhibits one or more activities of PI3K (e.g., by binding to and inhibiting one or more activities of PI3K, binding to and inhibiting expression of PI3K, and/or binding to and inhibiting one or more activities of a cell expressing PI3K, such as by inducing antibody-dependent cellular cytotoxicity, ADCC, or phagocytosis, ADCP), or (c) a nucleic acid that inhibits expression of PI3K (e.g., an antisense oligonucleotide, miRNA, siRNA, morpholino, CRISPR-based therapeutic, and the like). In some embodiments, the PI3K inhibitor is a small molecule inhibitor of PI3K (e.g., a competitive or non-competitive inhibitor). Non-limiting examples of PI3K inhibitors include GSK2636771, bupardisib (BKM120), AZD8186, copanlisib (BAY80-6946), LY294002, PX-866, TGX115, TGX126, BEZ235, SF1126, idelalisib (GS-1101, CAL-101), pictilisib (GDC-094), GDC0032, IPI145, INK1117 (MLN1117), SAR260301, KIN-193 (AZD6482), duvelisib, GS-9820, GSK2636771, GDC-0980, AMG319, pazobanib, and alpelisib (BYL719, Piqray), as well as pharmaceutically acceptable salts thereof. In some embodiments, the AKT inhibitor inhibits one or more activities of AKT (e.g., AKT1). In some embodiments, the targeted therapeutic/AKT inhibitor is (a) a small molecule that inhibits one or more enzymatic activities of AKT1, (b) an antibody that inhibits one or more activities of AKT1 (e.g., by binding to and inhibiting one or more activities of AKT1, binding to and inhibiting expression of AKT1, and/or binding to and inhibiting one or more activities of a cell expressing AKT1, such as by inducing antibody-dependent cellular cytotoxicity, ADCC, or phagocytosis, ADCP), or (c) a nucleic acid that inhibits expression of AKT1 (e.g., an antisense oligonucleotide, miRNA, siRNA, morpholino, CRISPR-based therapeutic, and the like). In some embodiments, the AKT1 inhibitor is a small molecule inhibitor of AKT1 (e.g., a competitive or non-competitive inhibitor). Non-limiting examples of AKT1 inhibitors include GSK690693, GSK2141795 (uprosertib), GSK2110183 (afuresertib), AZD5363, GDC-0068 (ipatasertib), AT7867, CCT128930, MK-2206, BAY 1125976, AKT1 and AKT2-IN-1, perifosine, and VIII, as well as pharmaceutically acceptable salts thereof. In some embodiments, the AKT1 inhibitor is a pan-Akt inhibitor.

In some embodiments (e.g., for treatment of tumors comprising a loss-of-function mutation in a PTCH1 gene), the targeted therapeutic is a hedgehog (Hh) inhibitor. In some embodiments, the targeted therapeutic/Hh inhibitor is (a) a small molecule that inhibits one or more enzymatic activities of Hh, (b) an antibody that inhibits one or more activities of MEK (e.g., by binding to and inhibiting one or more activities of Hh, binding to and inhibiting expression of Hh, and/or binding to and inhibiting one or more activities of a cell expressing Hh, such as by inducing antibody-dependent cellular cytotoxicity, ADCC, or phagocytosis, ADCP), or (c) a nucleic acid that inhibits expression of Hh (e.g., an antisense oligonucleotide, miRNA, siRNA, morpholino, CRISPR-based therapeutic, and the like). In some embodiments, the Hh inhibitor is a small molecule inhibitor of Hh (e.g., a competitive or non-competitive inhibitor). Non-limiting examples of Hh inhibitors include sonidegib, vismodegib, erismodegib, saridegib, BMS833923, PF-04449913, and LY2940680, as well as pharmaceutically acceptable salts thereof.

Therapeutic formulations of the targeted therapeutics used in accordance with the present invention are prepared for storage by mixing the therapeutic having the desired degree of purity with optional pharmaceutically acceptable carriers, excipients, or stabilizers in the form of lyophilized formulations or aqueous solutions. For general information concerning formulations, see, e.g., Gilman et al. (eds.) The Pharmacological Bases of Therapeutics, 8th Ed., Pergamon Press, 1990; A. Gennaro (ed.), Remington's Pharmaceutical Sciences, 18th Edition, Mack Publishing Co., Pennsylvania, 1990; Avis et al. (eds.) Pharmaceutical Dosage Forms: Parenteral Medications Dekker, New York, 1993; Lieberman et al. (eds.) Pharmaceutical Dosage Forms: Tablets Dekker, New York, 1990; Lieberman et al. (eds.), Pharmaceutical Dosage Forms: Disperse Systems Dekker, New York, 1990; and Walters (ed.) Dermatological and Transdermal Formulations (Drugs and the Pharmaceutical Sciences), Vol 1 19, Marcel Dekker, 2002.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride, phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, for example, those with complementary activities that do not adversely affect each other. The type and effective amounts of such medicaments depend, for example, on the amount and type of antagonist present in the formulation, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPO™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

It is to be understood that any of the above articles of manufacture may include an immunoconjugate described herein in place of or in addition to an antibody-based targeted therapeutic.

In some embodiments, the methods of the present disclosure comprise administration of a therapeutic agent or anti-cancer therapy in addition to the targeted therapy of the present disclosure. In some embodiments, the anti-cancer therapy is a small molecule inhibitor, an antibody, a cellular therapy (i.e., a cell-based therapy), or a nucleic acid. In some embodiments, the anti-cancer therapy is a chemotherapeutic agent, an anti-hormonal agent, an antimetabolite chemotherapeutic agent, a kinase inhibitor, a peptide, a gene therapy, a vaccine, a platinum-based chemotherapeutic agent, an immunotherapy, an antibody, or a checkpoint inhibitor.

In some embodiments, the anti-cancer therapy comprises a heat shock protein (HSP) inhibitor, a MYC inhibitor, an HDAC inhibitor, an immunotherapy, a neoantigen, a vaccine, or a cellular therapy.

In some embodiments, the second anti-cancer agent includes one or more of an immune checkpoint inhibitor, a chemotherapy, a VEGF inhibitor, an Integrin β3 inhibitor, a statin, an EGFR inhibitor, an mTOR inhibitor, a PI3K inhibitor, a MAPK inhibitor, or a CDK4/6 inhibitor.

In some embodiments, the anti-cancer therapy comprises a kinase inhibitor. In some embodiments, the methods provided herein comprise administering to the individual a kinase inhibitor, e.g., in combination with another anti-cancer therapy. In some embodiments, the kinase inhibitor is crizotinib, alectinib, ceritinib, lorlatinib, brigatinib, ensartinib (X-396), repotrectinib (TPX-005), entrectinib (RXDX-101), AZD3463, CEP-37440, belizatinib (TSR-011), ASP3026, KRCA-0008, TQ-B3139, TPX-0131, or TAE684

(NVP-TAE684). Additional examples of ALK kinase inhibitors that may be used according to any of the methods provided herein are described in examples 3-39 of WO2005016894, which is incorporated herein by reference.

In some embodiments, the anti-cancer therapy comprises a heat shock protein (HSP) inhibitor. In some embodiments, the methods provided herein comprise administering to the individual an HSP inhibitor, e.g., in combination with another anti-cancer therapy. In some embodiments, the HSP inhibitor is a Pan-HSP inhibitor, such as KNK423. In some embodiments, the HSP inhibitor is an HSP70 inhibitor, such as cmHsp70.1, quercetin, VER155008, or 17-AAD. In some embodiments, the HSP inhibitor is a HSP90 inhibitor. In some embodiments, the HSP90 inhibitor is 17-AAD, Debio0932, ganetespib (STA-9090), retaspimycin hydrochloride (retaspimycin, IPI-504), AUY922, alvespimycin (KOS-1022, 17-DMAG), tanespimycin (KOS-953, 17-AAG), DS 2248, or AT13387 (onalespib). In some embodiments, the HSP inhibitor is an HSP27 inhibitor, such as Apatorsen (OGX-427).

In some embodiments, the anti-cancer therapy comprises a MYC inhibitor. In some embodiments, the methods provided herein comprise administering to the individual a MYC inhibitor, e.g., in combination with another anti-cancer therapy. In some embodiments, the MYC inhibitor is MYCi361 (NUCC-0196361), MYCi975 (NUCC-0200975), Omomyc (dominant negative peptide), ZINC16293153 (Min9), 10058-F4, JKY-2-169, 7594-0035, or inhibitors of MYC/MAX dimerization and/or MYC/MAX/DNA complex formation.

In some embodiments, the anti-cancer therapy comprises a histone deacetylase (HDAC) inhibitor. In some embodiments, the methods provided herein comprise administering to the individual an HDAC inhibitor, e.g., in combination with another anti-cancer therapy. In some embodiments, the HDAC inhibitor is belinostat (PXD101, Beleodaq®), SAHA (vorinostat, suberoylanilide hydroxamine, Zolinza®), panobinostat (LBH589, LAQ-824), ACY1215 (Rocilinostat), quisinostat (JNJ-26481585), abexinostat (PCI-24781), pracinostat (SB939), givinostat (ITF2357), resminostat (4SC-201), trichostatin A (TSA), MS-275 (etinostat), Romidepsin (depsipeptide, FK228), MGCD0103 (mocetinostat), BML-210, CAY10603, valproic acid, MC1568, CUDC-907, CI-994 (Tacedinaline), Pivanex (AN-9), AR-42, Chidamide (CS055, HBI-8000), CUDC-101, CHR-3996, MPT0E028, BRD8430, MRLB-223, apicidin, RGFP966, BG45, PCI-34051, C149 (NCC149), TMP269, Cpd2, T247, T326, LMK235, C1A, HPOB, Nexturastat A, Befexamac, CBHA, Phenylbutyrate, MC1568, SNDX275, Scriptaid, Merck60, PX089344, PX105684, PX117735, PX117792, PX117245, PX105844, compound 12 as described by Li et al., Cold Spring Harb Perspect Med (2016) 6(10):a026831, or PX117445.

In some embodiments, the anti-cancer therapy comprises a VEGF inhibitor. In some embodiments, the methods provided herein comprise administering to the individual a VEGF inhibitor, e.g., in combination with another anti-cancer therapy. In some embodiments, the VEGF inhibitor is Bevacizumab (Avastin®), BMS-690514, ramucirumab, pazopanib, sorafenib, sunitinib, golvatinib, vandetanib, cabozantinib, levantinib, axitinib, cediranib, tivozanib, lucitanib, semaxanib, nindentanib, regorafinib, or aflibercept.

In some embodiments, the anti-cancer therapy comprises an integrin β3 inhibitor. In some embodiments, the methods provided herein comprise administering to the individual an integrin β3 inhibitor, e.g., in combination with another anti-cancer therapy. In some embodiments, the integrin β3 inhibitor is anti-avb3 (clone LM609), cilengitide (EMD121974, NSC, 707544), an siRNA, GLPG0187, MK-0429, CNTO95, TN-161, etaracizumab (MEDI-522), intetumumab (CNTO95) (anti-alphaV subunit antibody), abituzumab (EMD 525797/DI17E6) (anti-alphaV subunit antibody), JSM6427, SJ749, BCH-15046, SCH221153, or SC56631. In some embodiments, the anti-cancer therapy comprises an αIIbβ3 integrin inhibitor. In some embodiments, the methods provided herein comprise administering to the individual an αIIbβ3 integrin inhibitor, e.g., in combination with another anti-cancer therapy. In some embodiments, the αIIbβ3 integrin inhibitor is abciximab, eptifibatide (Integrilin®), or tirofiban (Aggrastat®).

In some embodiments, the anti-cancer therapy comprises a statin or a statin-based agent. In some embodiments, the methods provided herein comprise administering to the individual a statin or a statin-based agent, e.g., in combination with another anti-cancer therapy. In some embodiments, the statin or statin-based agent is simvastatin, atorvastatin, fluvastatin, pitavastatin, pravastatin, rosuvastatin, or cerivastatin.

In some embodiments, the anti-cancer therapy comprises a MAPK inhibitor. In some embodiments, the methods provided herein comprise administering to the individual a MAPK inhibitor, e.g., in combination with another anti-cancer therapy. In some embodiments, the MAPK inhibitor is SB203580, SKF-86002, BIRB-796, SC-409, RJW-67657, BIRB-796, VX-745, R03201195, SB-242235, or MW181.

In some embodiments, the anti-cancer therapy comprises an EGFR inhibitor. In some embodiments, the methods provided herein comprise administering to the individual an EGFR inhibitor, e.g., in combination with another anti-cancer therapy. In some embodiments, the EGFR inhibitor is cetuximab, panitumumab, lapatinib, gefitinib, vandetanib, dacomitinib, icotinib, osimertinib (AZD9291), afatanib, olmutinib, EGF816 (nazartinib), avitinib (AC0010), rociletinib (CO-1686), BMS-690514, YH5448, PF-06747775, ASP8273, PF299804, AP26113, or erlotinib. In some embodiments, the EGFR inhibitor is gefitinib or cetuximab.

In some embodiments, the anti-cancer therapy comprises a cancer immunotherapy, such as a checkpoint inhibitor, cancer vaccine, cell-based therapy, T cell receptor (TCR)-based therapy, adjuvant immunotherapy, cytokine immunotherapy, and oncolytic virus therapy. In some embodiments, the methods provided herein comprise administering to the individual a cancer immunotherapy, such as a checkpoint inhibitor, cancer vaccine, cell-based therapy, T cell receptor (TCR)-based therapy, adjuvant immunotherapy, cytokine immunotherapy, and oncolytic virus therapy, e.g., in combination with another anti-cancer therapy. In some embodiments, the cancer immunotherapy comprises a small molecule, nucleic acid, polypeptide, carbohydrate, toxin, cell-based agent, or cell-binding agent. Examples of cancer immunotherapies are described in greater detail herein but are not intended to be limiting. In some embodiments, the cancer immunotherapy activates one or more aspects of the immune system to attack a cell (e.g., a tumor cell) that expresses a neoantigen, e.g., a neoantigen expressed by a cancer of the disclosure (e.g., a neoantigen corresponding to a BCOR or BCORL1 nucleic acid molecule or polypeptide described herein). The cancer immunotherapies of the present disclosure are contemplated for use as monotherapies, or in combination approaches comprising two or more in any combination or number, subject to medical judgement. Any of the cancer immunotherapies (optionally as monotherapies or in combination with another cancer immunotherapy or other therapeutic agent described herein) may find use in any of the methods described herein.

In some embodiments, the cancer immunotherapy comprises a cancer vaccine. A range of cancer vaccines have been tested that employ different approaches to promoting an immune response against a cancer (see, e.g., Emens L A, Expert Opin Emerg Drugs 13(2): 295-308 (2008) and US20190367613). Approaches have been designed to enhance the response of B cells, T cells, or professional antigen-presenting cells against tumors. Exemplary types of cancer vaccines include, but are not limited to, DNA-based vaccines, RNA-based vaccines, virus transduced vaccines, peptide-based vaccines, dendritic cell vaccines, oncolytic viruses, whole tumor cell vaccines, tumor antigen vaccines, etc. In some embodiments, the cancer vaccine can be prophylactic or therapeutic. In some embodiments, the cancer vaccine is formulated as a peptide-based vaccine, a nucleic acid-based vaccine, an antibody based vaccine, or a cell based vaccine. For example, a vaccine composition can include naked cDNA in cationic lipid formulations; lipopeptides (e.g., Vitiello, A. et ah, J. Clin. Invest. 95:341, 1995), naked cDNA or peptides, encapsulated e.g., in poly(DL-lactide-co-glycolide) ("PLG") microspheres (see, e.g., Eldridge, et ah, Molec. Immunol. 28:287-294, 1991; Alonso et al, Vaccine 12:299-306, 1994; Jones et al, Vaccine 13:675-681, 1995); peptide composition contained in immune stimulating complexes (ISCOMS) (e.g., Takahashi et al, Nature 344:873-875, 1990; Hu et al, Clin. Exp. Immunol. 13:235-243, 1998); or multiple antigen peptide systems (MAPs) (see e.g., Tam, J. P., Proc. Natl Acad. Sci. U.S.A. 85:5409-5413, 1988; Tam, J. P., J. Immunol. Methods 196: 17-32, 1996). In some embodiments, a cancer vaccine is formulated as a peptide-based vaccine, or nucleic acid based vaccine in which the nucleic acid encodes the polypeptides. In some embodiments, a cancer vaccine is formulated as an antibody-based vaccine. In some embodiments, a cancer vaccine is formulated as a cell based vaccine. In some embodiments, the cancer vaccine is a peptide cancer vaccine, which in some embodiments is a personalized peptide vaccine. In some embodiments, the cancer vaccine is a multivalent long peptide, a multiple peptide, a peptide mixture, a hybrid peptide, or a peptide pulsed dendritic cell vaccine (see, e.g., Yamada et al, Cancer Sci, 104: 14-21), 2013). In some embodiments, such cancer vaccines augment the anti-cancer response.

In some embodiments, the cancer vaccine comprises a polynucleotide that encodes a neoantigen, e.g., a neoantigen expressed by a cancer of the disclosure (e.g., a neoantigen corresponding to a BCOR or BCORL1 nucleic acid molecule or polypeptide described herein). In some embodiments, the cancer vaccine comprises DNA that encodes a neoantigen, e.g., a neoantigen expressed by a cancer of the disclosure (e.g., a neoantigen corresponding to a BCOR or BCORL1 nucleic acid molecule or polypeptide described herein). In some embodiments, the cancer vaccine comprises RNA that encodes a neoantigen, e.g., a neoantigen expressed by a cancer of the disclosure (e.g., a neoantigen corresponding to a BCOR or BCORL1 nucleic acid molecule or polypeptide described herein). In some embodiments, the cancer vaccine comprises a polynucleotide that encodes a neoantigen, e.g., a neoantigen expressed by a cancer of the disclosure (e.g., a neoantigen corresponding to a BCOR or BCORL1 nucleic acid molecule or polypeptide described herein), as well as one or more additional antigens, neoantigens, or other sequences that promote antigen presentation and/or an immune response. In some embodiments, the polynucleotide is complexed with one or more additional agents, such as a liposome or lipoplex. In some embodiments, the polynucleotide(s) are taken up and translated by antigen presenting cells (APCs), which then present the neoantigen(s) via MHC class I on the APC cell surface.

In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, the cancer vaccine is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543), prostate cancer (NCT01619813), head and neck squamous cell cancer (NCT01166542), pancreatic adenocarcinoma (NCT00998322), and non-small cell lung cancer (NSCLC) (NCT 00861627); enadenotucirev (NG-348, PsiOxus, formerly known as ColoAdl), an adenovirus engineered to express a full length CD80 and an antibody fragment specific for the T-cell receptor CD3 protein, in ovarian cancer (NCT02028117), metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676), and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260), fallopian tube cancer, ovarian cancer (NCT 02759588); or CG0070 (Cold Genesys), an adenovirus engineered to express GM-CSF in bladder cancer (NCT02365818); anti-gp100; STINGVAX; GVAX; DCVaxL; and DNX-2401. In some embodiments, the cancer vaccine is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TGO1 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response. In some embodiments, the cancer vaccine comprises a vector-based tumor antigen vaccine. Vector-based tumor antigen vaccines can be used as a way to provide a steady supply of antigens to stimulate an anti-tumor immune response. In some embodiments, vectors encoding for tumor antigens are injected into an individual (possibly with pro-inflammatory or other attractants such as GM-CSF), taken up by cells in vivo to make the specific antigens, which then provoke the desired immune response. In some embodiments, vectors may be used to deliver more than one tumor antigen at a time, to increase the immune response. In addition, recombinant virus, bacteria or yeast vectors can trigger their own immune responses, which may also enhance the overall immune response.

In some embodiments, the cancer vaccine comprises a DNA-based vaccine. In some embodiments, DNA-based vaccines can be employed to stimulate an anti-tumor response. The ability of directly injected DNA that encodes an antigenic protein, to elicit a protective immune response has been demonstrated in numerous experimental systems. Vaccination through directly injecting DNA that encodes an antigenic protein, to elicit a protective immune response often produces both cell-mediated and humoral responses. Moreover, reproducible immune responses to DNA encoding various antigens have been reported in mice that last essentially for the lifetime of the animal (see, e.g., Yankauckas et al. (1993) DNA Cell Biol., 12: 771-776). In some embodiments, plasmid (or other vector) DNA that includes a sequence encoding a protein operably linked to regulatory elements required for gene expression is administered to individuals (e.g., human patients, non-human mammals, etc.). In some embodiments, the cells of the individual take up the administered DNA and the coding sequence is expressed. In some embodiments, the antigen so produced becomes a target against which an immune response is directed.

In some embodiments, the cancer vaccine comprises an RNA-based vaccine. In some embodiments, RNA-based vaccines can be employed to stimulate an anti-tumor response. In some embodiments, RNA-based vaccines comprise a self-replicating RNA molecule. In some embodiments, the self-replicating RNA molecule may be an alphavirus-derived RNA replicon. Self-replicating RNA (or "SAM") molecules are well known in the art and can be produced by using replication elements derived from, e.g., alphaviruses, and substituting the structural viral proteins with a nucleotide sequence encoding a protein of interest. A self-replicating RNA molecule is typically a +-strand molecule which can be directly translated after delivery to a cell, and this translation provides a RNA-dependent RNA polymerase which then produces both antisense and sense transcripts from the delivered RNA. Thus, the delivered RNA leads to the production of multiple daughter RNAs. These daughter RNAs, as well as collinear subgenomic transcripts, may be translated themselves to provide in situ expression of an encoded polypeptide, or may be transcribed to provide further transcripts with the same sense as the delivered RNA which are translated to provide in situ expression of the antigen.

In some embodiments, the cancer immunotherapy comprises a cell-based therapy. In some embodiments, the cancer immunotherapy comprises a T cell-based therapy. In some embodiments, the cancer immunotherapy comprises an adoptive therapy, e.g., an adoptive T cell-based therapy. In some embodiments, the T cells are autologous or allogeneic to the recipient. In some embodiments, the T cells are CD8+ T cells. In some embodiments, the T cells are CD4+ T cells. Adoptive immunotherapy refers to a therapeutic approach for treating cancer or infectious diseases in which immune cells are administered to a host with the aim that the cells mediate either directly or indirectly specific immunity to (i.e., mount an immune response directed against) cancer cells. In some embodiments, the immune response results in inhibition of tumor and/or metastatic cell growth and/or proliferation, and in related embodiments, results in neoplastic cell death and/or resorption. The immune cells can be derived from a different organism/host (exogenous immune cells) or can be cells obtained from the subject organism (autologous immune cells). In some embodiments, the immune cells (e.g., autologous or allogeneic T cells (e.g., regulatory T cells, CD4+ T cells, CD8+ T cells, or gamma-delta T cells), NK cells, invariant NK cells, or NKT cells) can be genetically engineered to express antigen receptors such as engineered TCRs and/or chimeric antigen receptors (CARs). For example, the host cells (e.g., autologous or allogeneic T-cells) are modified to express a T cell receptor (TCR) having antigenic specificity for a cancer antigen. In some embodiments, NK cells are engineered to express a TCR. The NK cells may be further engineered to express a CAR. Multiple CARs and/or TCRs, such as to different antigens, may be added to a single cell type, such as T cells or NK cells. In some embodiments, the cells comprise one or more nucleic acids/expression constructs/vectors introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g. chimeric). In some embodiments, a population of immune cells can be obtained from a subject in need of therapy or suffering from a disease associated with reduced immune cell activity. Thus, the cells will be autologous to the subject in need of therapy. In some embodiments, a population of immune cells can be obtained from a donor, such as a histocompatibility-matched donor. In some embodiments, the immune cell population can be harvested from the peripheral blood, cord blood, bone marrow, spleen, or any other organ/tissue in which immune cells reside in said subject or donor. In some embodiments, the immune cells can be isolated from a pool of subjects and/or donors, such as from pooled cord blood. In some embodiments, when the population of immune cells is obtained from a donor distinct from the subject, the donor may be allogeneic, provided the cells obtained are subject-compatible, in that they can be introduced into the subject. In some embodiments, allogeneic donor cells may or may not be human-leukocyte-antigen (HLA)-compatible. In some embodiments, to be rendered subject-compatible, allogeneic cells can be treated to reduce immunogenicity.

In some embodiments, the cell-based therapy comprises a T cell-based therapy, such as autologous cells, e.g., tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". Several approaches for the isolation, derivation, engineering or modification, activation, and expansion of functional anti-tumor effector cells have been described in the last two decades and may be used according to any of the methods provided herein. In some embodiments, the T cells are derived from the blood, bone marrow, lymph, umbilical cord, or lymphoid organs. In some embodiments, the cells are human cells. In some embodiments, the cells are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. In some embodiments, the cells may be allogeneic and/or autologous. In some embodiments, such as for off-the-shelf technologies, the cells are pluripotent and/or multipotent, such as stem cells, such as induced pluripotent stem cells (iPSCs).

In some embodiments, the T cell-based therapy comprises a chimeric antigen receptor (CAR)-T cell-based therapy. This approach involves engineering a CAR that specifically binds to an antigen of interest and comprises one or more intracellular signaling domains for T cell activation. The CAR is then expressed on the surface of engineered T cells (CAR-T) and administered to a patient, leading to a T-cell-specific immune response against cancer cells expressing the antigen. In some embodiments, the CAR specifically binds a neoantigen, such as a neoantigen corresponding to a BCOR or BCORL1 polypeptide provided herein.

In some embodiments, the T cell-based therapy comprises T cells expressing a recombinant T cell receptor (TCR). This approach involves identifying a TCR that specifically binds to an antigen of interest, which is then used to replace the endogenous or native TCR on the surface of engineered T cells that are administered to a patient, leading to a T-cell-specific immune response against cancer cells expressing the antigen. In some embodiments, the recombinant TCR specifically binds a neoantigen corresponding to a BCOR or BCORL1 polypeptide provided herein.

In some embodiments, the T cell-based therapy comprises tumor-infiltrating lymphocytes (TILs). For example, TILs can be isolated from a tumor or cancer of the present disclosure, then isolated and expanded in vitro. Some or all of these TILs may specifically recognize an antigen expressed by the tumor or cancer of the present disclosure. In some embodiments, the TILs are exposed to one or more neoantigens, e.g., a neoantigen corresponding to a BCOR or BCORL1 polypeptide provided herein, e.g., a neoantigen, in vitro after isolation. TILs are then administered to the patient (optionally in combination with one or more cytokines or other immune-stimulating substances).

In some embodiments, the cell-based therapy comprises a natural killer (NK) cell-based therapy. Natural killer (NK) cells are a subpopulation of lymphocytes that have spontaneous cytotoxicity against a variety of tumor cells, virus-infected cells, and some normal cells in the bone marrow and thymus. NK cells are critical effectors of the early innate immune response toward transformed and virus-infected cells. NK cells can be detected by specific surface markers, such as CD16, CD56, and CD8 in humans. NK cells do not express T-cell antigen receptors, the pan T marker CD3, or surface immunoglobulin B cell receptors. In some embodiments, NK cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art.

In some embodiments, the cell-based therapy comprises a dendritic cell (DC)-based therapy, e.g., a dendritic cell vaccine. In some embodiments, the DC vaccine comprises antigen-presenting cells that are able to induce specific T cell immunity, which are harvested from the patient or from a donor. In some embodiments, the DC vaccine can then be exposed in vitro to a peptide antigen, for which T cells are to be generated in the patient. In some embodiments, dendritic cells loaded with the antigen are then injected back into the patient. In some embodiments, immunization may be repeated multiple times if desired. Methods for harvesting, expanding, and administering dendritic cells are known in the art; see, e.g., WO2019178081. Dendritic cell vaccines (such as Sipuleucel-T, also known as APC8015 and PROVENGE®) are vaccines that involve administration of dendritic cells that act as APCs to present one or more cancer-specific antigens to the patient's immune system. In some embodiments, the dendritic cells are autologous or allogeneic to the recipient.

In some embodiments, the cancer immunotherapy comprises a TCR-based therapy. In some embodiments, the cancer immunotherapy comprises administration of one or more TCRs or TCR-based therapeutics that specifically bind an antigen expressed by a cancer of the present disclosure, e.g., an antigen corresponding to a BCOR or BCORL1 polypeptide of the disclosure. In some embodiments, the TCR-based therapeutic may further include a moiety that binds an immune cell (e.g., a T cell), such as an antibody or antibody fragment that specifically binds a T cell surface protein or receptor (e.g., an anti-CD3 antibody or antibody fragment).

In some embodiments, the immunotherapy comprises adjuvant immunotherapy. Adjuvant immunotherapy comprises the use of one or more agents that activate components of the innate immune system, e.g., HILTONOL™ (imiquimod), which targets the TLR7 pathway.

In some embodiments, the immunotherapy comprises cytokine immunotherapy. Cytokine immunotherapy comprises the use of one or more cytokines that activate components of the immune system. Examples include, but are not limited to, aldesleukin (PROLEUKIN®; interleukin-2), interferon alfa-2a (ROFERON®-A), interferon alfa-2b (INTRON®-A), and peginterferon alfa-2b (PEGINTRON®).

In some embodiments, the immunotherapy comprises oncolytic virus therapy. Oncolytic virus therapy uses genetically modified viruses to replicate in and kill cancer cells, leading to the release of antigens that stimulate an immune response. In some embodiments, replication-competent oncolytic viruses expressing a tumor antigen comprise any naturally occurring (e.g., from a "field source") or modified replication-competent oncolytic virus. In some embodiments, the oncolytic virus, in addition to expressing a tumor antigen, may be modified to increase selectivity of the virus for cancer cells. In some embodiments, replication-competent oncolytic viruses include, but are not limited to, oncolytic viruses that are a member in the family of myoviridae, siphoviridae, podpviridae, teciviridae, corticoviridae, plasmaviridae, lipothrixviridae, fuselloviridae, poxyiridae, iridoviridae, phycodnaviridac, baculoviridae, herpesviridae, adnoviridae, papovaviridae, polydnaviridae, inoviridae, microviridae, geminiviridae, circoviridae, parvoviridae, hepadnaviridae, retroviridae, cyctoviridae, reoviridae, bimaviridae, paramyxoviridae, rhabdoviridae, filoviridae, orthomyxoviridae, bunyaviridae, arenaviridae, Leviviridae, picomaviridae, sequiviridae, comoviridae, potyviridae, caliciviridae, astroviridae, nodaviridae, tetraviridae, tombusviridae, coronaviridae, glaviviridae, togaviridae, and barnaviridae. In some embodiments, replication-competent oncolytic viruses include adenovirus, retrovirus, reovirus, rhabdovirus, Newcastle Disease virus (NDV), polyoma virus, vaccinia virus (VacV), herpes simplex virus, picomavirus, coxsackie virus and parvovirus. In some embodiments, a replicative oncolytic vaccinia virus expressing a tumor antigen may be engineered to lack one or more functional genes in order to increase the cancer selectivity of the virus. In some embodiments, an oncolytic vaccinia virus is engineered to lack thymidine kinase (TK) activity. In some embodiments, the oncolytic vaccinia virus may be engineered to lack vaccinia virus growth factor (VGF). In some embodiments, an oncolytic vaccinia virus may be engineered to lack both VGF and TK activity. In some embodiments, an oncolytic vaccinia virus may be engineered to lack one or more genes involved in evading host interferon (IFN) response such as E3L, K3L, B18R, or B8R. In some embodiments, a replicative oncolytic vaccinia virus is a Western Reserve, Copenhagen, Lister or Wyeth strain and lacks a functional TK gene. In some embodiments, the oncolytic vaccinia virus is a Western Reserve, Copenhagen, Lister or Wyeth strain lacking a functional B18R and/or B8R gene. In some embodiments, a replicative oncolytic vaccinia virus expressing a tumor antigen may be locally or systemically administered to a subject, e.g. via intratumoral, intraperitoneal, intravenous, intra-arterial, intramuscular, intradermal, intracranial, subcutaneous, or intranasal administration.

In some embodiments, the anti-cancer therapy comprises an immune checkpoint inhibitor. In some embodiments, the methods provided herein comprise administering to the individual an immune checkpoint inhibitor, e.g., in combination with another anti-cancer therapy. In some embodiments, the methods provided herein comprise administering to an individual an effective amount of an immune checkpoint inhibitor. As is known in the art, a checkpoint inhibitor targets at least one immune checkpoint protein to alter the regulation of an immune response. Immune checkpoint proteins include, e.g., CTLA4, PD-L1, PD-1, PD-L2, VISTA, B7-H2, B7-H3, B7-H4, B7-H6, 2B4, ICOS, HVEM, CEACAM, LAIR1, CD80, CD86, CD276, VTCN1, MHC class I, MHC class II, GALS, adenosine, TGFR, CSF1R, MICA/B, arginase, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, IDO, OX40, and A2aR. In some embodiments, molecules involved in regulating immune checkpoints include, but are not limited to: PD-1 (CD279), PD-L1 (B7-H1, CD274), PD-L2 (B7-CD, CD273), CTLA-4 (CD152), HVEM, BTLA (CD272), a killer-cell immunoglobulin-like receptor (KIR), LAG-3 (CD223), TIM-3 (HAVCR2), CEACAM, CEACAM-1, CEACAM-3, CEACAM-5, GAL9, VISTA (PD-1H), TIGIT, LAIR1, CD160, 2B4, TGFRbeta, A2AR, GITR (CD357), CD80 (B7-1), CD86 (B7-2), CD276 (B7-H3), VTCNI (B7-H4), MHC class I, MHC class II, GALS, adenosine, TGFR, B7-H1, OX40 (CD134), CD94 (KLRD1), CD137 (4-1BB), CD137L (4-1BBL), CD40, IDO, CSF1R, CD40L, CD47, CD70 (CD27L), CD226, HHLA2, ICOS (CD278), ICOSL (CD275), LIGHT (TNFSF14, CD258), NKG2a, NKG2d, OX40L (CD134L), PVR (NECL5, CD155), SIRPa, MICA/B, and/or arginase. In some embodiments, an immune checkpoint inhibitor (i.e., a checkpoint inhibitor) decreases the activity of a checkpoint protein that negatively regulates immune cell function, e.g., in order to enhance T cell activation and/or an anti-cancer immune response. In other embodiments, a checkpoint inhibitor increases the activity of a checkpoint protein that positively regulates immune cell function, e.g., in order to enhance T cell activation and/or an anti-cancer immune response. In some embodiments, the checkpoint inhibitor is an antibody. Examples of checkpoint inhibitors include, without limitation, a PD-1 axis binding antagonist, a PD-L1 axis binding antagonist (e.g., an anti-PD-L1 antibody, e.g., atezolizumab (MPDL3280A)), an antagonist directed against a co-inhibitory molecule (e.g., a CTLA4 antagonist (e.g., an anti-CTLA4 antibody), a TIM-3 antagonist (e.g., an anti-TIM-3 antibody), or a LAG-3 antagonist (e.g., an anti-LAG-3 antibody)), or any combination thereof. In some embodiments, the immune checkpoint inhibitors comprise drugs such as small molecules, recombinant forms of ligand or receptors, or antibodies, such as human antibodies (see, e.g., International Patent Publication WO2015016718; Pardoll, Nat Rev Cancer, 12(4): 252-64, 2012; both incorporated herein by reference). In some embodiments, known inhibitors of immune checkpoint proteins or analogs thereof may be used, in particular chimerized, humanized or human forms of antibodies may be used.

In some embodiments, the checkpoint inhibitor is a PD-L1 axis binding antagonist, e.g., a PD-1 binding antagonist, a PD-L1 binding antagonist, or a PD-L2 binding antagonist. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1 LG1," "CD274," "B7-H," and "PDL1." An exemplary human PD-L1 is shown in UniProtKB/Swiss-Prot Accession No.Q9NZQ7.1. PD-L2 (programmed death ligand 2) is also referred to in the art as "programmed cell death 1 ligand 2," "PDCD1 LG2," "CD273," "B7-DC," "Btdc," and "PDL2." An exemplary human PD-L2 is shown in UniProtKB/Swiss-Prot Accession No. Q9BQ51. In some instances, PD-1, PD-L1, and PD-L2 are human PD-1, PD-L1 and PD-L2.

In some instances, the PD-1 binding antagonist is a molecule that inhibits the binding of PD-1 to its ligand binding partners. In a specific embodiment, the PD-1 ligand binding partners are PD-L1 and/or PD-L2. In another instance, a PD-L1 binding antagonist is a molecule that inhibits the binding of PD-L1 to its binding ligands. In a specific embodiment, PD-L1 binding partners are PD-1 and/or B7-1. In another instance, the PD-L2 binding antagonist is a molecule that inhibits the binding of PD-L2 to its ligand binding partners. In a specific embodiment, the PD-L2 binding ligand partner is PD-1. The antagonist may be an antibody, an antigen binding fragment thereof, an immunoadhesin, a fusion protein, or an oligopeptide. In some embodiments, the PD-1 binding antagonist is a small molecule, a nucleic acid, a polypeptide (e.g., antibody), a carbohydrate, a lipid, a metal, or a toxin.

In some instances, the PD-1 binding antagonist is an anti-PD-1 antibody (e.g., a human antibody, a humanized antibody, or a chimeric antibody), for example, as described below. In some instances, the anti-PD-1 antibody is selected from the group consisting of MDX-1 106 (nivolumab), MK-3475 (pembrolizumab, Keytruda®), MEDI-0680 (AMP-514), PDR001, REGN2810, MGA-012, JNJ-63723283, BI 754091, and BGB-108. In other instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some instances, the PD-1 binding antagonist is AMP-224. Other examples of anti-PD-1 antibodies include, but are not limited to, MEDI-0680 (AMP-514; AstraZeneca), PDR001

(CAS Registry No. 1859072-53-9; Novartis), REGN2810 (LIBTAYO® or cemiplimab-rwlc; Regeneron), BGB-108 (BeiGene), BGB-A317 (BeiGene), BI 754091, JS-001 (Shanghai Junshi), STI-A1110 (Sorrento), INCSHR-1210 (Incyte), PF-06801591 (Pfizer), TSR-042 (also known as ANB011; Tesaro/AnaptysBio), AM0001 (ARMO Biosciences), ENUM 244C8 (Enumeral Biomedical Holdings), or ENUM 388D4 (Enumeral Biomedical Holdings). In some embodiments, the PD-1 axis binding antagonist comprises tislelizumab (BGB-A317), BGB-108, STI-A1110, AM0001, BI 754091, sintilimab (IBI308), cetrelimab (JNJ-63723283), toripalimab (JS-001), camrelizumab (SHR-1210, INCSHR-1210, HR-301210), MEDI-0680 (AMP-514), MGA-012 (INCMGA 0012), nivolumab (BMS-936558, MDX1106, ONO-4538), spartalizumab (PDR001), pembrolizumab (MK-3475, SCH 900475, Keytruda®), PF-06801591, cemiplimab (REGN-2810, REGEN2810), dostarlimab (TSR-042, ANB011), FITC-YT-16 (PD-1 binding peptide), APL-501 or CBT-501 or genolimzumab (GB-226), AB-122, AK105, AMG 404, BCD-100, F520, HLX10, HX008, JTX-4014, LZM009, Sym021, PSB205, AMP-224 (fusion protein targeting PD-1), CX-188 (PD-1 probody), AGEN-2034, GLS-010, budigalimab (ABBV-181), AK-103, BAT-1306, CS-1003, AM-0001, TILT-123, BH-2922, BH-2941, BH-2950, ENUM-244C8, ENUM-388D4, HAB-21, H EIS-COI 11-003, IKT-202, MCLA-134, MT-17000, PEGMP-7, PRS-332, RXI-762, STI-1110, VXM-10, XmAb-23104, AK-112, HLX-20, SSI-361, AT-16201, SNA-01, AB122, PD1-PIK, PF-06936308, RG-7769, CAB PD-1 Abs, AK-123, MEDI-3387, MEDI-5771, 4H1128Z-E27, REMD-288, SG-001, BY-24.3, CB-201, IBI-319, ONCR-177, Max-1, CS-4100, JBI-426, CCC-0701, or CCX-4503, or derivatives thereof.

In some embodiments, the PD-L1 binding antagonist is a small molecule that inhibits PD-1. In some embodiments, the PD-L1 binding antagonist is a small molecule that inhibits PD-L1. In some embodiments, the PD-L1 binding antagonist is a small molecule that inhibits PD-L1 and VISTA or PD-L1 and TIM3. In some embodiments, the PD-L1 binding antagonist is CA-170 (also known as AUPM-170). In some embodiments, the PD-L1 binding antagonist is an anti-PD-L1 antibody. In some embodiments, the anti-PD-L1 antibody can bind to a human PD-L1, for example a human PD-L1 as shown in UniProtKB/Swiss-Prot Accession No.Q9NZQ7.1, or a variant thereof. In some embodiments, the PD-L1 binding antagonist is a small molecule, a nucleic acid, a polypeptide (e.g., antibody), a carbohydrate, a lipid, a metal, or a toxin.

In some instances, the PD-L1 binding antagonist is an anti-PD-L1 antibody, for example, as described below. In some instances, the anti-PD-L1 antibody is capable of inhibiting the binding between PD-L1 and PD-1, and/or between PD-L1 and B7-1. In some instances, the anti-PD-L1 antibody is a monoclonal antibody. In some instances, the anti-PD-L1 antibody is an antibody fragment selected from a Fab, Fab'-SH, Fv, scFv, or (Fab')2 fragment. In some instances, the anti-PD-L1 antibody is a humanized antibody. In some instances, the anti-PD-L1 antibody is a human antibody. In some instances, the anti-PD-L1 antibody is selected from YW243.55.S70, MPDL3280A (atezolizumab), MDX-1 105, MEDI4736 (durvalumab), or MSB0010718C (avelumab). In some embodiments, the PD-L1 axis binding antagonist comprises atezolizumab, avelumab, durvalumab (imfinzi), BGB-A333, SHR-1316 (HTI-1088), CK-301, BMS-936559, envafolimab (KN035, ASC22), CS1001, MDX-1105 (BMS-936559), LY3300054, STI-A1014, FAZ053, CX-072, INCB086550, GNS-1480, CA-170, CK-301, M-7824, HTI-1088 (HTI-131, SHR-1316), MSB-2311, AK-106, AVA-004, BBI-801, CA-327, CBA-0710, CBT-502, FPT-155, IKT-201, IKT-703, 10-103, JS-003, KD-033, KY-1003, MCLA-145, MT-5050, SNA-02, BCD-135, APL-502 (CBT-402 or TQB2450), IMC-001, KD-045, INBRX-105, KN-046, IMC-2102, IMC-2101, KD-005, IMM-2502, 89Zr-CX-072, 89Zr-DFO-6E11, KY-1055, MEDI-1109, MT-5594, SL-279252, DSP-106, Gensci-047, REMD-290, N-809, PRS-344, FS-222, GEN-1046, BH-29xx, or FS-118, or a derivative thereof.

In some embodiments, the checkpoint inhibitor is an antagonist of CTLA4. In some embodiments, the checkpoint inhibitor is a small molecule antagonist of CTLA4. In some embodiments, the checkpoint inhibitor is an anti-CTLA4 antibody. CTLA4 is part of the CD28-B7 immunoglobulin superfamily of immune checkpoint molecules that acts to negatively regulate T cell activation, particularly CD28-dependent T cell responses. CTLA4 competes for binding to common ligands with CD28, such as CD80 (B7-1) and CD86 (B7-2), and binds to these ligands with higher affinity than CD28. Blocking CTLA4 activity (e.g., using an anti-CTLA4 antibody) is thought to enhance CD28-mediated costimulation (leading to increased T cell activation/priming), affect T cell development, and/or deplete Tregs (such as intratumoral Tregs). In some embodiments, the CTLA4 antagonist is a small molecule, a nucleic acid, a polypeptide (e.g., antibody), a carbohydrate, a lipid, a metal, or a toxin. In some embodiments, the CTLA-4 inhibitor comprises ipilimumab (IB1310, BMS-734016, MDX010, MDX-CTLA4, MEDI4736), tremelimumab (CP-675, CP-675, 206), APL-509, AGEN1884, CS1002, AGEN1181, Abatacept (Orencia, BMS-188667, RG2077), BCD-145, ONC-392, ADU-1604, REGN4659, ADG116, KN044, KN046, or a derivative thereof.

In some embodiments, the anti-PD-1 antibody or antibody fragment is MDX-1106 (nivolumab), MK-3475 (pembrolizumab, Keytruda®), MEDI-0680 (AMP-514), PDR001, REGN2810, MGA-012, JNJ-63723283, BI 754091, BGB-108, BGB-A317, JS-001, STI-A1110, INCSHR-1210, PF-06801591, TSR-042, AM0001, ENUM 244C8, or ENUM 388D4. In some embodiments, the PD-1 binding antagonist is an anti-PD-1 immunoadhesin. In some embodiments, the anti-PD-1 immunoadhesin is AMP-224. In some embodiments, the anti-PD-L1 antibody or antibody fragment is YW243.55.S70, MPDL3280A (atezolizumab), MDX-1105, MED14736 (durvalumab), MSB0010718C (avelumab), LY3300054, STI-A1014, KN035, FAZ053, or CX-072.

In some embodiments, the immune checkpoint inhibitor comprises a LAG-3 inhibitor (e.g., an antibody, an antibody conjugate, or an antigen-binding fragment thereof). In some embodiments, the LAG-3 inhibitor comprises a small molecule, a nucleic acid, a polypeptide (e.g., an antibody), a carbohydrate, a lipid, a metal, or a toxin. In some embodiments, the LAG-3 inhibitor comprises a small molecule. In some embodiments, the LAG-3 inhibitor comprises a LAG-3 binding agent. In some embodiments, the LAG-3 inhibitor comprises an antibody, an antibody conjugate, or an antigen-binding fragment thereof. In some embodiments, the LAG-3 inhibitor comprises eftilagimod alpha (IMP321, IMP-321, EDDP-202, EOC-202), relatlimab (BMS-986016), GSK2831781 (IMP-731), LAG525 (IMP701), TSR-033, EVIP321 (soluble LAG-3 protein), BI 754111, IMP761, REGN3767, MK-4280, MGD-013, XmAb22841, INCAGN-2385, ENUM-006, AVA-017, AM-0003, iOnctura anti-LAG-3 antibody, Arcus Biosciences LAG-3 antibody, Sym022, a derivative thereof, or an antibody that competes with any of the preceding.

In some embodiments, the anti-cancer therapy comprises an immunoregulatory molecule or a cytokine. In some embodiments, the methods provided herein comprise administering to the individual an immunoregulatory molecule or a cytokine, e.g., in combination with another anti-cancer therapy. An immunoregulatory profile is required to trigger an efficient immune response and balance the immunity in a subject. Examples of suitable immunoregulatory cytokines include, but are not limited to, interferons (e.g., IFNα, IFNβ and IFNγ), interleukins (e.g., IL-1, IL-2, IL-3, IL-4, IL-5, IL-6, IL-7, IL-8, IL-9, IL-10, IL-12 and IL-20), tumor necrosis factors (e.g., TNFα and TNFβ), erythropoictin (EPO), FLT-3 ligand, glp10, TCA-3, MCP-1, MIF, MIP-1α, MIP-1β, Rantes, macrophage colony stimulating factor (M-CSF), granulocyte colony stimulating factor (G-CSF), or granulocyte-macrophage colony stimulating factor (GM-CSF), as well as functional fragments thereof. In some embodiments, any immunomodulatory chemokine that binds to a chemokine receptor, i.e., a CXC, CC, C, or CX3C chemokine receptor, can be used in the context of the present disclosure. Examples of chemokines include, but are not limited to, MIP-3α (Lax), MIP-3β, Hcc-1, MPIF-1, MPIF-2, MCP-2, MCP-3, MCP-4, MCP-5, Eotaxin, Tarc, Elc, I309, IL-8, GCP-2 Groα, Gro-β, Nap-2, Ena-78, Ip-10, MIG, I-Tac, SDF-1, or BCA-1 (Blc), as well as functional fragments thereof. In some embodiments, the immunoregulatory molecule is included with any of the treatments provided herein.

In some embodiments, the immune checkpoint inhibitor is monovalent and/or monospecific. In some embodiments, the immune checkpoint inhibitor is multivalent and/or multispecific.

In some embodiments, the anti-cancer therapy comprises an anti-cancer agent that inhibits expression of a BCOR or BCORL1 nucleic acid molecule or polypeptide. In some embodiments, the methods provided herein comprise administering to the individual an anti-cancer agent that inhibits expression of a BCOR or BCORL1 nucleic acid molecule or polypeptide, e.g., in combination with another anti-cancer therapy.

In some embodiments, the anti-cancer therapy comprises a nucleic acid molecule, such as a dsRNA, an siRNA, or an shRNA. In some embodiments, the methods provided herein comprise administering to the individual a nucleic acid molecule, such as a dsRNA, an siRNA, or an shRNA, e.g., in combination with another anti-cancer therapy. As is known in the art, dsRNAs having a duplex structure are effective at inducing RNA interference (RNAi). In some embodiments, the anti-cancer therapy comprises a small interfering RNA molecule (siRNA). dsRNAs and siRNAs can be used to silence gene expression in mammalian cells (e.g., human cells). In some embodiments, a dsRNA of the disclosure comprises any of between about 5 and about 10 base pairs, between about 10 and about 12 base pairs, between about 12 and about 15 base pairs, between about 15 and about 20 base pairs, between about 20 and 23 base pairs, between about 23 and about 25 base pairs, between about 25 and about 27 base pairs, or between about 27 and about 30 base pairs. As is known in the art, siRNAs are small dsRNAs that optionally include overhangs. In some embodiments, the duplex region of an siRNA is between about 18 and 25 nucleotides, e.g., any of 18, 19, 20, 21, 22, 23, 24, or 25 nucleotides. siRNAs may also include short hairpin RNAs (shRNAs), e.g., with approximately 29-base-pair stems and 2-nucleotide 3' overhangs. In some embodiments, a dsRNA, an siRNA, or an shRNA of the disclosure comprises a nucleotide sequence that is configured to hybridize to a BCOR or BCORL1 nucleic acid molecule provided herein. In some embodiments, a dsRNA, an siRNA, or an shRNA of the disclosure comprises a nucleotide sequence that is configured to hybridize to the BCOR or BCORL1 breakpoint of a fusion nucleic acid molecule provided herein. Methods for designing, optimizing, producing, and using dsRNAs, siRNAs, or shRNAs, are known in the art.

In some embodiments, the anti-cancer therapy comprises a chemotherapy. In some embodiments, the methods provided herein comprise administering to the individual a chemotherapy, e.g., in combination with another anti-cancer therapy. Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenishers such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethlylomithine (DMFO); retinoids, such as retinoic acid; capecitabine; carboplatin, procarbazine, plicomycin, gemcitabine, navelbine, famesyl-protein transferase inhibitors, transplatinum, and pharmaceutically acceptable salts, acids, or derivatives of any of the above.

Some non-limiting examples of chemotherapeutic drugs which can be combined with anti-cancer therapies of the present disclosure are carboplatin (Paraplatin), cisplatin (Platinol, Platinol-AQ), cyclophosphamide (Cytoxan, Neosar), docetaxel (Taxotere), doxorubicin (Adriamycin), erlotinib (Tarceva), etoposide (VePesid), fluorouracil (5-FU), gemcitabine (Gemzar), imatinib mesylate (Gleevec), irinotecan (Camptosar), methotrexate (Folex, Mexate, Amethopterin), paclitaxel (Taxol, Abraxane), sorafinib (Nexavar), sunitinib (Sutent), topotecan (Hycamtin), vincristine (Oncovin, Vincasar PFS), and vinblastine (Velban).

In some embodiments, the anti-cancer therapy comprises a kinase inhibitor. In some embodiments, the methods provided herein comprise administering to the individual a kinase inhibitor, e.g., in combination with another anti-cancer therapy. Examples of kinase inhibitors include those that target one or more receptor tyrosine kinases, e.g., BCR-ABL, B-Raf, EGFR, HER-2/ErbB2, IGF-IR, PDGFR-a, PDGFR-β, cKit, Flt-4, Flt3, FGFR1, FGFR3, FGFR4, CSF1R, c-Met, RON, c-Ret, or ALK; one or more cytoplasmic tyrosine kinases, e.g., c-SRC, c-YES, Abl, or JAK-2; one or more serine/threonine kinases, e.g., ATM, Aurora A & B, CDKs, mTOR, PKCi, PLKs, b-Raf, S6K, or STK11/LKB1; or one or more lipid kinases, e.g., PI3K or SKI. Small molecule kinase inhibitors include PHA-739358, nilotinib, dasatinib, PD166326, NSC 743411, lapatinib (GW-572016), canertinib (CI-1033), semaxinib (SU5416), vatalanib (PTK787/ZK222584), sutent (SU1 1248), sorafenib (BAY 43-9006), or leflunomide (SU101). Additional non-limiting examples of tyrosine kinase inhibitors include imatinib (Gleevec/Glivec) and gefitinib (Iressa).

In some embodiments, the anti-cancer therapy comprises an anti-angiogenic agent. In some embodiments, the methods provided herein comprise administering to the individual an anti-angiogenic agent, e.g., in combination with another anti-cancer therapy. Angiogenesis inhibitors prevent the extensive growth of blood vessels (angiogenesis) that tumors require to survive. Non-limiting examples of angiogenesis-mediating molecules or angiogenesis inhibitors which may be used in the methods of the present disclosure include soluble VEGF (for example: VEGF isoforms, e.g., VEGF121 and VEGF165; VEGF receptors, e.g., VEGFR1, VEGFR2; and co-receptors, e.g., Neuropilin-1 and Neuropilin-2), NRP-1, angiopoietin 2, TSP-1 and TSP-2, angiostatin and related molecules, endostatin, vasostatin, calreticulin, platelet factor-4, TIMP and CDAI, Meth-1 and Meth-2, IFNα, IFN-β and IFN-γ, CXCL10, IL-4, IL-12 and IL-18, prothrombin (kringle domain-2), antithrombin III fragment, prolactin, VEGI, SPARC, osteopontin, maspin, canstatin, proliferin-related protein, restin and drugs such as bevacizumab, itraconazole, carboxyamidotriazole, TNP-470, CM101, IFN-α platelet factor-4, suramin, SU5416, thrombospondin, VEGFR antagonists, angiostatic steroids and heparin, cartilage-derived angiogenesis inhibitory factor, matrix metalloproteinase inhibitors, 2-methoxyestradiol, tecogalan, tetrathiomolybdate, thalidomide, thrombospondin, prolactina v β3 inhibitors, linomide, or tasquinimod. In some embodiments, known therapeutic candidates that may be used according to the methods of the disclosure include naturally occurring angiogenic inhibitors, including without limitation, angiostatin, endostatin, or platelet factor-4. In another embodiment, therapeutic candidates that may be used according to the methods of the disclosure include, without limitation, specific inhibitors of endothelial cell growth, such as TNP-470, thalidomide, and interleukin-12. Still other anti-angiogenic agents that may be used according to the methods of the disclosure include those that neutralize angiogenic molecules, including without limitation, antibodies to fibroblast growth factor, antibodies to vascular endothelial growth factor, antibodies to platelet derived growth factor, or antibodies or other types of inhibitors of the receptors of EGF, VEGF or PDGF. In some embodiments, anti-angiogenic agents that may be used according to the methods of the disclosure include, without limitation, suramin and its analogs, and tecogalan. In other embodiments, anti-angiogenic agents that may be used according to the methods of the disclosure include, without limitation, agents that neutralize receptors for angiogenic factors or agents that interfere with vascular basement membrane and extracellular matrix, including, without limitation, metalloprotease inhibitors and angiostatic steroids. Another group of anti-angiogenic compounds that may be used according to the methods of the disclosure includes, without limitation, anti-adhesion molecules, such as antibodies to integrin alpha v beta 3. Still other anti-angiogenic compounds or compositions that may be used according to the methods of the disclosure include, without limitation, kinase inhibitors, thalidomide, itraconazole, carboxyamidotriazole, CM101, IFN-α, IL-12, SU5416, thrombospondin, cartilage-derived angiogenesis inhibitory factor, 2-methoxyestradiol, tetrathiomolybdate, thrombospondin, prolactin, and linomide. In one particular embodiment, the anti-angiogenic compound that may be used according to the methods of the disclosure is an antibody to VEGF, such as Avastin®/bevacizumab (Genentech).

In some embodiments, the anti-cancer therapy comprises an anti-DNA repair therapy. In some embodiments, the methods provided herein comprise administering to the individual an anti-DNA repair therapy, e.g., in combination with another anti-cancer therapy. In some embodiments, the anti-DNA repair therapy is a PARP inhibitor (e.g., talazoparib, rucaparib, olaparib), a RAD51 inhibitor (e.g., RI-1), or an inhibitor of a DNA damage response kinase, e.g., CHCK1 (e.g., AZD7762), ATM (e.g., KU-55933, KU-60019, NU7026, or VE-821), and ATR (e.g., NU7026).

In some embodiments, the anti-cancer therapy comprises a radiosensitizer. In some embodiments, the methods provided herein comprise administering to the individual a radiosensitizer, e.g., in combination with another anti-cancer therapy. Exemplary radiosensitizers include hypoxia radiosensitizers such as misonidazole, metronidazole, and trans-sodium crocetinate, a compound that helps to increase the diffusion of oxygen into hypoxic tumor tissue. The radiosensitizer can also be a DNA damage response inhibitor interfering with base excision repair (BER), nucleotide excision repair (NER), mismatch repair (MMR), recombinational repair comprising homologous recombination (HR) and non-homologous end-joining (NHEJ), and direct repair mechanisms. Single strand break (SSB) repair mechanisms include BER, NER, or MMR pathways, while double stranded break (DSB) repair mechanisms consist of HR and NHEJ pathways. Radiation causes DNA breaks that, if not repaired, are lethal. SSBs are repaired through a combination of BER, NER and MMR mechanisms using the intact DNA strand as a template. The predominant pathway of SSB repair is BER, utilizing a family of related enzymes termed poly-(ADP-ribose) polymerases (PARP). Thus, the radiosensitizer can include DNA damage response inhibitors such as PARP inhibitors.

In some embodiments, the anti-cancer therapy comprises an anti-inflammatory agent. In some embodiments, the methods provided herein comprise administering to the individual an anti-inflammatory agent, e.g., in combination with another anti-cancer therapy. In some embodiments, the anti-inflammatory agent is an agent that blocks, inhibits, or reduces inflammation or signaling from an inflammatory signaling pathway In some embodiments, the anti-inflammatory agent inhibits or reduces the activity of one or more of any of the following: IL-1, IL-2, IL-3, IL-4, IL-5, IL-6, IL-7, IL-8, IL-9, IL-10, IL-12, IL-13, IL-15, IL-18, IL-23; interferons (IFNs), e.g., IFNα, IFNβ, IFNγ, IFN-γ inducing factor (IGIF); transforming growth factor-β (TGF-β); transforming growth factor-α (TGF-α); tumor necrosis factors, e.g., TNF-α, TNF-β, TNF-RI, TNF-RII; CD23; CD30; CD40L; EGF; G-CSF; GDNF; PDGF-BB; RANTES/CCL5; IKK; NF-κB; TLR2; TLR3; TLR4; TL5; TLR6; TLR7; TLR8; TLR8; TLR9; and/or any cognate receptors thereof. In some embodiments, the anti-inflammatory agent is an IL-1 or IL-1 receptor antagonist, such as anakinra (Kineret®), rilonacept, or canakinumab. In some embodiments, the anti-inflammatory agent is an IL-6 or IL-6 receptor antagonist, e.g., an anti-IL-6 antibody or an anti-IL-6 receptor antibody, such as tocilizumab (ACTEMRA®), olokizumab, clazakizumab, sarilumab, sirukumab, siltuximab, or ALX-0061. In some embodiments, the anti-inflammatory agent is a TNF-α antagonist, e.g., an anti-TNFα antibody, such as infliximab (Remicade®), golimumab (Simponi®), adalimumab (Humira®), certolizumab pegol (Cimzia®) or etanercept. In some embodiments, the anti-inflammatory agent is a corticosteroid. Exemplary corticosteroids include, but are not limited to, cortisone (hydrocortisone, hydrocortisone sodium phosphate, hydrocortisone sodium succinate, Ala-Cort®, Hydrocort Acetate®, hydrocortone phosphate Lanacort®, Solu-Cortef®), decadron (dexamethasone, dexamethasone acetate, dexamethasone sodium phosphate, Dexasone®, Diodex®, Hexadrol®, Maxidex®), methylprednisolone (6-methylprednisolone, methylprednisolone acetate, methylprednisolone sodium succinate, Duralone®, Medralone®, Medrol®, M-Prednisol®, Solu-Medrol®), prednisolone (Delta-Cortef®, ORAPRED®, Pediapred®, Prezone®), and prednisone (Deltasone®, Liquid Pred®, Meticorten®, Orasone®), and bisphosphonates (e.g., pamidronate (Aredia®), and zoledronic acid (Zometac®).

In some embodiments, the anti-cancer therapy comprises an anti-hormonal agent. In some embodiments, the methods provided herein comprise administering to the individual an anti-hormonal agent, e.g., in combination with another anti-cancer therapy. Anti-hormonal agents are agents that act to regulate or inhibit hormone action on tumors. Examples of anti-hormonal agents include anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGACE® megestrol acetate, AROMASIN® exemestane, formestanie, fadrozole, RIVISOR® vorozole, FEMARA® letrozole, and ARIMIDEX® (anastrozole); anti-androgens such as flutamide, nilutamide, bicalutamide, leuprolide, and goserelin; troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

In some embodiments, the anti-cancer therapy comprises an antimetabolite chemotherapeutic agent. In some embodiments, the methods provided herein comprise administering to the individual an antimetabolite chemotherapeutic agent, e.g., in combination with another anti-cancer therapy. Antimetabolite chemotherapeutic agents are agents that are structurally similar to a metabolite, but cannot be used by the body in a productive manner. Many antimetabolite chemotherapeutic agents interfere with the production of RNA or DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOMED), azocytosine, deoxycytosine, pyridmidene, fludarabine (FLUDARA®), cladrabine, and 2-deoxy-D-glucose. In some embodiments, an antimetabolite chemotherapeutic agent is gemcitabine. Gemcitabine HCl is sold by Eli Lilly under the trademark GEMZAR®.

In some embodiments, the anti-cancer therapy comprises a platinum-based chemotherapeutic agent. In some embodiments, the methods provided herein comprise administering to the individual a platinum-based chemotherapeutic agent, e.g., in combination with another anti-cancer therapy. Platinum-based chemotherapeutic agents are chemotherapeutic agents that comprise an organic compound containing platinum as an integral part of the molecule. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

In some aspects, provided herein are therapeutic formulations comprising an anti-cancer therapy provided herein, and a pharmaceutically acceptable carrier, excipient, or stabilizer. A formulation provided herein may contain more than one active compound, e.g., an anti-cancer therapy provided herein and one or more additional agents (e.g., anti-cancer agents).

Acceptable carriers, excipients, or stabilizers are non-toxic to recipients at the dosages and concentrations employed, and include, for example, one or more of: buffers such as phosphate, citrate, and other organic acids; antioxidants, including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, or m-cresol; low molecular weight polypeptides (e.g., less than about 10 residues); proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); surfactants such as non-ionic surfactants; or polymers such as polyethylene glycol (PEG).

The active ingredients may be entrapped in microcapsules. Such microcapsules may be prepared, for example, by coacervation techniques or by interfacial polymerization, for example, hydroxymethylcellulose or gelatin-microcapsules and poly-(methylmethacylate) microcapsules, respectively; in colloidal drug delivery systems (for example, liposomes, albumin microspheres, microemulsions, nano-particles and nano-capsules); or in macroemulsions. Such techniques are known in the art.

Sustained-release compositions may be prepared. Suitable examples of sustained-release compositions include semi-permeable matrices of solid hydrophobic polymers containing an anti-cancer therapy of the disclosure. Such matrices may be in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Formulations to be used for in vivo administration are sterile. This is readily accomplished by filtration through sterile filtration membranes or other methods known in the art.

In some embodiments, the anti-cancer therapy is administered as a monotherapy. In some embodiments, the anti-cancer therapy is administered in combination with one or more additional anti-cancer therapies or treatments. In some embodiments, the one or more additional anti-cancer therapies or treatments include one or more anti-cancer therapies described herein. In some embodiments, the additional anti-cancer therapy comprises one or more of surgery, radiotherapy, chemotherapy, anti-angiogenic therapy, anti-DNA repair therapy, and anti-inflammatory therapy. In some embodiments, the additional anti-cancer therapy comprises an anti-neoplastic agent, a chemotherapeutic agent, a growth inhibitory agent, an anti-angiogenic agent, a radiation therapy, a cytotoxic agent, or combinations thereof. In some embodiments, an anti-cancer therapy may be administered in conjunction with a chemotherapy or chemotherapeutic agent. In some embodiments, the chemotherapy or chemotherapeutic agent is a platinum-based agent (including, without limitation cisplatin, carboplatin, oxaliplatin, and staraplatin). In some embodiments, an anti-cancer therapy may be administered in conjunction with a radiation therapy.

In some embodiments, the anti-cancer therapy for use in any of the methods described herein (e.g., as monotherapy or in combination with another therapy or treatment) is an anti-cancer therapy or treatment described by Pietrantonio et al., J Natl Cancer Inst (2017) 109(12) and/or by Wang et al., Cancers (2020) 12(2):426, which are hereby incorporated by reference.

IV. Articles of Manufacture or Kits

Provided herein are kits or articles of manufacture comprising one or more oligonucleotides for detecting a rearrangement in a BCOR gene. In some embodiments, the BCOR gene rearrangement results in an internal BCOR gene rearrangement or a fusion gene between BCOR and a gene selected from the group consisting of L3MBTL2, EP300, NUTM2G, MAP7D2, RALGPS1, RGAG1, CREBBP, ING3, NUGGC, and KMT2D.

Further provided herein are kits or articles of manufacture comprising a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor) and a package insert comprising instructions for using the targeted therapeutic in a method of treating or delaying progression of cancer, e.g., by administration to an individual from whom a sample comprising a BCOR gene rearrangement has been obtained.

Provided herein are kits or articles of manufacture comprising one or more oligonucleotides for detecting an alteration in a BCORL1 gene. In some embodiments, the BCORL1 gene alteration comprises a T513fs*22, P600fs*1, R945*, R1196*, R1265fs*4, L461fs*5, or H1426fs*29 mutation; an internal rearrangement; or a JAZF1-BCORL1, BCORL1-JAZF1, or EP300-BCORL1 fusion gene.

Further provided herein are kits or articles of manufacture comprising a targeted therapeutic (e.g., a CDK inhibitor, an MDM2 inhibitor, a tyrosine kinase inhibitor, a MEK inhibitor, an mTOR inhibitor, PIK3CA or AKT inhibitor, or a Hh inhibitor) and a package insert comprising instructions for using the targeted therapeutic in a method of treating or delaying progression of cancer, e.g., by administration to an individual from whom a sample comprising a BCORL1 gene alteration has been obtained.

In some embodiments, a kit provided herein comprises a reagent (e.g., one or more oligonucleotides, primers, probes or baits of the present disclosure) for detecting a BCOR or BCORL1 nucleic acid molecule provided herein. In some embodiments, the kit comprises a reagent (e.g., one or more oligonucleotides, primers, probes or baits of the present disclosure) for detecting a wild-type counterpart of a BCOR or BCORL1 nucleic acid molecule provided herein. In some embodiments, the reagent comprises one or more oligonucleotides, primers, probes or baits of the present disclosure capable of hybridizing to a BCOR or BCORL1 nucleic acid molecule provided herein, or to a wild-type counterpart of a BCOR or BCORL1 nucleic acid molecule provided herein. In some embodiments, the reagent comprises one or more oligonucleotides, primers, probes or baits of the present disclosure capable of distinguishing a BCOR or BCORL1 nucleic acid molecule provided herein from a wild-type counterpart of the BCOR or BCORL1 nucleic acid molecule provided herein. In some embodiments, the kit is for use according to any method of detecting BCOR or BCORL1 nucleic acid molecules known in the art or described herein, such as sequencing, PCR, in situ hybridization methods, a nucleic acid hybridization assay, an amplification-based assay, a PCR-RFLP assay, real-time PCR, sequencing, next-generation sequencing, a screening analysis, FISH, spectral karyotyping, MFISH, comparative genomic hybridization, in situ hybridization, sequence-specific priming (SSP) PCR, HPLC, and mass-spectrometric genotyping. In some embodiments, a kit provided herein further comprises instructions for detecting a BCOR or BCORL1 nucleic acid molecule of the disclosure, e.g., using one or more oligonucleotides, primers, probes or baits of the present disclosure.

Also provided herein are kits for detecting a BCOR or BCORL1 polypeptide of the disclosure. In some embodiments, a kit provided herein comprises a reagent (e.g., one or more antibodies of the present disclosure) for detecting a BCOR or BCORL1 polypeptide described herein. In some embodiments, the kit comprises a reagent (e.g., one or more antibodies of the present disclosure) for detecting the wild-type counterparts of a BCOR or BCORL1 polypeptide provided herein. In some embodiments, the reagent comprises one or more antibodies of the present disclosure capable of binding to a BCOR or BCORL1 polypeptide provided herein, or to wild-type counterparts of the BCOR or BCORL1 polypeptide provided herein. In some embodiments, the reagent comprises one or more antibodies of the present disclosure capable of distinguishing a BCOR or BCORL1 polypeptide provided herein from wild-type counterparts of a BCOR or BCORL1 polypeptide provided herein. In some embodiments, the kit is for use according to any protein or polypeptide detection assay known in the art or described herein, such as mass spectrometry (e.g., tandem mass spectrometry), a reporter assay (e.g., a fluorescence-based assay), immunoblots such as a Western blot, immunoassays such as enzyme-linked immunosorbent assays (ELISA), immunohistochemistry, other immunological assays (e.g., fluid or gel precipitin reactions, immunodiffusion, immunoelectrophoresis, radioimmunoassay (RIA), immunofluorescent assays), and analytic biochemical methods (e.g., electrophoresis, capillary electrophoresis, high performance liquid chromatography (HPLC), thin layer chromatography (TLC), hyperdiffusion chromatography). In some embodiments, the kit further comprises instructions for detecting a BCOR or BCORL1 polypeptide of the disclosure, e.g., using one or more antibodies of the present disclosure.

The article of manufacture may include, for example, a container and a label or package insert on or associated with the container. Suitable containers include, for example, bottles, vials, syringes, and the like. The container may be formed from a variety of materials such as glass or plastic. The container holds or contains a composition comprising the cancer medicament as the active agent and may have a sterile access port (e.g., the container may be an intravenous solution bag or a vial having a stopper pierceable by a hypodermic injection needle).

The article of manufacture may further include a second container comprising a pharmaceutically-acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

The article of manufacture of the present invention also includes information, for example in the form of a package insert, indicating that the composition is used for treating cancer, as described herein. The insert or label may take any form, such as paper or on electronic media such as a magnetically recorded medium (e.g., floppy disk), a CD-ROM, a Universal Serial Bus (USB) flash drive, and the like. The label or insert may also include other information concerning the pharmaceutical compositions and dosage forms in the kit or article of manufacture.

Expression Vectors, Host Cells and Recombinant Cells

Provided herein are vectors comprising a BCOR or BCORL1 nucleic acid molecule, a bait, a probe, or an oligonucleotide described herein, or fragments thereof.

In some embodiments, a vector provided herein comprises a BCOR or BCORL1 nucleic acid molecule described herein, or a nucleic acid molecule encoding a BCOR or BCORL1 polypeptide described herein.

In some embodiments, a vector provided herein is a nucleic acid molecule capable of transporting another nucleic acid to which it has been linked (e.g., BCOR or BCORL1 nucleic acid molecules, baits, probes, or oligonucleotides described herein, or fragments thereof). In some embodiments, a vector is a plasmid, a cosmid or a viral vector. The vector may be capable of autonomous replication, or it can integrate into a host DNA. Viral vectors (e.g., comprising BCOR or BCORL1 nucleic acid molecules, baits, probes, or oligonucleotides described herein, or fragments thereof) are also contemplated herein, including, e.g., replication defective retroviruses, adenoviruses and adeno-associated viruses.

In some embodiments, a vector provided herein comprises a BCOR or BCORL1 nucleic acid molecule, a bait, a probe, or an oligonucleotide of the disclosure in a form suitable for expression thereof in a host cell. In some embodiments, the vector includes one or more regulatory sequences operatively linked to the nucleotide sequence to be expressed. In some embodiments, the one or more regulatory sequences include promoters (e.g., promoters derived from polyoma, Adenovirus 2, cytomegalovirus and Simian Virus 40), enhancers, and other expression control elements (e.g., polyadenylation signals). In some embodiments, a regulatory sequence directs constitutive expression of a nucleotide sequence (e.g., BCOR or BCORL1 nucleic acid molecules, baits, probes, or oligonucleotides described herein, or fragments thereof). In some embodiments, a regulatory sequence directs tissue-specific expression of a nucleotide sequence (e.g., BCOR or BCORL1 nucleic acid molecules, baits, probes, or oligonucleotides described herein, or fragments thereof). In some embodiments, a regulatory sequence directs inducible expression of a nucleotide sequence (e.g., BCOR or BCORL1 nucleic acid molecules, baits, probes, or oligonucleotides described herein, or fragments thereof). Examples of inducible regulatory sequences include, without limitation, promoters regulated by a steroid hormone, by a polypeptide hormone, or by a heterologous polypeptide, such as a tetracycline-inducible promoter. Examples of tissue- or cell-type-specific regulatory sequences include, without limitation, the albumin promoter, lymphoid-specific promoters, promoters of T cell receptors or immunoglobulins, neuron-specific promoters, pancreas-specific promoters, mammary gland-specific promoters, and developmentally-regulated promoters. In some embodiments, a vector provided herein comprises a BCOR or BCORL1 nucleic acid molecule, a bait, a probe, or an oligonucleotide of the disclosure in the sense or the anti-sense orientation. In some embodiments, a vector (e.g., an expression vector) provided herein is introduced into host cells to thereby produce a polypeptide, e.g., a BCOR or BCORL1 polypeptide described herein, or a fragment or mutant form thereof.

In some embodiments, the design of a vector provided herein depends on such factors as the choice of the host cell to be transformed, the level of expression desired, and the like. In some embodiments, expression vectors are designed for the expression of BCOR or BCORL1 nucleic acid molecules, baits, probes, or oligonucleotides described herein, or fragments thereof, in prokaryotic or eukaryotic cells, such as *E. coli* cells, insect cells (e.g., using baculovirus expression vectors), yeast cells, or mammalian cells. In some embodiments, a vector described herein is transcribed and translated in vitro, for example using T7 promoter regulatory sequences and T7 polymerase. In some embodiments, a vector (e.g., an expression vector) provided herein comprises a BCOR or BCORL1 nucleic acid molecule described herein, wherein the nucleotide sequence of the BCOR or BCORL1 nucleic acid molecule described herein has been altered (e.g., codon optimized) so that the individual codons for each encoded amino acid are those preferentially utilized in the host cell.

Also provided herein are host cells, e.g., comprising BCOR or BCORL1 nucleic acid molecules, BCOR or BCORL1 polypeptides, baits, probes, vectors, or oligonucleotides of the disclosure. In some embodiments, a host cell (e.g., a recombinant host cell or recombinant cell) comprises a vector described herein (e.g., an expression vector described herein). In some embodiments, a BCOR or BCORL1 nucleic acid molecule, bait, probe, vector, or oligonucleotide provided herein further includes sequences which allow it to integrate into the host cell's genome (e.g., through homologous recombination at a specific site). In some embodiments, a host cell provided herein is a prokaryotic or eukaryotic cell. Non limiting examples of host cells include, without limitation, bacterial cells (e.g., *E. coli*), insect cells, yeast cells, or mammalian cells (e.g., human cells, rodent cells, mouse cells, rabbit cells, pig cells, Chinese hamster ovary cells (CHO), or COS cells, e.g., COS-7 cells, CV-1 origin SV40 cells). A host cell described herein includes the particular host cell, as well as the progeny of such a cell. Because certain modifications may occur in succeeding generations due to either mutation or environmental influences, such progeny may not, in fact, be identical to the parent host cell.

BCOR or BCORL1 nucleic acid molecules, baits, probes, vectors, or oligonucleotides of the disclosure may be introduced into host cells using any suitable method known in the art, such as conventional transformation or transfection techniques (e.g., using calcium phosphate or calcium chloride co-precipitation, DEAE-dextran-mediated transfection, lipofection, or electroporation).

Also provided herein are methods of producing a BCOR or BCORL1 polypeptide, e.g., by culturing a host cell described herein (e.g., into which a recombinant expression vector encoding a polypeptide has been introduced) in a suitable medium such that the BCOR or BCORL1 polypeptide is produced. In another embodiment, the method further includes isolating a BCOR or BCORL1 polypeptide from the medium or the host cell.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

The following exemplary embodiments are representative of some aspects of the invention:

Embodiment 1. A method of identifying an individual having cancer who may benefit from a treatment comprising a targeted therapeutic, the method comprising detecting a genetic alteration comprising a rearrangement in a B-cell lymphoma 6 (BCL6) corepressor (BCOR) gene or an alteration in a BCL6 corepressor-like protein 1 (BCORL1) gene in a sample from the individual, wherein the presence of the BCOR gene rearrangement or BCORL1 alteration in the sample identifies the individual as one who may benefit from the targeted therapeutic, wherein the targeted therapeutic is a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 2. A method of selecting a therapy for an individual having cancer, the method comprising detecting a genetic alteration comprising a rearrangement in a BCOR gene or an alteration in a BCORL1 gene in a sample from the individual, wherein the presence of the BCOR gene rearrangement or BCORL1 alteration in the sample identifies the individual as one who may benefit from a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 3. A method of identifying one or more treatment options for an individual having cancer, the method comprising:

(a) detecting a rearrangement in a BCOR gene or an alteration in a BCORL1 gene in a sample from the individual; and (b) generating a report comprising one or more treatment options identified for the individual based at least in part on the presence of the BCOR gene rearrangement or BCORL1 alteration in the sample, wherein the one or more treatment options comprise a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 4. A method of identifying one or more treatment options for an individual having cancer, the method comprising:

(a) acquiring knowledge of a rearrangement in a BCOR gene or an alteration in a BCORL1 gene in a sample from the individual; and (b) generating a report comprising one or more treatment options identified for the individual based at least in part on said knowledge, wherein the one or more treatment options comprise a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 5. A method of selecting treatment for an individual having cancer, comprising acquiring knowledge of a rearrangement in a BCOR gene or an alteration in a BCORL1 gene in a sample from an individual having cancer, wherein responsive to the acquisition of said knowledge: (i) the individual is classified as a candidate to receive treatment with a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor; and/or (ii) the individual is identified as likely to respond to a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 6. A method of treating or delaying progression of cancer, comprising administering to an individual an effective amount of a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor, wherein the cancer comprises a rearrangement in a BCOR gene or an alteration in a BCORL1 gene.

Embodiment 7. A method of treating or delaying progression of cancer, comprising, responsive to knowledge of a rearrangement in a BCOR gene or an alteration in a BCORL1 gene in a sample from an individual, administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 8. A method of treating or delaying progression of cancer, comprising:

(a) acquiring knowledge of a rearrangement in a BCOR gene or an alteration in a BCORL1 gene in a sample from an individual; and (b) responsive to said knowledge, administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 9. A method of treating or delaying progression of cancer, comprising:

(a) detecting a rearrangement in a BCOR gene or an alteration in a BCORL1 gene in a sample from an individual; and (b) administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 10. A method of monitoring an individual having cancer, comprising acquiring knowledge of a rearrangement in a BCOR gene or an alteration in a BCORL1 gene in a sample from the individual, wherein responsive to the acquisition of said knowledge, the individual is predicted to have increased risk of uterine sarcoma, as compared to an individual whose cancer does not comprise a rearrangement in a BCOR gene or an alteration in a BCORL1 gene.

Embodiment 11. A method of predicting survival of an individual having cancer, comprising acquiring knowledge of a rearrangement in a BCOR gene or an alteration in a BCORL1 gene in a sample from the individual, wherein responsive to the acquisition of said knowledge, the individual is predicted to have shorter survival, as compared to survival of an individual whose cancer does not comprise a rearrangement in a BCOR gene or an alteration in a BCORL1 gene.

Embodiment 12. A method of evaluating an individual having cancer, comprising acquiring knowledge of a rearrangement in a BCOR gene or an alteration in a BCORL1 gene in a sample from the individual, wherein responsive to the acquisition of said knowledge, the individual is predicted to have increased risk of recurrence, as compared to an individual whose cancer does not comprise a rearrangement in a BCOR gene or an alteration in a BCORL1 gene.

Embodiment 13. A method of screening an individual having cancer, comprising acquiring knowledge of a rearrangement in a BCOR gene or an alteration in a BCORL1 gene in a sample from the individual, wherein responsive to the acquisition of said knowledge, the individual is predicted to have increased risk of recurrence, as compared to an individual whose cancer does not comprise a rearrangement in a BCOR gene or an alteration in a BCORL1 gene.

Embodiment 14. The method of any one of embodiments 1-13, wherein the genetic alteration comprises a BCOR rearrangement.

Embodiment 15. The method of any one of embodiments 1-13, wherein the genetic alteration comprises a BCORL1 alteration.

Embodiment 16. The method of any one of embodiments 1-15, wherein the cancer further comprises one or more genomic alterations leading to increased expression and/or activity of Cyclin D/Cdk4 complex.

Embodiment 17. The method of embodiment 16, wherein the cancer further comprises amplification of an MDM2, FRS2, CCND2, or CDK4 gene.

Embodiment 18. The method of embodiment 16, wherein the cancer further comprises deletion of a CDKN2A or CDKN2B gene.

Embodiment 19. The method of embodiment 18, wherein the deletion is a homozygous deletion.

Embodiment 20. The method of any one of embodiments 16-19, wherein the targeted therapeutic is a CDK inhibitor.

Embodiment 21. The method of embodiment 20, wherein the CDK inhibitor is a CDK4/CDK6 inhibitor.

Embodiment 22. The method of embodiment 21, wherein the targeted therapeutic is (a) a small molecule that inhibits one or more enzymatic activities of CDK4, (b) an antibody that inhibits one or more activities of CDK4, or (c) a nucleic acid that inhibits expression of CDK4.

Embodiment 23. The method of embodiment 21, wherein the targeted therapeutic is palbociclib, ribociclib, or abemaciclib.

Embodiment 24. The method of any one of embodiments 16-19, wherein the targeted therapeutic is an MDM2 inhibitor.

Embodiment 25. The method of embodiment 24, wherein the targeted therapeutic is (a) a small molecule that inhibits one or more activities of MDM2, (b) an antibody that inhibits one or more activities of MDM2, or (c) a nucleic acid that inhibits expression of MDM2.

Embodiment 26. The method of embodiment 24, wherein the targeted therapeutic is nutlin-3a, RG7112, idasanutlin, AMG-232, MI-63, MI-291, MI-391, MI-77301, APG-115, DS-3032b, NVP-CGM097, or HDM-201.

Embodiment 27. The method of any one of embodiments 20-26, wherein the targeted therapeutic comprises a combination of a CDK inhibitor and an MDM2 inhibitor.

Embodiment 28. The method of any one of embodiments 1-14, wherein the cancer further comprises amplification of a PDGFRA, KDR, ERBB3, or KIT gene.

Embodiment 29. The method of embodiment 28, wherein the targeted therapeutic is a tyrosine kinase inhibitor.

Embodiment 30. The method of embodiment 29, wherein the targeted therapeutic is (a) a small molecule that inhibits one or more enzymatic activities of a tyrosine kinase, (b) an antibody that inhibits one or more activities of a tyrosine kinase, or (c) a nucleic acid that inhibits expression of a tyrosine kinase.

Embodiment 31. The method of embodiment 29, wherein the tyrosine kinase inhibitor is imatinib, crenolanib, linifanib, ninetedanib, axitinib, dasatinib, imetelstat, midostaurin, pazopanib, sorafenib, sunitinb, motesanib, masitinib, vatalanib, cabozanitinib, tivozanib, OSI-930, Ki8751, telatinib, dovitinib, tyrphostin AG 1296, amuvatinib, or a pharmaceutically acceptable salt thereof.

Embodiment 32. The method of any one of embodiments 1-15, wherein the cancer further comprises loss-of-function mutation in an NF1, NF2, mTOR, or PIK3RJ gene, or gain-of-function in an AKT1 gene.

Embodiment 33. The method of embodiment 32, wherein the targeted therapeutic is a MEK or mTOR inhibitor.

Embodiment 34. The method of embodiment 33, wherein the targeted therapeutic is (a) a small molecule that inhibits one or more enzymatic activities of MEK, (b) an antibody that inhibits one or more activities of MEK, or (c) a nucleic acid that inhibits expression of MEK.

Embodiment 35. The method of embodiment 33, wherein the MEK inhibitor is trametinib, cobimetinib, binimetinib, CI-1040, PD0325901, selumetinib, AZD8330, TAK-733, GDC-0623, refametinib, pimasertib, R04987655, RO5126766, WX-544, HL-085, or a pharmaceutically acceptable salt thereof.

Embodiment 36. The method of embodiment 33, wherein the targeted therapeutic is (a) a small molecule that inhibits one or more enzymatic activities of mTOR, (b) an antibody that inhibits one or more activities of mTOR, or (c) a nucleic acid that inhibits expression of mTOR.

Embodiment 37. The method of embodiment 33, wherein the mTOR inhibitor is temsirolimus, everolimus, ridaforolimus, dactolisib, GSK2126458, XL765, AZD8055, AZD2014, MLN128, PP242, NVP-BEZ235, LY3023414, PQR309, PKI587, OSI027, or a pharmaceutically acceptable salt thereof.

Embodiment 38. The method of embodiment 32, wherein the targeted therapeutic is a phosphatidylinositol 3-kinase (PI3K) or AKT1 inhibitor.

Embodiment 39. The method of embodiment 38, wherein the targeted therapeutic is (a) a small molecule that inhibits one or more enzymatic activities of PI3K, (b) an antibody that inhibits one or more activities of PI3K, or (c) a nucleic acid that inhibits expression of PI3K.

Embodiment 40. The method of embodiment 38, wherein the PI3K inhibitor is idelalisib, copanlisib, duvelisib, alpelisib, taselisib, perifosine, buparlisib, umbralisib, PX-866, dacolisib, CUDC-907, voxtalisib, ME-401, IPI-549, SF1126, RP6530, INK1117, pictilisib, XL147, Palomid 529, GSK1059615, ZSTK474, PWT33597, IC87114, TG100-115, CAL263, RP6503, PI-103, GNE-477, or AEZS-136.

Embodiment 41. The method of embodiment 38, wherein the targeted therapeutic is (a) a small molecule that inhibits one or more enzymatic activities of AKT1, (b) an antibody that inhibits one or more activities of AKT1, or (c) a nucleic acid that inhibits expression of AKT1.

Embodiment 42. The method of embodiment 38, wherein the AKT1 inhibitor is GSK690693, uprosertib, afuresertib, AZD5363, ipatasertib, AT7867, CCT128930, MK-2206, BAY1125976, or perifosine.

Embodiment 43. The method of any one of embodiments 1-13, wherein the cancer further comprises loss-of-function mutation in a PTCH1 gene.

Embodiment 44. The method of embodiment 41, wherein the targeted therapeutic is a Hh inhibitor.

Embodiment 45. The method of embodiment 44, wherein the targeted therapeutic is (a) a small molecule that inhibits one or more enzymatic activities of Hh, (b) an antibody that inhibits one or more activities of Hh, or (c) a nucleic acid that inhibits expression of Hh.

Embodiment 46. The method of embodiment 44, wherein the targeted therapeutic is selected from the group consisting of sonidegib, vismodegib, erismodegib, saridegib, BMS833923, PF-04449913, LY2940680, and pharmaceutically acceptable salts thereof.

Embodiment 47. The method of any one of embodiments 1-13 and 15-46, wherein the BCOR rearrangement results in a fusion gene between BCOR and ZC3H7B.

Embodiment 48. The method of embodiment 47, wherein a sample obtained from the cancer comprises spindle cells arranged in a fascicular growth pattern.

Embodiment 49. The method of any one of embodiments 1-13 and 15-46, wherein the BCOR rearrangement results in a fusion gene between BCOR and L3MBTL2, EP300, NUTM2G, MAP7D2, RALGPS1, RGAG1, CREBBP, ING3, NUGGC, or KMT2D.

Embodiment 50. The method of embodiment 49, wherein the fusion gene is BCOR-L3MBTL2, EP300-BCOR, BCOR-NUTM2G, BCOR-RALGPS1, BCOR-MAP7D2, RGAG1-BCOR, ING3-BCOR, BCOR-NUGGC, KMT2D-BCOR, or CREBBP-BCOR.

Embodiment 51. The method of any one of embodiments 1-13 and 15-46, wherein the BCOR rearrangement is an internal BCOR gene rearrangement characterized by a chromosome X inversion.

Embodiment 52. The method of any one of embodiments 49-51, wherein a sample obtained from the cancer comprises spindle, epithelioid, or small round cells.

Embodiment 53. The method of any one of embodiments 49-52, wherein the sample further comprises myxoid stroma.

Embodiment 54. The method of any one of embodiments 49-53, wherein the sample further comprises collagen fibrosis.

Embodiment 55. The method of any one of embodiments 49-54, wherein the sample further comprises spiral arterioles.

Embodiment 56. The method of any one of embodiments 49-55, wherein a sample obtained from the cancer is characterized by a mitotic count that is between about 3 per 10 high power fields (HPF) and about 30 per 10 HPF.

Embodiment 57. The method of any one of embodiments 1-13 and 15-46, wherein the BCORL1 alteration comprises a frameshift, nonsense, or truncating mutation.

Embodiment 58. The method of embodiment 57, wherein the BCORL1 alteration comprises a T513fs*22, P600fs*1, R945*, R1196*, R1265fs*4, L461fs*5, or H1426fs*29 mutation.

Embodiment 59. The method of any one of embodiments 1-13 and 15-46, wherein the BCORL1 alteration comprises a deletion.

Embodiment 60. The method of embodiment 59, wherein the deletion is a homozygous deletion.

Embodiment 61. The method of any one of embodiments 1-13 and 15-46, wherein the BCORL1 alteration comprises an internal BCORL1 rearrangement.

Embodiment 62. The method of any one of embodiments 1-13 and 15-46, wherein the BCORL1 alteration comprises a rearrangement resulting in a BCORL1 fusion gene.

Embodiment 63. The method of embodiment 62, wherein the BCORL1 rearrangement results in a fusion gene between BCORL1 and JAZF1 or EP300.

Embodiment 64. The method of embodiment 62, wherein the BCORL1 fusion gene is a JAZF1-BCORL1, BCORL1-JAZF1, or EP300-BCORL1 fusion gene.

Embodiment 65. The method of embodiment 64, wherein the BCORL1 fusion gene is a JAZF1-BCORL1 fusion gene comprising breakpoints at exon 3 of JAZF1 and exon 5 of BCORL1.

Embodiment 66. The method of embodiment 65, wherein the BCORL1 fusion gene is a JAZF1-BCORL1 fusion gene comprising exons 1-3 of JAZF1 fused to exons 5-12 of BCORL1.

Embodiment 67. The method of embodiment 64, wherein the BCORL1 fusion gene is a JAZF1-BCORL1 fusion gene comprising breakpoints at exon 3 of JAZF1 and exon 6 of BCORL1.

Embodiment 68. The method of embodiment 67, wherein the BCORL1 fusion gene is a JAZF1-BCORL1 fusion gene comprising exons 1-3 of JAZF1 fused to exons 6-12 of BCORL1.

Embodiment 69. The method of embodiment 64, wherein the BCORL1 fusion gene is a JAZF1-BCORL1 fusion gene comprising breakpoints at exon 3 of JAZF1 and exon 7 of BCORL1.

Embodiment 70. The method of embodiment 69, wherein the BCORL1 fusion gene is a JAZF1-BCORL1 fusion gene comprising exons 1-3 of JAZF1 fused to exons 7-12 of BCORL1.

Embodiment 71. The method of embodiment 64, wherein the BCORL1 fusion gene is a BCORL1-JAZF1 fusion gene comprising breakpoints at exon 4 of BCORL1 and exon 4 of JAZF1.

Embodiment 72. The method of embodiment 71, wherein the BCORL1 fusion gene is a BCORL1-JAZF1 fusion gene comprising exons 1-4 of BCORL1 fused to exons 4-5 of JAZF1.

Embodiment 73. The method of embodiment 64, wherein the BCORL1 fusion gene is an EP300-BCORL1 fusion gene comprising breakpoints at exon 31 of EP300 and exon 4 of BCORL1.

Embodiment 74. The method of embodiment 73, wherein the BCORL1 fusion gene is an EP300-BCORL1 fusion gene comprising exons 1-31 of EP300 fused to exons 4-12 of BCORL1.

Embodiment 75. The method of any one of embodiments 57-74, wherein a sample obtained from the cancer comprises spindle or epithelioid cells.

Embodiment 76. The method of any one of embodiments 57-75, wherein the sample further comprises myxoid stroma.

Embodiment 77. The method of any one of embodiments 57-76, wherein the sample further comprises collagen fibrosis.

Embodiment 78. The method of any one of embodiments 57-77, wherein the sample further comprises spiral arterioles.

Embodiment 79. The method of any one of embodiments 57-78, wherein a sample obtained from the cancer is characterized by a mitotic count that is between about 2 per 10 high power fields (HPF) and about 25 per 10 HPF.

Embodiment 80. The method of any one of embodiments 1-79, wherein the cancer is endometrial stromal sarcoma (ESS).

Embodiment 81. The method of embodiment 80, wherein the cancer is a high grade ESS.

Embodiment 82. The method of any one of embodiments 1-81, wherein the cancer is uterine sarcoma.

Embodiment 83. The method of embodiment 82, wherein the cancer is uterine adenosarcoma.

Embodiment 84. The method of any one of embodiments 1-83, wherein a sample obtained from the cancer exhibits expression of one or more of cyclin D1, CD10, and BCOR.

Embodiment 85. The method of any one of embodiments 1-83, wherein a sample obtained from the cancer exhibits cyclin D1 overexpression.

Embodiment 86. The method of any one of embodiments 1-85, wherein a sample obtained from the cancer does not exhibit desmin expression.

Embodiment 87. The method of any one of embodiments 1-86, wherein the cancer was previously classified as myxoid leiomyosarcoma.

Embodiment 88. The method of any one of embodiments 1-86, wherein a sample obtained from the cancer lacks a mutation in one or more of the TP53, BRCA2, PLAG1, RB1, ATRX, PTEN or MED12 genes.

Embodiment 89. The method of any one of embodiments 1-86, wherein a sample obtained from the cancer lacks a mutation in any of the TP53, BRCA2, PLAG1, RB1, ATRX, PTEN or MED12 genes.

Embodiment 90. The method of any one of embodiments 1-89, wherein a sample obtained from the cancer is characterized by intermediate or low tumor burden.

Embodiment 91. The method of any one of embodiments 1-89, wherein a sample obtained from the cancer is characterized by 19 or fewer mutations per megabase (Mb).

Embodiment 92. The method of any one of embodiments 1-89, wherein a sample obtained from the cancer is characterized by 6 or fewer mutations per megabase (Mb).

Embodiment 93. The method of any one of embodiments 1-92, wherein a sample obtained from the cancer is microsatellite stable.

Embodiment 94. The method of any one of embodiments 1-93, wherein the cancer is resistant or refractory to treatment with conventional chemotherapy.

Embodiment 95. The method of any one of embodiments 1-94, further comprising selectively enriching for one or more nucleic acids comprising a rearrangement in a BCOR gene or an alteration in a BCORL1 gene to produce an enriched sample.

Embodiment 96. The method of any one of embodiments 1-95, wherein the treatment or the one or more treatment options further comprise a second therapeutic agent.

Embodiment 97. The method of embodiment 96, wherein the second therapeutic agent comprises a chemotherapeutic agent, immune checkpoint inhibitor (ICI), cancer immunotherapy, cell-based therapy, or nucleic acid-based therapy.

Embodiment 98. The method of any one of embodiments 1-97, wherein the sample from the individual comprises fluid, cells, or tissue.

Embodiment 99. The method of embodiment 98, wherein the sample from the individual comprises a tumor biopsy or a circulating tumor cell.

Embodiment 100. The method of any one of embodiments 1-99, wherein the sample from the individual is a nucleic acid sample.

Embodiment 101. The method of embodiment 100, wherein the nucleic acid sample comprises mRNA, genomic DNA, circulating tumor DNA, cell-free DNA, or cell-free RNA.

Embodiment 102. The method of any one of embodiments 1-101, wherein the BCOR gene rearrangement or BCORL1 alteration is detected in the sample by one or more methods selected from the group consisting of a nucleic acid hybridization assay, an amplification-based assay, a polymerase chain reaction-restriction fragment length polymorphism (PCR-RFLP) assay, real-time PCR, sequencing, next-generation sequencing, a screening analysis, fluorescence in situ hybridization (FISH), spectral karyotyping, multicolor FISH (mFISH), comparative genomic hybridization, in situ hybridization, sequence-specific priming (SSP) PCR, high-performance liquid chromatography (HPLC), and mass-spectrometric genotyping.

Embodiment 103. The method of any one of embodiments 1-102, further comprising obtaining more than one sample from the individual at different time points.

Embodiment 104. A kit comprising a probe or bait for detecting a rearrangement in a BCOR gene or an alteration in a BCORL1 gene.

Embodiment 105. A vector comprising a rearrangement in a BCOR gene or an alteration in a BCORL1 gene, or fragments thereof.

Embodiment 106. A host cell comprising the vector of embodiment 105.

Embodiment 107. An antibody or antibody fragment that specifically binds to a polypeptide encoded by a BCOR fusion gene or an internal BCOR gene rearrangement.

Embodiment 108. The antibody of embodiment 107, wherein the BCOR fusion gene comprises a fusion between BCOR and a gene selected from the group consisting of L3MBTL2, EP300, NUTM2G, MAP7D2, RALGPS1, RGAG1, CREBBP, ING3, NUGGC, and KMT2D.

Embodiment 109. A kit comprising an antibody or antibody fragment that specifically binds to a polypeptide encoded by a BCOR fusion gene or an internal BCOR gene rearrangement.

Embodiment 110. The kit of embodiment 109, wherein the BCOR fusion gene comprises a fusion between BCOR and a gene selected from the group consisting of L3MBTL2, EP300, NUTM2G, MAP7D2, RALGPS1, RGAG1, CREBBP, ING3, NUGGC, and KMT2D.

Embodiment 111. An antibody or antibody fragment that specifically binds to a polypeptide encoded by a BCORL1 gene comprising:
- (a) a frameshift, nonsense, or truncating mutation;
- (b) an internal rearrangement; or
- (c) a fusion gene.

Embodiment 112. The antibody of embodiment 111, wherein the BCORL1 gene comprises:
- (a) a T513fs*22, P600fs*1, R945*, R1196*, R1265fs*4, L461fs*5, or H1426fs*29 mutation;
- (b) an internal rearrangement; or
- (c) a JAZF1-BCORL1, BCORL1-JAZF1, or EP300-BCORL1 fusion gene.

Embodiment 113. A kit comprising an antibody or antibody fragment that specifically binds to a polypeptide encoded by a BCORL1 gene comprising:
- (a) a frameshift, nonsense, or truncating mutation;
- (b) an internal rearrangement; or
- (c) a fusion gene.

Embodiment 114. The kit of embodiment 113, wherein the BCORL1 gene comprises:
- (a) a T513fs*22, P600fs*1, R945*, R1196*, R1265fs*4, L461fs*5, or H1426fs*29 mutation;
- (b) an internal rearrangement; or
- (c) a JAZF1-BCORL1, BCORL1-JAZF1, or EP300-BCORL1 fusion gene.

Embodiment 115. A method of detecting a rearrangement in B-cell lymphoma 6 (BCL6) corepressor (BCOR) gene, the method comprising detecting an internal BCOR gene rearrangement or a fusion gene between a BCOR gene and a L3MBTL2, EP300, NUTM2G, MAP7D2, RALGPS1, RGAG1, CREBBP, ING3, NUGGC, and KMT2D gene in a sample from an individual.

Embodiment 116. A method of diagnosing/assessing a rearrangement in B-cell lymphoma 6 (BCL6) corepressor (BCOR) gene, the method comprising:
- (a) detecting an internal BCOR gene rearrangement or a fusion gene between BCOR and L3MBTL2, EP300, NUTM2G, MAP7D2, RALGPS1, RGAG1, CREBBP, ING3, NUGGC, or KMT2D in a sample from an individual; and
- (b) providing a diagnosis/assessment of a rearrangement in a B-cell lymphoma 6 (BCL6) corepressor (BCOR) gene.

Embodiment 117. A method of diagnosing endometrial stromal sarcoma (ESS) in an individual, the method comprising:
- (a) detecting an internal rearrangement in B-cell lymphoma 6 (BCL6) corepressor (BCOR) gene rearrangement or a fusion gene between BCOR and L3MBTL2, EP300, NUTM2G, MAP7D2, RALGPS1, RGAG1, CREBBP, ING3, NUGGC, or KMT2D in a sample from the individual; and
- (b) providing a diagnosis of endometrial stromal sarcoma in the individual.

Embodiment 118. A method of diagnosing uterine sarcoma in an individual, the method comprising:
- (a) detecting an internal rearrangement in B-cell lymphoma 6 (BCL6) corepressor (BCOR) gene rearrangement or a fusion gene between BCOR and L3MBTL2, EP300, NUTM2G, MAP7D2, RALGPS1, RGAG1, CREBBP, ING3, NUGGC, or KMT2D in a sample from the individual; and
- (b) providing a diagnosis of uterine sarcoma in the individual.

Embodiment 119. A method of detecting a BCORL1 gene alteration, the method comprising detecting a BCORL1 gene comprising a frameshift, nonsense, or truncating mutation; deletion; internal rearrangement; or fusion gene in a sample from an individual.

Embodiment 120. A method of diagnosing/assessing a BCORL1 gene alteration, the method comprising:
- (a) detecting a BCORL1 gene comprising a frameshift, nonsense, or truncating mutation; deletion; internal rearrangement; or fusion gene in a sample from an individual, and
- (b) providing a diagnosis/assessment of a BCORL1 gene alteration.

Embodiment 121. A method of diagnosing endometrial stromal sarcoma (ESS) in an individual, the method comprising:
- (a) detecting a BCORL1 gene comprising a frameshift, nonsense, or truncating mutation; deletion; internal rearrangement; or fusion gene in a sample from the individual; and
- (b) providing a diagnosis of endometrial stromal sarcoma in the individual.

Embodiment 122. A method of diagnosing uterine sarcoma in an individual, the method comprising:
- (a) detecting a BCORL1 gene comprising a frameshift, nonsense, or truncating mutation; deletion; internal rearrangement; or fusion gene in a sample from the individual; and
- (b) providing a diagnosis of uterine sarcoma in the individual.

Embodiment 123. A method of detecting a rearrangement in a BCOR gene or an alteration in a BCORL1 gene, comprising:
- (a) providing a plurality of nucleic acids obtained from a sample from an individual, wherein the plurality of nucleic acids comprises nucleic acids encoding a BCOR gene or a BCORL1 gene;
- (b) optionally, ligating one or more adaptors onto one or more nucleic acids from the plurality of nucleic acids;
- (c) amplifying nucleic acids from the plurality of nucleic acids;
- (d) optionally, capturing a plurality of nucleic acids corresponding to the BCOR and/or BCORL1 gene(s);

(e) sequencing, by a sequencer, the plurality of nucleic acids to obtain a plurality of sequence reads corresponding to the BCOR and/or BCORL1 gene(s);

(f) analyzing the plurality of sequence reads; and (g) based on the analysis, detecting a rearrangement in the BCOR gene or an alteration in the BCORL1 gene.

Embodiment 124. The method of embodiment 123, wherein the plurality of nucleic acids corresponding to the BCOR and/or BCORL1 gene(s) are captured from the amplified nucleic acids by hybridization with a bait molecule.

Embodiment 125. The method of any one of embodiments 119-124, wherein the BCORL1 gene comprises:

(a) a T513fs*22, P600fs*1, R945*, R1196*, R1265fs*4, L461fs*5, or H1426fs*29 mutation;

(b) an internal rearrangement; or (c) a JAZF1-BCORL1, BCORL1-JAZF1, or EP300-BCORL1 fusion gene.

Embodiment 126. A system, comprising:

a memory configured to store one or more program instructions; and one or more processors configured to execute the one or more program instructions, the one or more program instructions when executed by the one or more processors are configured to:

(a) obtain a plurality of sequence reads of one or more nucleic acids, wherein the one or more nucleic acids are derived from a sample obtained from an individual, (b) analyze the plurality of sequence reads for the presence of a genetic alteration comprising a rearrangement in a B-cell lymphoma 6 (BCL6) corepressor (BCOR) gene or an alteration in a BCL6 corepressor-like protein 1 (BCORL1) gene, or of a portion thereof; and (c) detect, based on the analyzing, a rearrangement in a BCOR gene or an alteration in a BCORL1 gene, or a portion thereof, in the sample.

Embodiment 127. The system of embodiment 126, wherein the genetic alteration comprises a BCOR rearrangement.

Embodiment 128. The system of embodiment 127, wherein:

(a) the BCOR rearrangement results in a fusion gene between BCOR and ZC3H7B;

(b) the BCOR rearrangement results in a fusion gene between BCOR and L3MBTL2, EP300, NUTM2G, MAP7D2, RALGPS1, RGAG1, CREBBP, ING3, NUGGC, or KMT2D or (c) wherein the BCOR rearrangement is an internal BCOR gene rearrangement characterized by a chromosome X inversion.

Embodiment 129. The system of embodiment 126, wherein the genetic alteration comprises a BCORL1 alteration.

Embodiment 130. The system of embodiment 129, wherein the BCORL1 alteration comprises:

(a) a frameshift, nonsense, or truncating mutation;

(b) a deletion;

(c) an internal BCORL1 rearrangement; or (d) a rearrangement resulting in a BCORL1 fusion gene.

Embodiment 131. A non-transitory computer readable storage medium comprising one or more programs executable by one or more computer processors for performing a method, comprising:

(a) obtaining, using the one or more processors, a plurality of sequence reads of one or more nucleic acids, wherein the one or more nucleic acids are derived from a sample obtained from an individual;

(b) analyzing, using the one or more processors, the plurality of sequence reads for the presence of a genetic alteration comprising a rearrangement in a B-cell lymphoma 6 (BCL6) compressor (BCOR) gene or an alteration in a BCL6 corepressor-like protein 1 (BCORL1) gene, or of a portion thereof; and (c) detecting, using the one or more processors and based on the analyzing, a rearrangement in a BCOR gene or an alteration in a BCORL1 gene, or a portion thereof, in the sample.

Embodiment 132. The non-transitory computer readable storage medium of embodiment 131, wherein the genetic alteration comprises a BCOR rearrangement.

Embodiment 133. The non-transitory computer readable storage medium of embodiment 132, wherein:

(a) the BCOR rearrangement results in a fusion gene between BCOR and ZC3H7B;

(b) the BCOR rearrangement results in a fusion gene between BCOR and L3MBTL2, EP300, NUTM2G, MAP7D2, RALGPS1, RGAG1, CREBBP, ING3, NUGGC, or KMT2D; or (c) wherein the BCOR rearrangement is an internal BCOR gene rearrangement characterized by a chromosome X inversion.

Embodiment 134. The non-transitory computer readable storage medium of embodiment 131, wherein the genetic alteration comprises a BCORL1 alteration.

Embodiment 135. The non-transitory computer readable storage medium of embodiment 134, wherein the BCORL1 alteration comprises:

(a) a frameshift, nonsense, or truncating mutation;

(b) a deletion;

(c) an internal BCORL1 rearrangement; or (d) a rearrangement resulting in a BCORL1 fusion gene.

Embodiment 136. In vitro use of one or more oligonucleotides for detecting a rearrangement in a B-cell lymphoma 6 (BCL6) compressor (BCOR) gene, wherein the BCOR gene rearrangement results in an internal BCOR gene rearrangement or a fusion gene between BCOR and L3MBTL2, EP300, NUTM2G, MAP7D2, RALGPS1, RGAG1, CREBBP, ING3, NUGGC, or KMT2D.

Embodiment 137. A kit comprising one or more oligonucleotides for detecting a rearrangement in a B-cell lymphoma 6 (BCL6) compressor (BCOR) gene, wherein the BCOR gene rearrangement results in an internal BCOR gene rearrangement or a fusion gene between BCOR and L3MBTL2, EP300, NUTM2G, MAP7D2, RALGPS1, RGAG1, CREBBP, ING3, NUGGC, or KMT2D.

Embodiment 138. In vitro use of one or more oligonucleotides for detecting a BCORL1 gene alteration, wherein the BCORL1 gene alteration comprises a frameshift, nonsense, or truncating mutation; deletion; internal rearrangement; or fusion gene.

Embodiment 139. The use of embodiment 138, wherein the BCORL1 gene alteration comprises:

(a) a T513fs*22, P600fs*1, R945*, R1196*, R1265fs*4, L461fs*5, or H1426fs*29 mutation;

(b) an internal rearrangement; or (c) a JAZF1-BCORL1, BCORL1-JAZF1, or EP300-BCORL1 fusion gene.

Embodiment 140. A kit comprising one or more oligonucleotides for detecting a BCORL1 gene alteration, wherein the BCORL1 gene alteration comprises a frameshift, nonsense, or truncating mutation; deletion; internal rearrangement; or fusion gene.

Embodiment 141. The kit of embodiment 140, wherein the BCORL1 gene alteration comprises:

(a) a T513fs*22, P600fs*1, R945*, R1196*, R1265fs*4, L461fs*5, or H1426fs*29 mutation;

(b) an internal rearrangement; or (c) a JAZF1-BCORL1, BCORL1-JAZF1, or EP300-BCORL1 fusion gene.

Embodiment 142. A targeted therapeutic for use in a method of treating or delaying progression of cancer, wherein the method comprises administering the targeted therapeutic to an individual, wherein a rearrangement in a BCOR gene or an alteration in a BCORL1 gene is detected in a sample obtained from the individual, and wherein the targeted therapeutic is a CDK inhibitor, an MDM2 inhibitor, a tyrosine kinase inhibitor, a MEK inhibitor, an mTOR inhibitor, PIK3CA or AKT inhibitor, or a Hh inhibitor.

Embodiment 143. A targeted therapeutic for use in the manufacture of a medicament for treating or delaying progression of cancer, wherein the medicament is to be administered to an individual, wherein a rearrangement in a BCOR gene or an alteration in a BCORL1 gene has been detected in a sample obtained from the individual, and wherein the targeted therapeutic is a CDK inhibitor, an MDM2 inhibitor, a tyrosine kinase inhibitor, a MEK inhibitor, an mTOR inhibitor, PIK3CA or AKT inhibitor, or a Hh inhibitor.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Genomic Profiling of BCOR-Rearranged Uterine Sarcomas Reveals Novel Gene Fusion Partners and Frequent CDK4 Activation Comprehensive genomic profiling can identify not only BCOR-mutated cases which were not detected by other means, such as piecemeal FISH assays, but can also identify various specific gene rearrangements or the internal tandem duplication of a gene in a single molecular assay. In this study, targeted DNA- and RNA-based next generation sequencing and comprehensive genomic profiling were used to 1) determine the molecular landscape of BCOR-rearranged endometrial sarcomas, 2) to identify the novel BCOR fusion gene partners in uterine sarcomas and associated clinicopathological characteristics, and 3) to potentially unravel targetable genomic alterations in BCOR-rearranged uterine sarcomas.

Materials and Methods

BCOR-Rearranged Uterine Sarcoma Cohort

Approval for this study was obtained from the Western Institutional Review Board. A retrospective database search of a CLIA-certified and CAP-accredited reference molecular laboratory was performed for uterine sarcomas with genomic profiles that contained BCOR gene rearrangements or BCOR internal tandem duplication. The cases were previously assayed with comprehensive genomic profiling via both DNA- and RNA-based targeted next generation sequencing during the course of clinical care at other institutions. Clinicopathological data including patient age and sites of metastases were extracted from pathology reports. The pathologic diagnosis of uterine sarcoma and associated morphological features were centrally re-evaluated on routine H&E slides of tissue sections submitted for genomic profiling. Tumor staging for each case was assigned based on either the accompanying pathology report with respective synoptic reports or based on associated clinical documents containing tumor stage. One H&E slide, corresponding to the tissue that was submitted for genomic profiling, was available for each case for review of morphological features. Central re-review was performed by a United States board-certified, gynecologic pathologist (DIL).

Genomic Profiling

Next generation sequencing-based comprehensive genomic profiling was performed on hybridization-captured, adaptor ligation-based libraries using DNA and RNA extracted from formalin-fixed paraffin-embedded tumor in a CLIA- and CAP-certified laboratory. All samples forwarded for DNA and RNA extraction contained a minimum of 20% tumor cells. The samples were assayed using adaptor-ligation and hybrid capture next-generation sequencing for all coding exons from up to 406 cancer related genes, plus select introns from up to 31 genes frequently rearranged in cancer. Patient samples were sequenced and evaluated for genomic alterations including base substitutions, insertions, deletions, copy number alterations (amplifications and homozygous deletions), and for BCOR and other select gene fusions/rearrangements, as previously described (Lipson, D. et al. (2012) *Nat. Med.* 18:382-384; He, J. et al. (2016) *Blood* 127:3004-3014). The bioinformatics processes used in this study included Bayesian algorithms to detect base substitutions, local assembly algorithms to detect short insertions and deletions, a comparison with process-matched normal control samples to detect gene copy number alterations and an analysis of chimeric read pairs to identify gene fusions as previously described (Frampton, G. M. et al. (2013) *Nat. Biotechnol.* 31:1023-1031). To help visualize the sequencing data results, an oncoprint plot was generated with the online tools of the cbio portal as described by Gao et al. ((2013) *Sci. Signal* 6:p11) and Cerami et al. ((2012) *Cancer Discov.* 2:401-404).

Calculation of Tumor Mutational Burden and Microsatellite Instability

Tumor mutational burden was determined on 0.83-1.14 Mb of sequenced DNA using a mutation burden estimation algorithm that, based on the genomic alterations detected, extrapolates to the exome or the genome as a whole as previously described (Chalmers, Z. R. et al. (2017) *Genome Med.* 9:34). In this study, low tumor mutational burden scores were defined as $<6$ mut/Mb; intermediate tumor mutational burden was defined as scores of 6-19 mut/Mb, and high tumor mutational burden was defined as scores of $>=20$ mut/Mb. Assessment of microsatellite instability was performed from DNA sequencing across 114 loci as previously described (Chalmers, Z. R. et al. (2017) *Genome Med* 9:34). Each microsatellite locus had repeat length of 7-39 bp. The next-generation sequencing based "microsatellite instability score" was translated into categorical microsatellite instability high, microsatellite instability intermediate, or microsatellite stable by unsupervised clustering of specimens for which microsatellite instability status was previously assessed via gold standard methods (Chalmers, Z. R. et al. (2017) *Genome Med.* 9:34).

Statistical Analysis

Fisher's exact test was used in the statistical analysis comparing the frequency of CDK4 and MDM2 amplification and CDKN2A homozygous deletion in the cohort of BCOR-rearranged uterine sarcomas versus the cohort of uterine sarcomas harboring BCOR internal tandem duplication. Statistical significance was defined as $p<0.05$.

Results

A retrospective database search of 1,390 uterine sarcoma cases (including 270 endometrial stromal sarcomas, 939 uterine leiomyosarcomas and 181 undifferentiated uterine sarcomas), which had previously undergone comprehensive genomic profiling between 2010 and 2019, from the archives of a large CLIA-certified and CAP-accredited reference molecular laboratory, yielded 40 cases with BCOR gene rearrangements. Submitting previous diagnoses for the 40 cases with BCOR rearrangements from referring institutions included 22 cases of endometrial stromal sarcoma, 9 cases of high-grade undifferentiated uterine sarcoma, 8 cases of myxoid leiomyosarcoma and 1 case of recurrent uterine sarcoma derived from a uterine adenosarcoma with sarcomatous overgrowth. Based on genomics and morphology, the 8 cases with prior diagnoses of myxoid leiomyosarcoma were reclassified as BCOR-rearranged endometrial stromal sarcoma, similarly to previously described (Lewis, N. et al. (2018) *Mod. Pathol.* 31:674-684), based on morphology and lack of known driver mutations commonly found in either conventional uterine leiomyosarcoma (i.e. lack of TP53, RB1, ATRX, PTEN or MED12 alterations; see Mäkinen N. et al. (2016) *PLoS Genet.* 12:e1005850; Cuppens, T. et al. (2018) *Int. J. Cancer* 142:1230-1243; Elvin, J. A. et al. (2017) *Oncologist* 22:416-421) or in less studied and more genetically heterogeneous myxoid uterine leiomyosarcoma (i.e. lack of TP53 and BRCA2 mutations or PLAG1 rearrangements; see Schaefer, I. M. et al. (2017) *Histopathology* 70:1138-1146; Arias-Stella, J. A. et al. (2019) *Am. J Surg. Pathol.* 43:382-388; Yoon, J. Y. et al. (2019) *Mod. Pathol.* 32:1688-1697). Slides of the hysterectomy specimen for the uterine adenosarcoma case were not available to assess for classic adenosarcoma morphology (i.e. phyllodes architecture and peri-glandular cuffing or condensation).

In the cohort of 40 BCOR-rearranged uterine sarcoma cases, patient age ranged from 23 to 79 years with a median age of 54 years. Most tumors in the cohort were high stage and aggressive with spread of tumor beyond the uterus. Specifically, 18% of cases were stage I, 12% stage II, 32% stage III, and 38% stage IV. In addition, 18% (7 of 40) of tumors demonstrated lymph node metastasis; however, this is likely an underestimation, since a lymphadenectomy was not performed in all cases. Other sites of extra-uterine and distant metastasis in the cohort included ovary, fallopian tube, abdomen, colon, small intestine, omentum, lung, pleura and bone (vertebra, femur and humerus).

Figure 1B:
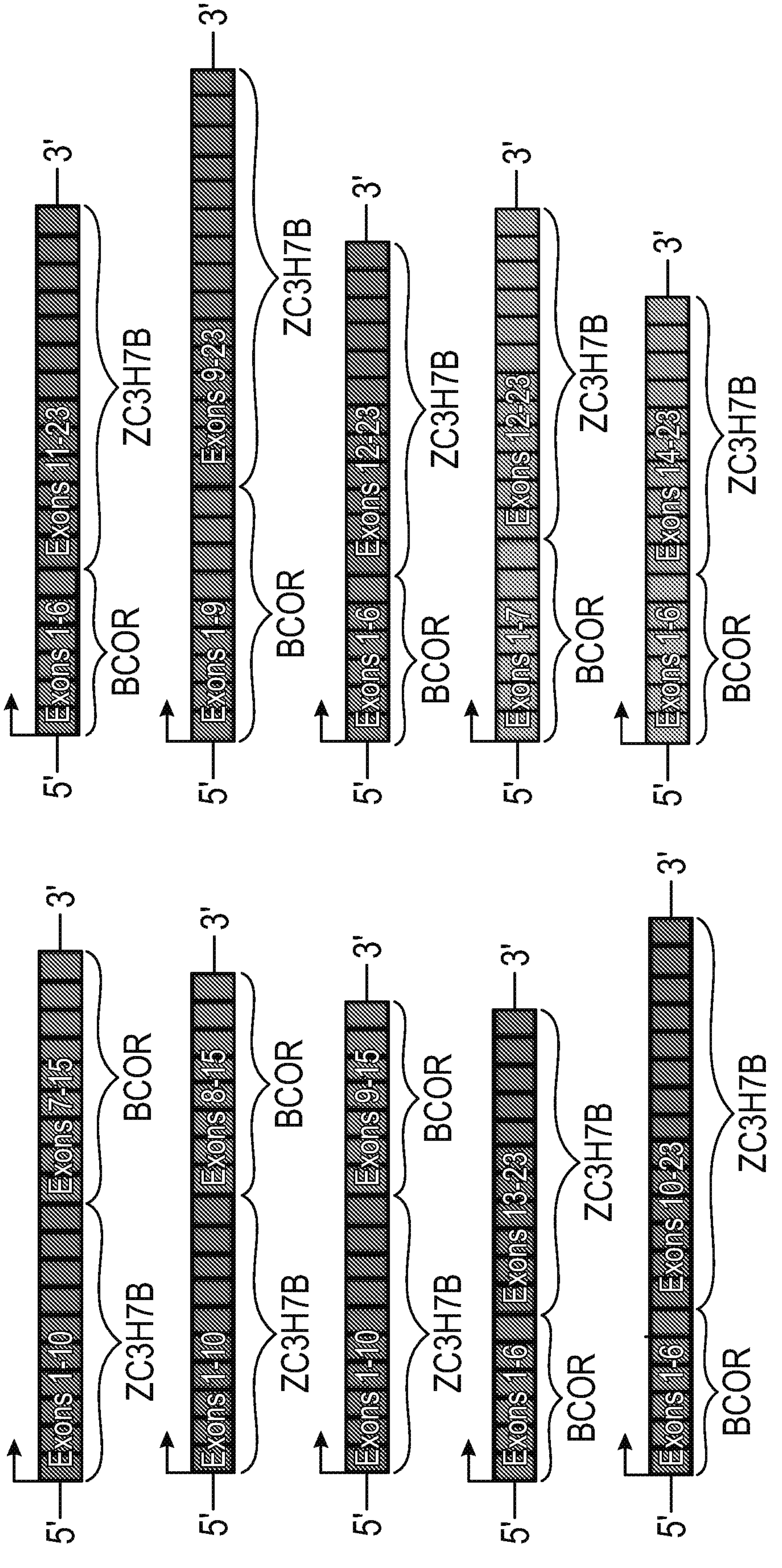
FIG. 1B provides schematic diagrams of RNA fusion transcripts involving BCOR and ZC3H7B identified in the uterine sarcoma cohort. Specific exons for BCOR and ZC3H7B identified for each fusion transcript are labeled.
Figure 1C:
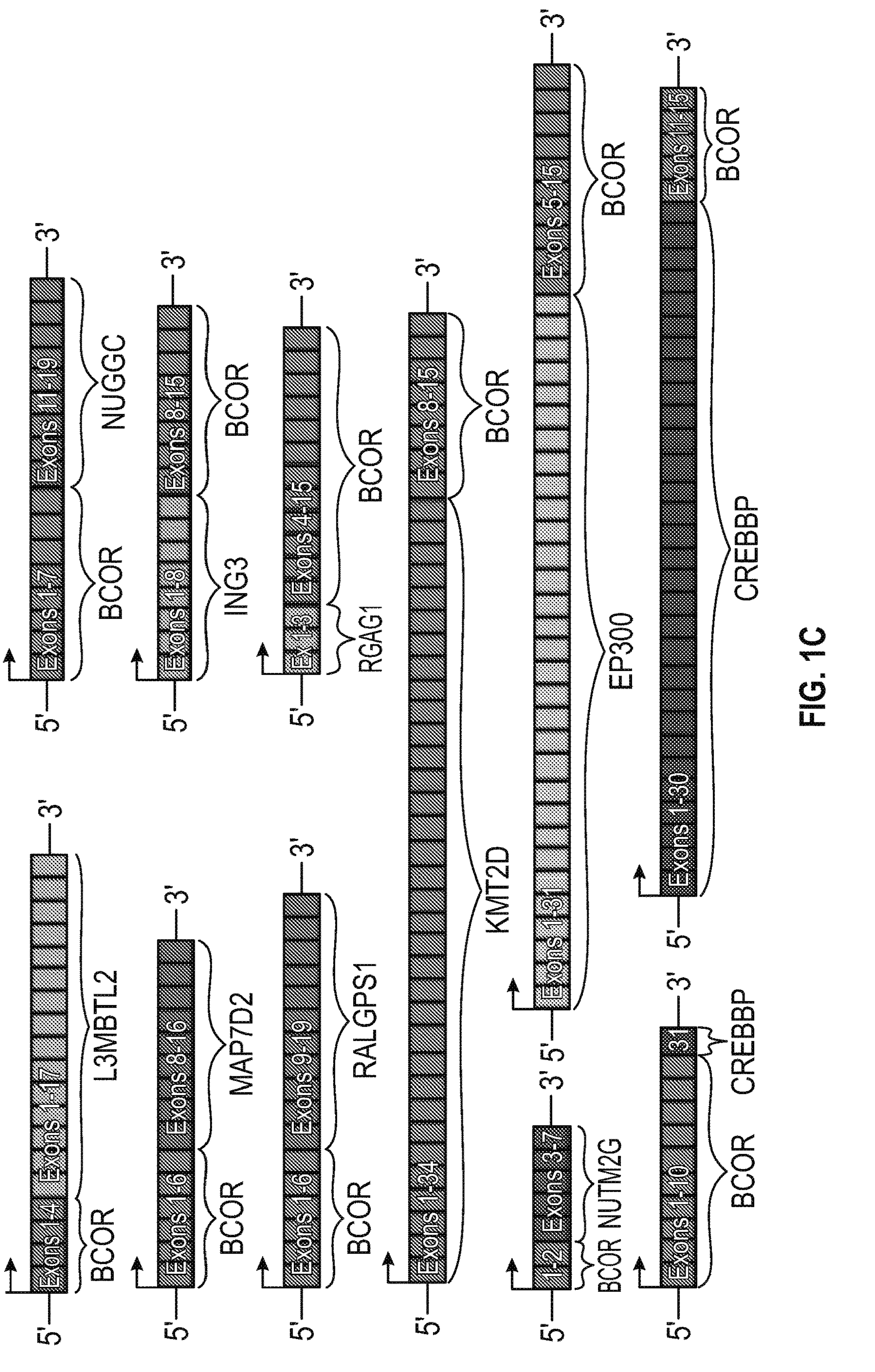
FIG. 1C provides schematic diagrams of RNA fusion transcripts of novel BCOR gene rearrangements involving BCOR and novel gene partners identified in the cohort. Specific exons for BCOR and the gene partner identified for each fusion transcript are labeled.
Figure 1D:
FIGS. 1D-1G show a uterine sarcoma (FIG. 1D) with ZC3H7B-BCOR gene rearrangement, as well as CDK4 and MDM2 amplification, with fascicular growth pattern (FIG. 1E) and fibromyxoid stroma (FIGS. 1F & 1G).
Figure 1E:
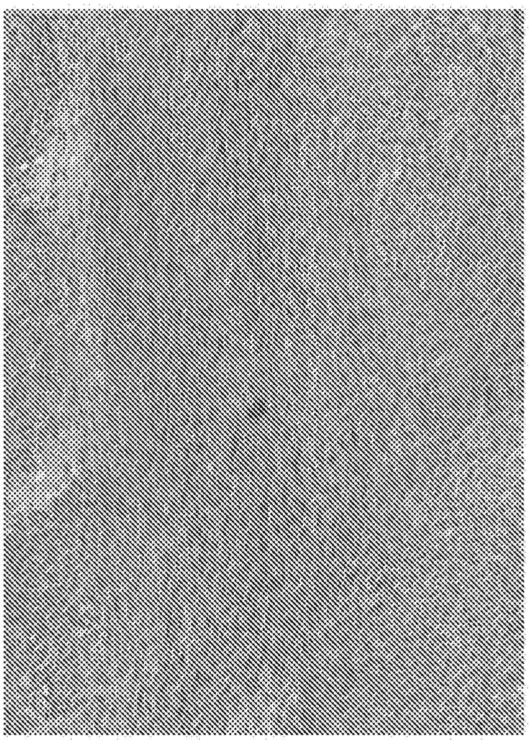
Figure 1F:
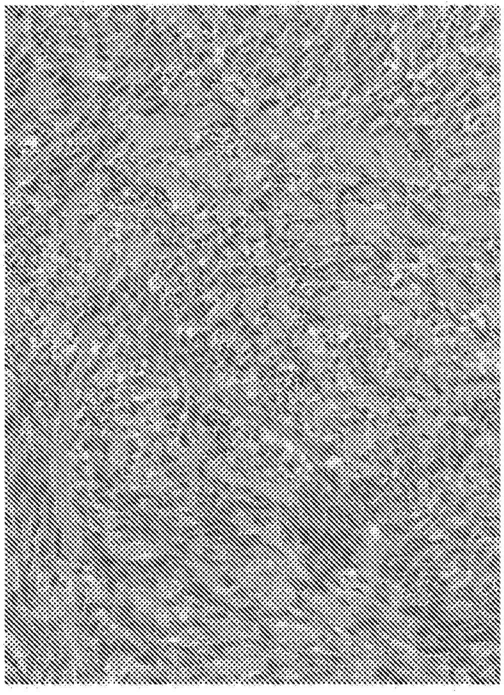
Figure 1G:
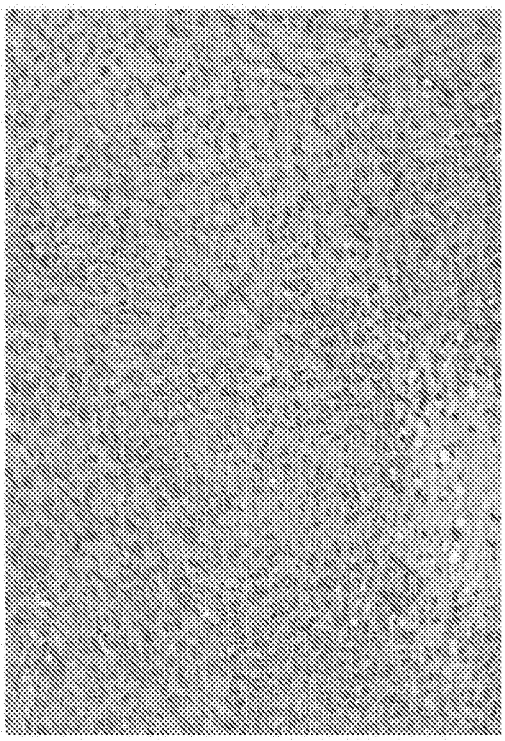
Figures 2A, 2B, 2C, 2D, 2E, 2F:
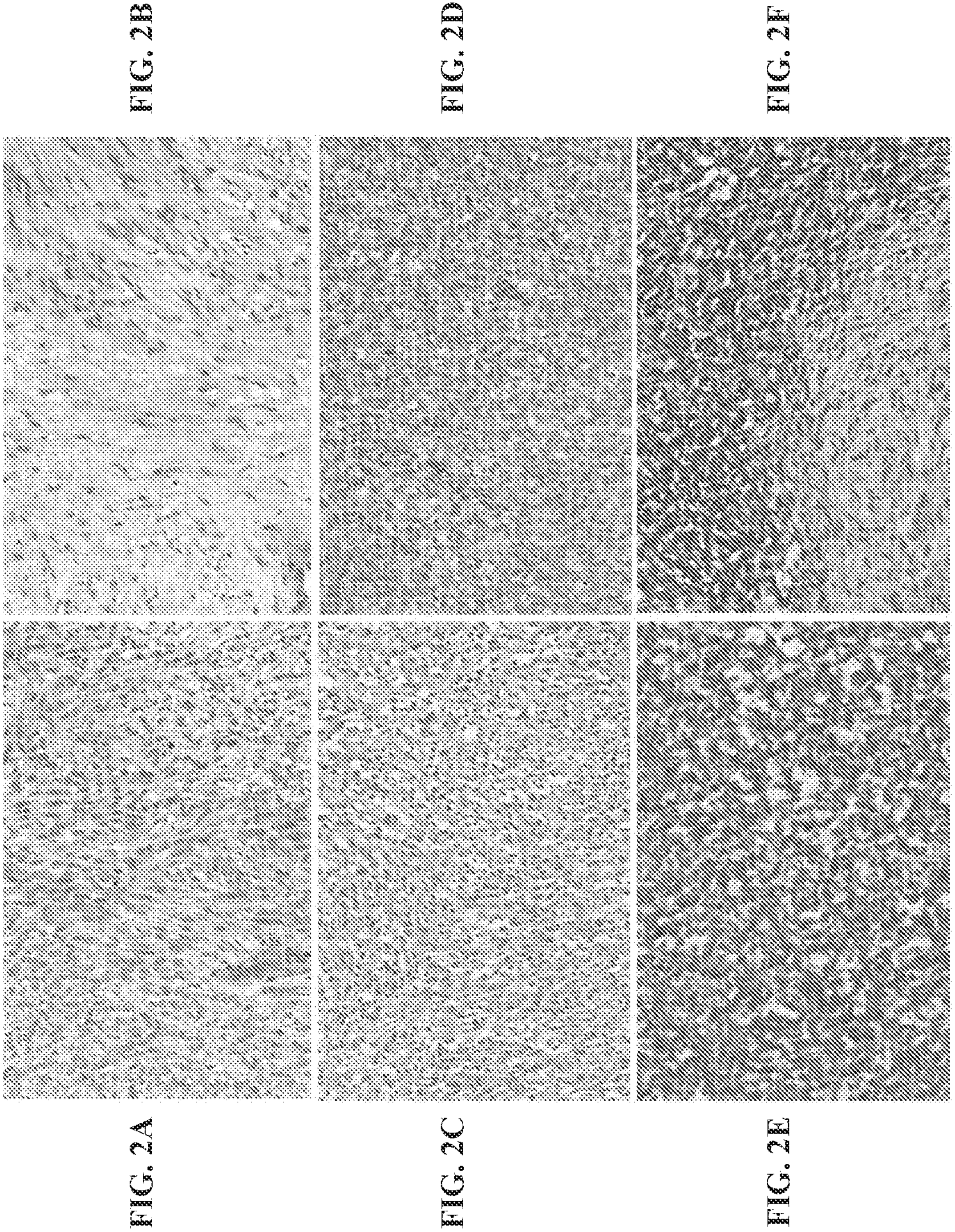
FIGS. 2A-2F show the morphological spectrum of uterine sarcomas with novel BCOR gene rearrangements.
Figures 3A, 3B, 3C, 3D, 3E, 3F:
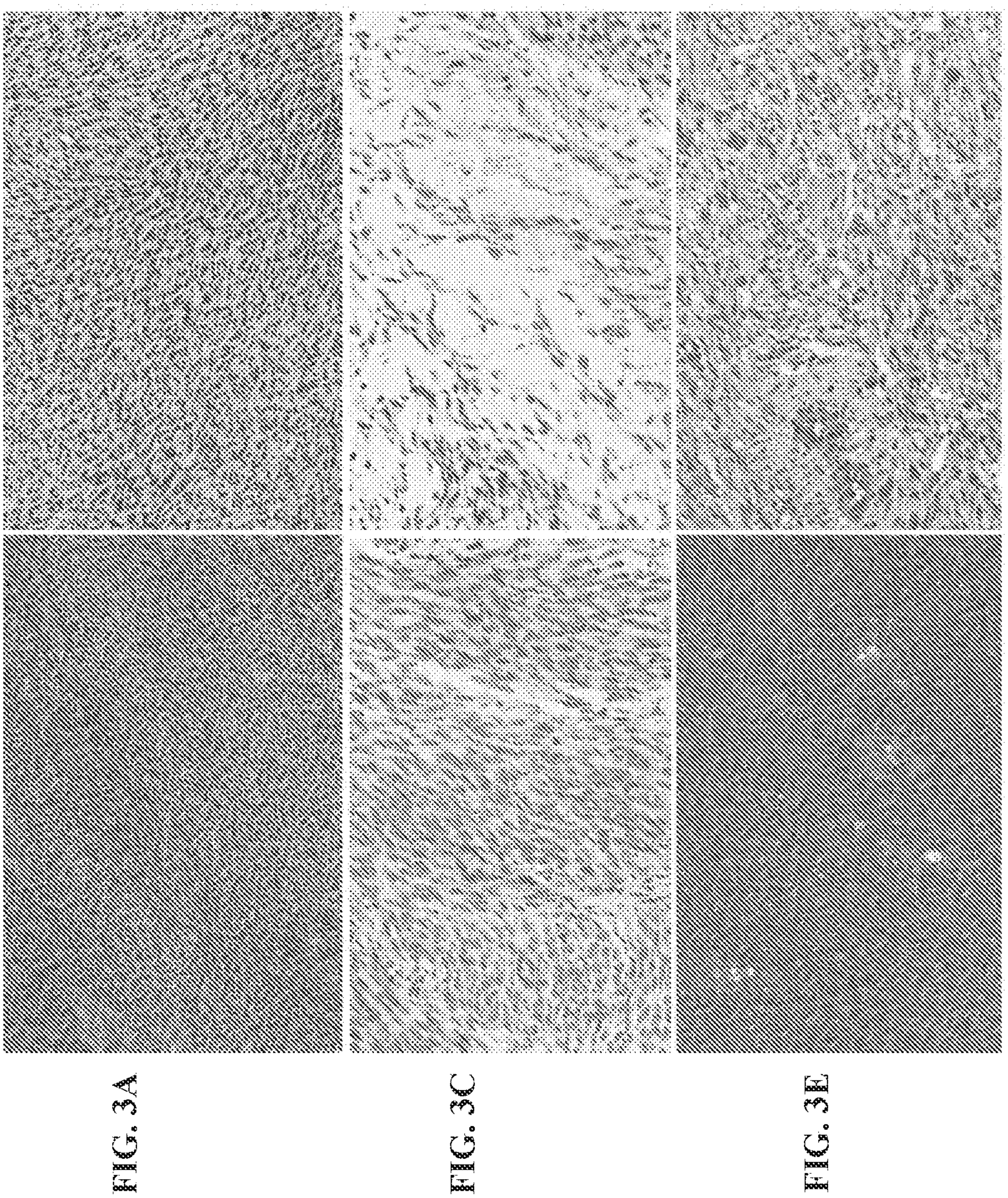
FIGS. 3A & 3B show metastatic uterine carcinoma with novel CREBBP-BCOR gene fusion with fascicular growth pattern (FIG. 3A) and spindle cell morphology with prominent myxoid stromal change (FIG. 3B).
FIGS. 3C & 3D show uterine sarcoma containing novel ING3-BCOR and BCOR-NUGGC rearrangements with hypercellular spindle cells (FIG. 3C) and more hypocellular myxoid background (FIG. 3D).
FIG. 3E shows uterine sarcoma harboring BCOR-L3MBTL2 and EP300-BCOR rearrangements with hypercellular morphology with spindle to oval nuclei and small arterioles.
FIG. 3F shows BCOR-MAP7D2 rearranged uterine sarcoma with fibromyxoid, spindle cell morphology and small arterioles.
Figures 3G, 3H, 3I, 3J, 3K, 3L:
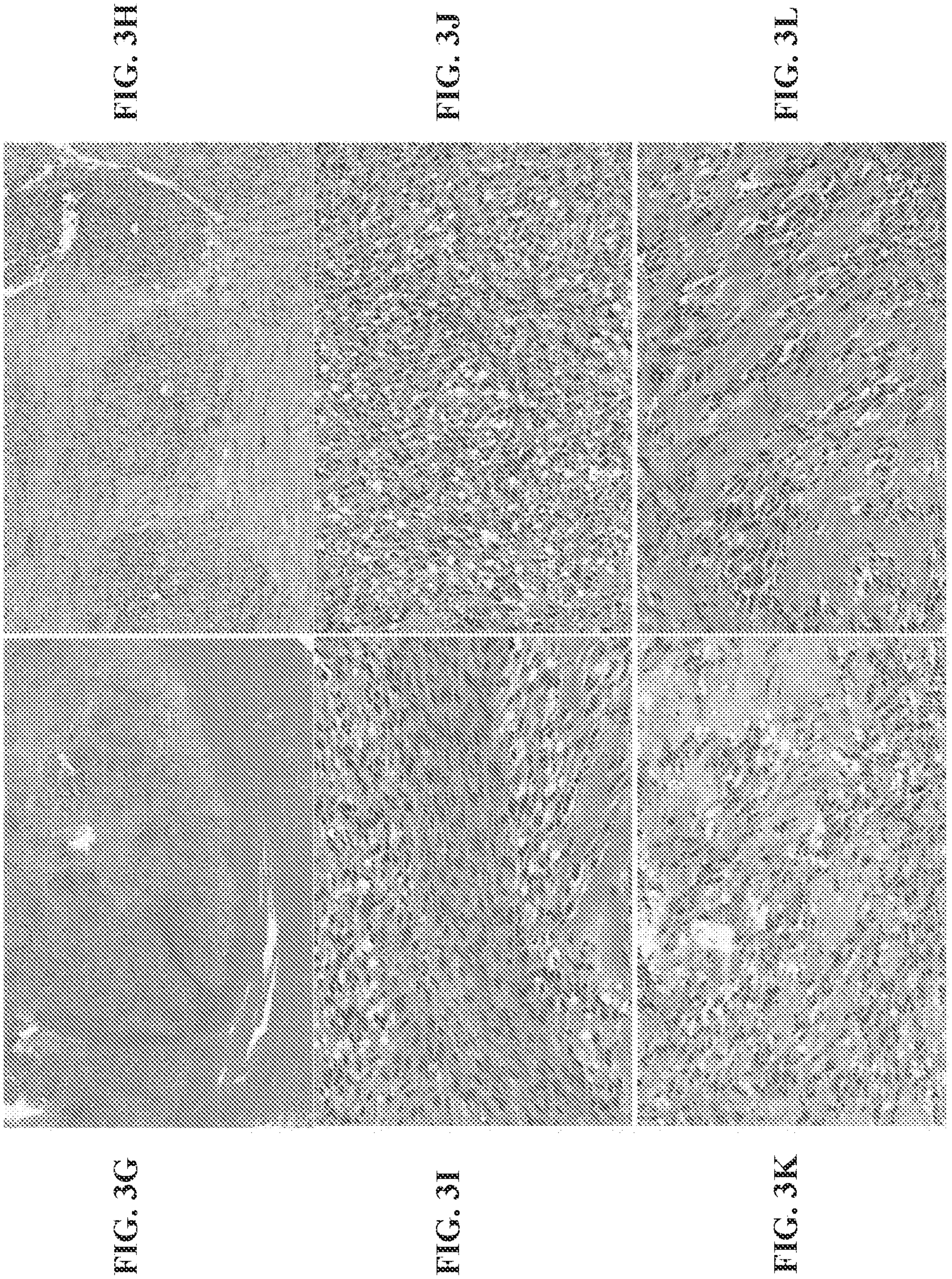
FIGS. 3G-L show high stage uterine sarcoma with novel BCOR-RALGPS1 gene rearrangement with broad front invasive growth pattern (FIG. 3G), hypercellular areas around vessels transitioning to hypocellular myxoid areas away from vessels (FIG. 3H), spindle cell, fascicular growth pattern (FIG. 3I), epithelioid morphology and clear cytoplasm (FIG. 3J), spindle cell morphology with myxoid stroma (FIG. 3K), and collagen plaques (FIG. 3L).

Retrospective molecular re-analysis of the 40 uterine sarcoma cases with BCOR gene rearrangement revealed that ZC3H7B was the most predominant gene rearrangement partner, as either ZC3H7B-BCOR fusions or as BCOR-ZC3H7B with the reciprocal ZC3H7B-BCOR fusion (FIG. 1B) in 31 cases (78%, 31 of 40). In addition, 8 cases (20%, 8 of 40) were identified with novel BCOR gene rearrangement partners, such as BCOR-L3MBTL2, EP300-BCOR, BCOR-NUTM2G, BCOR-RALGPS1, BCOR-MAP7D2, RGAG1-BCOR, ING3-BCOR, BCOR-NUGGC, KMT2D-BCOR and CREBBP-BCOR (FIG. 1C). One additional case (2%, 1 of 40) contained a BCOR internal gene rearrangement characterized by a chromosome X inversion fragment involving BCOR as a 3' rearrangement breakpoint at intron 6 without a gene rearrangement partner. Whole H&E slide images of tumor sections submitted for genomic profiling were centrally re-reviewed to assess morphological features. In this study, one H&E slide, corresponding to the tissue that was submitted for genomic profiling, was available for each case for review of morphological features. In this central review, tumors with ZC3H7B-BCOR and/or BCOR-ZC3H7B fusions were often characterized by spindle cells arranged in a fascicular growth pattern with little pleomorphism and varying degrees of myxoid or collagenous stromal change (FIGS. 1D-1G), as previously described (Lewis, N. et al. (2018) *Mod Pathol.* 31:674-684). In contrast, cases with novel rearrangements demonstrated sarcomas with spindle, epithelioid or small round cell components and varying degrees of fascicular growth pattern as well as myxoid or collagenous stromal change (Table 1; FIGS. 2A-3L).

TABLE 1

Morphological features of uterine sarcomas with novel BCOR rearrangements.

| n | BCOR fusion partner(s) | Atypia | Nuclei | Spindle cells | Small cells | Epithelioid cells | Collagen-fibrosis | Necrosis | Myxoid stroma | Mitotic Count | Spiral arterioles | Border |
|---|---|---|---|---|---|---|---|---|---|---|---|---|
| 1 | L3MBTL2 and EP300 | Moderate | Uniform | Present | Absent | Absent | Absent | Present | Absent | 30 per 10 HPF | Present | Unknown |
| 2 | NUTM2G | Moderate | Uniform | Absent | Present | Absent | Absent | Present | Present | 16 per 10 HPF | Absent | Infiltrative |
| 3 | MAP7D2 | Mild-Moderate | Uniform | Present | Absent | Present | Present | Present | Present | 3 per 10 HPF | Present | Infiltrative |
| 4 | RALGPS1 | Moderate | Uniform | Present | Absent | Present | Present | Absent | Present | 12 per 10 HPF | Absent | Broad front |
| 5 | RGAG1 | Moderate-severe | Variable | Present | Present | Present | Present | Present | Present | 18 per 10 HPF | Present | Infiltrative |
| 6 | CREBBP | Mild-Moderate | Uniform | Present | Absent | Absent | Absent | Absent | Present | 15 per 10 HPF | Present | Unknown |
| 7 | ING3 and NUGGC | Mild-Moderate | Uniform | Present | Absent | Absent | Absent | Present | Present | 8 per 10 HPF | Absent | Unknown |
| 8 | KMT2D | Moderate-severe | Uniform | Present | Present | Absent | Absent | Absent | Present | 28 per 10 HPF | Present | Unknown |
| 9 | None-chrX inversion | Moderate-severe | Uniform | Present | Absent | Present | Present | Present | Present | 24 per 10 HPF | Absent | Infiltrative |

The morphological features of cases with novel BCOR rearrangements are summarized in Table 1. Most tumors were characterized by spindle cells and variable amounts of small round cell morphology and/or epithelioid cells, often with clear cytoplasm, uniform nuclei and mild to moderate atypia (Table 1). However, a minority of cases exhibited moderate to severe atypia, characterized by nuclear enlargement, condensed chromatin and prominent nucleoli, often with an associated small round cell or epithelioid component (Table 1). Myxoid stroma was present in 89% of cases with novel BCOR rearrangements; tumor necrosis and collagen deposition/fibrosis were present in 67% of cases each; and spiral arterioles was present in 56% of cases (Table 1). Mitotic count across the nine cases with novel BCOR rearrangements ranged from 3 to 30 mitoses per 10 high power fields (Mean=17, Median=16 mitoses per 10 high power fields). The representative morphology of uterine sarcoma cases with novel BCOR rearrangements are illustrated in FIGS. 2A-3L.

Figure 4:
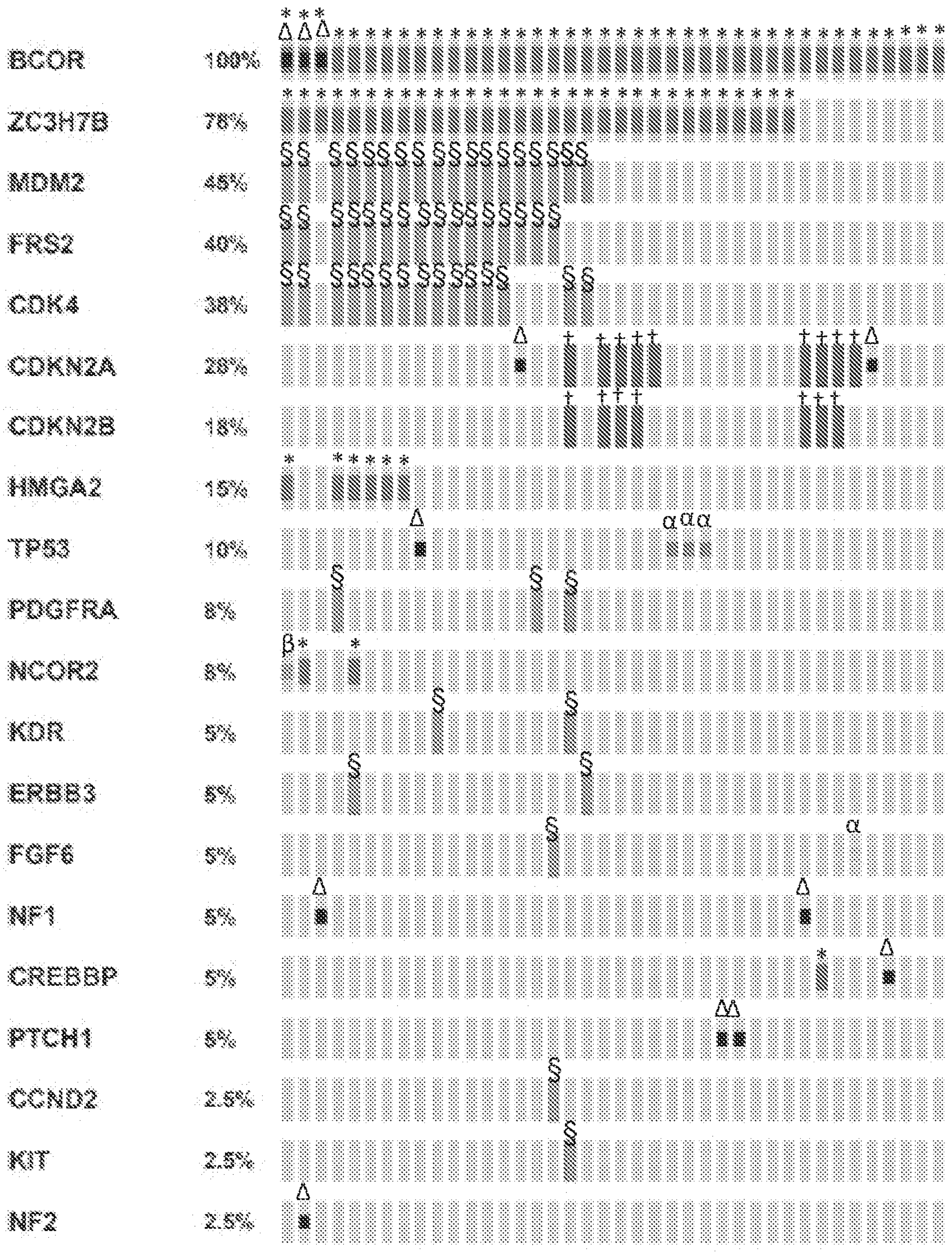
FIG. 4 shows the oncoprint of the BCOR-rearranged uterine sarcoma cohort, demonstrating genomic profiles with frequent activation of the cyclin D-CDK4 axis via CDK4 amplification and CDKN2A loss. *gene rearrangement; †homozygous deletion; § amplification; Δtruncating mutation; α oncogenic missense mutation; β non-frameshift insertion. Only recurrent and/or targetable alterations are shown.

Comprehensive genomic profiling, via targeted DNA- and RNA-based next-generation sequencing of up to 406 genes involved in tumorigenesis, revealed that most BCOR-rearranged uterine sarcomas had a low tumor mutation burden with the exception of one case which had intermediate tumor mutational burden. All tumors were also microsatellite stable. In addition to BCOR fusions, BCOR-rearranged uterine sarcomas exhibited high frequency of MDM2, FRS2 and CDK4 gene amplification in 45%, 40% and 38% of cases, respectively (FIG. 4). BCOR-rearranged uterine sarcomas also contained high frequency of homozygous deletion of (DKN24, which encodes $p16^{INK4a}$, an inhibitor of CDK4, and of CDKN2B in 28% and 18% of cases, respectively (FIG. 4). One additional case contained CCND2 gene amplification (FIG. 4), which encodes for cyclin D2, another activator of the CDK4 kinase similar to cyclin D1. CDK4 amplification and CDKN2A deletion appeared mutually exclusive, and CDK4 amplification occurred specifically in uterine sarcomas harboring canonical ZC3H7B-BCOR fusions and not in tumors with novel BCOR fusion partners (FIG. 4). Overall, genomic alterations leading to the activation of the cyclin D1-CDK4 kinase, via CDK4 amplification, CCND2 amplification or CDKN2A loss, occurred in 26 of 40 (65%) BCOR-rearranged uterine sarcoma cases.

Other targetable alterations in BCOR-rearranged uterine sarcomas included amplification of PDGFRA, KDR (encoding VEGFR2), ERBB3 and KIT in 8%, 5%, 5% and 2.5% of cases, respectively (FIG. 4), suggesting potential response to specific tyrosine kinase inhibitors. In contrast, inactivating truncating mutations in NF1 (specifically R1830C, N2387fs*1 and E1192fs*2) and NF2 (Y144*) occurred in 5% and 2.5%, suggesting potential response to MEK or mTOR inhibitors, respectively. At similar frequency, inactivating truncating mutations in targetable PTCH1 (T903fs*1 and K838fs*64) occurred in 5% of cases (FIG. 4).

Specifically in ZC3H7B-BCOR-rearranged uterine sarcoma, other potential driver events included genomic alterations in HMGA2, TP53 and NCOR2 (FIG. 4). Inactivating missense or truncating nonsense mutations in TP53 (Y103fs*46, R156P, R248Q and S240R) occurred in 10% (4 of 40) of cases (FIG. 4). Interestingly, co-rearrangements in HMGA2 occurred in 15% (6 of 40) of cases, while co-rearrangement of NCOR2 occurred in 5% (2 of 40) of BCOR-rearranged uterine sarcoma cases (FIG. 4). Specific HMGA2 fusion gene partners included CPSF6, MED13, MON2, RAB35, TAOK3, KSR2, KIF16B, OAS3 and LEMD3. Specific NCOR2 rearrangement gene partners included KDM2B and TMEM132D. A short variant NCOR2 alteration (Q510_P511insQQ) was identified in one additional case. Lastly, 8% (3 of 40) of cases exhibited co-occurring inactivating short variant truncating mutations of BCOR (L221fs*45, L1200*, T938fs*8) in addition to rearrangement (FIG. 4), suggesting potential loss of function BCOR.

Finally, genomic profiles were compared between BCOR-rearranged uterine sarcomas versus uterine sarcomas harboring BCOR internal tandem duplication in order to assess whether CDK4 and MDM2 amplification was specific to BCOR-rearranged uterine sarcomas. In an independent cohort of uterine sarcomas harboring BCOR internal tandem duplication (n=15) that had been previously evaluated by comprehensive genomic profiling, CDK4 and/or MDM2 amplification were identified in 0% (0 of 15) of cases (Table 2), suggesting that CDK4 and MDM2 amplification are specific to BCOR-rearranged uterine sarcomas. Statistical analysis by Fisher's Exact test revealed significantly higher frequency of CDK4 (p=0.0052) and MDM2 (p=0.001) amplification in BCOR-rearranged uterine sarcoma cases compared to cases with BCOR internal tandem duplication. In contrast, CDKN2A and CDKN2B homozygous deletion was present in 20% (3 of 15) of endometrial stromal sarcoma cases harboring BCOR internal tandem duplication that were analyzed (Table 2), which was at a comparable rate to BCOR-rearranged uterine sarcomas (p=0.73 for CDKN2A inactivating alterations by Fisher's Exact test). Other genes that had recurrent alterations in uterine sarcomas with BCOR internal tandem duplication were STAG2 (V212fs*13 and R439fs*9), PASK (S265fs*64 and A602V) and ARID1A (Q1334_R1335insQ and D1850fs*4) in 13%(2 of 15) of cases each (Table 2). The clinicopathological and morphological features of 11 of the 15 uterine sarcomas with BCOR internal tandem duplication within our cohort have been previously described by Juckett, L. T. et al. (2018) *Oncology* October: 1-9 (i.e. high frequency of metastatic tumors with small round cell and spindle cell morphology and fibromyxoid stromal changes).

TABLE 2

Comparative genomic features of uterine sarcomas harboring BCOR internal tandem duplication (ITD). BCOR reference transcript number NM_017745 was used in the analysis, in which BCOR internal tandem duplications occurred in exon 15, near the C-terminus.

| n | Age | Submitting diagnosis | BCOR ITD (NM_017745) | Other genomic alterations present |
|---|---|---|---|---|
| 1 | 42 | Endometrial stromal sarcoma | *1722Sext*33 | ARIDIA Q1334_R1335insQ |
| 2 | 59 | Endometrial stromal sarcoma | W1721_*1722ins32 | TP53 splice site, STAG2 V212fs*13 |

TABLE 2-continued

Comparative genomic features of uterine sarcomas harboring BCOR internal tandem duplication (ITD). BCOR reference transcript number NM_017745 was used in the analysis, in which BCOR internal tandem duplications occurred in exon 15, near the C-terminus.

| n | Age | Submitting diagnosis | BCOR ITD (NM_017745) | Other genomic alterations present |
|---|---|---|---|---|
| 3 | 44 | Endometrial stromal sarcoma | V1707_E1708ins30 | |
| 4 | 42 | Uterine sarcoma | E1708_W1709ins30 | CDKN2A/2B loss |
| 5 | 52 | Uterine sarcoma, high grade | W1721_*1722ins32 | |
| 6 | 44 | Endometrial stromal sarcoma | W1721_*1722ins32 | CTNNB1 S45P |
| 7 | 44 | Uterine sarcoma | K1687_E1688ins32 | PASK S265fs*64 |
| 8 | 32 | Endometrial stromal sarcoma | L1679_E1680ins30 | CDKN2A/2B loss |
| 9 | 46 | Endometrial stromal sarcoma | D1678_L1679ins30 | CDKN2A/2B loss |
| 10 | 56 | Endometrial stromal sarcoma | K1687_E1688ins32 | |
| 11 | 47 | Endometrial stromal sarcoma | D1678_L1679ins30 | |
| 12 | 59 | Endometrial stromal sarcoma | D1718_N1719ins33 | ARIDIA D1850fs*4 |
| 13 | 14 | Uterine sarcoma, high grade | D1718_N1719ins32 | PASK A602V, ATRX E1464del |
| 14 | 27 | Uterine leiomyosarcoma | K1687_E1688ins32 | STAG2 R439fs*9, SMARCB1 R373fs*3 |
| 15 | 53 | Uterine leiomyosarcoma | K1687_E1688ins32 | |

Conclusions

Here, the genomic spectrum and clinicopathological features of BCOR-rearranged uterine sarcomas were characterized. This cohort of 40 cases had several similarities to the findings of a smaller series (Lewis, N. et al. (2018) *Mod. Pathol.* 31:674-684) including; 1) similar median age of 54 years and age range of 20s to 70s in both studies, 2) aggressive tumors, 3) high frequency of lymph node metastasis and distant spread, and 4) frequent myxoid morphology, some of which mimicked and were previously diagnosed as myxoid leiomyosarcoma. Morphologically, most tumors with ZC3H7B-BCOR fusions in this cohort were characterized by fascicular growth pattern with spindle cell morphology and uniform nuclei with moderate atypia, no significant nuclear pleomorphism, but with myxoid and collagenous stromal changes, similarly to previously described (Hoang, L. N. et al. (2017) *Am. J. Surg. Pathol.* 41:12-24; Lewis, N. et al. (2018) *Mod. Pathol.* 31:674-684). In contrast, the uterine sarcomas with novel BCOR rearrangements demonstrated a mix of spindle, epithelioid or small round cell components and varying degrees of fascicular growth pattern and myxoid or collagenous stroma. In the retrospective study, long term follow-up data was not available to calculate survival; however, most tumors were high stage with metastasis to extra-uterine sites. The presence of high stage disease and distant metastasis supports the notion that BCOR-rearranged uterine sarcomas exhibit aggressive behavior. The high frequency of lymph node metastasis is not specific to BCOR-mutated uterine sarcomas as it has also been recently described in SMARCA4-deficient (Lin, D. I et al. (2019) *Mod. Pathol.* June doi: 10.1038/s41379-019-0303-z) uterine undifferentiated sarcomas.

Here, novel BCOR gene fusion partners were described, and the genomic landscape of these tumors was expanded with emphasis on driver and potentially targetable genomic alterations. Novel BCOR fusions in uterine sarcoma that were identified in the cohort included BCOR-L3MBTL2, EP300-BCOR, BCOR-NUTM2G, BCOR-RALGPS1, BCOR-MAP7D2, RGAG1-BCOR, ING3-BCOR, BCOR-NUGGC, KMT2D-BCOR and CREBBP-BCOR as well as a case with internal BCOR gene rearrangement without another gene partner. Of these fusions, EP300-BCOR and KMT2D-BCOR have been identified in other tumor types. For instance, recurrent EP300-BCOR fusions have been reported in central nervous system high-grade neuroepithelial tumors with BCOR alteration (Torre, M. et al. (2019) *J. Neuropathol. Exp. Neurol.* 78:305-314), while a KMT2D-BCOR fusion has been identified in undifferentiated small round cell sarcoma (Kao, Y. C. et al. (2018) *Am. J. Surg. Pathol.* 42:604-615). While it is thought that CREBBP-BCOR fusions have not been identified in other tumor types, CREBBP-BCORL1 and KDM2B-CREBBP fusions have been identified in ossifying fibromyxoid tumor and endometrial stromal sarcoma, respectively (Kao, Y. C. et al. (2017) *Genes, Chromosom. Cancer* 56:42-50; Micci, F. et al. (2016) *Genes Chromosom. Cancer* 55:834-846). BCORL1 is also a member of the PCR1 complex, and it acts interchangeably with BCOR within the PCR1 complex (Astolfi, A. et al. (2019) *Epigenomics* 11:835-855). Internal BCOR rearrangements without other gene partner have also been identified in four cases of Ewing-like undifferentiated small blue round cell sarcomas (Specht, K. et al. (2016) *Am. J. Surg. Pathol.* 40:433).

Based on morphology, the main histological differential diagnosis of BCOR-rearranged uterine sarcomas is myxoid leiomyosarcoma. In the cohort, 20% (8 of 40) cases of BCOR-rearranged uterine sarcomas were previously classified as uterine myxoid leiomyosarcoma. This rate is comparable to other BCOR-mutated sarcoma studies, in which 24% (4 of 17) of ZC3H7B-BCOR rearranged uterine sarcoma and 18% (2 of 11) of uterine sarcomas harboring BCOR internal tandem duplication were previously classified as myxoid leiomyosarcoma, respectively (Juckett, L. T. et al. (2018) Oncology October: 1-9; Lewis, N. et al. (2018) *Mod. Pathol.* 31:674-684). Morphologically, BCOR-rearranged uterine sarcoma and myxoid leiomyosarcoma may have overlapping myxoid morphological features. As seen in the cohort and in cases with BCOR internal tandem duplication (Juckett, L. T. et al. (2018) *Oncology* October: 1-9), BCOR-mutated uterine sarcomas may also exhibit small round cell and epithelioid morphology. Combination of morphology and immunohistochemistry and/or genomics may be helpful in identifying BCOR-rearranged uterine sarcoma. Known immunohistochemistry markers for BCOR-mutated uterine sarcomas are CD10, BCOR and cyclin D1, while they are generally negative for muscle markers (Lewis, N. et al. (2018) *Mod. Pathol.* 31:674-684; Ferreira, J. et al. (2018) *Virchows Arch.* 473:665-678). In contrast to BCOR-mutated uterine sarcomas, conventional uterine leiomyosarcomas frequently harbor alterations in T7P53, RB1, MED12, ATRX and PTEN (Mäkinen N. et al. (2016) *PLoS Genet.* 12:e1005850; Cuppens, T. et al. (2018) *Int. J. Cancer* 142:1230-1243; Elvin, J. A. et al. (2017) *Oncologist* 22:416-421). However, from limited literature, the genomics of myxoid leiomyosarcomas appear more heterogeneous with reported identification of TP53 and BRCA2 alterations and PLAG1 rearrangements (Schaefer, I. M. et al. (2017) *Histopathology* 70:1138-1146; Arias-Stella, J. A. et al. (2019) *Am. J. Surg. Pathol.* 43:382-388; Yoon, J. Y. et al. (2019) *Mod. Pathol.* 32:1688-1697).

Metastatic or recurrent endometrial stromal sarcomas or undifferentiated uterine sarcomas have limited therapeutic options besides chemotherapy and radiotherapy (Meurer, M. et al. (2019) *Int. J. Gynecol. Cancer* 29:691-698; Pautier, P. et al. (2014) *Int. J. Gynecol. Cancer* 24:S73-S77). The standard of care treatment of endometrial stromal sarcomas is surgery, including total abdominal hysterectomy, bilateral salpingo-oophorectomy and tumor debulking. In contrast to low-grade endometrial stromal sarcomas, which are very indolent with late recurrences, high grade endometrial sarcomas exhibit more aggressive behavior with poorer outcomes (Benson, C. and Miah, A. B. (2017) *Int. J. Womens Health* 9:597-606). Given the rarity of these tumors, there is limited data available on the efficacy of adjuvant chemotherapy in endometrial stromal sarcomas. Mainstay treatment of low grade endometrial stromal sarcomas may also include hormonal therapy due to high frequency of ER and PR expression in low-grade tumors, followed by systemic chemotherapy if there is hormonal therapy failure (Benson, C. and Miah, A. B. (2017) *Int. J. Womens Health* 9:597-606). However, both low-grade and high-grade endometrial stromal sarcomas are generally refractory and display minimal response to conventional cytotoxic chemotherapy agents leading to progressive and advanced disease (Benson, C. and Miah, A. B. (2017) *Int. J. Womens Health* 9:597-606). For instance, in patients with high-grade endometrial stromal sarcoma, partial or complete responses to doxorubicin-ifosfamide-based, combination of gemcitabine and docetaxel chemotherapy regimens or anthracycline-based therapy have been reported, although responses can be short lived (Malouf, G. G. et al. (2013) *Int. J. Gynaecol. Obstet.* 122:57-61; Hemming, M. L. et al. (2017) *Gynecol. Oncol.* 145:531-535). Therefore, in the chemotherapy refractory setting and if eligible, patients may be considered for clinical trials with novel agents.

The present disclosure demonstrates a high frequency of CDK4 gene amplification, CDKN2A homozygous gene deletion, combined with cyclin D1 protein overexpression by immunohistochemistry, suggesting that BCOR-mutated uterine tumors may be sensitive to CDK4/6 inhibition. In the overall cohort, genomic alterations leading to the activation of the cyclin D1-CDK4 kinase, via CDK4 amplification, CCND2 amplification or CDKN2A loss, occurred in 26 of 40 (65%) BCOR-rearranged uterine sarcoma cases. Currently, CDK4 inhibitors, such as palbociclib, ribociclib, and abemaciclib, are FDA-approved for the treatment of ER-positive and Her2-negative breast carcinomas, and they appear safe with low frequency of severe side effects (Turner, N.C. et al. (2015) *N. Engl. J. Med.* 373:209-219; Turner, N.C. et al. (2018) *N. Engl. J. Med.* 379:1926-1936). Although in a different uterine tumor type, but also supporting the concept of CDK4 inhibition in uterine sarcoma, a patient with uterine leiomyosarcoma harboring CDKN2A loss has responded to palbociclib treatment (Elvin, J. A. et al. (2017) *Oncologist* 22:416-421). However, published literature on CDK4 inhibition in endometrial stromal sarcoma is lacking, but it is worth noting that BCOR-mutated endometrial stromal sarcoma may be mistaken for leiomyosarcoma. Alternatively, since MDM2 is also amplified in 45% of cases and appears to be co-amplified with CDK4, another therapeutic intervention to consider would be MDM2 inhibitors. In this regard, combinations of MDM2 and CDK4 inhibitors are could also be explored in BCOR-rearranged uterine sarcoma.

Although clinical trials may be difficult to conduct in endometrial stromal sarcomas due to rarity and indolent behavior the of low-grade tumors, there are current clinical trials that have been designed based on genomic alterations rather than tumor type. For example, there are currently active clinical trials for FDA-approved CDK4 inhibitor drugs based on CDK4 status regardless of tumor type, such as: 1) Phase II multicenter trial of palbociclib in second line of advanced sarcomas with CDK4 overexpression (NCT03242382), 2) Targeted therapy directed by genetic testing in treating patients with advanced refractory solid tumors (The MATCH Screening Trial) (NCT02465060), 3) TAPUR: testing the use of Food and Drug Administration (FDA) approved drugs that target a specific abnormality in a tumor gene in people with advanced stage cancer (TAPUR) (NCT02693535, 4) Molecular profiling of advanced soft-tissue sarcomas (MULTISARC) (NCT03784014), and 5) Study of the CDK4/6 Inhibitor Abemaciclib in solid tumors harboring genetic alterations in genes encoding D-type cyclins or amplification of CDK4 or CDK6 (NCT03310879). Therefore, identification of CDK4 amplification or inactivating mutation of CDKN2A may be useful for clinical trial enrollment in refractory BCOR-rearranged uterine sarcoma patients that fail conventional therapy and in which current standard treatments may no longer be clinically effective.

Less frequent, but targetable genomic alterations in receptor kinases were identified in the BCOR-rearranged uterine sarcoma cohort, suggesting potential benefit of kinase inhibitors in a small subset of patients. In <10% of BCOR-rearranged uterine sarcomas, alterations in PDGFRA, KDR (encoding VEGFR2), KIT or ERBB3 were identified, suggesting potential response to specific tyrosine kinase inhibitors (Silva, E. et al. (2015) *Breast J.* 21:205-207; Debiec-Rychter, M. et al. (2004) *Eur. J. Cancer* 40:689-695). In a minority of patients, inactivating truncating mutations in NF1 or NF2 were present, implicating response to MEK inhibitors (See, W. L. et al. (2012) *Cancer Res.* 72:3350-3359) or mTOR inhibitors (Ali, S. M. et al. (2015) *Eur. Urol.* 67:1195-1196). Finally, rare inactivating truncating mutations were identified in PTCH1 suggesting potential response to Sonidegib or Vismodegib (Von Hoff, D. D. et al. (2009) *N. Engl. J. Med.* 361:1164-1172).

In conclusion, the clinicopathologic, morphological and molecular features of the largest group of BCOR-rearranged uterine sarcomas to date were identified and reported. The present disclosure expands on the overall distinct molecular characteristics of theses tumors, which were identified by comprehensive molecular profiling. These data demonstrate the usefulness of comprehensive genomic profiling in identifying novel BCOR rearrangements and targetable genomic alterations in this new group of uterine sarcomas, as correct identification of this molecularly defined subset of uterine sarcoma may have important diagnostic and potential targeted therapeutic implications. Finally, these results provide a key resource to guide future preclinical, clinical and pathological studies in BCOR-mutated uterine sarcomas.

Example 2: Clinicopathological and Genomic Characterization of BCORL1-Driven High-Grade Endometrial Stromal Sarcomas and Uterine Adenosarcomas Inactivating truncating short variant mutations (e.g., nonsense and frameshift mutations) in BCORL1, a transcriptional corepressor homologous to BCOR, are present in myelodysplastic syndrome (MDS) and acute myeloid leukemia (AML), but have not been previously reported in uterine sarcoma or adenosarcoma. Considering the homology and related biological functions to BCOR, molecular alterations of BCORL1 may also define a distinct subset of uterine sarcomas. In this example, targeted DNA- and RNA-based next generation sequencing and comprehensive genomic profiling were used (1) to investigate the mutational landscape of BCORL1 in uterine sarcomas, (2) to determine whether molecular alterations of BCORL1 drive the oncogenesis of a distinct subset of endometrial stromal sarcomas, and (3) to compare the clinicopathological and molecular features of BCOR-versus BCORL1-altered uterine sarcomas.

Materials and Methods

BCORL1-Altered Uterine Sarcoma and Adenosarcoma Cohorts

Approval for this study was obtained from the Western Institutional Review Board (Protocol No. 20152817). A retrospective database search of a CLIA-certified and CAP-accredited reference molecular laboratory was performed for uterine sarcomas and adenosarcomas with genomic profiles containing all classes of pathogenic BCORL1 genomic alterations. The database originally contained 1,445 uterine sarcomas (278 endometrial stromal sarcomas, 963 uterine leiomyosarcomas and 204 uterine sarcomas NOS) as well as 86 uterine adenosarcomas. The cases were previously assayed with comprehensive genomic profiling (CGP) via both DNA- and RNA-based targeted next generation sequencing (NGS) during the course of clinical care at other institutions. Clinicopathological data including age and sites of metastases were extracted from pathology reports and available clinical documents. The pathologic diagnosis of uterine sarcoma, endometrial stromal sarcoma, and adenosarcoma and associated morphological features were centrally re-evaluated on routine H&E slides of tissue sections submitted for genomic profiling. Low-grade atypia was defined as the appearance resembling classic low-grade endometrial stromal sarcoma. High-grade atypia was defined as at least moderate to severe nuclear atypia with nuclear enlargement, coarse chromatin, pleomorphism and prominent nucleoli.

Genomic Profiling and Biomarker Analysis

NGS-based CGP was performed on hybridization-captured, adaptor ligation-based libraries using DNA and RNA extracted from formalin-fixed paraffin-embedded tumor tissue. All samples forwarded for DNA and RNA extraction contained a minimum of 20% tumor cells. The samples were assayed for all coding exons from up to 406 cancer related genes, in addition to select introns from up to 31 genes. Patient samples were sequenced and evaluated for all classes of genomic alterations, including base substitutions, insertions, deletions, copy number alterations (amplifications and homozygous deletions), and fusions/rearrangements, as previously described (Lipson, D., et al. (2012) *Nat Med* 18:382-384; He, J., et al. (2016) *Blood* 127:3004-3014; Frampton, G. M., et al. (2013) *Nat Biotechnol* 31:1023-1031). Oncoprints of genomic data were generated with the cBio portal (Gao, J., et al. (2013) *Sci Signal* 6:pl1: Cerami, E., et al. (2012) *Cancer Discov* 2:401-404).

Calculation of Tumor Mutational Burden and Microsatellite Instability

Tumor mutational burden (TMB) was determined on 0.79-1.14 Mb of sequenced DNA using a mutation burden estimation algorithm (Chalmers, Z. R. et al. (2017) *Genome Med* 9:34). In this study, low TMB was defined as <10 mut/Mb, since a score of at least 10 mut/Mb is currently an FDA-approved companion diagnostic biomarker for immunotherapy (FDA (2020) *FDA approves pembrolizumab for adults and children with TMB-H solid tumors*. Available from: https://www.fda.gov/drugs/drug-approvals-and-databases/fda-approves-pembrolizumab-adults-and-children-tmb-h-solid-tumors). Assessment of microsatellite instability was performed from DNA next-generation sequencing across 114 loci (Chalmers, Z. R. et al. (2017) *Genome Med* 9:34).

Genomic Ancestry Analysis

Predominant genetic ancestry was assessed using a single nucleotide polymorphism (SNP) based approach (Connelly, C. F. et al. (2018) *Cancer Research: AACR* 1227-1227). Briefly, germline SNPs were characterized in the publicly available 1000 Genomes database and used to train and validate a classifier to bin individuals into one of five inferred population groups, estimated to be of predominantly African, European, Admixed American, South Asian, or East Asian ethnic origin.

Statistical Analysis

Fisher's exact test was used to assess differences among categorical variables. The statistical tests were 2-sided and used a significance threshold of $p<0.05$. Reported p values were not adjusted for multiple testing.

Results

BCORL1-Altered Endometrial Stromal Sarcomas

Figure 5A:
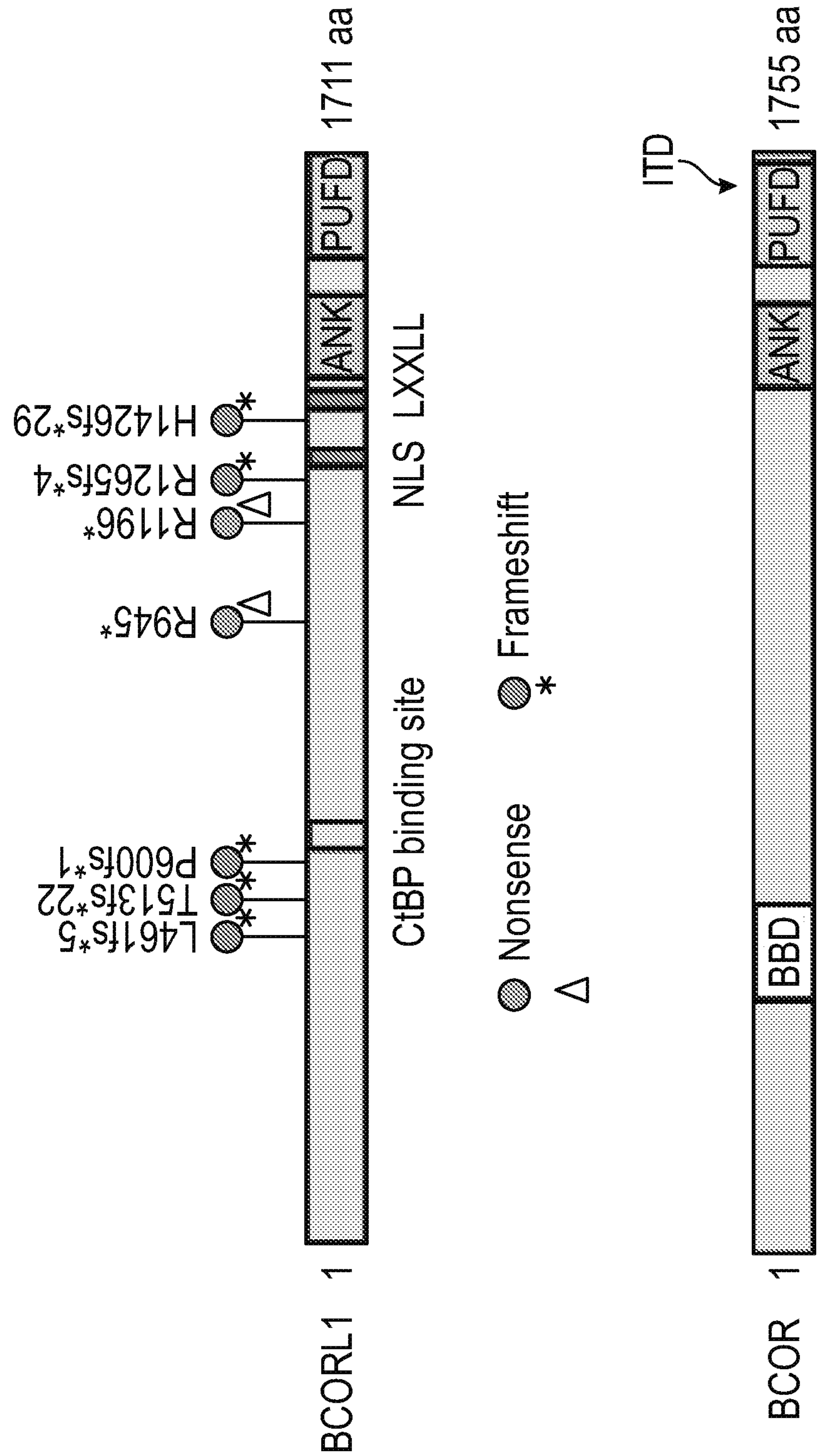
FIGS. 5A & 5B depict the mutational landscape of BCORL1 across endometrial stromal sarcoma and uterine adenosarcoma cohorts.
Figure 5B:
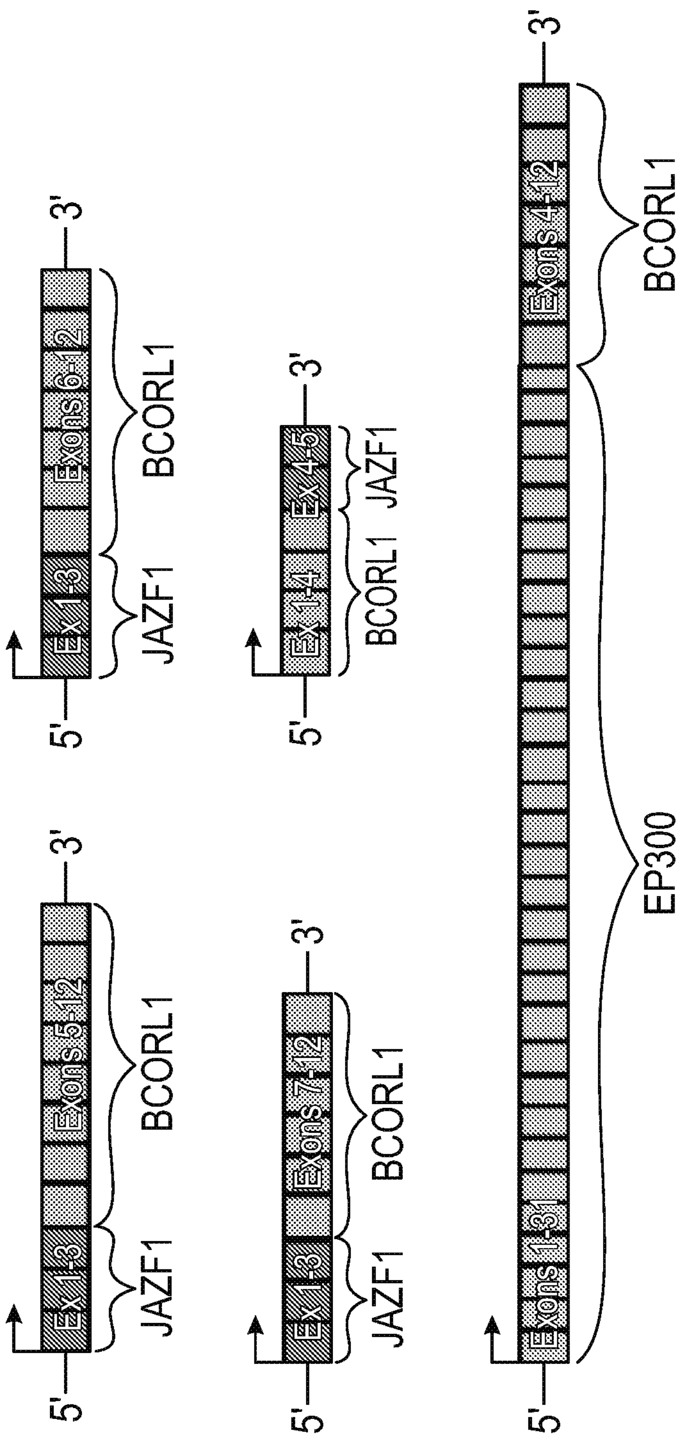

A retrospective analysis of a research database of 1,445 uterine sarcoma cases (including 278 endometrial stromal sarcomas, 963 uterine leiomyosarcomas and 204 uterine sarcomas NOS), which had previously undergone comprehensive genomic profiling between 2010 and 2020 during the course of clinical care at various institutions, led to the identification of 12 BCORL1-altered uterine sarcomas with striking resemblance to BCOR-altered high-grade endometrial stromal sarcoma (see Example 1). These 12 uterine sarcoma cases contained different classes of BCORL1 genomic alterations, and included 5 cases with BCORL1 rearrangements or fusions (JAZF1-BCORL1, EP300-BCORL1, or internal BCORL1 rearrangement), 5 cases with truncating BCORL1 short variants, nonsense or frameshift mutations (T513fs*22, P600fs*1, R945*, R1196*, or R1265fs*4), and 2 cases with homozygous BCORL1 gene deletion (FIG. 5A and Table 3). The case with an internal BCORL1 alteration exhibited a chromosome X deletion, resulting in loss of exon 8 and intron 9 of BCORL1. Three cases harbored recurrent JAZF1-BCORL1 or reciprocal BCORL1-JAZF1-fusions, and one case harbored a novel EP300-BCORL1 fusion (FIG. 5B and Table 3). The submitted diagnoses from referring outside institutions for the 12 cases with BCORL1 alterations included 7 endometrial stromal sarcomas, 2 high-grade uterine sarcomas, 2 myxoid uterine leiomyosarcomas and 1 uterine spindle cell neoplasm consistent with leiomyosarcoma (Table 3). Based on genomics and morphology, the 3 cases with prior diagnoses of leiomyosarcoma were reclassified as BCORL1-altered endometrial stromal sarcoma, as previously described for BCOR-altered endometrial sarcomas mimicking myxoid leiomyosarcomas (Lewis, N., et al. (2018) *Mod Pathol* 31:674-684; Lin, D. I., et al. (2020) *Gynecol Oncol* 157: 357-366; Example 1), based on morphology and lack of known driver mutations commonly found in either conventional uterine leiomyosarcoma (i.e., lack of TP53, ATRX, PTEN or MED12 alterations) (Mäkinen, N., et al. (1026) *PLOS Genet* 12:e1005850; Cuppens, T., et al. (2018) *Int J Cancer* 142:1230-1243; Elvin, J. A., et al. (2017) *Oncologist* 22:416-421) or in myxoid uterine leiomyosarcoma (i.e., lack of TP53 and BRCA2 mutations or PLAG1 rearrangements) (Schaefer, I. M., et al. (2017) *Histopathology* 70:1138-1146; Arias-Stella, J. A., et al. (2019) *Am J Surg Pathol* 43:382-388; Yoon, J-Y., et al. (2019) *Mod Pathol* 32:1688-1697). For instance, one case (case #10) was previously diagnosed as myxoid uterine leiomyosarcoma. However, the frameshift BCORL1 T513fs*22 short variant mutation was the only genomic alteration identified in this case, with no other co-occurring alterations.

In this cohort of 12 BCORL1-altered uterine sarcoma cases, the median age was 57.5 years (range 33-79 years) (Table 3). Most tumors were aggressive with extra-uterine spread and/or recurrences after total hysterectomy (Table 3). Sites of metastasis included peri-aortic and obturator lymph nodes, pelvic sidewall, omentum, pancreas, small and large intestine, bladder, rectum and vagina. Of patients with available clinical follow-up, 4 died of disease at 11, 11, 64 and 73 months after total abdominal hysterectomy, respectively (Table 3, case #1, #5, #7 and #12).

TABLE 3

Clinicopathological features of BCORL1-altered uterine sarcomas (cases #1-12) and uterine adenosarcomas (cases #13-18).

| n | BCORL1 genomic alteration | Age | Submitting diagnosis | Biopsy proven sites of metastasis or extension | Follow-up |
|---|---|---|---|---|---|
| 1 | JAZF1-BCORL1 fusion | 59 | Recurrent endometrial stromal sarcoma | Pelvic peritoneum, omentum and pancreas | Died at 64 months after hysterectomy. |
| 2 | EP300-BCORL1 fusion | 56 | Metastatic endometrial stromal sarcoma | Peri-aortic lymph node | Not available. |
| 3 | Internal BCORL1 rearrangement | 72 | Metastatic endometrial stromal sarcoma | Small intestine | Not available. |
| 4 | JAZF1-BCORL1 fusion | 46 | Low to high grade endometrial stromal sarcoma | Small and large intestine, right obdurator | Not available. |
| 5 | BCORL1 R1265fs*4 | 66 | Recurrent low grade endometrial stromal sarcoma | Bladder, rectum | Died at 73 months after hysterectomy. |
| 6 | BCORL1 R1196* | 66 | Low grade endometrial stromal sarcoma | Not applicable | Alive at 28 months after hysterectomy. |
| 7 | BCORL1 homozygous deletion | 38 | High grade endometrial stromal sarcoma | Pelvis; stage IV per test requisition sheet | Died at 11 months after diagnosis. |
| 8 | JAZF1-BCORL1 fusion | 79 | High grade uterine sarcoma | Vagina; stage IV per test requisition sheet | Not available. |
| 9 | BCORL1 homozygous deletion | 48 | High grade uterine sarcoma | Pelvis, omentum, retroperitoneum | Alive at 22 months after hysterectomy with recurrence refractory to gemcitabine and docetaxel followed by adriamycin. |
| 10 | BCORL1 T513fs*22 | 33 | Myxoid uterine leiomyosarcoma | Cervix, right uterine sidewall | Not available. |
| 11 | BCORL1 R945* | 56 | Myxoid uterine leiomyosarcoma | Right adnexa, left pelvic sidewall | Alive at 12 months after hysterectomy. |
| 12 | BCORL1 P600fs*1 | 74 | Spindle cell neoplam most consistent with leiomyosarcoma | None available; stage IV per test requisition sheet | Died at 11 months after hysterectomy. |
| 13 | JAZF1-BCORL1 fusion | 63 | Metastatic malignant spindle cell neoplasm consistent with sarcomatous component of prior uterine adenosarcoma with sarcomatous overgrowth | Abdomen | Alive at 59 months after hyserectomy. |
| 14 | BCORL1 L461fs*5 | 45 | Uterine adenosarcoma with sarcomatous overgrowth comprising 90% of the tumor (CD10, ER, PR positive) | Vagina | Not available. |

TABLE 3-continued

Clinicopathological features of BCORL1-altered uterine sarcomas (cases #1-12) and uterine adenosarcomas (cases #13-18).

| n | BCORL1 genomic alteration | Age | Submitting diagnosis | Biopsy proven sites of metastasis or extension | Follow-up |
|---|---|---|---|---|---|
| 15 | BCORL1 H1426fs*29 | 71 | Metastatic sarcoma (CD10 positive) consitent with spread from prior uterine adenosarcoma. | Lung | Died at 13 months after hysterectomy. |
| 16 | JAZF1-BCORL1 fusion | 75 | Recurrent metastatic myxoid spindle cell sarcoma with prior history of uterine adenosarcoma. | Large intestine, peritoneum, peri-iliac artey, presacrum, femur | Not available. |
| 17 | JAZF1-BCORL1 fusion | 67 | Metastatic spindle cell sarcoma consistent with recurrence of uterine of adenosarcoma. | Small and large intestine | Alive at 46 months after hysterectomy. |
| 18 | JAZF1-BCORL1 fusion | 63 | Residual uterine adenosarcoma status post neoajdvant radiation therapy | None available | Alive at 12 months 9 after hysterectomy. |

Most tumors were characterized by spindle cells and variable amounts of epithelioid cells with clear to pale cytoplasm (Table 4). No small round cell morphology, or heterologous or sex cord stromal elements were identified in any case. Uniform nuclei and mild to moderate atypia were observed in 57% of cases, while 43% of cases harbored severe nuclear atypia, characterized by nuclear enlargement, condensed chromatin and prominent nucleoli, often associated with the epithelioid component (FIGS. 6A-6F, FIGS. 7A-7F, and FIGS. 8A-8F). Myxoid stroma was present in 83% of cases, while collagen stromal fibrosis was present in 50% of cases. Tumor necrosis and spiral arterioles were present in 42% and 25% of cases, respectively. Mitotic count across the twelve cases with BCORL1 alterations ranged from 2 to 25 mitoses per 10 high power fields (mean=9.5, median=8.5 mitoses, range 2-25 mitoses per 10 high-power fields).

TABLE 4

Morphological features of BCORL1-altered uterine sarcomas (cases #1-12) and of the sarcomatous component of uterine adenosarcomas with BCORL1 alterations (cases #13-18).

| n | BCORL1 alteration | Atypia | Nuclei | Spindle cells | Epithelioid cells | Small cells | Myxoid stroma | Collagen fibrosis | Hypocellular fibromyxoid | Spiral arterioles | Necrosis | Mitotic count |
|---|---|---|---|---|---|---|---|---|---|---|---|---|
| 1 | JAZF1-BCORL1 fusion | Moderate to severe | Mild pleomorphism | Present | Present | Absent | Present | Absent | Present | Absent | Absent | 25 per 10 HPF |
| 2 | EP300-BCORL1 fusion | Moderate | Mild pleomorphism | Present | Present | Absent | Present | Absent | Absent | Absent | Present | 2 per 10 HPF |
| 3 | Internal BCORL1 rearrange-ment | Mild to moderate | Uniform | Present | Present | Absent | Absent | Present | Present | Absent | Absent | 8 per 10 HPF |
| 4 | JAZF1-BCORL1 fusion | Moderate | Mild pleomorphism | Present | Present | Absent | Focal | Absent | Absent | Absent | Present | 17 per 10 HPF |
| 5 | BCORL1 RI265fs*4 | Moderate to severe | Uniform | Present | Present | Absent | Present | Present | Present | Absent | Absent | 5 per 10 HPF |
| 6 | BCORL1 RI196* | Mild to moderate | Uniform | Present | Absent | Absent | Absent | Absent | Absent | Present | Absent | 2 per 10 HPF |
| 7 | BCORL1 homozygous deletion | Mild to moderate | Uniform | Present | Present | Absent | Present | Focal | Present | Present | Present | 15 per 10 HPF |
| 8 | JAZF1-BCORL1 fusion | Moderate to severe | Focal pleomorphism | Present | Present | Absent | Present | Focal | Present | Absent | Present | 10 per 10 HPF |
| 9 | BCORL1 homozygous deletion | Moderate to focal severe | Focal pleomorphism | Present | Focal | Absent | Present | Present | Present | Present | Absent | 9 per 10 HPF |
| 10 | BCORL1 T513fs*22 | Moderate | Uniform | Present | Absent | Absent | Present | Present | Present | Absent | Absent | 2 per 10 HPF |
| 11 | BCORL1 R945* | Mild to moderate | Uniform | Present | Absent | Absent | Present | Absent | Present | Absent | Absent | 4 per 10 HPF |
| 12 | BCORL1 P600fs*1 | Moderate to severe | Mild pleomorphism | Present | Focal | Absent | Focal | Absent | Absent | Absent | Present | 15 per 10 HPF |

TABLE 4-continued

Morphological features of BCORL1-altered uterine sarcomas (cases #1-12) and of the sarcomatous component of uterine adenosarcomas with BCORL1 alterations (cases #13-18).

| n | BCORL1 alteration | Atypia | Nuclei | Spindle cells | Epithelioid cells | Small cells | Myxoid stroma | Collagen fibrosis | Hypocellular fibromyxoid | Spiral arterioles | Necrosis | Mitotic count |
|---|---|---|---|---|---|---|---|---|---|---|---|---|
| 13 | JAZF1-BCORL1 fusion | Moderate to severe | Focal pleomorphism | Present | Focal | Absent | Present | Absent | Absent | Absent | Absent | 7 per 10 HPF |
| 14 | BCORL1 L461fs*5 | Mild to moderate | Uniform | Present | Absent | Absent | Absent | Absent | Absent | Present | Present | 36 per 10 HPF |
| 15 | BCORL1 H1426fs*29 | Moderate to severe | Pleomorphism | Present | Absent | Absent | Present | Absent | Absent | Absent | Present | 10 per 10 HPF |
| 16 | JAZF1-BCORL1 fusion | Moderate to severe | Multifocal pleomorphism | Present | Present | Absent | Present | Focal | Present | Absent | Present | 13 per 10 HPF |
| 17 | JAZF1-BCORL1 fusion | Moderate to severe | Multifocal pleomorphism | Present | Absent | Absent | Present | Present | Present | Present | Absent | 25 per 10 HPF |
| 18 | JAZF1-BCORL1 fusion | Moderate to severe | Pleomorphism | Present | Present | Absent | Present | Present | Present | Absent | Absent | 3 per 10 HPF |

Figures 8A, 8B, 8C, 8D, 8E, 8F:
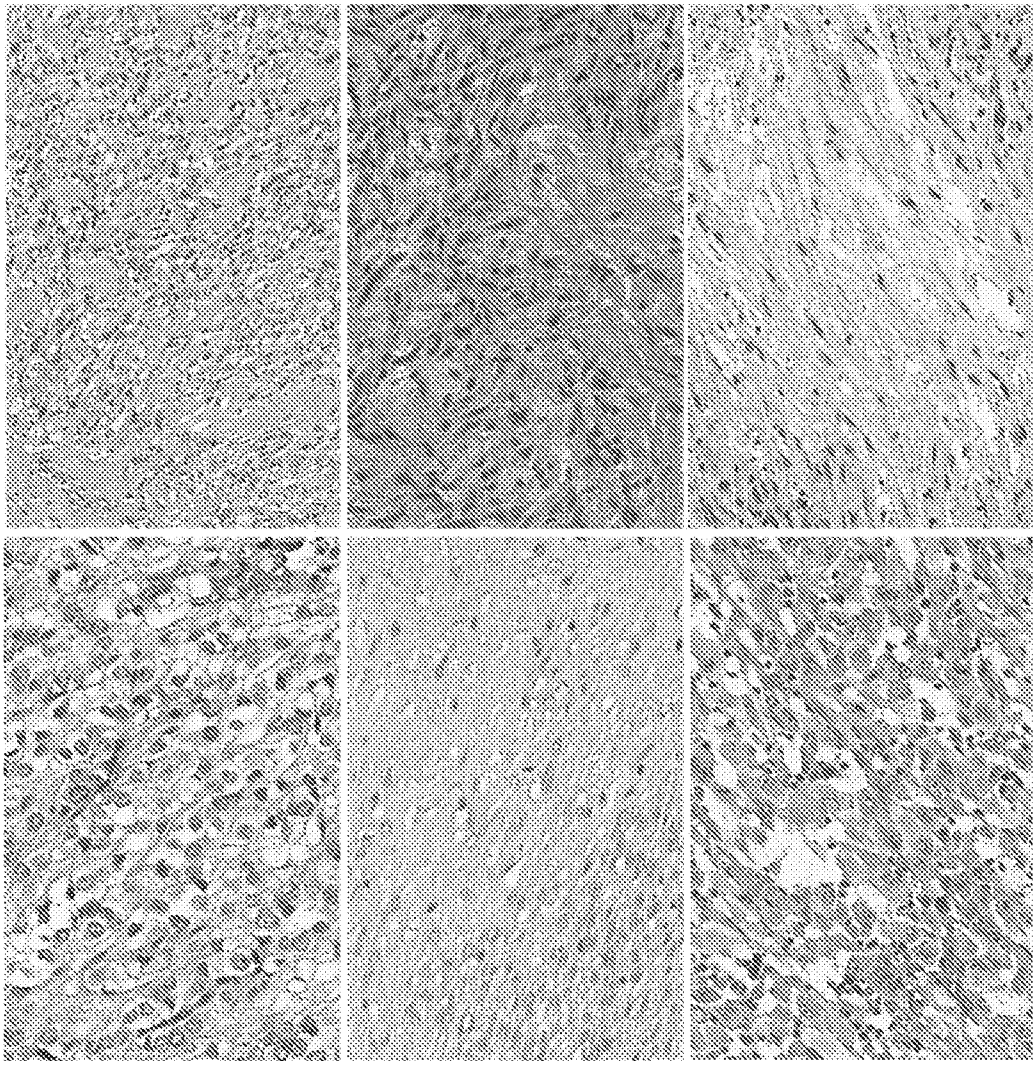
FIGS. 8A-8F show the morphology of uterine sarcomas with short variant BCORL1 mutations.
Figure 9A:
FIGS. 9A-9F show the morphology of uterine adenosarcomas with BCORL1 alterations.
Figure 9B:
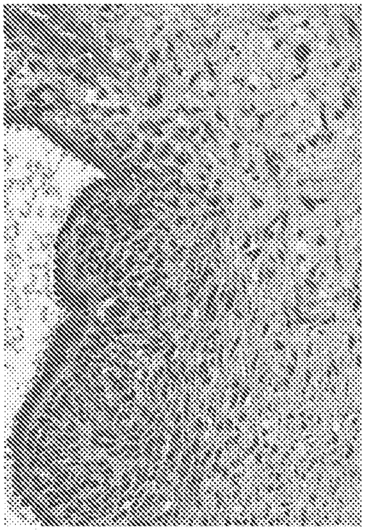
Figure 9C:
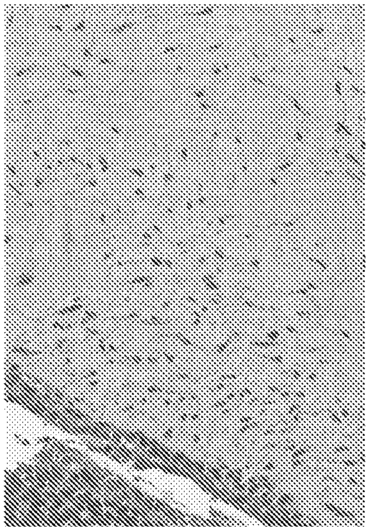
Figure 9D:
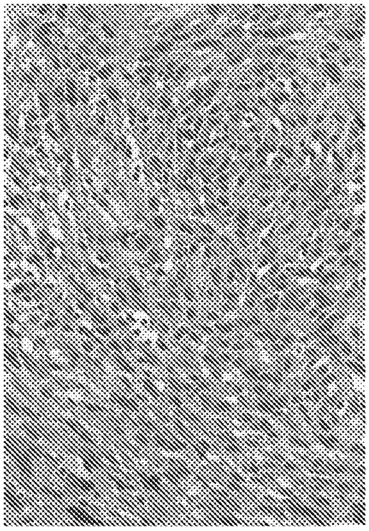
Figure 9E:
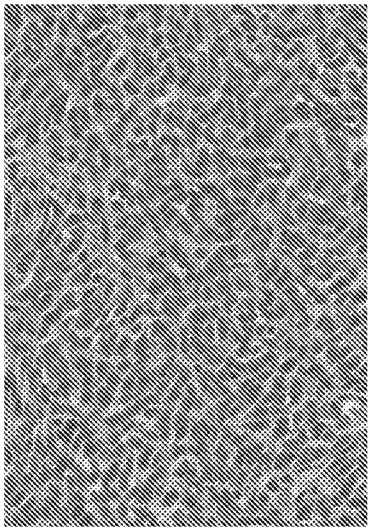
Figure 9F:
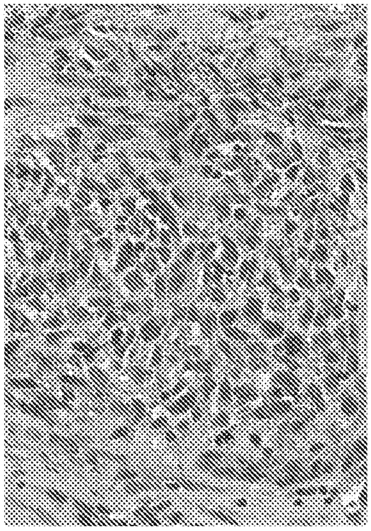

One case (case #5) also contained a JAFZ1-SUZ12 fusion, which is classically associated with low-grade endometrial stromal sarcoma. However, this case (case #5) also harbored a co-occurring BCORL1 R1265fs*4 frameshift mutation and demonstrated an associated epithelioid component with higher grade nuclear atypia, as well as myxoid and collagen fibrosis components, reminiscent of BCOR-altered endometrial stromal sarcoma (FIGS. 8A-8C). Overall, 11 of 12 cases demonstrated striking resemblance to previously described BCOR-altered endometrial stromal sarcomas in the form of myxoid stromal change, collagen fibrosis and/or epithelioid components (Lewis, N., et al. (2018) *Mod Pathol* 31:674-684; Lin, D. I., et al. (2020) *Gynecol Oncol* 157:357-366; Example 1). One exception was a uterine sarcoma with a BCORL1 R1196* mutation (case #6), which exhibited classic low-grade endometrial stromal sarcoma morphology with low-grade spindle cells in a tongue-like pattern of infiltration and devoid of myxoid, collagen fibrosis or epithelioid components. Interestingly, this case also harbored an EPC1-PHF7 fusion, which is characteristic of low-grade endometrial stromal sarcoma.

Figure 10A:
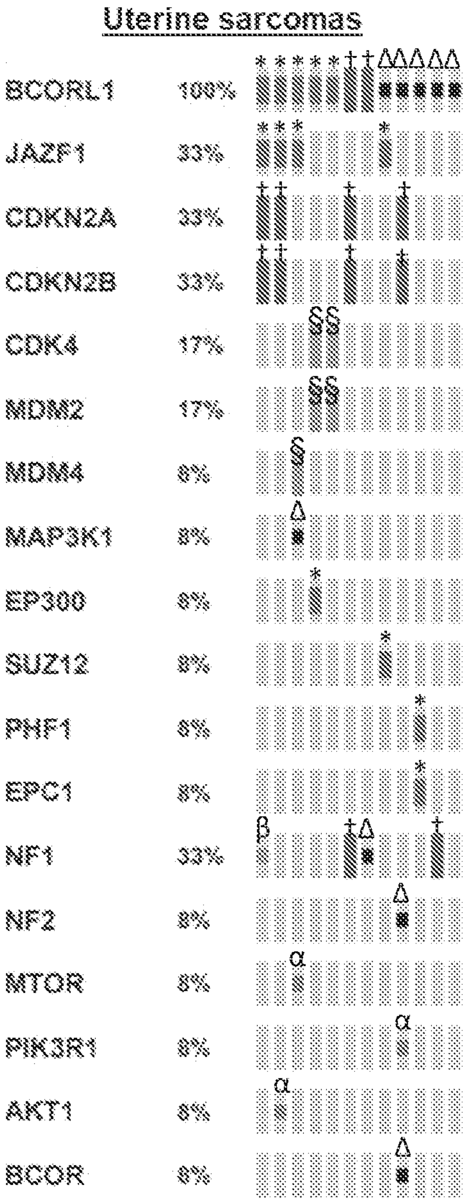
FIGS. 10A-10B show the oncoprint of cohorts of BCORL1-altered uterine sarcomas (FIG. 10A) and uterine adenosarcomas with BCORL1 alterations (FIG. 10B), demonstrating genomic profiles with frequent activation of the cyclin D-CDK4 axis via CDK4 and CDKN2A alterations. *gene rearrangement; †homozygous deletion; § amplification; Δtruncating, frameshift, or nonsense short variant mutation; α oncogenic missense mutation; β truncating splice site mutation.
Figure 10B:
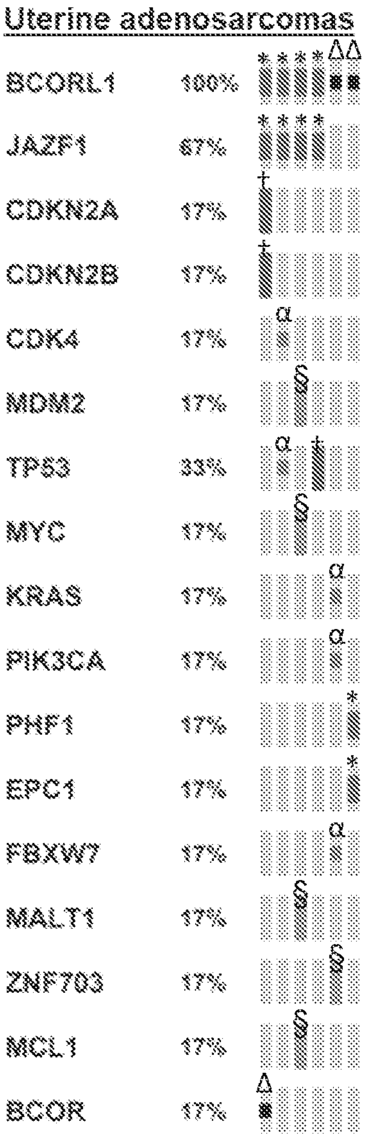

Comprehensive genomic profiling revealed that BCORL1-altered uterine sarcomas were microsatellite stable and had a low tumor mutation burden, arguing against immune checkpoint therapies based on these biomarkers. In addition to BCORL1 alterations, high frequency of homozygous deletion of CDKN2A and CDKN2B was present in 33% of BCORL1-altered uterine sarcomas, while CDK4 and MDM2 gene amplification was present in 17% of cases (FIGS. 10A-10B). Therefore, overall genomic alterations leading to the activation of the cyclin D1-CDK4 kinase pathway, via CDK4 amplification or CDKN2A loss, occurred in 6 of 12 (50%) BCORL1-altered uterine sarcoma cases at a comparable rate as seen with previously described BCOR-rearranged endometrial stromal sarcomas (Lin, D. I., et al. (2020) *Gynecol Oncol* 157:357-366; Example 1) (50% vs. 65%, p=0.5).

Other targetable alterations in BCORL1-altered uterine sarcomas included homozygous deletion or inactivating truncating mutations of NF1 (W267* and E291*) that were observed in 33% of cases (FIGS. 10A-10B). The frequency of NF1 alterations in BCORL1-mutated uterine sarcoma was higher than that seen in BCOR-rearranged endometrial stromal sarcoma (33% vs. 5%, p=0.02). Another notable difference was a higher frequency of alterations in the NF2-mTOR pathway in 25% of BCORL1-altered uterine sarcoma compared with 2.5% in BCOR-rearranged endometrial stromal sarcoma (p=0.03) (FIGS. 10A-10B). Specific alterations in the NF2-mTOR pathway included NF2 K550fs*2 and PIK3R1 D560Y in one case as well as mTOR C1483Y or AKT1 E17K in two additional cases.

BCORL1-Altered Uterine Adenosarcomas

The extent of BCORL1 genomic alterations in other uterine tumors was also assessed. In a database of mutations, uterine adenosarcomas was the only other type of uterine tumor that harbored JAZF1-BCORL1 fusion. Out of 86 predominantly advanced uterine adenosarcomas, six cases with BCORL1 genomic alterations were identified, including four cases with JAZF1-BCORL1 fusion and two cases with BCORL1 short variant frameshift mutations L461fs*5 or H1426fs*29 (FIG. 5A and Table 3, cases #13-18). The median age of this cohort was 65 years (range 45-75 years) (Table 3, cases #13-18). Sites of extra-uterine and distant metastasis for BCORL1-altered uterine adenosarcomas included vagina, lung, peritoneum, small and large intestine, pre-sacrum, and femur. Recurrences or metastasis of these cases contained only the sarcomatous component. Of patients with available clinical follow-up, one patient died of disease at 13 months after total abdominal hysterectomy (Table 3, case #15).

Most cases of BCORL1-altered uterine adenosarcomas were recurrent metastasis of only the sarcomatous component, and the original hysterectomy specimen was available for only one case to assess peri-glandular cuffing and phyllodes-like architecture of the epithelial-mesenchymal component (FIGS. 9A-9F). The sarcomatous components were characterized by spindle cells and variable amounts of epithelioid cells. Moderate to severe atypia, and myxoid or hypocellular fibromyxoid stroma were present in most cases (FIGS. 9A-9F and Table 4, cases #13-18). No small round cell morphology, sex-cord stromal, or heterologous elements were identified in any case. Mitotic count in sarcomatous component across the adenosarcoma cases ranged from 3 to 36 mitoses per 10 high power fields (mean=11.5, median=15.7 mitoses per 10 high-power fields). Like the BCORL1-uterine sarcoma cohort, one adenosarcoma case with a BCORL1 L461fs*5 frameshift mutation also harbored an EPC1-PHF1 fusion, and the morphology of the sarcomatous component of this case resembled classic low-grade endometrial stromal sarcoma (FIGS. 9A-9F). Otherwise, five (of six) uterine adenosarcoma cases had morphological features that resembled either BCORL1- or BCOR-altered uterine sarcomas.

Like BCORL1-altered uterine sarcomas, uterine adenosarcomas with BCORL1 alterations were microsatellite stable and had a low tumor mutation burden. In addition, the frequencies of alterations in CDKN2A (17%), CDK4 (17%), and MDM2 (17%) were similar in BCORL1-altered uterine adenosarcomas and BCORL1-altered uterine sarcomas (FIGS. 10A-10B). In contrast, TP53 alterations were present only in BCORL1-altered uterine adenosarcomas (33%), while no NF1 alterations were identified in BCORL1-altered adenosarcomas (FIGS. 10A-10B). A co-occurrence of both BCORL1 and BCOR alterations in the same case was also identified in 1 of 6 uterine adenosarcoma and 1 of 12 uterine sarcoma, respectively (FIGS. 10A-10B). In these 2 cases, the co-occurring BCOR alterations in were BCOR L1262fs*29 and S543*, and not the classical BCOR internal tandem duplications previously described within exon 15 of BCOR in high-grade endometrial stromal sarcomas (Lin, D. I., et al. (2020) *Gynecol Oncol* 157:357-366; Example 1).

Ancestral Analysis of BCORL1-Altered Uterine Sarcoma and Adenosarcomas

Genetic ancestry analysis was available for 11 BCORL1-altered uterine sarcomas, and for 5 BCORL1-altered uterine adenosarcomas. Of the BCORL1-altered uterine sarcomas for which genetic ancestry analysis was available, 7 of 11 (64%) BCORL1-mutated uterine sarcoma patients were of European descent, while 2 of 11 (18%) patients were of African descent, and 2 of 11 (18%) patients were of admixed American descent. Additionally, of the BCOR-altered uterine adenosarcomas for which genetic ancestry analysis was available, 4 of 5 (80%) BCORL1-mutated uterine adenosarcoma patients were of European descent, while 1 of 5 (20%) uterine adenosarcoma patients was of East Asian descent.

BCORL1 Alterations in Other Uterine Mesenchymal Tumors

In contrast to BCORL1 fusions or rearrangements, which were specific to uterine sarcomas and uterine adenosarcomas in the genomic database, a missense and a short variant BCORL1 mutation were also identified in one conventional uterine leiomyosarcoma and one uterine inflammatory myofibroblastic tumor. The conventional uterine leiomyosarcoma had a BCORL1 V1096I missense mutation, TP53, RB1, and MED12 co-alterations, and classic leiomyosarcoma morphology, without myxoid features. The uterine inflammatory myofibroblastic tumor had a BCORL1 R1196* nonsense mutation, a co-occurring RANBP2-ALK1 fusion and myxoid features. In these two cases, the morphology and genomic profiles were compatible with conventional leiomyosarcoma and inflammatory myofibroblastic tumors with co-occurring BCORL1 short variant mutations. Notably, the type of BCORL1 mutation identified in the conventional uterine leiomyosarcoma was a point mutation, BCORL1 V10961, in contrast to the nonsense and frameshift mutations that were identified in the other BCORL1-mutated uterine sarcomas with myxoid features.

CONCLUSIONS

Here, it was assessed whether molecular alterations in BCORL1, a transcriptional corepressor homologous to BCOR, defined a distinct subset of uterine sarcomas similar to BCOR. The molecular landscape of BCORL1 genomic alterations across various uterine mesenchymal malignancies was examined, and the clinicopathological and genomic features of uterine sarcomas that are driven by BCORL1 genomic alterations were characterized. Notedly, the cohort of 12 BCORL1-altered uterine sarcoma cases had several similarities to the findings previously described for BCOR-rearranged high grade endometrial stromal sarcomas (Lewis, N., et al. (2018) *Mod Pathol* 31:674-684; Lin, D. I., et al. (2020) *Gynecol Oncol* 157:357-366; Example 1). These similarities included: (1) similar median age of mid-50 years and age range of 20-30 years to 70 years in both types, (2) aggressive behavior with refractory recurrences, (3) striking morphological resemblance with hypocellular fibromyxoid areas, collagen fibrosis, and high-grade epithelioid components, (4) frequent myxoid stroma, some of which mimicked and were previously diagnosed as myxoid uterine leiomyosarcoma, and (5) frequent co-occurring genomic alterations leading to the activation of the cyclin D1-CDK4 kinase pathway, via CDK4 amplification or CDKN2A loss. These results suggest that similarly to BCOR, genomic alterations in BCORL1 drive the pathogenesis of a distinct subset of high-grade endometrial stromal sarcomas.

However, BCORL1 alterations were not specific to uterine sarcomas and were also identified in the sarcomatous component of aggressive uterine adenosarcomas. Interestingly, the sarcomatous overgrowth and metastasis of BCORL1-altered adenosarcomas exhibited morphological overlap with both BCORL1- and BCOR-altered uterine sarcomas with frequent myxoid stromal change, hypocellular fibromyxoid areas and high-grade epithelioid components. These results suggest that sarcomatous component of a subset (7%) of uterine adenosarcomas may be derived from a BCORL1-altered high-grade endometrial stromal sarcoma. Notably, within the uterine adenosarcoma database, two uterine adenosarcoma cases with either BCOR rearrangement (BCOR-NUGGC) or BCOR internal tandem duplication (not shown) were also identified, suggesting a subset of uterine adenosarcomas may be similarly driven by a BCOR-altered high-grade endometrial stromal sarcoma component.

Figure 6A:
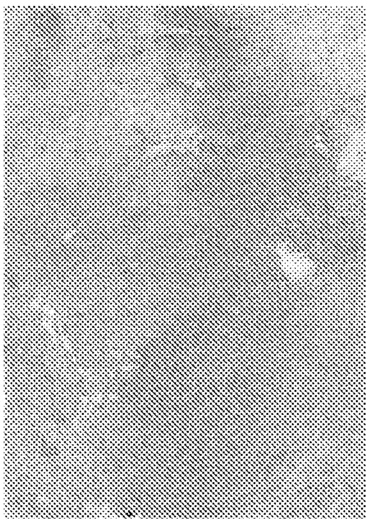
FIGS. 6A-6F show the morphological spectrum of endometrial stromal sarcomas with BCORL1 fusions.
Figure 6B:
Figure 6C:
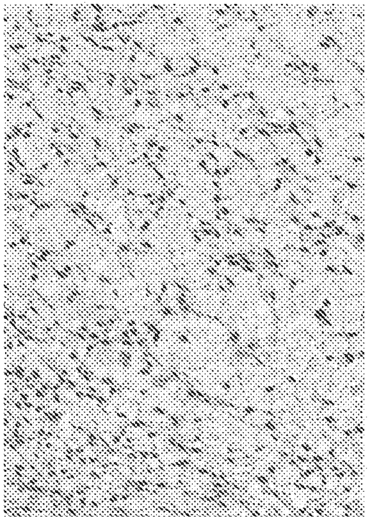
Figure 6D:
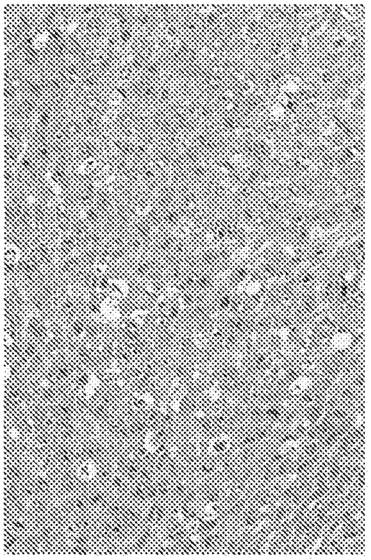
Figure 6E:
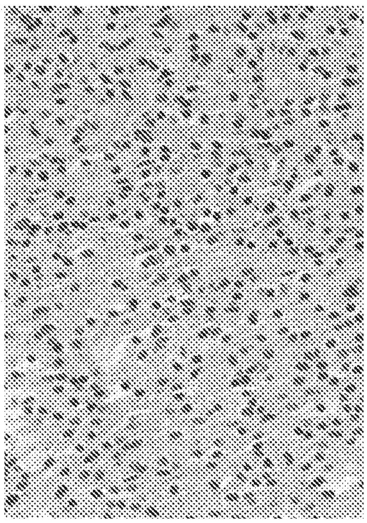
Figure 6F:
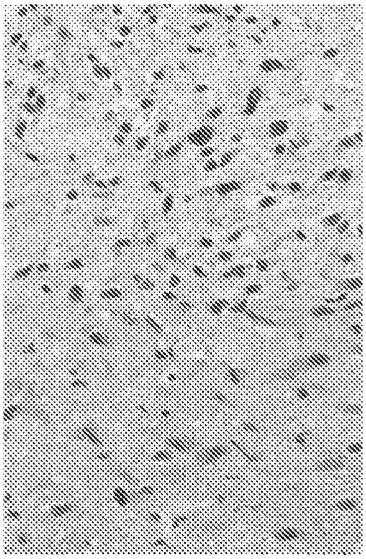
Figure 7A:
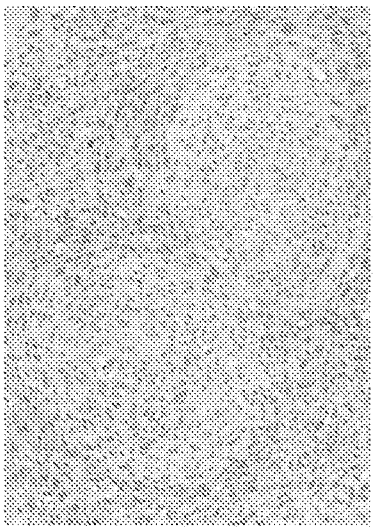
FIGS. 7A-7F show the morphological features of endometrial stromal sarcomas with homozygous BCORL1 gene deletion.
Figure 7B:
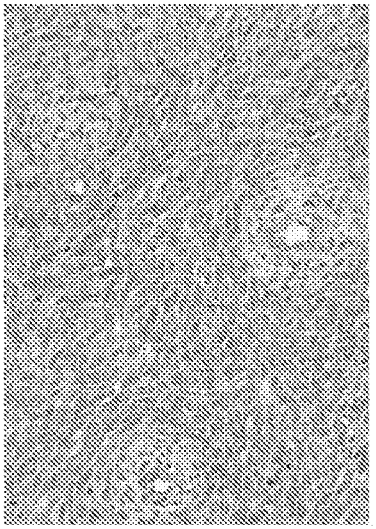
Figure 7C:
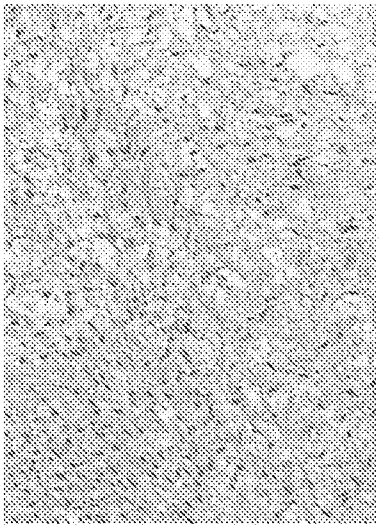
Figure 7D:
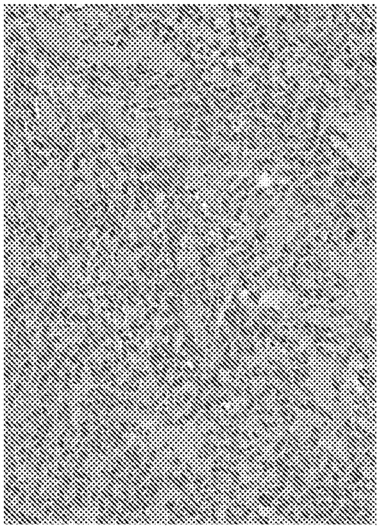
Figure 7E:
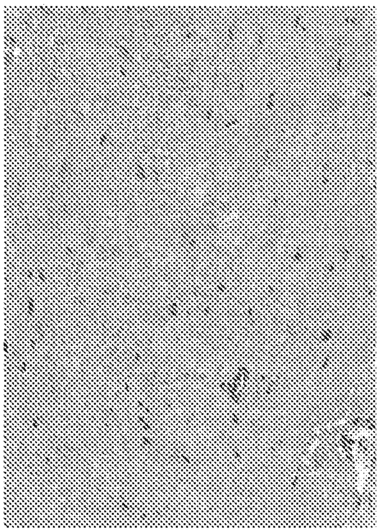
Figure 7F:
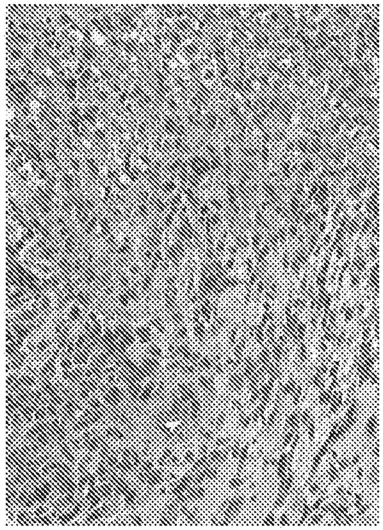

Most of the short variant BCORL1 alterations in the uterine sarcomas or adenosarcomas were nonsense mutations or out-of-frame insertions that are predicted to encode truncated proteins lacking the last C-terminal LXXLL nuclear receptor recruitment motif and ANK and PUFD domains, which are involved in protein-protein interactions and transcriptional regulation (Plevin, M. J., et al. (2005) *Trends Biochem. Sci.* 30:66-69) (FIG. 6A). In addition, two uterine sarcoma cases with homozygous BCORL1 loss were identified. These results suggest that a subset of uterine sarcomas and adenosarcomas are driven by BCORL1 loss of function within the PRC1 transcriptional complex, leading to transcriptional de-regulation. Supporting this notion, two BCORL1-mutated cases also exhibited co-occurring BCOR alterations (FIG. 10A-10B), likely further contributing to PRC1 transcriptional dysfunction. In addition, none of the BCORL1 short variant alterations were subclonal (defined as BCORL1 next-generation sequencing variant allele frequency less than 10% of tumor purity). While loss of heterozygosity of second the BCORL1 could not be determined, BCORL1 is located on the X chromosome, and the second BCORL1 allele may be subject to complete chromosome X inactivation in females (Carrel. L., and Willard, H. F. (2005) *Nature* 434:400-404).

While JAFZ1-BCORL1 or EP300-BCORL1 fusions and homozygous BCORL1 deletion appeared specific to uterine sarcomas or adenosarcomas, a BCORL1 point mutation and a BCORL1 nonsense mutation were also identified in one conventional uterine leiomyosarcoma and one myxoid inflammatory myofibroblastic tumor. However, the morphology and genomic profiles of these two cases were different than BCORL1-altered uterine sarcomas and compatible with the diagnoses. Moreover, short variant BCORL1 frameshift or nonsense mutations were also identified in endometrial carcinomas and carcinosarcomas, especially in a microsatellite instability setting. Defects in the mismatch repair system often results in frameshift mutations, and therefore most of the BCORL1 short variant mutations in endometrial carcinoma or carcinosarcoma were likely secondary mutations due to microsatellite instability rather than primary driver mutations as seen in microsatellite stable uterine sarcomas or adenosarcomas.

Here, novel BCORL1 rearrangements in uterine sarcomas such as EP300-BCORL1 are reported, as well as a case of uterine sarcoma with internal BCORL1 gene rearrangement without another gene partner. Interestingly, similar EP300-BCOR and internal BCOR rearrangements have also been previously identified in BCOR-rearranged high-grade endometrial stromal sarcomas, which also demonstrated similar spindle, epithelioid and myxoid morphology (Lin, D. I., et al. (2020) *Gynecol Oncol* 157:357-366; Example 1).

Like BCOR-rearranged endometrial stromal sarcomas, BCORL1-altered uterine sarcomas and adenosarcomas exhibited high frequencies of CDK4 amplification and CDKN2A homozygous gene deletion. Genomic alterations leading to the activation of the cyclin D1-CDK4 kinase, via CDK4 amplification or CDKN2A loss, occurred in 50% and 34% BCORL1-altered uterine sarcomas or adenosarcomas, respectively. Future investigation would be of interest to determine whether refractory tumors with CDK4 and CDKN2A alterations are responsive to CDK4 inhibitors, such as palbociclib, ribociclib, and abemaciclib, in patients that fail conventional therapy and in which current standard treatments may no longer be clinically effective. CDK4 inhibitors are currently FDA-approved for the treatment of ER-positive and HER2-negative breast carcinomas with minimal side effects (Turner, N.C., et al. (2015) *N Engl J Med* 373:209-219; Turner, N.C., et al. (2018) *N Engl J* 379:1926-1936).

In contrast to BCOR-rearranged uterine sarcomas in which only a small minority exhibited NF1 (5%) or NF2 (2.5%) alterations (Lin, D. I., et al. (2020) *Gynecol Oncol* 157:357-366; Example 1), BCORL1-altered uterine sarcomas harbored inactivating NF1 mutations or alterations of the mTOR-NF2-AKT pathway in 33% and 25% of cases, respectively. For these reasons, based on response in other tumor types (See, W. L., et al. (2012) *Cancer Res* 72:3350-3359; Ali, S. M., et al. (2015) *Eur Urol* 67:1195-1196), off-label use of MEK inhibitors or mTOR inhibitors as single agents or in combination with other therapies could also be considered in a subset of BCORL1-mutated uterine sarcomas that are refractory to conventional cytotoxic chemotherapy.

This Example demonstrates the value of next-generation sequencing-based comprehensive genomic profiling for identifying BCORL1-mutated uterine sarcomas, since the BCORL1 nonsense and frameshift mutations observed here would not have been detected by either FISH or sarcoma fusion panels, similarly to the previously described BCOR internal tandem duplications (ITDs) within exon 15 of BCOR in high-grade endometrial stromal sarcomas. Therefore, during the pathological work-up of a uterine sarcoma case, a negative FISH or sarcoma fusion panel result for BCOR or BCORL1 may warrant reflex testing to a next-generation sequencing based assay for a more comprehensive evaluation of either BCOR or BCORL1.

In conclusion, the clinicopathological and molecular features of uterine sarcomas and adenosarcomas driven by BCORL1 genomic alterations were evaluated. BCORL1-altered uterine sarcomas and the sarcomatous component of adenosarcomas with BCORL1 alterations had striking morphological resemblance to previously described BCOR-rearranged high-grade endometrial stromal sarcomas. Given homologous gene structures, related biological functions of BCORL1 and BCOR and similar clinicopathological features, BCORL1-altered uterine sarcomas may represent a new subtype of high-grade endometrial stromal sarcomas, which may also include the sarcomatous component of a subset of BCORL1-mutated uterine adenosarcomas. This new group of aggressive BCORL1-mutated uterine mesenchymal tumors may mimic myxoid leiomyosarcomas and should also be considered in the differential diagnosis of myxoid uterine mesenchymal neoplasms.

What is claimed is:

1. A method of treating or delaying progression of cancer, comprising, responsive to knowledge of a rearrangement in a BCOR gene in a sample from an individual, administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor; wherein the BCOR rearrangement: (a) results in a fusion gene between BCOR and L3MBTL2, EP300, NUTM2G, MAP7D2, RALGPS1, RGAG1, ING3, NUGGC, or KMT2D; or (b) is an internal BCOR gene rearrangement characterized by a chromosome X inversion; wherein the cancer is uterine sarcoma.

2. A method of treating or delaying progression of cancer, comprising:

(a) acquiring knowledge of a rearrangement in a BCOR gene in a sample from an individual; wherein the BCOR rearrangement: (a) results in a fusion gene between BCOR and L3MBTL2, EP300, NUTM2G, MAP7D2, RALGPS1, RGAG1, ING3, NUGGC, or KMT2D; or (b) is an internal BCOR gene rearrangement characterized by a chromosome X inversion; and (b) responsive to said knowledge, administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor;

wherein the cancer is uterine sarcoma.

3. A method of treating or delaying progression of cancer, comprising:

(a) detecting a rearrangement in a BCOR gene in a sample from an individual; wherein the BCOR rearrangement: (a) results in a fusion gene between BCOR and L3MBTL2, EP300, NUTM2G, MAP7D2, RALGPS1, RGAG1, ING3, NUGGC, or KMT2D; or (b) is an internal BCOR gene rearrangement characterized by a chromosome X inversion; and (b) administering to the individual an effective amount of a treatment that comprises a targeted therapeutic comprising a CDK inhibitor, an MDM2 inhibitor, a tyrosine kinase inhibitor, a MEK inhibitor, an mTOR inhibitor, PIK3CA or AKT inhibitor, or a Hh inhibitor;

wherein the cancer is uterine sarcoma.

4. The method of claim 3, wherein the cancer is endometrial stromal sarcoma (ESS).

5. The method of claim 3, wherein a sample obtained from the cancer is:

(a) characterized by 19 or fewer mutations per megabase (Mb); and/or (b) microsatellite stable.

6. The method of claim 3, wherein the cancer is resistant or refractory to treatment with conventional chemotherapy.

7. The method of claim 3, further comprising selectively enriching for one or more nucleic acids comprising a rearrangement in a BCOR gene to produce an enriched sample.

8. The method of claim 3, wherein the treatment further comprises a second therapeutic agent that comprises a chemotherapeutic agent, immune checkpoint inhibitor (ICI), cancer immunotherapy, cell-based therapy, or nucleic acid-based therapy.

9. The method of claim 3, wherein the sample from the individual comprises fluid, cells, or tissue.

10. The method of claim 9, wherein the sample from the individual comprises a tumor biopsy, a circulating tumor cell, or a nucleic acid sample that comprises mRNA, genomic DNA, circulating tumor DNA, cell-free DNA, or cell-free RNA.

* * * * *